US012180523B2

(12) United States Patent
Tholl et al.

(10) Patent No.: US 12,180,523 B2
(45) Date of Patent: Dec. 31, 2024

(54) SOUTHERN GREEN STINK BUG PHEROMONE SYNTHESIS ENZYMES AND USES THEREOF

(71) Applicant: VIRGINIA TECH INTELLECTUAL PROPERTIES, INC., Blacksburg, VA (US)

(72) Inventors: Dorothea Tholl, Blacksburg, VA (US); Jason Lancaster, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 576 days.

(21) Appl. No.: 17/291,604

(22) PCT Filed: Sep. 28, 2019

(86) PCT No.: PCT/US2019/053708
§ 371 (c)(1),
(2) Date: May 5, 2021

(87) PCT Pub. No.: WO2020/096711
PCT Pub. Date: May 14, 2020

(65) Prior Publication Data
US 2021/0388335 A1  Dec. 16, 2021

Related U.S. Application Data

(60) Provisional application No. 62/756,392, filed on Nov. 6, 2018.

(51) Int. Cl.
*C12N 15/82* (2006.01)
*C12N 9/88* (2006.01)
*C12P 5/00* (2006.01)

(52) U.S. Cl.
CPC ........... *C12N 9/88* (2013.01); *C12N 15/8243* (2013.01); *C12P 5/007* (2013.01)

(58) Field of Classification Search
None
See application file for complete search history.

(56) References Cited

U.S. PATENT DOCUMENTS

2012/0094386 A1  4/2012  Mendez et al.
2016/0244773 A1  8/2016  Inoue et al.

OTHER PUBLICATIONS

Venter et al. Accession ABL18121, Deposited Sep. 27, 2001.*
"International Search Report and Written Opinion issued by the United States Patent Office, as International Searching Authority", for PCT/US2019/053708 on Feb. 6, 2020.
"Invitation to Pay Additional Fees issued by the United States Patent Office, as International Searching Authority", for PCT/US19/53708 on Dec. 16, 2019.
Lancaster, et al., "Nezara viridula terpene synthase (TPS) mRNA, complete cds", The Journal of Antibiotics, vol. 68, No. 6, pp. 1-2, Jan. 9, 2020.
Yamada, et al., "Novel terpenes generated by heterologous expression of bacterial terpene synthase genes in an engineered Streptomyces host", J. Antibiot (Tokyo), vol. 68, No. 6, pp. 385-394, Jun. 2015.
Little and Croteau, 2002 Arch Biochem Biophys, Jun. 1;402(1): 120-35. doi: 10.1016/S0003-9861(02)00068-1.
Belles et al. 2005. Annual Review in Entomology, 2005, 50, 181-199.
Pickett et al. 2013. Nat. Prod. Rep 30:1277-1283).
Sobotnik et al. 2008. J Chem Ecol: 34:478-486).
Honda 1981. J. Chem Ecol. 7:1089-1113.
Omura et al. 2006. J Chem Ecol. 32:1999-2012.
Bodemann et al. 2012. Proc RSoc B. 279:4126-4134 ).
Lee and Kim. 2018. FEMS Microbiol. Lett. 1:365(17).
Müller and Buchbauer. 2011. Flavour Frag J 26:357-377.
Stokl and Steiger. 2017. Curr Opp Insct Sci 24:36-42.
Blomquist and Vogt. 2003. PNAS 113:2922-2927.
Jurenka. 2004. Insect pheromone biosynthesis. In: Schulz (ed.) Chemistry of pheromones and other Semiochemicals I, vol. 239. Topics in current Chemistry. pp 97-131.
Yew and Chung. 2015. Prog Lipid Res. 59:88-105.
Cai et al. 2002. Phytochemistry.61:523-529.
Tillman et al. 1999. Insect Biochem Mol Biol. 29:481-514.
Bartelt et al. 2001. J. Chem Ecol. 27:2397-2423.
Brown et al. 2006. J. Cehm Ecol. 32:2489-2499.
Dewhirst et al. 2010. Aphid pheromones. In: Litwack G. (ed) Vitamins and hormones: pheromones, vol. 83. Academic Press, pp. 551-574.
Sillam-Dusses et al. 2009. J. Insct Physiol 55:751-757.
Tholl. 2015. Adv. Biochem Eng—Biotechnol. 148:63-106.
Chen et al. 2011. Plant J. 66:212-229.
Christianson. 2017. Chem Rev. 117-11570-11648.
Degenhardt et al. 2009. Phytochemistry. 70:1621-1637.
Dickschat. 2016. Nat Prod Rep. 33:87-110.
Noriega. 2014. Juvenile hormone biosynthesis in insects: what is new, what do we know, and what questions remain? ISRN Zoology 967361.
Cusson et al. 2006. Proteins. 65:742-758.
Ma et al. 2010. Insect Biochem. Mol. Biol. 40:552-561.
Sen et al. 2007. Insect Biochem Mol. Biol. 37:819-828.
Taban et al. 2009. Arch Insect Biochem Physiol. 71:88-104.
Vandermoten et al. 2008. FEBS Lett. 582:1928-1934.
Frick et al. 2013. PNAS. 110:56-61.
Lewis et al. 2008. Insect Mol Biol. 17:437-443.
Gilg et al. 2009. Naturwissenschaften 96:731-735.
Gilg et al. 2005. PNAS 102:9769-9765.
Beran et al. 2016. PNAS. 113:2922-2927.

(Continued)

*Primary Examiner* — Medina A Ibrahim
(74) *Attorney, Agent, or Firm* — Carin R. Miller, Esq.; Johnson, Marcou, Isaacs & Nix, LLC

(57) ABSTRACT

Described herein are engineered polynucleotides and vectors capable of encoding one or more engineered southern green stink bug pheromone synthesis enzymes. Also described herein are engineered southern green stink bug pheromone synthesis enzymes. Also described herein are methods of making modified plants capable of expressing one or more southern green stink bug pheromone synthesis enzymes.

20 Claims, 17 Drawing Sheets
Specification includes a Sequence Listing.

(56) References Cited

OTHER PUBLICATIONS

Beran et al. 2016. J Chem Ecol. 42:748-755.
Weber et al. 2018. CRC Press, Boca Raton, pp. 677-725.
Khrimian et al. 2014. J Chem Ecol 40:1260-1268.
Weber et al. 2014. J Chem Ecol. 40:1251-1259.
Zahn et al. 2008. J Chem Ecol 34:238-251.
Lancaster et al. 2018. PNAS 1150: 115: E8534-E8641.
Aldrich et al. 1987. J Exp. Zool. 244: 171-175.
Harris and Todd. 1980. Entomol Exp Appl. 27:117-126.
Cribb et al. 2006. J Morphol 267: 831-840.
Brezot et al. 1994. J Chem Ecol. 20:4133-3147.
Brezot et al. 1993 J Chem Ecol.
Baker et al. 1987. J Chem Soc Chem Commun: 414-416.
Tholl et al. 2005. Plant. J. 42:757-771.
Wallrapp et al. 2013. PNAS. 110:E1196-E1202.
Bolger et al. 2014 Bioinformatics. Aug. 1, 2014;30(15):2114-20. doi: 10.1093/bioinformatics/btu170.
Grabherr et al. 2011. Nature Biotechnology vol. 29, pp. 644-652.
Langmead and Salzberg. 2012. PNAS 115:E8634-E8641.
Livak and Schmittgen. 2001. Methods 25:402-408.
Sparks et al. 2017. Insects 8:55.

\* cited by examiner

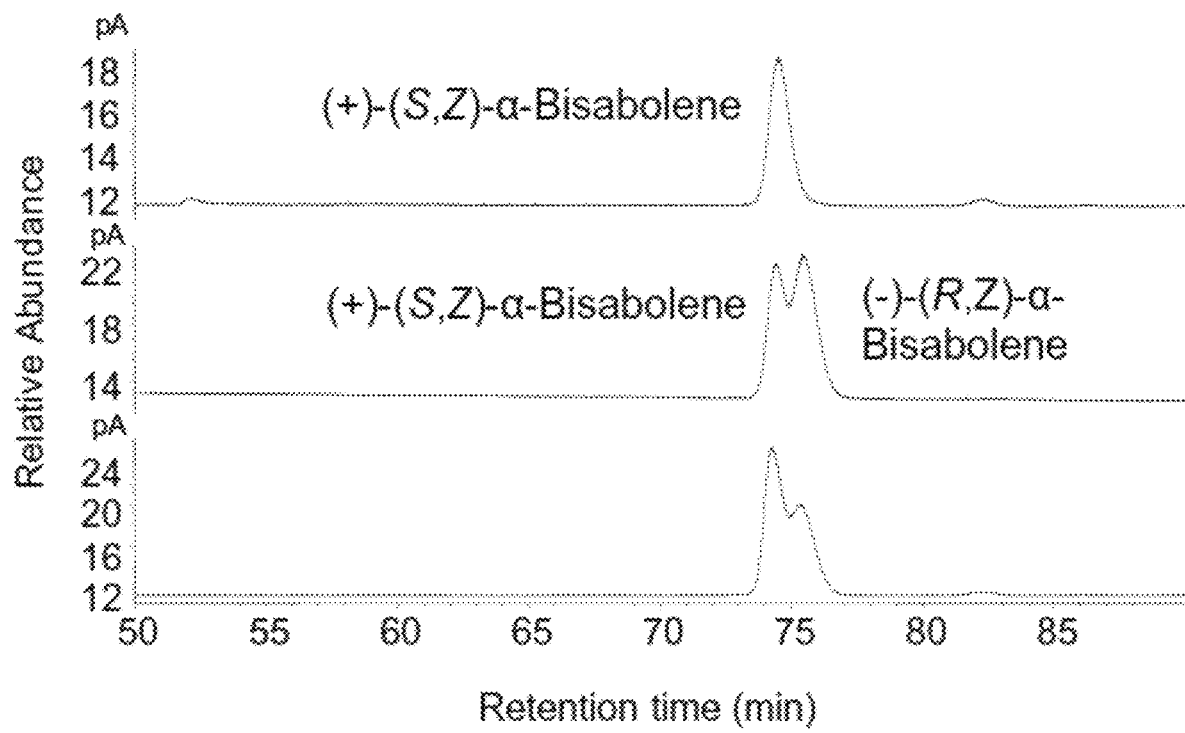
FIG. 3
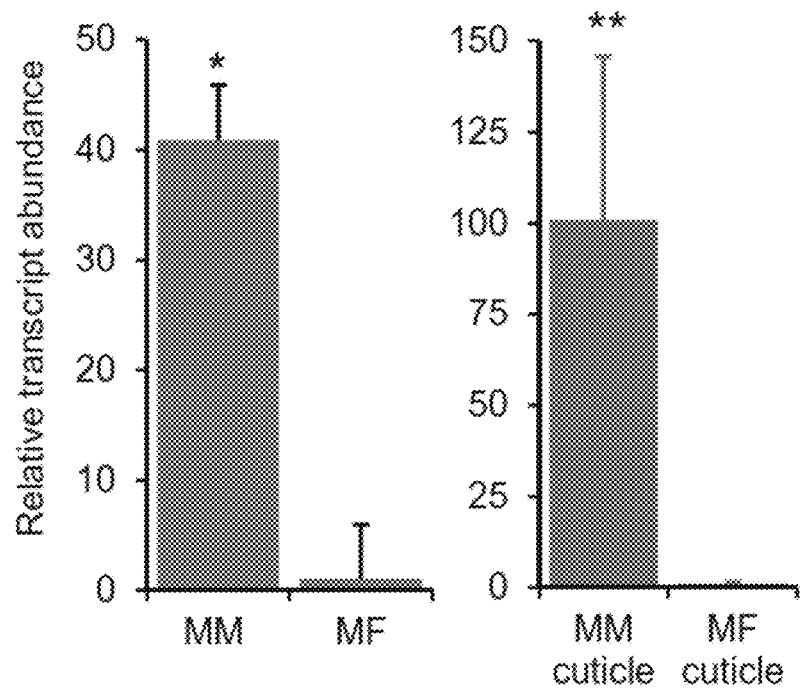
FIG. 4A  FIG. 4B

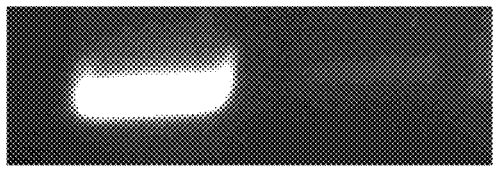 NvTPS
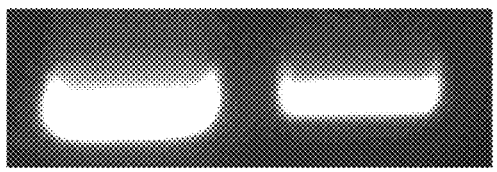 NvFPPS
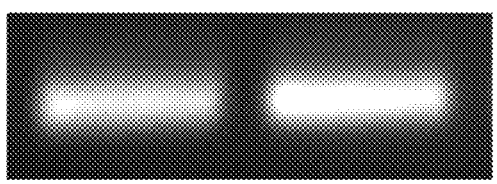 RpS4
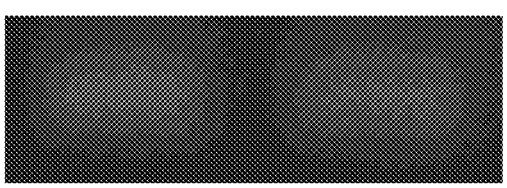 18S
FIG. 8A
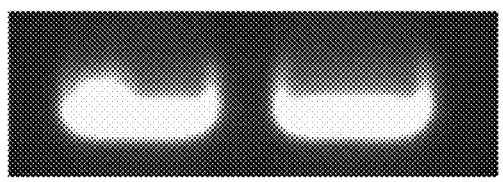 NvTPS
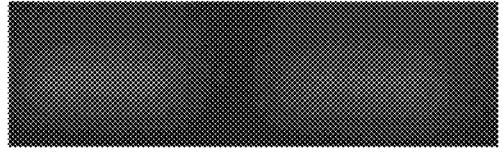 18S
FIG. 8B

FIG. 9 (ctd.)

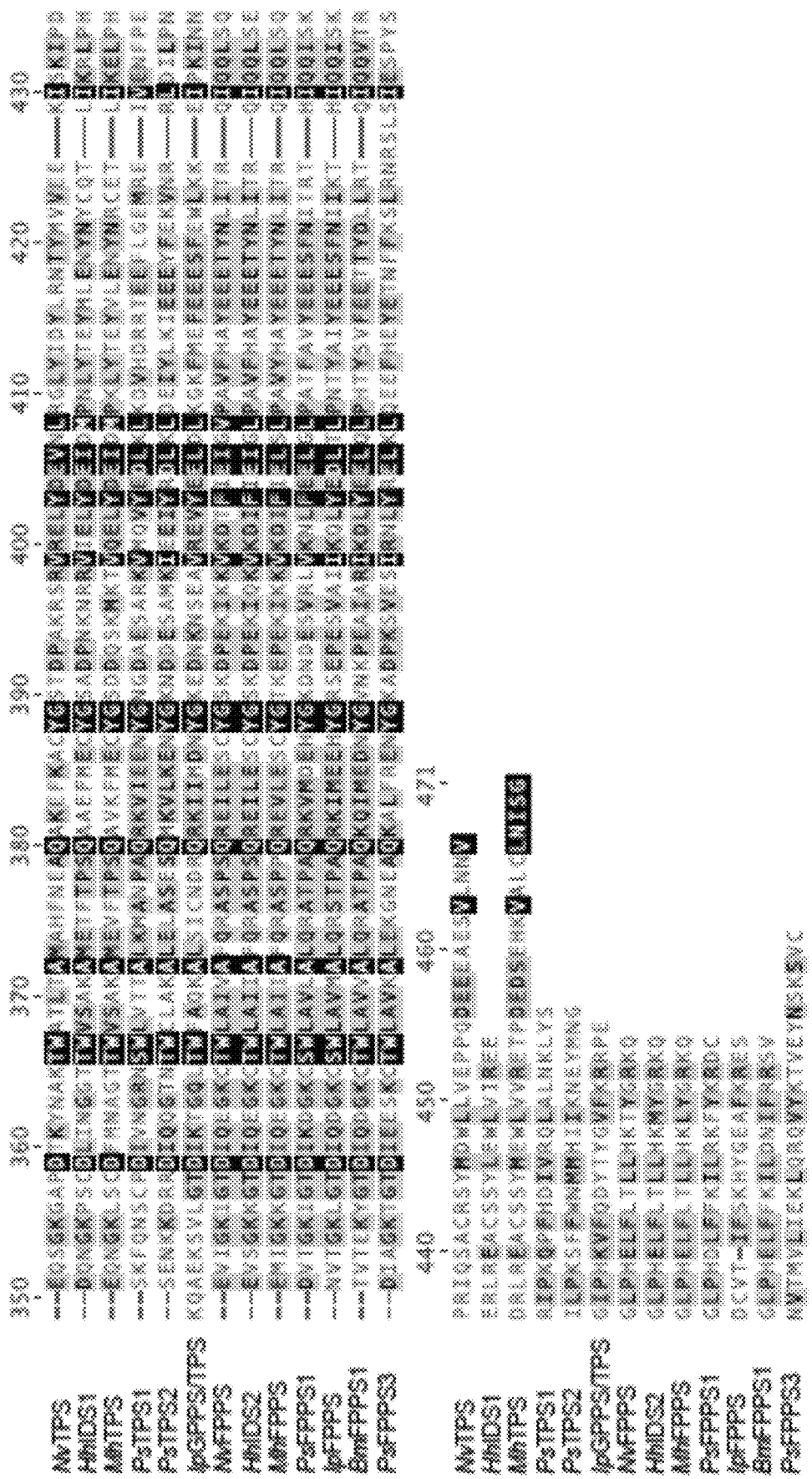
FIG. 9 (ctd.)

| Gene | Query Sequences (tblastn) | *N. viridula* Acc. Nos. |
|---|---|---|
| *NvIDS1/ NvTPS* | *Murgantia histrionica* TPS (MG662378) | MG748543 |
| | *Murgantia histrionica* FPPS (MG662379) | |
| | *Ips pini* FPPS (AAX55631.1) | |
| | *Ips pini* GPPS/TPS (AY953508) | |
| *NvIDS2/ NvFPPS* | *Murgantia histrionica* TPS (MG662378) | MG748544 |
| | *Murgantia histrionica* FPPS (MG662379) | |
| | *Ips pini* FPPS (AAX55631.1) | |
| | *Ips pini* GPPS/TPS (AY953508) | |
| *NvIDS3* | *Murgantia histrionica* TPS (MG662378) | MG748545 |
| | *Murgantia histrionica* FPPS (MG662379) | |
| | *Ips pini* FPPS (AAX55631.1) | |
| | *Ips pini* GPPS/TPS (AY953508) | |

FIG. 11

|        | MhTPS  | HhTPS  | NvTPS  | MhFPPS | HhFPPS | NvFPPS |
|--------|--------|--------|--------|--------|--------|--------|
| MhTPS  |        | 80.43% | 38.18% | 22.63% | 23.28% | 23.04% |
| HhTPS  | 80.43% |        | 38.17% | 23.84% | 24.75% | 24.02% |
| NvTPS  | 38.18% | 38.17% |        | 17.96% | 18.58% | 17.85% |
| MhFPPS | 22.63% | 23.84% | 17.96% |        | 87.68% | 86.70% |
| HhFPPS | 23.28% | 24.75% | 18.58% | 87.68% |        | 88.83% |
| NvFPPS | 23.04% | 24.02% | 17.85% | 86.70% | 88.83% |        |

FIG. 12

SEQUENCE LISTING

<160> NUMBER OF SEQ ID NOS: 101

<210> SEQ ID NO 1
<211> LENGTH: 1137
<212> TYPE: DNA
<213> ORGANISM: Nezara viridula

<400> SEQUENCE: 1
atggcagcaa gggcacccgt acacctcaga ggatttattg caagagtcgc ccttaacaag 60
aaaaatcttc atgcaagaca taagctagac acagatattg acaaatatta ttacacgctc 120
cacaatgtaa taattccaga ttttatggat atggttaagg aaataccagg ttatccagaa 180
aggattaaga agtgcgttgc tcacaccacc ccatcatatt ttgaaggatg ggccttcagc 240
accgaattaa tatacaaaac agtggcagat aaacaacatc aaacagaaag gaacttagaa 300
aagtgtagaa tcatcagagc tttgatggat atgagctatg cgatggcagg aatacttgat 360
gactatgttg acaaaggtga gttcagacga ggtaagaagg tttgggcttc cgtgtgtgag 420
ggaggccaag aagctgcaat ctacgactcc attgctgtca cctacttgat gtcacttatg 480
gttaagcgcc acttcggtac ggatccagga tatagcaagc tgatagaatt atttaatatg 540
gttcctggca cagcggcgat agggaacacg ctggatatcc ttgaccgtca cgacacaaac 600
tactatgatg atacaatgtg gaaacattcc gtccaaaaca aagcagcaaa tactgtattt 660
cctgcagcaa ctgctggcct aattcatgca ggagtactct gtgatgacct acttgataga 720
actagtgaag tgtttggcta cactggacat ctgtttcaag tctgggatga tttcatggaa 780
cactacgctg tgaaagaaca atctggcaaa ggtgctccag ataccaaata taacgcaaaa 840
acttgggcaa cgttgactgc aatggcccac tttaatgaag cccaagccaa ggagtttaag 900
gcctgctacg ggtccaccga tccagccaaa agatcgagag tgcgcgaact atatgatgaa 960
gtgaatttac gaggactata tattgattat ctcagaaata cttatatggt cgtggaagaa 1020
aaaatcagca aaattcccga tcccagaata caaagtgcct gtagaagcta catggattgg 1080
ttgcttgttg aaccacccca ggatgaagaa gaagctgaaa gcgtattaaa taactga 1137

<210> SEQ ID NO 2
<211> LENGTH: 1212
<212> TYPE: DNA
<213> ORGANISM: Nezara viridula

<400> SEQUENCE: 2
atgccacttg caaaactgtg cgcgaaaaaa ctttcaagcc ctttaatgaa attatgttac 60
cctaatttga acggaaaatt gccctttagt aatttatcta atatcttaga caattcttct 120
ttaaaatttc atagctgcaa tcctcatatt acctgcagag ggcttagcac agttgcacta 180
cgtccacaga ctataacaaa agatgataag agagatttta tggctgtatt tccagacatt 240
gttcgggatt tgacacaact gaatcctgga atatcagatc tcagtacttt aatttctaag 300
attatgcaat ataatgtatc aggaggaaag aaagtaagag ggctgactgt tgtttatagt 360
tatcgcatgc ttgctcctga ccatgcttta acaccagaaa acatcaggct ggcccagatt 420
ttagggtggt gcgttgaaat gctccaagga tttttcttag ttattgatga tcttgctgat 480
cagtctataa ctagaagggg aagaccctgt tggtatagaa atcctgatgt tggacttcgt 540
gctggttctg atgctcttct tatacagtca ggaacttttc aactgcttca acaacattgc 600
aaagatagag agttctatat tgatcttgtt gaattatttt tggatgctgt aaggcgtact 660
acctatggac aaacattaga tcacgtttct tcatttccta acatcactca cttaacaatg 720

```
gataggtata actttatcac aaaatataaa acatcgtact acactttcca tttgccagta    780
gccactgcaa tgtatatggc tggtatttac aatactgaat tgcatcgtca agctaaaagt    840
gttttacttg aaatgggaca ttactttcaa gttcaggatg actatcttga tgtgtttggt    900
gatgaagaag ttatcggaaa gataggtact gatattcagg aaggaaagtg cacatggcta    960
gctattgttg catttcaaag agcttcacca tctcagagag aaattttaga gtcctgctat   1020
ggaagtaaag acccagaaaa aattaaaaaa gtgaaggata cttttataga aattggtgtt   1080
cctgcagttt ttcatgctta tgaagaagaa acatataatt tgatcacaag acaaatacaa   1140
caattaagtc aaggcctgcc tcatgaatta tttcttacat tattacataa acatatggc    1200
agaaagcagt ag                                                       1212
```

<210> SEQ ID NO 3
<211> LENGTH: 1134
<212> TYPE: DNA
<213> ORGANISM: Nezara viridula

<400> SEQUENCE: 3

```
atggcagcaa gggcatcggt aaatctaaga ggttttttag caagagtcgc gcaaaataag     60
gaaaatgttc atgtaagaca taagttggac acagaaattg acaaatatta taagacactc    120
cacaatgtag tcattccaga ttgtatggat ttggtgaagg aaataccagg ttatccacaa    180
agggttaaag agtgcatttc acacaccacc ccatcatatt atgacgggtg gaacttcagc    240
atcgaattaa tgtataaaac agtggcagat gaacaccatc aaacagaaaa gaacttggaa    300
aagtgtagaa tactcagagc cttgaaggat atgagctatg cgatggcagg tatagttgat    360
gactatgctg ataaaggtga atacagacat ggtaagaagg tttgggcttc catatgcgaa    420
ggaggccaag aagctgcaat ctacgactcc gtcgcagtca actacttgat actactgatg    480
cttcatcgcc acttcaggaa tgatccagga tacagcaggc tgttagaact atataatatg    540
gttcctggca cagcagcgat aggaaacacg ctggatatcc ttgaccgtta caactcaaac    600
tacagtgatg atatatggaa acatactgtc caaaacaaag caatgaattc aatatgtact    660
gcaggaggta caggcctagt tcatgctgga gttatctgtg atgacctgat tgctaaaact    720
tgtgatgttt ttcgctacac tggacttctg tttcaagtgt gggatgattt catggaatac    780
tatgctttgc aagaacaatc tggtaaaggt tctccagata gcgaatataa tataaaatcc    840
tgggcaactg tgactgcaat ggcccacttt aatgaagccc aagctaagga gtttagggcc    900
tgctacgggt ccagcgatcc agccaaaaga tcaagagtgc gggagctgta tgatgaagtg    960
aatttaccag gactatacat ggattatctt agaaatattc atatgacaat ggaaaaaaaa   1020
attagcatta ttccaaatcc aagaatacga agcgcctgca ctagctatat ggaatggttg   1080
ctcgttgaac cacccaacgt tgaagaacaa attgaaagaa taaagtgta ttaa          1134
```

<210> SEQ ID NO 4
<211> LENGTH: 378
<212> TYPE: PRT
<213> ORGANISM: Nezara viridula

<400> SEQUENCE: 4

```
Met Ala Ala Arg Ala Pro Val His Leu Arg Gly Phe Ile Ala Arg Val
1               5                   10                  15

Ala Leu Asn Lys Lys Asn Leu His Ala Arg His Lys Leu Asp Thr Asp
            20                  25                  30
```

```
Ile Asp Lys Tyr Tyr Tyr Thr Leu His Asn Val Ile Ile Pro Asp Phe
        35                  40                  45

Met Asp Met Val Lys Glu Ile Pro Gly Tyr Pro Glu Arg Ile Lys Lys
 50                  55                  60

Cys Val Ala His Thr Thr Pro Ser Tyr Phe Glu Gly Trp Ala Phe Ser
 65                  70                  75                  80

Thr Glu Leu Ile Tyr Lys Thr Val Ala Asp Lys Gln His Gln Thr Glu
                 85                  90                  95

Arg Asn Leu Glu Lys Cys Arg Ile Ile Arg Ala Leu Met Asp Met Ser
                100                 105                 110

Tyr Ala Met Ala Gly Ile Leu Asp Asp Tyr Val Asp Lys Gly Glu Phe
            115                 120                 125

Arg Arg Gly Lys Lys Val Trp Ala Ser Val Cys Glu Gly Gly Gln Glu
130                 135                 140

Ala Ala Ile Tyr Asp Ser Ile Ala Val Thr Tyr Leu Met Ser Leu Met
145                 150                 155                 160

Val Lys Arg His Phe Gly Thr Asp Pro Gly Tyr Ser Lys Leu Ile Glu
                165                 170                 175

Leu Phe Asn Met Val Pro Gly Thr Ala Ala Ile Gly Asn Thr Leu Asp
                180                 185                 190

Ile Leu Asp Arg His Asp Thr Asn Tyr Tyr Asp Asp Thr Met Trp Lys
            195                 200                 205

His Ser Val Gln Asn Lys Ala Ala Asn Thr Val Phe Pro Ala Ala Thr
210                 215                 220

Ala Gly Leu Ile His Ala Gly Val Leu Cys Asp Leu Leu Asp Arg
225                 230                 235                 240

Thr Ser Glu Val Phe Gly Tyr Thr Gly His Leu Phe Gln Val Trp Asp
                245                 250                 255

Asp Phe Met Glu His Tyr Ala Val Lys Glu Gln Ser Gly Lys Gly Ala
                260                 265                 270

Pro Asp Thr Lys Tyr Asn Ala Lys Thr Trp Ala Thr Leu Thr Ala Met
            275                 280                 285

Ala His Phe Asn Glu Ala Gln Ala Lys Glu Phe Lys Ala Cys Tyr Gly
290                 295                 300

Ser Thr Asp Pro Ala Lys Arg Ser Arg Val Arg Glu Leu Tyr Asp Glu
305                 310                 315                 320

Val Asn Leu Arg Gly Leu Tyr Ile Asp Tyr Leu Arg Asn Thr Tyr Met
                325                 330                 335

Val Val Glu Glu Lys Ile Ser Lys Ile Pro Asp Pro Arg Ile Gln Ser
            340                 345                 350

Ala Cys Arg Ser Tyr Met Asp Trp Leu Leu Val Glu Pro Pro Gln Asp
355                 360                 365

Glu Glu Glu Ala Glu Ser Val Leu Asn Asn
370                 375

<210> SEQ ID NO 5
<211> LENGTH: 403
<212> TYPE: PRT
<213> ORGANISM: Nezara viridula

<400> SEQUENCE: 5

Met Pro Leu Ala Lys Leu Cys Ala Lys Lys Leu Ser Ser Pro Leu Met
 1               5                  10                  15

Lys Leu Cys Tyr Pro Asn Leu Asn Gly Lys Leu Pro Phe Ser Asn Leu
                20                  25                  30
```

Ser Asn Ile Leu Asp Asn Ser Ser Leu Lys Phe His Ser Cys Asn Pro
         35                  40                  45

His Ile Thr Cys Arg Gly Leu Ser Thr Val Ala Leu Arg Pro Gln Thr
 50                  55                  60

Ile Thr Lys Asp Asp Lys Arg Asp Phe Met Ala Val Phe Pro Asp Ile
 65                  70                  75                  80

Val Arg Asp Leu Thr Gln Leu Asn Pro Gly Ile Ser Asp Leu Ser Thr
                 85                  90                  95

Leu Ile Ser Lys Ile Met Gln Tyr Asn Val Ser Gly Gly Lys Lys Val
                100                 105                 110

Arg Gly Leu Thr Val Val Tyr Ser Tyr Arg Met Leu Ala Pro Asp His
                115                 120                 125

Ala Leu Thr Pro Glu Asn Ile Arg Leu Ala Gln Ile Leu Gly Trp Cys
            130                 135                 140

Val Glu Met Leu Gln Gly Phe Phe Leu Val Ile Asp Asp Leu Ala Asp
145                 150                 155                 160

Gln Ser Ile Thr Arg Arg Gly Arg Pro Cys Trp Tyr Arg Asn Pro Asp
                165                 170                 175

Val Gly Leu Arg Ala Gly Ser Asp Ala Leu Leu Ile Gln Ser Gly Thr
                180                 185                 190

Phe Gln Leu Leu Gln Gln His Cys Lys Asp Arg Glu Phe Tyr Ile Asp
            195                 200                 205

Leu Val Glu Leu Phe Leu Asp Ala Val Arg Thr Thr Tyr Gly Gln
210                 215                 220

Thr Leu Asp His Val Ser Ser Phe Pro Asn Ile Thr His Leu Thr Met
225                 230                 235                 240

Asp Arg Tyr Asn Phe Ile Thr Lys Tyr Lys Thr Ser Tyr Tyr Thr Phe
                245                 250                 255

His Leu Pro Val Ala Thr Ala Met Tyr Met Ala Gly Ile Tyr Asn Thr
                260                 265                 270

Glu Leu His Arg Gln Ala Lys Ser Val Leu Leu Glu Met Gly His Tyr
            275                 280                 285

Phe Gln Val Gln Asp Asp Tyr Leu Asp Val Phe Gly Asp Glu Glu Val
290                 295                 300

Ile Gly Lys Ile Gly Thr Asp Ile Gln Glu Gly Lys Cys Thr Trp Leu
305                 310                 315                 320

Ala Ile Val Ala Phe Gln Arg Ala Ser Pro Ser Gln Arg Glu Ile Leu
                325                 330                 335

Glu Ser Cys Tyr Gly Ser Lys Asp Pro Glu Lys Ile Lys Lys Val Lys
            340                 345                 350

Asp Thr Phe Ile Glu Ile Gly Val Pro Ala Val Phe His Ala Tyr Glu
            355                 360                 365

Glu Glu Thr Tyr Asn Leu Ile Thr Arg Gln Ile Gln Gln Leu Ser Gln
370                 375                 380

Gly Leu Pro His Glu Leu Phe Leu Thr Leu Leu His Lys Thr Tyr Gly
385                 390                 395                 400

Arg Lys Gln

<210> SEQ ID NO 6
<211> LENGTH: 562
<212> TYPE: PRT
<213> ORGANISM: Nezara viridula

<400> SEQUENCE: 6

-continued

```
Met Ser Ile Ser Ala Ala Thr Pro Val Ile Ser Val Pro Ser Ala Val
1               5                   10                  15

Leu Ser Ala Thr Ser Val Phe Tyr Phe Leu Leu Val Pro Ala Leu Val
            20                  25                  30

Leu Trp Tyr Val Tyr Trp Arg Met Ser Arg Arg His Met Ile Glu Leu
            35                  40                  45

Ala Ser Lys Ile Pro Gly Pro Pro Gly Leu Pro Ile Leu Gly Asn Ala
        50                  55                  60

Leu Gln Phe Thr Gly Ser Ser His Asp Ile Phe Glu Arg Val Tyr Ser
65                  70                  75                  80

Tyr Ser Phe Glu Tyr Lys Asp Val Thr Arg Val Trp Ile Gly Pro Arg
                85                  90                  95

Leu Val Ile Phe Leu Val Asp Pro Arg Asp Val Glu Leu Ile Leu Ser
                100                 105                 110

Ser His Val Tyr Ile Asp Lys Ser Arg Glu Tyr Arg Phe Phe Arg Pro
        115                 120                 125

Trp Leu Gly Asn Gly Leu Leu Ile Ser Ser Gly Pro Lys Trp Arg Ala
        130                 135                 140

His Arg Lys Leu Ile Ala Pro Thr Phe His Leu Asn Val Leu Lys Ser
145                 150                 155                 160

Phe Ile Asp Leu Phe Asn Ala Asn Ser Arg His Val Ile Lys Lys Leu
                165                 170                 175

Glu Lys Glu Leu Gly Lys Glu Phe Asp Cys His Asp Tyr Met Ser Glu
                180                 185                 190

Ala Thr Val Glu Ile Leu Leu Glu Thr Ala Met Gly Val Ser Lys Lys
            195                 200                 205

Thr Gln Asp Gln Ser Gly Tyr Asp Tyr Ala Met Ala Val Met Lys Met
        210                 215                 220

Cys Asp Ile Leu His Leu Arg His Thr Lys Phe Trp Leu Arg Pro Asp
225                 230                 235                 240

Ser Ile Phe Asn Leu Thr Lys Tyr Gly Lys Ile Gln Glu Asn Leu Leu
                245                 250                 255

Ala Thr Ile His Gly Leu Thr Arg Lys Val Ile Arg Lys Lys Ala
            260                 265                 270

Asp Phe Ala Lys Gly Ile Arg Gly Ser Thr Ala Glu Val Pro Lys Glu
        275                 280                 285

Leu Gln Thr Lys Asn Tyr Glu Ser Lys Val Glu Gln Lys Ala Thr Val
    290                 295                 300

Glu Gly Leu Ser Tyr Gly Gln Ser Ala Gly Leu Lys Asp Asp Leu Asp
305                 310                 315                 320

Val Asp Asp Asn Asp Ile Gly Glu Lys Lys Arg Met Ala Phe Leu Asp
                325                 330                 335

Leu Met Ile Glu Ala Ser Gln Asn Gly Val Val Ile Asn Asp Glu Glu
        340                 345                 350

Ile Lys Glu Gln Val Asp Thr Ile Met Phe Glu Gly His Asp Thr Thr
        355                 360                 365

Ala Ala Gly Ser Ser Phe Phe Leu Cys Met Met Gly Val His Gln His
        370                 375                 380

Ile Gln Asp Arg Val Ile Gln Glu Leu Asp Glu Ile Phe Gly Asp Ser
385                 390                 395                 400

Asp Arg Pro Ala Thr Phe Ala Asp Thr Leu Glu Met Lys Tyr Leu Glu
                405                 410                 415
```

-continued

```
Arg Cys Leu Met Glu Thr Leu Arg Leu Tyr Pro Pro Val Pro Ile Ile
            420                 425                 430

Ala Arg Glu Met Lys Glu Asp Leu Lys Leu Ala Ser Gly Asp Tyr Thr
            435                 440                 445

Ile Pro Ala Gly Ala Thr Val Val Ile Gly Thr Phe Lys Leu His Arg
            450                 455                 460

Lys Pro Glu Ile Tyr Pro Asn Pro Asn Lys Phe Asp Pro Asp Asn Phe
465                 470                 475                 480

Leu Pro Glu Arg Thr Ala Asn Arg His Tyr Tyr Ala Phe Val Pro Phe
            485                 490                 495

Ser Ala Gly Pro Arg Ser Cys Val Gly Arg Lys Tyr Ala Met Leu Lys
            500                 505                 510

Leu Lys Ile Leu Leu Ser Thr Ile Leu Arg Asn Tyr Arg Val Tyr Ser
            515                 520                 525

Asp Val Lys Glu Glu Asp Phe Lys Leu Gln Ala Asp Ile Ile Leu Lys
            530                 535                 540

Arg Ser Asp Gly Phe Arg Ile Arg Leu Glu Pro Arg Lys Arg Ala Ala
545                 550                 555                 560

Lys Ala
```

<210> SEQ ID NO 7
<211> LENGTH: 554
<212> TYPE: PRT
<213> ORGANISM: Nezara viridula

<400> SEQUENCE: 7

```
Phe Gly Ser Ser Val Asn Asn Lys Lys Met Ile Ala Val Phe Thr Phe
1               5                   10                  15

Leu Ile Val Thr Ala Ala Thr Leu Tyr Tyr Ile Lys Trp Arg Ser Glu
            20                  25                  30

Arg Lys Arg Leu Tyr Glu Leu Ala Glu Lys Ile Pro Gly Pro Glu Leu
        35                  40                  45

Leu Pro Leu Ala Ser Lys Ala Phe Ser Ile Leu Lys Asn His Asn Thr
50                  55                  60

Leu Leu Lys Tyr Ile Tyr Asp Leu Ser Phe Ile Pro Glu Tyr Gln Asn
65                  70                  75                  80

Val Ala Lys Leu Trp Leu Gly Ser Arg Leu Val Val Gly Leu Val His
            85                  90                  95

Pro Lys Asp Val Glu Ile Ile Leu Ser Ser Asn Val His Leu Lys Lys
        100                 105                 110

Ser Gln Glu Tyr Lys Leu Phe Glu Pro Trp Phe Gly Asn Gly Leu Leu
    115                 120                 125

Ile Ser Ser Gly Glu Thr Trp Arg His Gln Arg Lys Met Ile Ala Pro
130                 135                 140

Thr Phe His Leu Asn Ile Leu Lys Arg Phe Met Asp Glu Phe Asn Arg
145                 150                 155                 160

Asn Ser Gln Arg Val Ile Glu Arg Met Arg Lys Glu Asn Gly Lys Met
            165                 170                 175

Phe Asp Cys His Asp Tyr Met Ser Glu Ile Met Val Glu Thr Leu Ile
        180                 185                 190

Glu Thr Val Met Gly Val Lys Gln Glu Ser Gln Asn Arg Glu Cys Phe
    195                 200                 205

Ser Tyr Ala His Ser Val Met Asp Leu Cys Asp Ile Leu His Thr Arg
210                 215                 220
```

His Thr Arg Pro Trp Tyr Arg Pro Glu Tyr Leu Phe Lys Leu Thr Asn
225                 230                 235                 240

Met Ser Lys Glu Trp Asp Arg Asn Leu Gln Asn Ile Phe Asn Leu Thr
            245                 250                 255

Asn Arg Val Phe Asn Thr Lys Lys Glu Asp Cys Ile Lys Asn Lys Ser
        260                 265                 270

Lys Glu Ser Thr Met Thr Lys Glu Asp Val Lys Glu Thr Lys Val
    275                 280                 285

Glu Thr Lys Ile Glu Thr His Ser Asp Glu Lys Phe Ser Tyr Gly Gln
290                 295                 300

Ala Ala Gly Leu Lys Asp Asp Leu Asp Asp Asn Glu Ile Gly Glu
305                 310                 315                 320

Lys Lys Arg Leu Pro Phe Leu Glu Ser Leu Ile Asp Arg Ser Gln Asn
                325                 330                 335

Gly Asp Lys Leu Thr Asp Gln Asp Ile Ile Asp Gln Val Asn Thr Ile
            340                 345                 350

Met Phe Glu Gly His Asp Thr Thr Ala Ala Gly Ser Ser Phe Phe Leu
        355                 360                 365

Cys Val Met Gly Asp Arg Gln Asp Ile Gln Ala Lys Cys Ile Glu Glu
    370                 375                 380

Ile Asp Ser Ile Phe Gly Asp Ser Asp Arg Pro Val Thr Phe Gln Asp
385                 390                 395                 400

Thr Ile Glu Met Lys Tyr Leu Glu Arg Cys Ile Met Glu Thr Leu Arg
                405                 410                 415

Leu Phe Pro Pro Val Pro Leu Ile Ala Arg Glu Leu Gly Gln Asp Val
            420                 425                 430

Gln Leu Met Ser Glu Asn Ile Leu Leu Pro Lys Gly Cys Ala Val Val
        435                 440                 445

Ile Gly Thr Phe Lys Leu His Arg Arg Ala Asp Ile Tyr Val Asp Pro
    450                 455                 460

Asp Asn Phe Asp Pro Asp Arg Phe Leu Pro Glu Asn Ala Val Asn Arg
465                 470                 475                 480

His Tyr Tyr Ser Phe Val Pro Phe Ser Ala Gly Pro Arg Ser Cys Val
                485                 490                 495

Gly Arg Lys Tyr Ala Met Leu Lys Leu Lys Ile Leu Leu Ala Asn Ile
            500                 505                 510

Leu Arg Asn Phe Arg Val Lys Gln Gly Lys Pro Met Lys Asp Trp Gln
        515                 520                 525

Leu Gln Ala Asp Ile Ile Leu Lys Arg Ser Asp Lys Phe Glu Ile Thr
    530                 535                 540

Leu Glu Pro Arg Arg Val Gln Lys Val Cys
545                 550

<210> SEQ ID NO 8
<211> LENGTH: 550
<212> TYPE: PRT
<213> ORGANISM: Nezara viridula

<400> SEQUENCE: 8

Met Asp Ser Gln Glu Leu Asp His Ser Glu Leu Arg Ser Arg Leu Tyr
1               5                   10                  15

Ser Ile Ser Ser Leu Ile Leu Pro Ile Phe Ile Leu Tyr Val Gly
            20                  25                  30

Trp Arg Leu Ala Asn Lys Arg Phe Ile Glu Leu Ala Glu Lys Ile Pro
        35                  40                  45

```
Gly Pro Pro Gly Leu Pro Ile Ile Gly Asn Ala Leu Glu Leu Arg Gly
 50                  55                  60

Thr Pro Asn Glu Ile Phe Glu Asn Leu Tyr Ser Lys Ser Glu Ile Tyr
 65                  70                  75                  80

Pro Asp Val Ala Arg Val Trp Ala Gly Pro Arg Leu Leu Val Phe Leu
                 85                  90                  95

Thr Asn Pro Ala Asp Ile Glu Ile Val Leu Ser Ser His Asp His Leu
            100                 105                 110

Asp Lys Ser Ala Glu Tyr Asp Phe Leu Arg Pro Trp Leu Gly Asn Gly
        115                 120                 125

Leu Leu Val Ser Thr Gly Glu Lys Trp Arg Ser His Arg Lys Ile Ile
130                 135                 140

Ala Pro Thr Phe His Leu Asn Val Leu Arg Ser Phe Met Glu Arg Phe
145                 150                 155                 160

Asn Arg Asn Ser Lys Lys Thr Leu Glu Arg Leu Ala Lys Glu Gly Asp
                165                 170                 175

Asn Glu Phe Asp Ile His Asp Tyr Met Ser Glu Phe Thr Val Glu Val
            180                 185                 190

Leu Ile Glu Thr Val Met Gly Val Lys Lys Glu Asn Glu Gly Arg Ser
        195                 200                 205

Cys Phe Asp Tyr Ala Gln Ala Val Met Lys Leu Cys Asp Ile Val His
210                 215                 220

Leu Arg His Thr Lys Phe Tyr Leu Arg Pro Asp Leu Val Phe Tyr Ser
225                 230                 235                 240

Ser Lys Tyr Gly Ser Glu Gln Lys Ser Leu Ser Val Ile His Gly
                245                 250                 255

Leu Thr Glu Lys Val Leu Lys Val Lys Lys Ala Gln Phe Glu Asn Lys
            260                 265                 270

Ile Gln Asp Lys His Gln Glu Thr Ala Glu Lys Glu Val Leu Lys Glu
        275                 280                 285

Thr Ser Glu Ser Lys Glu Gly Phe Ser Tyr Gly Gln Ala Ser Gly Leu
290                 295                 300

Lys Asp Asp Leu Asp Val Glu Asp Ile Gly Glu Lys Lys Arg Asn Ala
305                 310                 315                 320

Phe Leu Glu Ser Ile Leu Glu Arg Ala Ala Asn Asn Asp Ser Ile Asn
                325                 330                 335

Asp Lys Glu Val Lys Glu Gln Leu Asp Thr Ile Met Phe Glu Gly His
            340                 345                 350

Asp Thr Thr Ala Ala Ser Ser Phe Phe Leu Cys Met Met Ala Ala
        355                 360                 365

His Pro Asp Ile Gln Lys Cys Tyr Glu Glu Ile Met Arg Val Leu
370                 375                 380

Gly Asp Ser Asp Arg Asp Ile Thr Phe Asn Asp Ile Leu Glu Met Lys
385                 390                 395                 400

Tyr Leu Glu Arg Cys Leu Met Glu Thr Leu Arg Leu Tyr Pro Pro Val
                405                 410                 415

Pro Ile Ile Ala Arg Gln Pro Lys Lys Glu Phe Lys Leu Ala Ser Lys
            420                 425                 430

Asn Leu Ile Ile Pro Ala Asn Cys Thr Val Val Ile Gly Ile Ile Lys
        435                 440                 445

Leu His Arg Arg Ala Asp Ile Tyr Pro Asn Pro Glu Lys Phe Asp Pro
450                 455                 460
```

```
Asp Asn Phe Leu Pro Glu Lys Ser Ala Ser Arg His Tyr Tyr Ser Phe
465                 470                 475                 480

Ile Pro Phe Ser Ala Gly Pro Arg Ser Cys Val Gly Arg Lys Tyr Ala
                485                 490                 495

Met Leu Lys Leu Lys Thr Ile Leu Ala Ser Thr Leu Arg Ala Phe Tyr
            500                 505                 510

Val Lys Pro Gly Tyr Thr Glu Glu Trp Lys Leu Lys Ala Asp Ile
        515                 520                 525

Ile Leu Lys Arg Ala Asp Gly Phe Arg Ile Lys Leu Glu Pro Arg Lys
        530                 535                 540

Glu Thr Asn Thr Lys Asn
545                 550
```

<210> SEQ ID NO 9
<211> LENGTH: 532
<212> TYPE: PRT
<213> ORGANISM: Nezara viridula

<400> SEQUENCE: 9

```
Met Asp Leu Leu Thr Phe Phe Gly Ala Val Leu Thr Ala Ala Ile Ala
1               5                   10                  15

Gly Tyr Gly Ala Phe Trp Tyr Ser Arg Arg Leu Tyr Glu Leu Ala
            20                  25                  30

Ala Lys Ile Pro Gly Pro Thr Ser Leu Pro Leu Leu Gly Thr Leu Ser
            35                  40                  45

Glu Phe Ser Gly Gly Ala His Met Val Phe Glu Asn Met Val Lys Lys
50                  55                  60

Cys His Glu Tyr Gly Asp Val Ile Lys Phe Trp Ile Gly Pro Arg Leu
65                  70                  75                  80

Leu Val Phe Leu Ala Asp Pro Ala Asp Ile Glu Leu Ile Leu Ser Ser
                85                  90                  95

His Val His Ile Asp Lys Ala Pro Glu Tyr Gln Phe Phe Gln Pro Trp
            100                 105                 110

Leu Gly Asp Gly Leu Leu Ile Ser Thr Gly Asn Lys Trp Arg Asn His
        115                 120                 125

Arg Lys Leu Ile Ala Pro Thr Phe His Leu Asn Ile Leu Lys Ser Phe
130                 135                 140

Ile Pro Leu Phe Asn Ser Asn Ser Arg Gly Val Ala Thr Lys Leu Lys
145                 150                 155                 160

Lys Glu Val Gly Lys Glu Phe Asp Cys His Asp Tyr Met Ser Glu Ala
                165                 170                 175

Thr Val Glu Ile Leu Leu Glu Thr Ala Met Gly Val Asn Lys Lys Thr
            180                 185                 190

Gln Glu Ser Gly Tyr Glu Tyr Ala Met Ala Val Met Lys Met Cys Asp
        195                 200                 205

Ile Leu His Leu Arg Gln Thr Lys Leu Trp Leu Arg Pro Asn Ile Ile
210                 215                 220

Phe Tyr Leu Thr Ser Leu Gly Lys Leu Gln Asp Lys Leu Leu Asn Ile
225                 230                 235                 240

Ile His Ser Leu Thr Lys Lys Val Leu Lys Ile Arg Met Glu Glu Tyr
                245                 250                 255

Lys Asn Asn Gly Ser Lys Leu Pro Gly Asn Val Thr Phe Val Thr Gly
            260                 265                 270

Asp Asp Gly Lys Ile Gln Val Glu Gly Asp Phe Ser Phe Gly His Ser
        275                 280                 285
```

```
Lys Gly Ile Lys Asp Asp Leu Asp Glu Asp Ile Gly Glu Lys Lys Arg
            290                 295                 300

Leu Ala Phe Leu Asp Leu Leu Ile Asp Ala Ser Gln Gly Gly Lys Leu
305                 310                 315                 320

Thr Asp Glu Glu Ile Gln Asn Gln Val Asp Thr Ile Met Phe Glu Gly
                325                 330                 335

His Asp Thr Thr Ala Ala Ala Ser Ser Phe Phe Leu Cys Glu Met Ala
            340                 345                 350

Ala Arg Pro Asp Ile Gln Glu Lys Cys Ile Glu Glu Leu Asn Lys Ile
            355                 360                 365

Phe Gly Asp Ser Asp Arg Pro Val Thr Phe Glu Asp Thr Leu Glu Met
370                 375                 380

Lys Tyr Ile Glu Arg Cys Leu Met Glu Thr Leu Arg Met Tyr Pro Pro
385                 390                 395                 400

Val Pro Val Ile Ala Arg Glu Leu Gln His Glu Leu Lys Leu Ala Ser
                405                 410                 415

Arg Asp Leu Val Ile Pro Ala Lys Cys Thr Val Ile Val Ala Thr Phe
            420                 425                 430

Lys Leu His Arg Lys Glu Asn Ile Tyr Pro Asn Pro Asn Val Phe Asp
            435                 440                 445

Pro Asp Asn Phe Leu Pro Glu Arg Ser Ala Ser Arg His Tyr Tyr Ser
450                 455                 460

Tyr Val Pro Phe Ser Ala Gly Pro Arg Ser Cys Val Gly Arg Lys Tyr
465                 470                 475                 480

Ala Met Leu Lys Leu Lys Val Leu Ile Ala Thr Ile Leu Arg Lys Tyr
                485                 490                 495

Lys Val Leu Pro Gly Lys Lys Glu Ala Asp Trp Lys Leu Gln Gly Asp
            500                 505                 510

Ile Ile Leu Lys Arg Thr Asp Gly Phe Gly Ile Arg Val Glu Pro Arg
            515                 520                 525

Thr Ser Ser Val
    530

<210> SEQ ID NO 10
<211> LENGTH: 551
<212> TYPE: PRT
<213> ORGANISM: Nezara viridula

<400> SEQUENCE: 10

Ser Thr Ile Lys Ser Ser Leu Asp Arg Arg Gln Glu Gln His Ser Glu
1               5                   10                  15

Gly Gly Met Asp Ile Leu Gly Ile Asp Ser Ile Leu Val Ala Gly Leu
            20                  25                  30

Thr Ala Ala Ile Ala Ala Tyr Gly Tyr Phe Trp Phe Ser Arg Arg Arg
        35                  40                  45

Leu Tyr Glu Leu Ala Ser Lys Ile Pro Gly Pro Ala Gly Tyr Pro Phe
    50                  55                  60

Ile Gly Asn Ala Leu Arg Phe Ile Gly Gly Ala Asp Thr Leu Phe Lys
65                  70                  75                  80

Asn Val Phe Ser Arg Thr Leu Glu Tyr Gly Asp Val Val Lys Met Trp
                85                  90                  95

Val Gly Pro Arg Leu Leu Val Phe Leu Thr Asn Pro Ala Asp Ile Glu
            100                 105                 110

Leu Ile Leu Ser Ser His Val His Ile Asp Lys Ala Pro Glu Tyr Arg
```

```
            115                 120                 125
Leu Phe Glu Pro Trp Leu Gly Asp Gly Leu Ile Ser Thr Gly Glu
130                 135                 140

Lys Trp Arg Asn His Arg Lys Leu Ile Ala Pro Thr Phe His Leu Asn
145                 150                 155                 160

Val Leu Lys Ser Phe Ile Pro Thr Phe Asn Ser Asn Ser Val Asp Val
                165                 170                 175

Val Lys Lys Leu Lys Gln Asp Val Gly Arg Glu Phe Asp Ala His Asp
            180                 185                 190

Tyr Met Ser Glu Ala Thr Val Glu Ile Leu Leu Glu Thr Ala Met Gly
            195                 200                 205

Val Asn Lys Lys Thr Gln Lys Asn Gly Tyr Glu Tyr Ala Met Ala Val
210                 215                 220

Met Gly Leu Ser Asn Ile Leu His Leu Arg His Thr Lys Leu Trp Leu
225                 230                 235                 240

Arg Pro Asp Phe Ile Phe Asn Met Thr Ser Leu Ser Lys Leu Gln Glu
                245                 250                 255

Lys Leu Leu Asn Val Ile His Ser Leu Thr Arg Lys Val Phe Asn Ile
            260                 265                 270

Arg Met Asp Glu Tyr Lys Lys Asn Gly Ser Lys Ile Ile Ser Thr Thr
            275                 280                 285

Pro Glu Asp Asn Ala Lys Val Gln Ala Glu Gly Asp Tyr Ala Phe Gly
290                 295                 300

His Ser Lys Gly Ile Lys Asp Asp Leu Asp Asp Glu Ile Gly Glu Lys
305                 310                 315                 320

Lys Arg Met Ala Phe Leu Asp Leu Leu Ile Asp Ala Ser Gln Gly Gly
                325                 330                 335

Gly Lys Leu Thr Ser Glu Glu Ile Gln His Gln Ile Asp Thr Ile Met
            340                 345                 350

Phe Glu Gly His Asp Thr Thr Ala Ala Gly Ser Ser Phe Phe Leu Ala
            355                 360                 365

Met Met Ala Ala Arg Pro Asp Ile Gln Glu Lys Cys Val Glu Glu Val
370                 375                 380

Lys Arg Ile Phe Gly Asp Ser Asn Arg Pro Val Thr Phe Gln Asp Thr
385                 390                 395                 400

Leu Glu Met Lys Tyr Ile Glu Arg Cys Leu Met Glu Thr Leu Arg Met
                405                 410                 415

Tyr Pro Pro Val Pro Ile Ile Ala Arg Glu Leu Lys Gln Glu Leu Lys
            420                 425                 430

Leu Ala Ser Cys Asp Leu Thr Ile Pro Ala His Cys Thr Val Val Val
            435                 440                 445

Asn Thr Phe Met Leu His Arg Lys Pro Asp Ile Tyr Ser Ser Pro Asn
            450                 455                 460

Tyr Phe Asp Pro Asp Asn Phe Leu Pro Glu Lys Ser Ala Ser Arg His
465                 470                 475                 480

Tyr Tyr Ser Tyr Ile Pro Phe Ser Ala Gly Pro Arg Ser Cys Val Gly
                485                 490                 495

Arg Lys Tyr Ala Val Leu Lys Leu Lys Val Met Leu Ala Thr Ile Leu
            500                 505                 510

Arg Asn Tyr Arg Ile Leu Pro Gly Lys Lys Glu Lys Asp Trp Lys Leu
            515                 520                 525

Gln Gly Asp Ile Ile Leu Lys Arg Ala Asp Gly Phe Pro Leu Val Met
530                 535                 540
```

```
Glu Pro Arg Ala Ile Lys Val
545                 550

<210> SEQ ID NO 11
<211> LENGTH: 537
<212> TYPE: PRT
<213> ORGANISM: Nezara viridula

<400> SEQUENCE: 11

Met Ala Glu Val Thr Ser Phe Asp Val Phe Ser Ser Tyr Leu Pro
1               5                   10                  15

Gln Ser Lys Arg Val Tyr Lys Ser Pro Cys Arg Asn Leu Leu Pro Val
                20                  25                  30

Asn Ser Glu Met Val Arg Leu Phe Lys Leu Gln Lys Val Leu Ser Ser
            35                  40                  45

Ala Ile Ser Ala Leu Ser Asp Val Ile Ser Cys Leu Tyr Ser Trp Thr
        50                  55                  60

Arg Phe Tyr Trp Met Val Ser Arg Leu Pro Gly Leu Pro Leu Thr His
65                  70                  75                  80

Ser Tyr Lys Gln Trp Glu Gly Phe Gln Ser Lys Tyr Asn Ala Leu Asn
                85                  90                  95

Thr Leu Val Lys Trp Arg Glu Lys Tyr Lys Thr Phe His Lys Val Tyr
            100                 105                 110

Ile Ser Phe Leu Pro Val Ile Phe Ala Tyr Ser Pro Glu Leu Ile Gln
        115                 120                 125

Glu Leu Leu Ser Lys Gln Lys His Asn Asp Lys Gly Lys Val Tyr
130                 135                 140

His Thr Leu Leu Pro Leu Leu Gly Asp Gly Leu Ile Thr Ser Lys Gly
145                 150                 155                 160

Glu Lys Trp Phe Ala His Arg Arg Met Leu Thr Pro Ala Phe His Ser
                165                 170                 175

Asn Ile Leu Glu Ser Phe Phe Glu Thr Phe Lys Ser Glu Thr Asn Thr
            180                 185                 190

Tyr Ile Asn Ser Leu Lys Asp Ser Glu Leu Thr Lys Gly Tyr Gly Asp
        195                 200                 205

Ile Cys Pro His Thr Arg Arg Leu Thr Leu Lys Phe Ile Cys Glu Thr
210                 215                 220

Ala Met Gly Phe Ser Glu Leu Ala Asp Cys Lys Glu Ala Glu Ala Val
225                 230                 235                 240

Ile Lys Ser Met His Lys Leu Glu Glu Ile Ala Thr Leu Arg Val Ile
                245                 250                 255

His Pro Trp Leu Leu Ser Asp Ser Ile Phe Lys Met Ser Ala Leu Tyr
            260                 265                 270

Lys Glu Leu Asn Glu Asn Lys Lys Ile Leu His Asn Phe Ser Asn Thr
        275                 280                 285

Leu Ile Lys Arg Lys Ser Ile Leu Lys Arg Leu Arg Asn Pro
290                 295                 300

Tyr Leu Glu Val His Lys Arg Lys Glu Ile Phe Leu Asp Gln Leu Ile
305                 310                 315                 320

Leu Gln Gln Leu Gln Gly Ile Lys Ile Thr Asp Glu Asp Ile Arg Asp
                325                 330                 335

Gln Val Asn Thr Phe Met Phe Ala Gly His Asn Thr Thr Gln Leu Ala
            340                 345                 350

Ile Asn Tyr Cys Ile Tyr Leu Phe Gly Arg Tyr Lys Asp Val Gln Glu
```

```
            355                 360                 365
Thr Ala His Asn Glu Leu Glu Glu Ile Phe Asn Asp Ser Asn Arg Glu
            370                 375                 380

Pro Thr Leu Asp Asp Leu Arg Asn Met Glu Tyr Leu Asp Arg Cys Ile
385                 390                 395                 400

Lys Glu Ala Leu Arg Leu Tyr Pro Ser Val Pro Ile Ile Ala Arg Lys
                405                 410                 415

Leu Thr Glu Asp Gln Pro Ile Gly Lys His Ile Leu Pro Lys Asp Thr
            420                 425                 430

Asp Cys Phe Ile Ile Pro Tyr Val Thr His Arg Asn Pro Glu Gln Phe
                435                 440                 445

Pro Asn Pro Glu Val Phe Asp Pro Asp Asn Phe Leu Pro Glu Arg Ile
450                 455                 460

Asn Asn Arg His Pro Tyr Ser Tyr Ile Pro Phe Ser Ala Gly Pro Arg
465                 470                 475                 480

Asn Cys Ile Gly Lys Arg Phe Ala Asn Ile Ala Glu Lys Thr Val Leu
                485                 490                 495

Ser Trp Ile Leu Arg Glu Phe Lys Ile Glu Ser Lys Leu Lys Gln Glu
                500                 505                 510

Asp Leu Lys Leu Ile Pro Ser Thr Val Leu Ile Pro Ser Gly Gly Leu
            515                 520                 525

Gln Val Lys Leu Thr Pro Arg Lys Cys
            530                 535

<210> SEQ ID NO 12
<211> LENGTH: 528
<212> TYPE: PRT
<213> ORGANISM: Nezara viridula

<400> SEQUENCE: 12

Met Met Asp Lys Pro Ser Val Met Glu Glu Leu Leu Ala Glu Cys Ile
1               5                   10                  15

Ile Tyr Trp Leu Phe Ile Leu Gly Ile Ile Val Ser Ser Val Val Ala
            20                  25                  30

Leu His Tyr Tyr Leu Ser Lys Arg Arg Tyr Tyr Gln Leu Ala Arg Lys
        35                  40                  45

Ile Pro Ala Pro Pro Gly Leu Pro Ile Ile Gly His Ala Phe Asn Ile
    50                  55                  60

Leu Met Gly Thr Glu Glu Ala Phe Arg Asn Val Trp Asn Thr Met Ser
65                  70                  75                  80

Asp Cys Asp Val Cys Lys Leu Trp Leu Gly Thr Arg Leu Phe Val Phe
                85                  90                  95

Ile Lys Asn Pro Ala Asp Ile Glu Leu Val Leu Asn Ser Arg Ile His
            100                 105                 110

Leu Cys Lys Pro Ser Glu Ser Asn Leu Leu Lys Thr Cys Leu Gly Asp
        115                 120                 125

Gly Ile Asn Thr Val Ser Gly Cys Gln Trp Lys Ser Tyr Arg Gln Leu
    130                 135                 140

Ile Ala Pro Met Phe Gln Trp Ser Gln Thr Phe Gln Pro Ile Leu Arg
145                 150                 155                 160

Asn Tyr Ser Arg Ile Leu Asp Asp Arg Leu Leu Lys Asn Val Gly Lys
                165                 170                 175

Asp Ile Asp Cys Tyr Asn Tyr Met Ser Asp Ala Val Met Glu Leu Leu
            180                 185                 190
```

```
Leu Ile Ser Ile Phe Gly Glu Asn Thr Asp Thr Glu Ser Lys Lys
            195                 200                 205

Tyr Phe Glu Ala Ile Gln Lys Leu Lys Glu Ile Ile Arg Tyr Arg Gln
210                 215                 220

Asn Lys Phe Trp Leu His Pro Asp Leu Ile Phe Asn Leu Thr Lys Tyr
225                 230                 235                 240

Ser Lys Leu Gln Lys Asp Leu Leu Arg Ile Ile Asn Arg Phe Thr Arg
                245                 250                 255

Gln Ala Ile Lys Asn Arg Lys Arg Ala Leu Met Glu Gln Gly Tyr Gly
                260                 265                 270

Trp Pro Lys Asn Gly Tyr Phe Glu Asp Gln Asn Gly Asn Ile Glu His
                275                 280                 285

Asn Asn Asn Ile Thr Thr Cys Leu Lys Glu Gly Asp Arg Ser Pro Ser
                290                 295                 300

Leu Leu Glu Leu Met Met Glu Val Ser His Asn Gly Thr Thr Leu Met
305                 310                 315                 320

Asp Ser Glu Ile Gln Asn Gln Val Asp Ala Leu Val Leu Glu Gly Leu
                325                 330                 335

Asp Thr Thr Ala Leu Thr Gly Ser Phe Phe Leu Gly Val Met Ala Asp
                340                 345                 350

Arg Pro Asp Ile Gln Glu Arg Cys Ala Ile Glu Leu Ser Gln Ile Phe
                355                 360                 365

Gly Asp Ser Asp Arg Gln Val Thr Phe Glu Asp Thr Leu Gln Met Lys
                370                 375                 380

Tyr Leu Glu Arg Cys Leu Met Glu Thr Leu Arg Ile His Pro Pro Val
385                 390                 395                 400

Pro Phe Ile Thr Arg Glu Leu Gln Gln Glu Leu Arg Leu Ala Ser Thr
                405                 410                 415

Cys Leu Thr Ile Pro Ala Asn Ser Thr Leu Met Val Asp Val Lys Lys
                420                 425                 430

Leu His Met Asn Glu Glu Leu Tyr Ser Ser Pro Asp Val Phe Asp Pro
                435                 440                 445

Asp Asn Phe Leu Leu Glu Lys Cys Val Ser Arg His Tyr Tyr Ser Phe
450                 455                 460

Ile Pro Phe Ser Ala Gly Pro Arg Ser Cys Val Gly Thr Lys Tyr Ser
465                 470                 475                 480

Met Leu Ser Leu Lys Val Leu Leu Ser Ser Ile Leu Arg Lys Tyr Lys
                485                 490                 495

Ile Phe Pro Ser Ser Gly Gln Glu Ser Ala Ser Met Met Thr Lys Asp
                500                 505                 510

Thr Arg Arg Thr Glu Arg Phe Val Ile Lys Met Glu His Arg Lys Arg
                515                 520                 525

<210> SEQ ID NO 13
<211> LENGTH: 546
<212> TYPE: PRT
<213> ORGANISM: Nezara viridula

<400> SEQUENCE: 13

Met Phe Arg Met Thr Asp Trp Thr Ser Asp Leu Gln Thr Val Ala Phe
1               5                   10                  15

Phe Ala Ala Val Val Pro Leu Leu Tyr Tyr Val Tyr Trp Arg Ile Ala
                20                  25                  30

Asn Arg Arg Leu Leu Gln Leu Ala Ala Lys Ile Pro Gly Pro Pro Gly
                35                  40                  45
```

```
Leu Pro Leu Leu Gly Asn Leu Glu Phe Thr Gly Ser Pro Thr Glu
    50                  55                  60

Ile Phe Glu Lys Leu Val Glu Lys Ser Tyr Gln Tyr Glu Asp Val Ile
65                  70                  75                  80

Lys Val Trp Phe Gly Pro Arg Leu Phe Val Phe Leu Thr Asn Pro Val
                85                  90                  95

Asp Ile Glu Val Leu Leu Thr Ser Thr Glu His Ile Glu Lys Ser Val
            100                 105                 110

Glu Tyr Asp Phe Met Lys Pro Trp Leu Gly Asp Gly Leu Leu Ile Ser
        115                 120                 125

Ser Gly Gln Lys Trp Phe Thr His Arg Lys Val Ile Ala Gln Thr Phe
130                 135                 140

His Leu Asn Ile Leu Arg Ser Phe Leu Gly Lys Phe Asn Glu Asn Ala
145                 150                 155                 160

Lys Lys Leu Val Lys Tyr Phe Glu Asp Glu Thr Gly Asn Glu Phe Asp
                165                 170                 175

Cys Arg Arg Tyr Met Cys Lys Tyr Thr Ala Glu Thr Leu Ile Asp Thr
            180                 185                 190

Val Met Gly Ala Asp Lys Asp Gln Leu Gly Phe Glu Ser Pro Val Tyr
        195                 200                 205

Ser Gly Ala Thr Thr Lys Leu Cys Glu Leu Val His Leu Arg His Thr
210                 215                 220

Lys Leu His Phe Arg Ser Asp Leu Leu Phe Asn Ser Thr Lys His Gly
225                 230                 235                 240

Phe Glu His Lys Lys Phe Val Ser Leu Val His Asp Phe Ser Ala Lys
                245                 250                 255

Val Ile Lys Phe Lys Lys Ser Gln Arg Glu Leu Leu Lys Pro Ser Pro
            260                 265                 270

Phe Ile Glu Lys Phe Asp Asp Ile Arg Lys Glu Asp Lys Ser Leu Thr
        275                 280                 285

His Tyr Glu Lys Ser Thr Gly Ile Ser Tyr Gly Gln Ser Ser Gly Leu
290                 295                 300

Lys Asp Asp Leu Asp Asn Glu Val Ile Gly Arg Lys Lys Lys Cys Ala
305                 310                 315                 320

Phe Leu Asp Thr Leu Leu Glu Lys Glu Ala Asn Arg Glu Val Phe Ser
                325                 330                 335

Met Lys Asp Val Gln Asp Gln Ile Asp Thr Leu Met Phe Glu Gly His
            340                 345                 350

Asp Thr Thr Ala Gly Val Ser Ser Met Phe Leu Cys Leu Met Ala Thr
        355                 360                 365

Asn Leu Asp Val Gln Ala Lys Cys Val Glu Glu Leu Glu Lys Ile Phe
370                 375                 380

Gly Asp Ser Asp Arg Asp Val Thr Phe Glu Asp Thr Tyr Glu Met Lys
385                 390                 395                 400

Tyr Leu Glu Arg Cys Val Met Glu Thr Leu Arg Ile Tyr Ser Pro Val
                405                 410                 415

Pro Val Ile Ala Arg Asn Leu Lys Lys Glu Leu Thr Leu Val Thr Asn
            420                 425                 430

Asn Ile Thr Leu Pro Val Ser Thr Thr Val Ile Val Ala Ile Phe Lys
        435                 440                 445

Leu His Arg Arg Glu Asp Leu Tyr Pro Asn Ser Glu Lys Phe Asn Pro
450                 455                 460
```

-continued

```
Asp Asn Phe Ile Gln Glu Lys Thr Ala Ala Arg Ser Phe Tyr Ser Phe
465                 470                 475                 480

Ile Pro Phe Ser Ala Gly Pro Arg Ser Cys Val Gly Arg Lys Tyr Ala
                485                 490                 495

Ile Leu Lys Leu Lys Val Val Leu Ser Thr Ile Leu Arg Asn Tyr Gln
            500                 505                 510

Ile Thr Thr Ser Cys Pro Met Glu Ser Trp Lys Leu Gln Ala Asp Ile
        515                 520                 525

Thr Leu Lys Arg Thr Asp Gly Phe Lys Ile Lys Leu Ile Pro Arg Lys
530                 535                 540

Asn Ala
545

<210> SEQ ID NO 14
<211> LENGTH: 494
<212> TYPE: PRT
<213> ORGANISM: Nezara viridula

<400> SEQUENCE: 14

Ala Ala Ile Ala Ile Val Leu Ile Leu Leu Ser Ile Ile Thr Leu
1               5                   10                  15

Leu Ile Ser Arg Val Ile Arg Asp Leu Phe Lys Leu Lys Gly Ile Pro
            20                  25                  30

Gly Pro Trp Glu Leu Pro Phe Leu Ala Glu Leu Arg Met Ile Leu Leu
        35                  40                  45

Pro Phe Thr Val Leu Tyr Pro Val Leu Gln Lys Tyr Ile Glu Asp Tyr
    50                  55                  60

Gly Gly Val Cys Ala Ile Tyr Arg Thr Gly Arg Val Tyr Val Met Leu
65              70                  75                  80

Ser Glu Pro Glu Thr Val Glu Pro Val Leu Ser Ser Tyr Asn His Ile
                85                  90                  95

Lys Lys Gly Asp Tyr Asp Tyr Ala Phe Leu Arg Pro Trp Leu Arg Asp
            100                 105                 110

Gly Leu Leu Leu Ser Asp Gly Ser Lys Trp Arg Asn Arg Arg Lys Leu
        115                 120                 125

Leu Thr Pro Ala Phe His Phe Lys Ile Leu Glu Asp Gly Met Lys Cys
130                 135                 140

Leu Thr Glu Lys Ser Glu Glu Ile Thr Glu Lys Leu Leu Ala Thr Lys
145                 150                 155                 160

Gly Glu Pro Thr Asp Leu Glu Asp Ile Ile Arg Ser Thr Leu Gly
                165                 170                 175

Ala Ile Leu Glu Thr Ala Met Gly Val Pro Ser Ser Asp Ala Asn Gly
            180                 185                 190

Tyr Gln Gln His Gln Glu Tyr Gln Ser Lys Ile Lys Gly Ile Thr
        195                 200                 205

Glu Ser Ile Met Arg Arg Tyr Tyr Arg Leu Trp Lys His Ile Glu Ser
    210                 215                 220

Leu Tyr Arg Leu Ser Ser Glu Gly Lys Glu Phe Phe Asn Asp Val Asn
225                 230                 235                 240

Arg Leu Gln Leu Phe Thr Lys Lys Val Ile Lys Asp Arg Lys Gln Leu
                245                 250                 255

Tyr Leu Ile Glu Arg Asp Ser Lys Pro Gly Asp Lys Ser Lys Ile
            260                 265                 270

Lys Pro Phe Leu Asp Cys Leu Ile Glu Leu Asn Val Ser Thr Pro Gly
        275                 280                 285
```

-continued

```
Ala Ile Ser Glu Asp Gly Ile Ala Glu Glu Val Asp Thr Phe Met Phe
            290                 295                 300

Glu Gly His Asp Thr Thr Ala Ser Ala Leu Asn Ser Ala Leu Phe Leu
305                 310                 315                 320

Leu Ala Asn Asn Pro Ile Glu Gln Glu Lys Ala Ala Glu Glu Gln Met
                325                 330                 335

Glu Ile Phe Gly Asp Asp Asn Arg Val Pro Ser Thr His Asp Leu Asn
            340                 345                 350

Lys Met Glu Tyr Leu Asp Met Val Ile Lys Glu Val Leu Arg Leu Tyr
        355                 360                 365

Pro Ser Val Pro Ile Ile Thr Arg Ser Leu Thr Glu Asp Leu Lys Ile
    370                 375                 380

Asn Glu Ser Ile Thr Val Pro Ala Gly Cys Ile Ala Ala Ile Met Pro
385                 390                 395                 400

Tyr Phe Val His Arg Ser Ala Lys His Trp Asp Asn Pro Glu Glu Phe
                405                 410                 415

Arg Pro Glu Arg Phe Asp Thr Gly Ile Ser Arg His Pro Phe Ser Phe
            420                 425                 430

Ile Pro Phe Ser Ala Gly Pro Arg Asn Cys Ile Gly Gln Lys Phe Ala
        435                 440                 445

Met Met Glu Met Lys Thr Met Leu Ser Ala Ile Leu Arg Lys Cys Lys
    450                 455                 460

Leu Glu Pro Val Thr Thr Ser Phe Glu Ile Ile Pro Thr Val Val Leu
465                 470                 475                 480

Lys Ser Asp Gln Pro Ile Leu Ile Lys Val Leu Pro Arg Lys
                485                 490

<210> SEQ ID NO 15
<211> LENGTH: 483
<212> TYPE: PRT
<213> ORGANISM: Nezara viridula

<400> SEQUENCE: 15

Met Phe Glu Ala Leu Tyr Ala Val Val Val Phe Leu Val Gly Leu
1               5                   10                  15

Ile Leu Lys Lys Trp Trp Asp Gln Lys Ile Pro Gly Pro Arg Gly Leu
            20                  25                  30

Pro Ile Met Gly Ile Ala Leu Glu Leu Ala Gln Ile Pro Pro Arg Asp
        35                  40                  45

Ile Phe Ala Lys Ile Asp Ser Leu Arg Gln Thr Tyr Ser Gly Ile Phe
    50                  55                  60

Glu Met Lys Ile Met Thr Asp Ser Tyr Val Met Leu Thr Asp Pro Glu
65                  70                  75                  80

Ser Val Glu Pro Leu Leu Ser Ser Lys His Ile Lys Lys Gly Ile
                85                  90                  95

Phe Asp Tyr Lys Phe Trp Arg Leu Phe Leu Gly Asp Gly Leu Leu
                100                 105                 110

Ser Asp Gly Ala Lys Trp His His Arg Arg Lys Val Leu Thr Pro Thr
            115                 120                 125

Phe His Phe Lys Ile Leu Glu Asp Ala Met Thr Ser Leu Val Lys Asn
        130                 135                 140

Ala Gln Ser Leu Thr Glu Gln Phe Leu Asp Thr Glu Gly Lys Pro Thr
145                 150                 155                 160

Asp Val Gly Asn Ile Ile Arg Ser Ser Thr Leu Lys Val Ile Cys Glu
```

```
            165                 170                 175
Thr Ala Met Gly Val Lys Leu Asn Thr Asp Asp Glu Thr Gln Asn Lys
            180                 185                 190

Tyr Val Glu Ala Val Lys Arg Ile Pro Glu Ala Ile Ile Leu Arg Tyr
            195                 200                 205

Leu Lys Phe Trp Leu His Ser Asp Phe Val Tyr Asn Leu Thr Lys Asp
210             215                 220

Gly Arg Asn Phe Lys Lys Asp Leu Asn Leu Ala His Ser Phe Thr Lys
225             230                 235                 240

Lys Ile Ile Ser Glu Arg Arg Met Leu Tyr Lys Asn Gln Lys Ala Asp
                245                 250                 255

Asn Ser Glu Asn Lys Ser Lys Lys Ala Phe Leu Asp Cys Leu Leu
            260                 265                 270

Glu Met Gly Glu Ala Leu Thr Asp Gln Asp Ile Cys Glu Val Asp
            275                 280                 285

Thr Phe Met Phe Glu Gly His Asp Thr Thr Ser Ala Asn Leu Val Phe
            290                 295                 300

Ser Leu Phe Leu Leu Ala Asn His Pro Glu Glu Gln Glu Lys Val Val
305             310                 315                 320

Glu Glu Leu Ile Glu Ile Phe Gly Glu Thr Asp Arg Pro Thr Leu
                325                 330                 335

Ser Asp Leu Ala Lys Met Asn Tyr Leu Glu Met Val Ile Lys Glu Ser
            340                 345                 350

Leu Arg Leu Tyr Pro Ser Val Pro Leu Ile Ser Arg Ser Leu Thr Glu
            355                 360                 365

Asp Leu Lys Leu Gly Ala Asp Val Ile Ile Pro Ala Gly Tyr Thr Ala
            370                 375                 380

Val Val Ala Pro Phe Leu Val His Arg Ser Lys Thr His Trp Glu Asn
385             390                 395                 400

Pro Glu Glu Phe Arg Pro Glu Arg Phe Met Pro Gly Thr Pro Arg His
                405                 410                 415

Pro Phe Ala Phe Ile Pro Phe Ser Ala Gly Pro Arg Asn Cys Ile Gly
            420                 425                 430

Gln Lys Phe Ala Met Met Glu Leu Lys Thr Met Leu Ser Ser Val Leu
            435                 440                 445

Arg Lys Cys Lys Leu Glu Ala Val Thr Lys Glu Val Asn Ile Leu Pro
            450                 455                 460

Thr Gly Ile Ile Lys Ser Glu Glu Thr Ile Leu Met Lys Ile Tyr Lys
465             470                 475                 480

Arg Asn Leu

<210> SEQ ID NO 16
<211> LENGTH: 458
<212> TYPE: PRT
<213> ORGANISM: Nezara viridula

<400> SEQUENCE: 16

Met Trp Met Met Val Ala Val Ile Leu Cys Leu Ile Cys Val Leu Leu
1               5                   10                  15

Val Leu Phe Val Gly Tyr Leu Ala Ile Tyr Trp Lys Pro Ser Arg Leu
                20                  25                  30

Pro Gly Pro Arg Gly Leu Pro Tyr Phe Gly Ile Ala Phe Ser Met Ile
            35                  40                  45

Gly Ile Thr Ser Lys Asp Ile Ile His His Leu Met Lys Trp Phe Glu
```

```
                    50                  55                  60
Glu Tyr Gly Asp Ile Phe Glu Phe Gln Ile Leu Gly Gln Lys Tyr Val
 65                  70                  75                  80

Phe Val Thr Asp Pro Gln Leu Leu Gln Pro Ile Leu Ser Ser Asn Thr
                 85                  90                  95

Asn Ile Thr Lys Gly Arg Phe Glu Tyr Ser Phe Arg Pro Met Phe
            100                 105                 110

Asn Asp Gly Leu Ile Ile Ser Asp Gly Asp Lys Trp Arg Thr Arg Arg
            115                 120                 125

Lys Leu Leu Thr Pro Ser Phe His Phe Lys Ile Leu Glu Thr Ser Ile
        130                 135                 140

Glu Ser Val Gly Arg Asn Thr Glu Glu Phe Val Ser His Leu Leu Lys
145                 150                 155                 160

Ser Asn Gly Lys Ala Thr Glu Ile Glu Asp His Ile Tyr Leu Leu Thr
                165                 170                 175

Phe Lys Ile Ile Cys Glu Thr Ala Met Gly Val Lys Leu Asn Thr Val
            180                 185                 190

Asp Asn Gln Gln Asn Glu Tyr Ile Lys Ala Ser Lys Ile Cys His Asp
        195                 200                 205

Ser Thr Val Tyr Arg Tyr Leu Arg Ile Trp Leu Phe Pro Asp Phe Ile
    210                 215                 220

Tyr Arg Leu Cys Lys Val Gly Lys Thr Phe Phe Lys Cys Leu Asp Val
225                 230                 235                 240

Ile His Asn Phe Ala Asp Gln Val Ile Lys Ser Arg Lys Glu Leu Phe
                245                 250                 255

Ile Ala Glu Lys Asn Asp Phe Thr Asn Lys Asp Ser Lys Arg Lys Ala
            260                 265                 270

Lys Asn Thr Phe Leu Asp Asn Leu Leu Glu Leu Asp Asp Ser Asn Pro
        275                 280                 285

Gly Leu Phe Thr Lys Ser Asp Ile Arg Glu Glu Val Asp Thr Phe Met
    290                 295                 300

Ile Ala Gly His Asn Pro Thr Ala Ala Leu Lys Phe Leu His Phe
305                 310                 315                 320

Leu Leu Ala Asn His Pro Asp Val Gln Glu Lys Val His Asp Glu Gln
                325                 330                 335

Val Glu Ile Tyr Gly Asp Asp Lys Arg Thr Pro Thr Ala Gln Asp Leu
            340                 345                 350

His Lys Met Ile Tyr Leu Glu Met Val Ile Lys Glu Thr Leu Arg Leu
        355                 360                 365

Tyr Pro Ser Ile Pro Leu Tyr Ser Arg Leu Leu Asp Lys Asp Leu Gln
    370                 375                 380

Ile Asp Glu Lys Thr Ile Ile Pro Ala Gly Cys Asn Val Ala Val Phe
385                 390                 395                 400

Asn Tyr Cys Val His Arg Ser Lys Lys His Trp Asp Asn Pro Glu Glu
                405                 410                 415

Phe Val Pro Glu Arg Phe Val Pro Gly Ile Glu Arg His Pro Tyr Ser
            420                 425                 430

Phe Ile Pro Phe Ser Ala Gly Pro Arg Asn Cys Ile Gly Gln Lys Tyr
        435                 440                 445

Ala Met Met Glu Leu Lys Thr Ile Met Pro
    450                 455

<210> SEQ ID NO 17
```

-continued

```
<211> LENGTH: 502
<212> TYPE: PRT
<213> ORGANISM: Nezara viridula

<400> SEQUENCE: 17
```

| | | | | | | | | | | | | | | |
|---|---|---|---|---|---|---|---|---|---|---|---|---|---|---|
| Met | Ile | Val | Ile | Trp | Gly | Leu | Ser | Cys | Val | Met | Val | Phe | Val | |
| 1 | | | | 5 | | | | | 10 | | | | | 15 |

Arg Phe Leu Val Lys Asn Trp Lys Pro Ser Met Leu Pro Gly Pro Arg
            20                25              30

Gly Phe Pro Tyr Phe Gly Ala Ala Phe Ser Val Val Gly Ile Ser Ser
       35               40              45

Lys Asp Ile Ile Pro Leu Ile Ile Lys Trp Cys Asp Glu Tyr Gly Lys
50                55              60

Met Phe Gly Val Lys Met Leu Gly Ala Asn Tyr Val Phe Val Ser Glu
65                70              75              80

Pro Glu Leu Val Lys Pro Leu Thr Ser Ile Asn Ile Thr Lys
            85              90              95

Gly Arg Phe Glu Tyr Ser Phe Leu Lys Leu Ile Phe Asn Asp Gly Leu
            100            105           110

Ile Val Ser Asp Gly Glu Lys Trp Arg Ser Asn Arg Arg Leu Leu Thr
            115            120           125

Pro Ser Phe His Asn Lys Ile Leu Lys Ser Ser Val Glu Thr Val Gly
            130            135           140

Arg Asn Ala Glu Glu Phe Val Ser Gln Leu Leu Ala Ser Asp Gly Lys
145                150              155              160

Pro Ile Asp Ile Glu Asp Thr Thr His Leu Leu Thr Leu Lys Ile Ile
                165              170           175

Cys Glu Thr Ala Met Gly Val Lys Leu Asn Thr Lys Asp Lys Gln Gln
            180            185           190

Asn Glu Tyr Val Lys Ala Ser Arg Ile Cys His Asp Thr Leu Val Tyr
            195            200           205

Arg Tyr Leu Arg Phe Trp Leu Phe Pro Asp Phe Ile Phe Arg Arg Ser
            210            215           220

Asp Val Gly Lys Arg Phe Ile Lys Ser Leu Lys Leu Ile His Glu Val
225                230              235              240

Ala Asp Gln Val Ile Lys Lys Arg Lys Glu Leu Tyr Ile Ala Glu Lys
                245              250           255

Asn Glu Ser Lys Asn Glu Asp Ser Arg Lys Lys Glu Arg Asn Ala Phe
            260            265           270

Leu Asp Asn Leu Leu Glu Leu Val Asp Ser Asn Pro Asp Leu Phe Asn
            275            280           285

Glu Ser Asn Ile Arg Glu Glu Val Asp Thr Phe Leu Ile Ala Gly His
            290            295           300

Asn Pro Ser Ala Ala Thr Leu Lys Phe Leu His Phe Ile Leu Ala Asn
305                310              315              320

Arg Pro Asp Val Gln Glu Lys Leu Tyr Asp Glu Gln Val Asp Ile Phe
                325              330           335

Gly Asp Ser Lys Arg Met Thr Thr Ala Gln Asp Leu Glu Lys Met Thr
            340            345           350

Tyr Leu Lys Met Val Ile Asn Glu Thr Leu Arg Leu Tyr Pro Thr Ile
            355            360           365

Pro Leu Tyr Ser Arg Cys Leu Lys Glu Asp Leu Leu Ile Asp Glu Lys
            370            375           380

Thr Ile Ile Pro Ala Gly His Thr Val Ala Val Phe Thr Tyr Ala Val

```
                385                 390                 395                 400
His Arg Ser Lys Lys His Trp Asp Asn Pro Glu Glu Phe Ile Pro Glu
                    405                 410                 415

Arg Phe Ala Pro Gly Ile Glu Ile His Pro Phe Ser Phe Leu Pro Phe
                420                 425                 430

Ser Ala Gly Pro Arg Asn Cys Ile Gly Gln Lys Tyr Ala Met Met Glu
                435                 440                 445

Leu Lys Ile Ile Ile Ser Thr Leu Val Arg Gln Cys Trp Leu Glu Pro
            450                 455                 460

Val Thr Thr Ser Val Ser Leu Asp Tyr Gly Ile Thr Leu Asn Pro Val
465                 470                 475                 480

Glu Pro Ile Ile Val Lys Ala Ile Pro Arg Asn Gly Thr Arg Arg Met
                485                 490                 495

Ile Pro Glu Arg Asn Ser
                500

<210> SEQ ID NO 18
<211> LENGTH: 501
<212> TYPE: PRT
<213> ORGANISM: Nezara viridula

<400> SEQUENCE: 18

Met Met Ser Ile Thr Leu Gly Leu Ile Cys Val Leu Leu Val Leu
1               5                   10                  15

Ala Ser Phe Tyr Arg Lys Pro Ser Thr Leu Pro Gly Pro Arg Gly Leu
                20                  25                  30

Pro Tyr Phe Gly Asn Val Trp Leu Tyr Met Ile Gly Arg Ser Ser Lys
            35                  40                  45

Asp Ile Ile Pro Phe Leu Lys Tyr Phe Val Asn Tyr Tyr Gly Asn Ile
    50                  55                  60

Phe Glu Leu Gln Ile Phe Gly Met Asn Tyr Val Phe Gly Ser Glu Ala
65                  70                  75                  80

Glu Leu Val Lys Pro Ile Leu Thr Ser His Thr Asn Ile Thr Lys Gly
                85                  90                  95

Arg Phe Glu Trp Ser Phe Phe Lys Pro Met Phe Arg Asp Gly Val Ile
            100                 105                 110

Ile Ser Glu Gly Glu Lys Trp Arg Thr Arg Arg Lys Ile Leu Glu Pro
        115                 120                 125

Ser Phe His Phe Lys Ile Leu Lys Arg Ser Ile Glu Ser Val Ala Arg
    130                 135                 140

Tyr Ala Glu Glu Tyr Val Ser Asn Leu Leu Asn Ser Glu Gly Lys Pro
145                 150                 155                 160

Thr Glu Ile Glu Asp Met Ile Tyr Leu Leu Thr Leu Lys Ile Ile Cys
                165                 170                 175

Glu Thr Ala Met Gly Val Lys Leu Asn Thr Glu Asp Arg Gln Gln Asn
            180                 185                 190

Glu Tyr Val Lys Ala Ser Lys Leu Cys His Asp Gly Ala Val Tyr Arg
        195                 200                 205

Phe Phe Lys Leu Trp Leu Tyr Pro Asp Phe Ile Tyr Arg Arg Ser Asn
    210                 215                 220

Ala Gly Lys Thr Phe Phe Arg Ser Val Asp Ile Ile His Asp Phe Ala
225                 230                 235                 240

Thr Gln Val Ile Arg Asn Arg Lys Glu Leu Phe Ile Ala Glu Lys Thr
                245                 250                 255
```

```
Gly Ser Asn Asn Gln Asp Ser Thr Lys Lys Glu Lys Asn Ala Phe Leu
            260                 265                 270

Asp Asn Leu Leu Glu Leu Asp Asp Ser Asn Pro Gly Leu Phe Thr Glu
            275                 280                 285

Ser Asp Ile Glu Glu Val Ser Thr Phe Met Ile Ala Gly His Asn
            290                 295                 300

Pro Ser Ala Ala Thr Leu Lys Phe Leu His Phe Val Leu Ala Asn Arg
305                 310                 315                 320

Pro Asp Val Gln Glu Lys Leu Tyr Asp Glu Gln Met Glu Ile Phe Gly
                    325                 330                 335

Asn Asp Lys Arg Ile Pro Thr Gly Gln Asp Leu Gln Lys Met Ile Tyr
            340                 345                 350

Leu Glu Met Val Ile Lys Glu Thr Leu Arg Leu Tyr Pro Ile Val Pro
            355                 360                 365

Phe Gln Ser Arg Leu Leu Glu Glu Asp Leu Gln Ile Asp Glu Asn Thr
            370                 375                 380

Ile Ile Pro Ala Gly His His Phe Val Val Ser Phe Ser Ile His
385                 390                 395                 400

Arg Ser Lys Lys His Trp Asp Asn Pro Glu Glu Phe Ile Pro Glu Arg
                    405                 410                 415

Phe Ala Pro Gly Asn Ile Ile Asn Pro Phe Ser Phe Ile Pro Phe Ser
            420                 425                 430

Ala Gly Pro Arg Ser Cys Ile Gly Gln Lys Tyr Ala Met Met Glu Met
            435                 440                 445

Lys Thr Ile Met Ser Thr Val Val Arg Gln Cys Trp Leu Glu Pro Val
450                 455                 460

Thr Thr Ser Ile Thr Leu Asp Tyr Gly Ile Ile Leu Lys Ser Ala Glu
465                 470                 475                 480

Pro Ile Ile Val Lys Ala Phe Pro Arg Asn Glu Asn Gln Arg Ile Asn
                    485                 490                 495

Tyr Lys Arg Asn Asn
            500

<210> SEQ ID NO 19
<211> LENGTH: 490
<212> TYPE: PRT
<213> ORGANISM: Nezara viridula

<400> SEQUENCE: 19

Met Met Leu Met Cys Leu Leu Ala Ala Leu Cys Gly Phe Leu Thr Leu
1               5                   10                  15

Arg Leu Trp Arg Arg Pro Arg Gly Pro Pro Gly Pro Pro Ala Ile
            20                  25                  30

Pro Tyr Phe Gly Gln Ala Phe Arg Leu Leu Ser Ile Ala Glu Arg Asp
            35                  40                  45

Ile Leu Pro Leu Phe Lys Glu Trp Phe Asp Thr Tyr Gly Ser Val Val
            50                  55                  60

Gln Val Glu Met Leu Gly Asn Val Tyr Val Leu Leu Ser Glu Pro Glu
65                  70                  75                  80

Ser Leu Glu Pro Val Leu Ser Ser Val His Ile Ser Lys Gly Tyr
            85                  90                  95

Trp Glu Tyr Leu Phe Phe Arg Pro Trp Leu Asn Asp Gly Leu Leu Leu
            100                 105                 110

Ser Thr Gly Asp Lys Trp Arg Leu Arg Arg Lys Leu Leu Thr Pro Ser
            115                 120                 125
```

```
Phe His Phe Lys Ile Leu Glu Ser Phe Leu Gly Gly Ile Ser Lys Asn
    130                 135                 140

Ser Glu Thr Tyr Val Glu Ser Ile Leu Glu Ser Gly Gly Lys Pro Leu
145                 150                 155                 160

Asp Ile Gln Glu Pro Ile Arg Met Ala Thr Leu Lys Ile Ile Cys Glu
                165                 170                 175

Thr Ala Met Gly Val Thr Leu Ser Thr Asp Asn Glu Glu Gln Asn Ala
            180                 185                 190

Phe Ile Thr Ala Ile Lys Asp Ala Ser Glu Gly Ile Val Leu Arg Tyr
        195                 200                 205

Leu Thr Phe Trp Leu Tyr Ser Asp Phe Ile Tyr Arg Arg Ser Glu Phe
210                 215                 220

Gly Lys Lys Phe Tyr Asn Ser Ile Asp Thr Leu Gln Ser Phe Ser Lys
225                 230                 235                 240

Lys Val Ile Arg Arg Lys Gln Leu Tyr Gln Ser Glu Lys Ser Asp
                245                 250                 255

Val Gly Glu Gly Asn Lys Ser Arg Arg Lys Ala Phe Leu Asp Leu Leu
            260                 265                 270

Leu Glu Val Glu Asp Ser Asn Pro Gly Leu Phe Thr Glu Ala Asp Ile
        275                 280                 285

Gln Glu Glu Val Asp Thr Phe Met Phe Glu Gly His Asp Thr Val Ser
    290                 295                 300

Ala Ala Ile Ile Phe Ser His Phe Leu Leu Ala Asn His Pro Asn Val
305                 310                 315                 320

Gln Glu Lys Ala Phe Lys Glu Gln Asp Gly Ile Phe Gly Asn Asp Asp
                325                 330                 335

Arg Pro Ala Ser Met Gln Asp Leu Gln Arg Met Thr Tyr Leu Glu Met
            340                 345                 350

Val Ile Lys Glu Thr Leu Arg Leu Tyr Pro Ser Val Pro Phe His Ser
        355                 360                 365

Arg Lys Leu Tyr Gln Asp Leu Arg Ile Asp Asp Asn Thr Val Val Pro
370                 375                 380

Ala Gly Gln Ser Val Gly Ile Leu Thr Phe Tyr Ile His Arg Ser Thr
385                 390                 395                 400

Arg His Trp Asp Asp Pro Glu Leu Phe Ile Pro Glu Arg Phe Asp Pro
                405                 410                 415

Glu Ile Ser Arg His Pro Phe Ser Tyr Ile Pro Phe Ser Ala Gly Pro
            420                 425                 430

Arg Asn Cys Ile Gly Gln Lys Leu Ala Met Met Glu Ile Lys Thr Leu
        435                 440                 445

Leu Ser Thr Val Leu Arg Asn Cys Ile Leu Glu Pro Val Thr Lys Ser
450                 455                 460

Val Asp Pro Val Ala Ser Val Ile Ile Arg Asn Leu Asp Pro Ile Ile
465                 470                 475                 480

Leu Lys Val Val Pro Arg Pro Arg Ala Ala
                485                 490

<210> SEQ ID NO 20
<211> LENGTH: 489
<212> TYPE: PRT
<213> ORGANISM: Nezara viridula

<400> SEQUENCE: 20

Met Leu Leu Leu Leu Leu Ser Leu Ala Leu Leu Phe Ile Val Trp Trp
```

```
  1               5                  10                 15
Lys Ser Ile Pro Ser Ser Lys Phe Arg Glu Ala Gly Ser Thr Ile Pro
                 20                 25                 30

Gly Pro Lys Ala Tyr Pro Val Val Gly Asn Leu Phe Asn Phe Lys Leu
                 35                 40                 45

Thr Gly Pro Ser Ala Leu Lys His Trp Glu Arg Tyr Thr Lys Ile Tyr
     50                 55                 60

Gly Asn Thr Phe Arg Ile Trp Ile Gly Pro His Leu Gln Ile Phe Thr
 65              70                 75                 80

Ile Glu Pro Asp Asp Ile Gln Thr Ile Phe Ser Ser Lys Met Ser Thr
                 85                 90                 95

Lys Ser Asn Ser Tyr Lys Ala Leu Glu Ser Trp Leu Gly Thr Gly Leu
                100                105                110

Leu Ile Ser Asn Gly Asn Leu Trp His Gln Arg Arg Lys Ala Ile Thr
                115                120                125

Pro Thr Phe His Phe Lys Ile Leu Glu Ser Phe Val Pro Ile Phe Tyr
                130                135                140

Lys Cys Gly Ile Ile Leu Val Asn Cys Leu Lys Glu Lys Val Gly Lys
145                150                155                160

Val Pro Phe Asp Ile Thr Pro Tyr Met Ser Asn Cys Ala Leu Asp Val
                165                170                175

Val Ala Glu Thr Ala Met Gly Thr Glu Val Lys Ala Gln Thr Asn Pro
                180                185                190

His Asp Glu Tyr Pro Lys Ser Val Leu Arg Met Thr Lys Leu Leu Ala
                195                200                205

Asp Lys Met Tyr Asn Pro Tyr Trp Asn Leu Leu Glu Pro Ile Tyr Thr
                210                215                220

Leu Leu Gly Lys Lys Glu Glu Thr Asp Leu Leu Lys Leu Leu Ser
225                230                235                240

Thr Phe Pro Leu Glu Leu Leu Lys Arg Lys Glu Asn Glu Lys Asn Asn
                245                250                255

His Pro Ser Ser Arg Glu Asn Gly Glu Asn Lys Asn Ile Ala Phe Leu
                260                265                270

Glu Leu Leu Val Arg Ile Lys Glu Thr Lys Asn Pro Ala Phe Lys Ser
                275                280                285

Glu Gln Asp Ile Lys Asp Glu Val Val Thr Phe Met Phe Glu Gly His
                290                295                300

Asp Thr Ser Ser Met Ala Leu Val Tyr Thr Phe Trp Leu Leu Gly Leu
305                310                315                320

His Ser Glu Ile Gln Glu Ala Leu Phe Gln Glu Val Ser Gln Thr Leu
                325                330                335

Val Gly Lys Ile Pro Ser Met Glu Asp Tyr His Lys Met Asp Leu Leu
                340                345                350

Asn Arg Val Leu Lys Glu Ser Leu Arg Leu Tyr Ser Pro Val Pro Leu
                355                360                365

Val Ser Arg Met Ile Thr Glu Glu Ile Val Leu Pro Gly Ser Gly Tyr
                370                375                380

Arg Leu Pro Ala Gly Thr Gln Val Val Ser Met Tyr Ser Leu His
385                390                395                400

Arg Arg Ala Asp Leu Phe Pro Glu Pro Glu Lys Phe Asn Pro Asp Arg
                405                410                415

Phe Leu Glu Pro Ile Lys His Pro Phe Ala Tyr Val Pro Phe Ala Ala
                420                425                430
```

```
Gly Pro Arg Asn Cys Ile Gly Gln Lys Phe Val Met Leu Glu Leu Lys
            435                 440                 445

Val Ile Val Ser Leu Val Val Leu Asn Phe Glu Ile His Ser Ser Asn
450                 455                 460

Lys Asn Leu Lys Leu Thr Arg Asp Ile Leu Leu Arg Cys Leu Asn Gly
465                 470                 475                 480

Pro Asn Val Ser Leu Thr Leu Arg Lys
                485

<210> SEQ ID NO 21
<211> LENGTH: 493
<212> TYPE: PRT
<213> ORGANISM: Nezara viridula

<400> SEQUENCE: 21

Met Asp Phe Phe Leu Tyr Leu Ser Ala Ile Leu Ala Val Leu Leu Ile
1               5                   10                  15

Trp Leu Leu Phe Pro Asn Arg Met Ser Arg Met Ala Arg Lys Ile Pro
            20                  25                  30

Gly Pro Arg Ala Leu Pro Ile Phe Gly Asn Ile Phe Asn Phe Ile Val
        35                  40                  45

Ile Gly Pro Lys Ala Pro Glu Cys Trp Lys Lys Gln Met Glu Thr Tyr
50                  55                  60

Gly Asn Thr Phe Arg Val Trp Leu Gly Pro Gln Leu His Val Phe Met
65                  70                  75                  80

Val Asp Pro Glu Asp Ile Lys Ala Ile Leu Ser Ser Gln Ser Leu Leu
                85                  90                  95

Thr Lys Ser Glu Ser Tyr Lys Thr Leu Val Pro Trp Leu Lys Thr Gly
            100                 105                 110

Leu Leu Val Ser Thr Gly Lys Leu Trp Gln Met Arg Arg Lys Ala Ile
        115                 120                 125

Thr Pro Thr Phe His Phe Lys Ile Leu Asp Glu Phe Val Pro Ile Phe
130                 135                 140

Tyr Lys Cys Ser Lys Ile Leu Leu Asp Cys Ile Lys Asp Lys Val Gly
145                 150                 155                 160

Gln Glu Pro Phe Leu Ile Thr Gly Phe Met Ser Asn Cys Ala Leu Asp
                165                 170                 175

Thr Ile Ala Glu Thr Ala Met Gly Thr Glu Leu Lys Ala Gln Thr Asn
            180                 185                 190

Pro Gln Ser Glu Tyr Pro Thr Ser Ile Leu Arg Met Thr Thr Val Leu
        195                 200                 205

Val Glu Arg Val Ala Asn Pro Leu Leu Gly Met Glu Pro Leu Tyr Thr
210                 215                 220

Leu Ser Gly Arg Arg Lys Val Glu Ser Asp Leu Leu Lys Ile Leu Phe
225                 230                 235                 240

Ser Leu Pro Arg Glu Val Ile Arg Gly Lys Lys Tyr Phe Lys Ser Asn
                245                 250                 255

Arg Lys Asn Ile Thr Pro Ser Asp Glu Ala Phe Gly Ile Lys Lys Lys
            260                 265                 270

Thr Ala Phe Leu Glu Leu Leu Leu Glu Met Lys Glu Asn Asn Ala Pro
        275                 280                 285

Ala Phe Gln Thr Asp Lys Asp Val Gln Asp Glu Val Ile Thr Phe Met
290                 295                 300

Phe Glu Gly His Asp Thr Thr Thr Met Ala Leu Thr Tyr Thr Thr Trp
```

-continued

```
305                 310                 315                 320
Leu Leu Gly Met His Pro Asp Glu Gln Glu Lys Leu Tyr Gln Glu Val
                325                 330                 335

Ser Ser Ile Leu Glu Gly Lys Ala Glu Pro Ser Met Glu Asp Tyr Ser
            340                 345                 350

Lys Met Glu Tyr Leu Glu Arg Val Ile Lys Glu Ser Leu Arg Leu Tyr
        355                 360                 365

Pro Pro Val Pro Ile Ile Gly Arg Glu Ala Ile Glu Asp Val Leu Leu
    370                 375                 380

Pro Ser Ser Gly Phe Leu Ile Pro Lys Gly Thr Gln Ile Thr Ile Ile
385                 390                 395                 400

Ile Tyr Ala Leu His Arg Arg Glu Asp Leu Phe Pro Asp Ala Glu Lys
                405                 410                 415

Phe Asn Pro Asp Arg Phe Leu Glu Gln Gln Lys His Pro Tyr Ala Phe
            420                 425                 430

Leu Pro Phe Ser Ala Gly Pro Arg Asn Cys Ile Gly Gln Lys Phe Ala
        435                 440                 445

Met Leu Glu Leu Lys Val Met Ile Ser Asn Leu Val Leu His Tyr Lys
    450                 455                 460

Ile Lys Ser Lys Lys Asp Met Ile Leu Asn Pro Glu Met Leu Leu Arg
465                 470                 475                 480

Ser Glu Asn Gly Pro Tyr Ile Ser Ile Thr Pro Arg Asn
                485                 490

<210> SEQ ID NO 22
<211> LENGTH: 477
<212> TYPE: PRT
<213> ORGANISM: Nezara viridula

<400> SEQUENCE: 22

Trp Leu Leu Thr Pro Glu Lys Arg Leu Arg Glu Met Gly Asn Lys Ile
1               5                   10                  15

Pro Gly Pro Thr Pro Tyr Pro Leu Val Gly Asn Ile Phe Asn Phe Asn
            20                  25                  30

Ile Phe Gly Ile Lys Ala Leu Asp Asp Trp Lys Tyr Cys Met Asn Lys
        35                  40                  45

Tyr Gly Arg Thr Phe Arg Phe Trp Leu Gly Pro Gln Leu His Ile Phe
    50                  55                  60

Ile Thr Glu Pro Glu Asp Ile Gln Met Leu Leu Ser Ser Gln Thr Leu
65                  70                  75                  80

Ile Thr Lys Ser Glu Ala Tyr Tyr Thr Leu Glu Ser Trp Leu Gly Ser
                85                  90                  95

Gly Leu Leu Val Ser Thr Gly Glu Leu Trp Gln Arg Arg Arg Lys Ala
            100                 105                 110

Ile Thr Pro Thr Phe His Phe Lys Ile Leu Asp Glu Phe Val Pro Thr
        115                 120                 125

Phe Asn Lys Cys Ala Asn Thr Leu Val Lys Ile Leu Lys Asp Lys Val
    130                 135                 140

Ser Lys Gly Phe Phe Pro Leu Thr Asp Phe Met Ser His Cys Ala Leu
145                 150                 155                 160

Asp Ala Val Ala Glu Thr Ala Met Gly Thr Glu Ile Lys Ala Gln Thr
                165                 170                 175

Asn Pro Ile Gly Glu Tyr Pro Ser Ser Val Val Lys Met Thr Thr Thr
            180                 185                 190
```

```
Leu Met Glu Lys Ile Gly Asn Pro Leu Leu Gly Met Glu Pro Leu Tyr
            195                 200                 205

Thr Met Ser Gly Arg Arg Thr Arg Glu Asp His Leu Leu Asn Ile Leu
    210                 215                 220

Phe Ser Leu Pro Leu Glu Val Ile Arg Lys Lys Glu Asn Glu Lys Asn
225                 230                 235                 240

Ser Pro Thr Asp Ser Ser Pro Thr Glu Glu Ala Phe Gly Val Lys Lys
            245                 250                 255

Lys Thr Ala Phe Leu Glu Tyr Leu Leu Lys Met Lys Arg Asp Asn Val
                260                 265                 270

Pro Ala Phe Gln Thr Glu Lys Asp Ile Lys Asp Glu Val Met Thr Phe
            275                 280                 285

Met Phe Glu Gly His Asp Thr Thr Thr Met Ala Leu Thr Phe Ala Val
    290                 295                 300

Trp Leu Leu Gly Leu His Gln Asp Ile Gln Glu Glu Leu Tyr Arg Glu
305                 310                 315                 320

Val Ser Gly Ile Leu Val Gly Gln Glu Pro Thr Met Glu Asp Tyr Gln
                325                 330                 335

Lys Met Thr Tyr Leu Glu Arg Val Leu Lys Glu Thr Ile Arg Leu Tyr
            340                 345                 350

Pro Ser Val Pro Ile Val Ala Arg Lys Ala Thr Gln Asp Val Val Leu
        355                 360                 365

Pro Ser Cys Gly Tyr Thr Val Pro Lys Gly Ala His Leu Asp Val Ile
    370                 375                 380

Ile Leu Ala Leu Gln Arg Arg Glu Asp Leu Phe Thr Asp Pro Asp Lys
385                 390                 395                 400

Phe Asn Pro Asp Arg Tyr Phe Glu Pro Gln Lys His Pro Tyr Ala Tyr
                405                 410                 415

Ile Pro Phe Ser Ala Gly Pro Arg Asn Cys Ile Gly Gln Lys Phe Ala
            420                 425                 430

Met Leu Asp Met Lys Val Ile Val Ser Asn Leu Val Leu Asn Tyr Lys
    435                 440                 445

Ile Glu Ser Asp Glu Asp Ile Ile Val Ser Pro Glu Met Ile Leu Arg
450                 455                 460

Thr Lys Lys Gly Pro Asn Ile Arg Leu Ile Ser Arg Asn
465                 470                 475

<210> SEQ ID NO 23
<211> LENGTH: 494
<212> TYPE: PRT
<213> ORGANISM: Nezara viridula

<400> SEQUENCE: 23

Met Tyr Met Ile Leu Ile Thr Leu Ala Leu Gly Ala Phe Met Ile Trp
1               5                   10                  15

Trp Leu Phe Arg Pro Glu Lys Arg Leu Arg Glu Met Gly Asn Lys Ile
            20                  25                  30

Pro Gly Pro Lys Ala Tyr Pro Ile Val Gly Asn Ile Phe Asn Phe Asn
        35                  40                  45

Leu Tyr Gly Ile Asn Gly Pro Lys Asp Trp Lys Glu Cys Ile Glu Lys
    50                  55                  60

Tyr Gly Pro Thr Phe Arg Val Trp Leu Gly Pro Gln Leu His Ile Ile
65              70                  75                  80

Ile Ala Glu Pro Glu Asp Ile Gln Ala Leu Ser Ser Lys Thr Leu Ile
                85                  90                  95
```

Thr Lys Ser Asp Ala Tyr Ser Ala Leu Gln Pro Trp Leu Gly Thr Gly
            100                 105                 110

Leu Leu Leu Ser Thr Gly Glu Leu Trp Gln Arg Arg Lys Ala Ile
        115                 120                 125

Thr Pro Thr Phe His Phe Lys Ile Leu Asp Gln Phe Val Pro Thr Phe
    130                 135                 140

Ser Lys Cys Ala Asn Thr Leu Leu Lys Val Leu Lys Asp Lys Val Gly
145                 150                 155                 160

Lys Gly Phe Phe Pro Leu Thr His Ile Ile Ser Asp Cys Ala Leu Asp
                165                 170                 175

Ser Val Ala Glu Thr Val Met Gly Thr Glu Leu Asn Ala Met Thr Asn
            180                 185                 190

Pro Ile Gly Glu Tyr Pro Thr Ala Ile Glu Arg Met Thr Leu Leu Leu
        195                 200                 205

Met Glu Lys Ile Lys Asn Pro Leu Leu Gly Met Glu Pro His Tyr Thr
    210                 215                 220

Leu Ser Gly Arg Arg Lys Lys Glu Lys His Leu Leu Asn Ile Leu Phe
225                 230                 235                 240

Ser Leu Pro Leu Glu Val Ile Arg Lys Lys Glu Ile Glu Asn Ile Asp
                245                 250                 255

Val Arg Asp Asp Ser Asp Ala Ser Gly Asp Ala Val Leu Gly Val Lys
            260                 265                 270

Arg Lys Ala Ala Leu Leu Glu Leu Leu Lys Met Lys Arg Asp Lys
        275                 280                 285

Val Pro Ala Phe Gln Thr Glu Lys Asp Val Lys Asp Glu Val Ile Thr
    290                 295                 300

Phe Met Phe Glu Gly His Asp Thr Thr Thr Ser Ser Leu Thr Phe Ala
305                 310                 315                 320

Ile Trp Ile Leu Gly Lys His Gln Asp Val Gln Glu Glu Val Tyr Arg
                325                 330                 335

Glu Val Ser Glu Ile Leu Val Gly Gln Glu Pro Thr Tyr Glu Asp Phe
            340                 345                 350

Gln Lys Met Thr Tyr Leu Asp Arg Val Leu Lys Glu Ser Met Arg Leu
        355                 360                 365

Tyr Pro Ala Val Pro Ile Val Ala Arg Gln Ala Thr His Asp Val Val
    370                 375                 380

Leu Pro His Asn Gly Tyr Thr Ile Pro Lys Gly Ala Tyr Leu Asn Val
385                 390                 395                 400

Met Ile Tyr Pro Leu His Arg Arg Glu Asp Leu Phe Pro Asp Ser Glu
                405                 410                 415

Lys Phe Asn Pro Asp Arg His Leu Lys Pro His Lys His Ala Tyr Ala
            420                 425                 430

Tyr Ile Pro Phe Ser Ala Gly Pro Arg Asn Cys Ile Gly Gln Lys Phe
        435                 440                 445

Ala Met Leu Asn Met Lys Val Ile Ile Ser Ser Leu Leu Leu Ser Tyr
    450                 455                 460

Lys Ile Glu Ser Asn Asp Asp Leu Ile Val Tyr Pro Glu Leu Leu Leu
465                 470                 475                 480

Arg Thr Lys Lys Gly Pro Tyr Ile Arg Leu Thr Pro Arg Asn
                485                 490

<210> SEQ ID NO 24
<211> LENGTH: 518

```
<212> TYPE: PRT
<213> ORGANISM: Nezara viridula

<400> SEQUENCE: 24
```

| | | | | | | | | | | | | | | | |
|---|---|---|---|---|---|---|---|---|---|---|---|---|---|---|---|
| Pro | Leu | Leu | Lys | Gln | Cys | Ser | Ile | Phe | Ile | Leu | Ala | Arg | Asp | His | Tyr |
| 1 | | | | 5 | | | | | 10 | | | | | 15 | |
| Ile | Ser | His | Ser | Lys | Ser | Arg | Met | Glu | Phe | Leu | Leu | Ser | Leu | Ala | |
| | | | 20 | | | | | 25 | | | | | 30 | | |
| Leu | Gly | Ala | Phe | Ile | Leu | Trp | Trp | Met | Phe | Ser | Ser | Pro | Lys | Arg | Leu |
| | | | 35 | | | | | 40 | | | | | 45 | | |
| Arg | Glu | Leu | Gly | Asn | Arg | Phe | Pro | Gly | Pro | Arg | Thr | Tyr | Pro | Ile | Val |
| | 50 | | | | | 55 | | | | | 60 | | | | |
| Gly | Asn | Ile | Phe | Asn | Phe | Gln | Ile | Ile | Gly | Pro | Asn | Ala | Pro | Gln | Cys |
| 65 | | | | | 70 | | | | | 75 | | | | | 80 |
| Trp | Ser | Asn | Phe | Ser | Lys | Lys | Tyr | Gly | Tyr | Thr | Met | Arg | Phe | Trp | Leu |
| | | | | 85 | | | | | 90 | | | | | 95 | |
| Gly | Pro | Glu | Leu | His | Ile | Phe | Val | Ser | Glu | Pro | Asp | Asp | Met | Gln | Met |
| | | | 100 | | | | | 105 | | | | | 110 | | |
| Ile | Leu | Ser | Ser | Gln | Thr | Leu | Ile | Thr | Lys | Ser | Thr | Ser | Tyr | Lys | Leu |
| | | | 115 | | | | | 120 | | | | | 125 | | |
| Leu | Asp | Ser | Trp | Leu | Gly | Met | Gly | Leu | Leu | Leu | Ser | Thr | Gly | Asn | Leu |
| | 130 | | | | | 135 | | | | | 140 | | | | |
| Trp | Gln | Met | Arg | Arg | Lys | Ala | Ile | Thr | Pro | Thr | Phe | His | Phe | Lys | Ile |
| 145 | | | | | 150 | | | | | 155 | | | | | 160 |
| Leu | Glu | Lys | Phe | Ile | Pro | Thr | Phe | Asn | Lys | Cys | Ala | Asn | Thr | Leu | Val |
| | | | | 165 | | | | | 170 | | | | | 175 | |
| Asn | Cys | Leu | Lys | Asp | Lys | Ala | Asp | Lys | Gly | Tyr | Phe | Asn | Ile | Ile | Asp |
| | | | 180 | | | | | 185 | | | | | 190 | | |
| Tyr | Met | Ser | Asn | Cys | Ala | Leu | Asp | Ala | Ile | Ala | Glu | Thr | Ala | Met | Gly |
| | | | 195 | | | | | 200 | | | | | 205 | | |
| Thr | Glu | Ile | Lys | Ala | Gln | Thr | Asn | Pro | Leu | Glu | Lys | Tyr | Pro | Arg | Ser |
| | 210 | | | | | 215 | | | | | 220 | | | | |
| Leu | Ser | Arg | Met | Thr | Lys | Tyr | Leu | Ile | Glu | Arg | Val | Arg | Asn | Pro | Leu |
| 225 | | | | | 230 | | | | | 235 | | | | | 240 |
| Leu | Ser | Met | Glu | Pro | Ile | Tyr | Thr | Leu | Ser | Gly | Arg | Arg | Lys | Glu | Glu |
| | | | | 245 | | | | | 250 | | | | | 255 | |
| Ala | Lys | His | Leu | Asp | Val | Leu | Phe | Ser | Leu | Pro | Leu | Glu | Val | Leu | Glu |
| | | | 260 | | | | | 265 | | | | | 270 | | |
| Lys | Lys | Lys | Asn | Glu | Lys | Ile | Asn | Thr | Leu | Asn | Glu | Thr | Glu | Pro | Leu |
| | | | 275 | | | | | 280 | | | | | 285 | | |
| Glu | Glu | Asp | Tyr | Gly | Ala | Lys | Lys | Thr | Ala | Phe | Leu | Glu | Met | Leu | |
| | 290 | | | | | 295 | | | | | 300 | | | | |
| Leu | Glu | Met | Lys | Gln | Lys | Asn | Ile | Pro | Gly | Phe | Arg | Ser | Asp | Lys | Asp |
| 305 | | | | | 310 | | | | | 315 | | | | | 320 |
| Ile | Lys | Asp | Glu | Val | Met | Thr | Phe | Met | Phe | Glu | Gly | His | Asp | Thr | Thr |
| | | | | 325 | | | | | 330 | | | | | 335 | |
| Thr | Thr | Val | Leu | Ser | Tyr | Thr | Ile | Trp | Leu | Ile | Gly | Met | His | Pro | Asp |
| | | | 340 | | | | | 345 | | | | | 350 | | |
| Ile | Gln | Glu | Glu | Leu | Tyr | Lys | Asp | Leu | Lys | Glu | Ile | Thr | Glu | Asp | Ser |
| | | | 355 | | | | | 360 | | | | | 365 | | |
| Glu | Leu | Thr | Ile | Asp | Val | Tyr | His | Lys | Met | His | Tyr | Leu | Glu | Arg | Ile |
| | 370 | | | | | 375 | | | | | 380 | | | | |
| Ile | Lys | Glu | Ser | Leu | Arg | Leu | Tyr | Pro | Pro | Val | Pro | Ala | Phe | Gly | Arg |
| 385 | | | | | 390 | | | | | 395 | | | | | 400 |

```
Leu Ala Thr Gln Asp Ile Val Leu Pro Thr Ser Gly Tyr Val Ile Pro
            405                 410                 415

Ala Gly Ala Gln Val Asp Leu Val Val Tyr Leu Leu His Arg Arg Glu
        420                 425                 430

Asp Leu Phe Pro Glu Pro Glu Lys Phe Asn Pro Asp Arg Phe Leu Glu
        435                 440                 445

Pro Ala Lys His Pro Phe Ala Tyr Ile Pro Phe Ser Ala Gly Pro Arg
    450                 455                 460

Asn Cys Ile Gly Gln Lys Phe Ala Met Leu Asp Leu Lys Ala Ile Ile
465                 470                 475                 480

Ser His Val Val Leu Asn Tyr Lys Ile Glu Ser Asp Ser Asn Leu Glu
                485                 490                 495

Val Asn Pro Glu Met Leu Leu Arg Thr Ser Lys Gly Pro Asn Val Lys
            500                 505                 510

Leu Thr Ala Arg Asn Gln
        515

<210> SEQ ID NO 25
<211> LENGTH: 511
<212> TYPE: PRT
<213> ORGANISM: Nezara viridula

<400> SEQUENCE: 25

Met Asp Met Ser Val Val Ile Trp Ile Ile Val Met Gly Val Gly Trp
1               5                   10                  15

Ala Trp Pro Tyr Leu Leu Leu Gly Ile Val Leu Leu Leu Ile Tyr Lys
            20                  25                  30

Phe Tyr Asn Ser Arg Ser Phe Lys Leu Leu Ser Ala Ile Pro Ser Thr
        35                  40                  45

Asn Ala Pro Arg Phe Ile Gly His Thr Leu Asp Phe Leu Thr Met His
    50                  55                  60

Pro Ser Asn Ile Leu Ser Phe Met Leu Gln Leu Phe Asp Lys Asn Lys
65                  70                  75                  80

Thr Asn Lys Asn Val Met Ala Ile Trp Thr Gly Pro Phe Cys Phe Val
                85                  90                  95

Tyr Leu Arg Thr Leu Pro Asp Ile Glu Lys Leu Leu Ser Asp Asn Gln
            100                 105                 110

Gln Leu Arg Lys Ser Ile Asn Tyr Ile Tyr Leu Glu Pro Trp Leu Gly
        115                 120                 125

Gln Gly Leu Ile Asn Ser Asp Gly Thr Ile Trp Gln Arg His Arg Lys
    130                 135                 140

Met Ile Thr Pro Ser Phe His Phe Lys Ile Leu Glu Gly Phe Leu Glu
145                 150                 155                 160

Ile Met Asn Ser Lys Leu Asp Ile Phe Ser Glu Val Leu Glu Lys Lys
                165                 170                 175

Val Gly Asn Gly Tyr Phe Asp Ile Glu Pro Leu Ile Ala Asn Tyr Ser
            180                 185                 190

Leu Asp Val Ile Thr Glu Thr Ala Met Ser Thr Asn Val Asp Ala Gln
        195                 200                 205

Arg Thr Asn Ser Glu Phe Ile Asp Cys Ile Lys Ser Leu Thr Glu Val
    210                 215                 220

Ile Ile Ile Arg Ser Val Arg Ile Met Tyr Phe Phe Gln Pro Ile Phe
225                 230                 235                 240

Asn Leu Ser Pro Tyr Lys Asn Gln Glu Ser Lys Ser Ile Asn Tyr Val
```

```
                        245                 250                 255
Asn Lys Tyr Ile Ala Lys Ile Leu Glu Asn Lys Arg Thr Glu Ala Lys
                260                 265                 270

Asn Ile Lys Lys Asp Glu Asn Val Glu Asn Asp Ile Gly Ala Lys Glu
            275                 280                 285

Lys Leu Ala Leu Leu Asp Met Leu Leu Gln Leu Gln Phe Ser Asn Ala
        290                 295                 300

Lys Ile Thr Asp Lys Glu Ile Tyr Asp Glu Val Asn Thr Phe Met Phe
305                 310                 315                 320

Ala Gly His Asp Thr Val Ser Ser Ala Leu Ser Phe Val Ile Tyr Asn
                325                 330                 335

Leu Ala Val His Gln Asp Val Gln Glu Lys Val Tyr Ala Glu Val Met
                340                 345                 350

Glu Val Leu Gly Asp Ser Lys Pro Thr Tyr Gln Ser Leu Met Asn Phe
            355                 360                 365

Lys Tyr Leu Glu Arg Val Ile Lys Glu Thr Met Arg Leu Tyr Pro Ser
        370                 375                 380

Val Pro Tyr Ile Gly Arg Arg Leu Lys Lys Asp Met Pro Ile Thr Asp
385                 390                 395                 400

Gly His Ile Val Pro Lys Asp Ser Asp Val Ala Val Phe Ile Tyr Asp
                405                 410                 415

His His Arg Asn Pro Glu Asn Phe Pro Asp Pro Glu Lys Phe Asp Pro
                420                 425                 430

Asp Arg Phe Leu Pro Glu Asn Ile Ala Lys Arg His Pro Tyr Ala Tyr
            435                 440                 445

Ile Pro Phe Ser Ala Gly Ser Arg Asn Cys Ile Gly Gln Lys Phe Ala
        450                 455                 460

Met Met Glu Gln Leu Ala Thr Val Ser His Leu Leu Arg Gln Phe Arg
465                 470                 475                 480

Ile Ser Ile Glu Pro Gly Phe Val Met Lys Pro Ile Ser His Ile Val
                485                 490                 495

Leu Arg Pro Asn Val Glu Gly Val Arg Ile Lys Leu Thr Lys Arg
            500                 505                 510

<210> SEQ ID NO 26
<211> LENGTH: 469
<212> TYPE: PRT
<213> ORGANISM: Nezara viridula

<400> SEQUENCE: 26

Met Leu Ile Leu Phe Gly Ile Leu Leu Thr Ala Leu Phe Leu Leu Arg
1               5                   10                  15

Phe Phe Cys Arg His Phe Asn Tyr Tyr Lys Leu Ala Leu Arg Leu Pro
            20                  25                  30

Tyr Ala Lys Lys Ala Pro Leu Ile Gly His Ala Leu Asn Leu Trp Val
        35                  40                  45

Asp Lys Asp Glu Leu Leu Asp Lys Ile Leu Glu Ile Gly Glu Pro
    50                  55                  60

Asp Asn Lys Arg Ser Ile Gln Glu His Gly Val Leu Ala Val Trp Ile
65                  70                  75                  80

Gly Pro Met Ala Ile Val Leu Val His Asp Leu Gln Asp Ile Glu Gln
                85                  90                  95

Ile Leu Thr Ser Arg Asp Leu Thr Arg Lys Ser Tyr Gln Tyr Lys Phe
            100                 105                 110
```

-continued

```
Phe Glu Pro Trp Leu Gly Gln Gly Leu Phe Thr Ala Ser Gly Pro His
            115                 120                 125
Trp Tyr Ser His Arg Lys Leu Ile Thr Pro Ala Phe His Phe Lys Ile
130                 135                 140
Leu Glu Lys Phe Ile Pro Ile Phe Asn Ala Asn Ile Asp Ile Tyr Leu
145                 150                 155                 160
Arg Lys Leu Asp Glu Lys Val Gly Lys Gly Ser Phe Asn Ile Glu Asn
                165                 170                 175
Tyr Ile Ala Tyr Leu Ser Leu Asp Ile Ile Ala Glu Thr Ala Met Asp
            180                 185                 190
Ala Lys Ile Asn Ala Gln Lys Glu Glu Ser Pro Tyr Ala Gln Lys Val
        195                 200                 205
Lys Asp Met Thr Glu Thr Ile Leu Leu Arg Gly Cys Arg Leu Leu Tyr
210                 215                 220
Tyr Ser Asp Val Ile Phe Ser Leu Ser Ser Leu Gly Arg Arg Gln Lys
225                 230                 235                 240
Arg Ser Lys Arg Phe Ile Asp Asn Phe Ile Asn Asp Leu Val Lys Arg
                245                 250                 255
Lys Lys Glu Glu Arg Asn Arg Ile Gln Leu Thr Lys Asn Asn Lys Asn
            260                 265                 270
Asn Ser Glu Ile Asp Glu Lys Glu Arg Val Ala Leu Met Asp Val Leu
        275                 280                 285
Leu Glu Thr Gln Asn Arg Ser Ser His Phe Thr Asp Lys Asp Ile Leu
290                 295                 300
Asp Glu Val Asn Thr Phe Met Phe Gly Gly His Asp Thr Ile Thr Ser
305                 310                 315                 320
Cys Ile Asn Phe Thr Leu Tyr Leu Leu Ser Lys His Pro Thr Ile Gln
                325                 330                 335
Glu Glu Val Leu Arg Glu Ile Glu Ser Val Ile Gly Glu Glu Lys Phe
            340                 345                 350
Thr Leu Ser Asn Leu Gln Gln Leu Lys Tyr Leu Glu Arg Val Ile Lys
        355                 360                 365
Glu Ser Leu Arg Ile Leu Pro Val Gly Pro Phe Met Gln Arg Ala Ala
370                 375                 380
Glu Lys Asp Ile Lys Leu Arg Ser Gly Tyr Val Leu Pro Ala Gly Cys
385                 390                 395                 400
Thr Ile Ile Met Met Ile Tyr Ala Leu His Arg Asn Pro Glu Tyr Phe
                405                 410                 415
Pro Asn Pro Glu Gln Phe Asp Pro Asp Arg Phe Leu Pro Glu Asn Cys
            420                 425                 430
Leu Asn Arg His Pro Tyr Ala Tyr Leu Pro Phe Ser Ala Gly Pro Arg
        435                 440                 445
Asn Cys Ile Gly Gln Lys Phe Ala Leu Leu Glu Met Lys Ala Ile Ile
450                 455                 460
Ala Ala Thr Ile Arg
465

<210> SEQ ID NO 27
<211> LENGTH: 522
<212> TYPE: PRT
<213> ORGANISM: Nezara viridula

<400> SEQUENCE: 27

Gly Gln Asn Asp Arg Gly Ala Pro Thr Leu Tyr Arg Pro Pro Ala Ala
1               5                   10                  15
```

-continued

```
Gln Ser Phe Ala Thr Ser Leu Pro Glu Asp Met Ile Ile Leu Val Leu
         20                  25                  30
Leu Ala Ile Val Val Leu Phe Val Tyr Leu Leu Ser Pro Asp Ala
 35                  40                  45
Lys Thr Arg Lys Cys Gly Gln Gln Ile Pro Gly Pro Lys Pro Trp Pro
         50                  55                  60
Leu Ile Gly Asn Leu Phe Asp Met Glu Leu Gly His Lys Gly Val Lys
65                   70                  75                  80
Thr Tyr Asn Gly Phe Gln Ala Lys Tyr Gly His Val Ile Arg Tyr Trp
                 85                  90                  95
Leu Gly Ser Lys Leu Ala Val Leu Leu Ser Asp Ala Asp Ala Glu
         100                 105                 110
Val Leu Phe Arg Asp Thr Gln Asn Leu Gly Lys Ala Asp Val Tyr Lys
         115                 120                 125
Phe Met His Pro Trp Leu Gly Thr Gly Leu Leu Thr Ser Thr Gly His
 130                 135                 140
Lys Trp Phe Gln Arg Arg Lys Ala Ile Thr Pro Thr Phe His Phe Lys
145                  150                 155                 160
Val Leu Asp Gln Phe Ile Glu Val Phe Glu Arg Lys Ser Thr Ile Leu
                 165                 170                 175
Val Glu Cys Leu Lys Ser Met Ala Asn Gly Gln Ser Phe Asp Ile His
         180                 185                 190
Pro Phe Val Ser Arg Tyr Ser Leu Asp Val Ile Cys Glu Thr Ala Met
         195                 200                 205
Gly Thr Ser Val Asp Ala Gln Asn Asn Ile Glu Ser Glu Tyr Phe Asn
         210                 215                 220
Ala Ile Arg Thr Val Ala Asp Cys Ile Val Thr Arg Ile Leu Lys Phe
225                  230                 235                 240
Trp Leu His Pro Asn Phe Ile Tyr Arg Phe Ser Arg Leu Ser Lys Gln
                 245                 250                 255
His Asp Ala Ala Leu Arg Val Val His Gly Phe Ser Lys Lys Val Ile
         260                 265                 270
Ser Glu Gln Asp Arg Leu Asn Asn Lys Glu Gln Leu His Asn Asp Lys
         275                 280                 285
Glu Ser Asp Thr Gly Met Lys Lys Arg Thr Ala Phe Leu Lys Leu Leu
 290                 295                 300
Ile Glu Met Lys Arg Gln Gln Asn Gly Ala Phe Thr Ser Glu Asp Asp
305                  310                 315                 320
Ile Arg Glu Glu Val Asp Thr Phe Met Phe Glu Gly Phe Asp Thr Thr
                 325                 330                 335
Ala Ser Ala Ile Ser Phe Ala Ile Tyr Glu Phe Gly Arg His Pro Asn
         340                 345                 350
Ile Gln Glu Thr Ala Tyr His Glu Val Arg Asp Ala Phe Ala Gly Glu
         355                 360                 365
Thr Ala Leu Thr Ile Glu Cys Leu Asn Asn Leu Lys Tyr Leu Glu Arg
         370                 375                 380
Phe Ile Lys Glu Val Leu Arg Leu Tyr Pro Ser Val Pro Met Ile Ala
385                  390                 395                 400
Arg Glu Ile Cys Lys Asp Ile Lys Ile Pro Ser Gly Tyr Leu Ile Pro
                 405                 410                 415
Ala Gly Ser Ile Ala Thr Val Val Ile Gly Gly Ile His Arg Asn Lys
         420                 425                 430
```

```
Lys Tyr Tyr Lys Asn Pro Asp Lys Phe Asp Pro Asp Arg Phe Leu Pro
            435                 440                 445

Glu Asn Met Val Asn Arg His Pro Tyr Ser Tyr Val Pro Phe Ser Ala
450                 455                 460

Gly Ser Arg Asn Cys Ile Gly Gln Lys Phe Ala Met Leu Glu Met Lys
465                 470                 475                 480

Ala Ser Leu Ser His Ile Leu Leu Asn Tyr Glu Ile Gly Thr Thr Glu
                485                 490                 495

Glu Ser Lys Tyr Gly Met Leu Leu Thr Leu Gln Ser Phe Asn Gly Gln
            500                 505                 510

Asn Val Trp Leu Lys Pro Arg Arg Thr Ala
        515                 520

<210> SEQ ID NO 28
<211> LENGTH: 496
<212> TYPE: PRT
<213> ORGANISM: Nezara viridula

<400> SEQUENCE: 28

Met Leu Ala Ile Ile Leu Val Val Leu Ala Ala Tyr Ala Phe Tyr Gln
1               5                   10                  15

Tyr Ser Val Trp Thr Phe Asp Tyr Trp Lys Arg Lys Val Pro His
            20                  25                  30

Pro Pro Pro Val Pro Leu Phe Gly Asn Ile Lys Glu Val Val Leu Met
            35                  40                  45

Lys Gln Tyr Pro Gly His Cys His Gln Gln Ile Tyr Lys Met Tyr Pro
        50                  55                  60

Asn Glu Lys Phe Val Gly Leu Tyr Gln Leu Arg Met Pro Ser Leu Leu
65                  70                  75                  80

Ile Arg Asp Pro Ser Leu Val Lys Gln Cys Leu Ile Lys Asp Phe Asp
                85                  90                  95

His Phe Phe Asp Arg Gly Phe His Thr Asp Glu Glu Arg Glu Pro Leu
            100                 105                 110

Thr Gly His Leu Val Ser Leu Thr Gly Thr Arg Trp Lys Leu Leu Arg
        115                 120                 125

Thr Lys Leu Thr Pro Val Phe Ser Ser Gly Lys Ile Lys Gln Met Phe
130                 135                 140

Pro Leu Leu Leu Asp Cys Ser Asp Gln Leu Arg Asp Phe Ile Lys Thr
145                 150                 155                 160

Gln Met Gly Gly Lys Glu Gly Val Leu Glu Met Arg Glu Val Thr Ala
                165                 170                 175

Arg Phe Thr Thr Asp Val Ile Gly Thr Val Ala Phe Gly Leu Gln Phe
            180                 185                 190

Glu Ser Met Ser Gly Asp Ser Val Phe Arg Gln Met Gly Lys Arg Ala
        195                 200                 205

Leu Gln Pro Thr Val Ala Gly Ala Leu Ala Lys Ala Met Arg Cys Phe
210                 215                 220

Thr Pro Lys Leu Phe Asp Leu Leu Lys Met Arg Thr Phe Pro Glu Glu
225                 230                 235                 240

Ile Asn Ser Phe Phe Thr Asn Val Val Ser Glu Thr Met Lys Gln Arg
                245                 250                 255

Thr Glu Ala Asn Tyr Gly Arg Asn Asp Phe Leu Gln Leu Met Met Gln
            260                 265                 270

Leu Arg Asp Ala Ser Gly Ala Asp Ile Ala Lys Asn Asp Ile Glu Leu
        275                 280                 285
```

Asn Asp Gln Val Ile Ala Ala Gln Ala Phe Val Phe Phe Leu Ala Gly
            290                 295                 300

Phe Glu Thr Ser Ser Thr Thr Leu Ser Tyr Cys Leu Tyr Glu Leu Ala
305                 310                 315                 320

Lys Asn Arg Gln Cys Gln Glu Ala Val Phe Asn Glu Ile Gln Glu Val
                325                 330                 335

Met Lys Lys His Gly Glu Leu Ser Tyr Glu Ala Val Ser Asp Met Ile
            340                 345                 350

Tyr Leu Glu Gln Val Leu Leu Glu Thr Met Arg Met Tyr Pro Pro Val
            355                 360                 365

Gly Asn Leu Cys Arg Val Cys Thr Lys Pro Tyr Arg Ile Pro Gly Thr
            370                 375                 380

Asp Ile Gln Leu Asp Glu Gly Val Ser Leu Val Ile Pro Val Phe Ala
385                 390                 395                 400

Leu His His Asp Pro Glu Leu Tyr Pro Asp Pro Glu Ser Phe Ile Pro
                405                 410                 415

Glu Arg Phe Thr Asp Lys Glu Leu Gln Lys Ala Pro Tyr Tyr Leu Pro
            420                 425                 430

Phe Gly Gly Gly Pro Arg Ile Cys Ile Gly Gln Arg Phe Ala Met Ile
            435                 440                 445

Glu Met Lys Leu Ala Leu Leu Arg Leu Leu Glu Asn Tyr Thr Phe Ser
450                 455                 460

Leu Ser Ser Lys Thr Pro Pro Glu Leu Pro Val Glu Pro Lys Ser Phe
465                 470                 475                 480

Ile Met Ala Pro Ile Gly Gly Ile Trp Leu Asn Leu Asn Ala Arg Ser
                485                 490                 495

<210> SEQ ID NO 29
<211> LENGTH: 492
<212> TYPE: PRT
<213> ORGANISM: Nezara viridula

<400> SEQUENCE: 29

Lys Tyr Tyr Val Ser Val Tyr Asp Leu Trp Glu Lys Arg Gly Ile Pro
1               5                   10                  15

Tyr Tyr Pro Ser Thr Phe Pro Phe Gly Cys Ser Tyr Gln Ile Leu Thr
                20                  25                  30

His Ser Arg Phe Pro Gly Tyr Ile His Asp Glu Met Tyr Lys Lys Leu
            35                  40                  45

Ala Pro Asn Pro Met Phe Gly Leu Phe Val Met Arg Val Pro Met Leu
50                  55                  60

Gln Ile Arg Asp Pro Asp Leu Ile Gln Leu Ile Leu Thr Lys Glu Phe
65                  70                  75                  80

Ser His Phe Arg Glu Arg Met Phe Ile Lys Ile Ser Glu Lys Asp Val
                85                  90                  95

Leu Asn Gln His Leu Phe Asn Leu Asp Gly Glu Arg Trp Arg Ala Leu
            100                 105                 110

Arg Leu Lys Leu Thr Pro Thr Phe Thr Ser Gly Lys Met Lys Ala Met
            115                 120                 125

Phe Pro Leu Phe Leu Asn Cys Ala Glu Ala Phe Asp Ser Leu Ile Leu
            130                 135                 140

Ser Lys Ile Gly Cys Asp Val Asp Val Lys Asp Leu Ile Gly Arg Leu
145                 150                 155                 160

Met Thr Asp Ile Ile Cys Ser Cys Ala Phe Gly Leu Asp Ser Asn Thr

```
            165                 170                 175

Ile Lys Glu Pro Asp His Lys Leu Arg Gln Ile Gly Ala Gln Val Phe
            180                 185                 190

Lys Met Asn Phe Met Asp Lys Val Lys Ile Ala Ile Leu Gln Ala Met
        195                 200                 205

Pro Lys Leu Ala Asn Lys Ile Glu Ala Arg Phe Thr Pro Lys Glu Thr
    210                 215                 220

Glu Asp Tyr Ile Val Lys Leu Val Glu Asn Thr Ile Glu Tyr Arg Glu
225                 230                 235                 240

Lys Asn Ile Lys Arg Asn Asp Phe Leu Asp Leu Ile Gln Leu
        245                 250                 255

Lys Asn Lys Gly Thr Val Gly Asp Asp Leu Lys Asp Glu Ile Glu Glu
        260                 265                 270

Gln Lys Cys Gln Pro Phe Glu Leu Thr Ile Gly Leu Met Ala Ala Gln
        275                 280                 285

Cys Phe Val Phe Leu Val Ala Gly Phe Glu Thr Ser Ser Ser Val Gln
    290                 295                 300

Ser Phe Cys Leu Tyr Glu Leu Ala Ile Asn Gln Asp Ile Gln Thr Arg
305                 310                 315                 320

Val Lys Lys Glu Ile Asp Glu Lys Ile Glu Lys His Gly Gly Leu Thr
            325                 330                 335

Tyr Gln Ala Val Lys Glu Met Glu Tyr Leu Asp Met Val Ile Ser Glu
        340                 345                 350

Thr Met Arg Lys Tyr Pro Thr Leu Pro Ile Leu Met Arg Tyr Cys Ser
            355                 360                 365

Lys Ser Ile Thr Thr Pro Tyr Gly Tyr Lys Ile Glu Ala Gly Asp Thr
        370                 375                 380

Ile Ile Ile Pro Val Trp Ser Leu His His Asp Pro Glu Tyr Tyr Pro
385                 390                 395                 400

Asn Pro Glu Lys Phe Asp Pro Glu Arg Phe Ser Pro Gln Asn Met Glu
                405                 410                 415

Ser Ile Asn Pro Tyr Thr Tyr Leu Pro Phe Gly Glu Gly Pro Arg Met
            420                 425                 430

Cys Ile Gly Met Arg Phe Gly Lys Leu Gln Thr Lys Val Gly Leu Ile
        435                 440                 445

Thr Ile Leu Arg Asn Cys Arg Val Glu Pro Cys Ala Ala Thr Lys Ile
    450                 455                 460

Pro Leu Val Ile Gly Pro Ser Pro Met Leu Thr Ile Pro Lys Asp Pro
465                 470                 475                 480

Ile Glu Leu Lys Leu Val Pro Arg Ser Ser Ser
                485                 490

<210> SEQ ID NO 30
<211> LENGTH: 510
<212> TYPE: PRT
<213> ORGANISM: Nezara viridula

<400> SEQUENCE: 30

Met Leu Thr Ile Leu Ile Gly Leu Leu Ile Pro Leu Trp Leu Phe Tyr
1               5                   10                  15

Lys Tyr Tyr Val Ser Val Tyr Asn Phe Trp Glu Ser Arg Gly Ile Ala
            20                  25                  30

Ser Glu Pro Gly Arg Phe Pro Phe Gly Asn Lys Leu Gln Leu Val Thr
        35                  40                  45
```

```
Met Asn Lys Ser Gln Ala Leu Val Ile Asp Lys Met Tyr Lys Lys Phe
    50                  55                  60

Glu Ser Gln Pro Tyr Phe Gly Phe Tyr Val Leu Arg Ser Ala Leu Leu
 65              70                  75                  80

Val Val Lys Asp Pro Glu Ile Ile Arg Leu Ile Met Ala Lys Asp Phe
                 85                  90                  95

Ser His Phe Arg Asp Arg Phe Pro Ala Arg Val Phe Thr Ser Lys Glu
                100                 105                 110

Asp Lys Leu Gln His His Leu Phe Asn Leu Gly Gly Glu Lys Trp Arg
            115                 120                 125

Ala Leu Arg Ile Lys Leu Thr Pro Thr Phe Thr Ser Gly Lys Leu Lys
    130                 135                 140

Gly Met Phe Pro Leu Phe Ile Ala Cys Ala Glu Asp Leu Ser Lys Met
145                 150                 155                 160

Leu Ile Ser Gln Ile Asp Lys Pro Val Asn Val Lys Asp Ile Thr Ala
                165                 170                 175

Cys Tyr Thr Thr Asp Thr Val Cys Asn Cys Val Phe Gly Trp Glu Asn
                180                 185                 190

Asn Ser Ile Asn Glu Lys Glu Asn Lys Met Arg Lys Leu Gly Gln Thr
            195                 200                 205

Val Leu Glu Ile Ser Lys Thr Val Leu Leu Lys Arg Met Leu Arg Asn
    210                 215                 220

Ile Phe Pro Gly Ile Ala Lys Leu Leu Lys Leu Arg Ile Val Ser Asn
225                 230                 235                 240

Glu Ile Glu Asp Ser Leu Ile Lys Met Val Gly Asp Thr Ile Ala Tyr
                245                 250                 255

Arg Glu Ala Asn Gly Ile Lys Arg Asn Asp Phe Leu Asp Leu Leu Ile
            260                 265                 270

Gln Leu Lys Asn Lys Gly Ser Val Glu Asp Val Lys Lys Asn Gly
    275                 280                 285

Asn Asp Thr Thr Ala Glu Pro Val Glu Met Asp Leu Gly Met Leu Thr
    290                 295                 300

Ala Gln Cys Phe Val Phe Phe Val Ala Gly Phe Glu Thr Ser Ser Ser
305                 310                 315                 320

Val Gln Ser Tyr Cys Leu Tyr Glu Leu Ala Leu Asn Pro Glu Ile Gln
                325                 330                 335

Lys Lys Leu Arg Glu Glu Ile Asn Ala Thr Ile Asn Lys His Gly Gly
            340                 345                 350

Ile Thr Tyr Gln Ala Ile Gln Glu Met Glu Tyr Leu Asp Met Val Val
    355                 360                 365

Ser Glu Thr Met Arg Met Tyr Pro Thr Leu Pro Ala Leu Asn Arg His
370                 375                 380

Cys Thr Lys Asp Tyr Thr Thr Pro Ser Gly Gln Lys Ile Lys Lys Gly
385                 390                 395                 400

Asp Asp Ile Ile Ile Pro Leu Tyr Ser Leu Gln Arg Asp Glu Lys Tyr
                405                 410                 415

Phe Pro Glu Pro Lys Lys Phe Asp Pro Glu Arg Phe Ser Lys Thr Asn
                420                 425                 430

Lys Tyr Lys Ile Asn Pro Phe Thr Tyr Met Pro Phe Gly Glu Gly Pro
            435                 440                 445

Arg Asn Cys Ile Gly Ser Arg Phe Gly Leu Ile Gln Thr Lys Val Gly
    450                 455                 460

Leu Ile Thr Ile Leu Lys Asn Tyr Glu Val Cys Lys Thr Glu Glu Thr
```

```
                465                 470                 475                 480
Gln Val Pro Leu Glu Phe Arg Gly Ser Gly Val Ile Ala Met Thr Lys
                    485                 490                 495

Gly Pro Ile Thr Leu Lys Leu Ser Pro Lys Pro Ser Asp Tyr
                    500                 505                 510

<210> SEQ ID NO 31
<211> LENGTH: 500
<212> TYPE: PRT
<213> ORGANISM: Nezara viridula

<400> SEQUENCE: 31

Met Leu Val Gly Val Val Ile Ile Val Gly Leu Leu Trp Leu Phe Tyr
1               5                   10                  15

Lys His Trp Ile Ser Asn Tyr Ser Tyr Trp Lys Lys Arg Gly Ile Pro
                20                  25                  30

Phe Tyr Pro Ala Glu Phe Pro Tyr Gly Ser Asp Pro Asn Phe Val Lys
            35                  40                  45

Leu Lys Lys Phe Lys Gly Tyr Thr Met Asp Lys Met Tyr His Glu Phe
        50                  55                  60

Ala Pro His Pro Met Phe Gly Ile Val Val Leu Arg Lys Pro Met Leu
65                  70                  75                  80

Ile Val Lys Asp Pro Glu Leu Ile Gln Met Val Leu Thr Lys Glu Phe
                85                  90                  95

Ser His Phe Arg Asp Arg Gly Ile Phe Lys Leu Pro Lys Arg Asp Thr
            100                 105                 110

Ile Asn His His Leu Phe Asn Leu Glu Gly Glu Lys Trp Lys Ala Ile
        115                 120                 125

Arg Met Lys Leu Thr Pro Thr Phe Thr Ser Gly Lys Leu Lys Thr Met
130                 135                 140

Phe Pro Leu Ile Ile Ser Cys Ala Glu Asn Phe Ser Ser Leu Leu Leu
145                 150                 155                 160

Ser Met Ala Asp Ser Lys Val Asp Ile Lys Glu Leu Ala Gly Arg Phe
                165                 170                 175

Thr Ala Asp Val Ile Ser Ser Cys Ala Phe Gly Leu Glu Ile Asp Ile
            180                 185                 190

Met Asn Asn Pro Asp Asn Lys Leu Arg Arg Ile Gly Ile Glu Arg Val
        195                 200                 205

Lys Val Lys Thr Leu Lys Lys Leu Asn Thr Leu Thr Gln Ile Phe
210                 215                 220

Pro Ala Leu Ser Thr Ile Leu Pro Ala Arg Ser Asn Glu Ser Glu Glu
225                 230                 235                 240

Gln Asn Tyr Val Ile Asn Leu Val Lys Ser Ile Ile Glu Gln Arg Glu
                245                 250                 255

Asn Asn Gly Ile Val Arg Asn Asp Phe Ile Asp Val Leu Ile Lys Leu
            260                 265                 270

Lys Asn Lys Gly Asn Leu Gly Asp Asp Ala Gln Glu Thr Glu Pro
        275                 280                 285

Phe Glu Met Thr Ile Glu Leu Met Ala Ala Gln Cys Phe Val Phe Phe
290                 295                 300

Ile Ala Gly Phe Glu Thr Ser Ser Ser Val Gln Ser Phe Cys Leu Tyr
305                 310                 315                 320

Glu Leu Ala Leu His Gln Asp Ile Gln Ser Arg Leu Ile Lys Glu Ile
                325                 330                 335
```

-continued

```
Asp Glu Thr Ile Glu Lys Asn Gly Ser Leu Thr Tyr Lys Ala Val Gln
                340                 345                 350

Glu Met Glu Tyr Leu Asp Met Val Ile Ser Glu Thr Ser Arg Lys Tyr
            355                 360                 365

Pro Thr Val Pro Thr Leu Val Arg Gln Cys Thr Lys Ser Val Thr Leu
        370                 375                 380

Ser Thr Gly Gln Asn Ile Glu Lys Asp Thr Met Ile Ile Ile Pro Val
385                 390                 395                 400

Trp Ser Leu His His Asp Ser Gln Tyr Phe Met Asp Pro Asp Lys Phe
                405                 410                 415

Asp Pro Glu Arg Phe Ser Lys Glu Asn Arg Asp Ser Ile Val Pro Tyr
            420                 425                 430

Thr Tyr Leu Pro Phe Gly Glu Gly Pro Arg Met Cys Ile Gly Met Arg
        435                 440                 445

Phe Gly Leu Leu Gln Thr Lys Val Gly Val Val Thr Leu Leu Arg Lys
450                 455                 460

Phe Arg Val Glu Pro Cys Glu Thr Asn Ile Pro Leu Val Ile Gly
465                 470                 475                 480

Gly Asn Ser Ala Thr Thr Ala Ser Asp Lys Pro Ile Ile Lys Leu
                485                 490                 495

Ile Ala Arg Tyr
            500

<210> SEQ ID NO 32
<211> LENGTH: 514
<212> TYPE: PRT
<213> ORGANISM: Nezara viridula

<400> SEQUENCE: 32

Ala Thr Ser Arg Arg Ile Val Leu Leu Gln Leu Pro Tyr Lys Met Leu
1               5                   10                  15

Phe Gly Val Thr Ile Ile Ala Gly Leu Leu Trp Leu Phe Tyr Lys His
            20                  25                  30

Trp Val Ser Val Tyr Thr His Trp Lys Glu Lys Gly Ile Pro Phe His
        35                  40                  45

Pro Ala Lys Phe Pro Phe Gly Ser His Pro Asn Leu Val Lys Leu Lys
    50                  55                  60

Glu Tyr Arg Gly Tyr Thr Ile Asp Lys Met Tyr His Arg Phe Ala Pro
65                  70                  75                  80

His Pro Met Phe Gly Ile Phe Phe Leu Arg Ser Pro Met Leu Ile Val
                85                  90                  95

Arg Asp Pro Glu Thr Ile Gln Leu Ile Leu Thr Lys Glu Phe Ser His
            100                 105                 110

Phe Arg Asp Arg Arg Ile Leu Lys Ile Ser Glu Lys Asp Val Leu Asn
        115                 120                 125

His His Leu Phe Tyr Leu Gln Gly Glu Lys Trp Arg Asp Leu Arg Met
    130                 135                 140

Lys Leu Thr Pro Thr Phe Thr Ser Gly Lys Leu Lys Ala Met Phe Pro
145                 150                 155                 160

Leu Phe Ile Ser Cys Ala Glu Ser Phe Ser Ser Leu Leu Leu Ser Lys
                165                 170                 175

Ser Asp Ser Lys Ile Asp Ile Lys Glu Leu Met Ser Arg Phe Thr Ala
            180                 185                 190

Asp Val Ile Cys Ser Cys Ala Phe Gly Leu Glu Leu Asp Val Ile Asn
        195                 200                 205
```

His Pro Asp Ser Lys Leu Arg Met Ile Gly Ile Glu Lys Ile Lys Leu
    210                 215                 220

Gln Phe Leu Gln Lys Leu Lys Met Ala Ala Thr Ile Leu Phe Pro Ala
225                 230                 235                 240

Leu Ser Thr Leu Leu Asn Met Arg Phe Thr Ser Leu Glu Asp Glu Lys
                245                 250                 255

Tyr Ile Leu Asn Leu Val Lys Lys Ile Val Glu Gln Arg Glu Lys Asn
            260                 265                 270

Gly Ile Val Arg Asn Asp Phe Ile Asp Leu Leu Met Gln Ser Lys Asn
        275                 280                 285

Lys Gly Asn Gln Gly Asp Asn Glu Gln Glu Phe Glu Lys Thr Phe Glu
    290                 295                 300

Ile Thr Leu Glu Leu Met Ala Ala Gln Cys Tyr Val Phe Phe Leu Ala
305                 310                 315                 320

Gly Phe Glu Thr Ser Ser Ser Leu Gln Ser Phe Cys Leu Tyr Glu Leu
                325                 330                 335

Ala Leu His Gln Asp Ile Gln Ser Arg Leu Ile Lys Glu Ile Asn Glu
            340                 345                 350

Lys Ile Glu Asn Asn Asn Gly Leu Thr Tyr Lys Ala Leu His Glu Met
        355                 360                 365

Glu Tyr Leu Asp Met Ile Ile Ser Glu Thr Ser Arg Lys Tyr Pro Thr
    370                 375                 380

Leu Pro Met Leu Tyr Arg Ser Cys Thr Lys Pro Ile Ile Leu Pro Ser
385                 390                 395                 400

Gly His Lys Ile Glu Gln Asp Thr Ile Ile Ser Ile Pro Thr Trp Ser
                405                 410                 415

Leu His Asp Pro Gln Tyr Phe Pro Asp Pro Glu Lys Phe Asp Pro
            420                 425                 430

Gln Arg Phe Ser Gln Glu Asn Arg Gly Ser Ile Val Pro Tyr Thr Tyr
        435                 440                 445

Leu Pro Phe Gly Glu Gly Pro Arg Met Cys Ile Gly Met Arg Phe Gly
    450                 455                 460

Leu Leu Gln Thr Lys Val Gly Ile Val Thr Leu Leu Gln Lys Cys Lys
465                 470                 475                 480

Val Glu Thr Cys Glu Asp Thr Lys Ile Pro Leu Val Met Gly Gly Ile
                485                 490                 495

Ser Ala Thr Thr Ala Pro Asp Glu Pro Ile Ile Ile Lys Leu Ile Ala
                500                 505                 510

Arg Ser

<210> SEQ ID NO 33
<211> LENGTH: 507
<212> TYPE: PRT
<213> ORGANISM: Nezara viridula

<400> SEQUENCE: 33

Met Phe Met Thr Ile Tyr Leu Val Ala Leu Ala Phe Phe Leu Leu Tyr
1               5                   10                  15

Lys Phe Trp Thr Ser Asn Tyr Ser Tyr Trp Lys Asp Arg Asp Ile Pro
            20                  25                  30

His Ile Pro Pro Val Phe Pro Phe Gly Ser Ser Arg Asp Leu Ala Leu
        35                  40                  45

Gln Arg Gly Phe Gln Gly Asp Ile Trp Ser Glu Leu Tyr Arg Lys Cys
    50                  55                  60

```
Ser Ser Gln Pro Phe Phe Gly Val His Ile Met Arg Thr Pro Phe Leu
 65              70                  75                  80

Val Met Arg Asp Pro Glu Met Ile Arg Phe Val Leu Ala Ser Ser Phe
                 85                  90                  95

Phe Asn Phe Arg Asp Arg Gln Pro Phe Lys Arg Ser Arg Glu Pro Leu
            100                 105                 110

Thr His His Leu Phe Asn Leu Glu Gly Glu Gln Trp Arg Ala Leu Arg
        115                 120                 125

Thr Lys Leu Thr Ala Thr Phe Thr Ser Gly Lys Leu Arg Gly Met Phe
    130                 135                 140

Pro Leu Phe Leu Ser Cys Ser Glu Ser Leu Asp Ser Ile Leu Gln Thr
145                 150                 155                 160

Asn Val Asn Lys Val Ile Asp Val Lys Asp Ile Thr Ala Arg Phe Ser
                165                 170                 175

Thr Asp Ile Ile Gly Ser Cys Ala Phe Gly Met Asp Met Asp Ser Ile
            180                 185                 190

Ser Asn Pro Asn Ser Glu Phe Arg Lys Ile Gly Ile Glu Ile Phe Lys
        195                 200                 205

Leu Lys Asn Ser Thr Arg Ile Lys Leu Ala Leu Val Asn Thr Phe Pro
    210                 215                 220

Asp Ile Met Lys Leu Phe Ser Pro Arg Phe Thr Pro Lys Ser Val Glu
225                 230                 235                 240

Lys Phe Ile Leu Arg Ala Val Ser Gly Thr Ile Glu His Arg Leu Arg
                245                 250                 255

Tyr Gly Ile Lys Arg Lys Asp Phe Ile Asp Leu Leu Met Ile Leu Lys
            260                 265                 270

Tyr Met Asn Gly Asp Lys Lys Ser Asp Asp Ile Pro Lys Leu Asn
        275                 280                 285

Leu Asn Asp Met Thr Met Glu Met Met Ala Ala Gln Cys Phe Val Phe
    290                 295                 300

Phe Thr Ala Gly Phe Glu Thr Ser Gly Ser Val Gln Ser Cys Cys Leu
305                 310                 315                 320

Tyr Glu Leu Ala Leu Asn Gln Asn Ile Gln Asn Arg Val Gln Lys Glu
                325                 330                 335

Ile Asp His Met Thr Glu His Tyr Gly Gly Leu Thr Tyr Glu Ala Val
            340                 345                 350

His Lys Met Val Phe Leu Asp Met Val Ile Ala Glu Thr Met Arg Lys
        355                 360                 365

Tyr Pro Thr Leu Pro Ser Leu Thr Arg Phe Ser Thr Glu Arg Thr Val
    370                 375                 380

Leu Pro Ser Gly His Val Ile Asp Lys Gly Val Arg Val Leu Ile Pro
385                 390                 395                 400

Val Trp Ala Leu His Arg Asp Pro Leu Leu Phe Pro Glu Pro Glu Lys
                405                 410                 415

Phe Asp Pro Glu Arg Phe Ser Asp Asn Met Ala Leu Ile Lys Pro
            420                 425                 430

Phe Ser Tyr Leu Pro Phe Gly Glu Gly Pro Arg Met Cys Ile Gly Lys
        435                 440                 445

Arg Phe Gly Leu Leu Gln Thr Lys Met Gly Leu Ile Thr Val Leu Lys
    450                 455                 460

Lys Tyr Arg Val Glu Pro Thr Ser Lys Thr Glu Ile Pro Leu Asp Phe
465                 470                 475                 480
```

Ser Pro Lys Cys Ile Leu Ile Thr Ala Thr Glu Gly Pro Ile His Leu
                485                 490                 495

Arg Leu Val Glu Arg Thr Asp His Cys Pro Ser
            500                 505

<210> SEQ ID NO 34
<211> LENGTH: 533
<212> TYPE: PRT
<213> ORGANISM: Nezara viridula

<400> SEQUENCE: 34

Phe Asp Asn Trp Leu Tyr Leu Asn Thr Leu Phe Phe Ile Gln Leu Phe
1               5                   10                  15

Ser Leu Lys Gln Val His Thr Phe Asn Glu Met Phe Ala Ile Ile Ile
            20                  25                  30

Ser Leu Val Val Ile Ala Ala Val Val Tyr Tyr Arg Arg Tyr Arg Ser
        35                  40                  45

Phe Tyr Ser His Trp Asp Lys Arg Gly Ile Pro Ala Ile Pro Gly Ser
    50                  55                  60

Val Pro Trp Gly Ser Tyr Ser Ser Arg Ser His Met Arg Gln Tyr Gln
65                  70                  75                  80

Gly Phe Ser Leu Asp Lys Phe Tyr Lys Met Thr Asn His Pro Tyr
                85                  90                  95

Phe Gly Phe Tyr Asp Met Arg Ser Pro Ile Leu Ile Ala Lys Asp Pro
            100                 105                 110

Glu Val Ile Arg Leu Ile Leu Thr Lys Glu Phe Ser His Phe Ile Asp
        115                 120                 125

Arg Thr Tyr Thr Gly Leu Pro Lys Thr Asp Pro Leu Leu His Tyr Gln
    130                 135                 140

Leu Phe Ser Leu Ser Gly Asn Lys Trp Arg Ala Leu Arg Thr Lys Leu
145                 150                 155                 160

Thr Pro Thr Phe Thr Ser Gly Arg Met Lys Ala Met Phe Pro Leu Phe
                165                 170                 175

Leu Asp Cys Ala Gln Gly Leu Asn Ser Leu Leu Trp Ser Arg Val Gly
            180                 185                 190

Ser Ile Val Asp Val Lys Asp Ala Val Ala Arg Phe Thr Thr Asp Val
        195                 200                 205

Ile Cys Ser Cys Ala Phe Gly Leu Gln Thr Asn Thr Val Val Glu Pro
    210                 215                 220

Asn His Pro Leu Arg Lys Ala Ala Ala Asp Phe Leu Ala Phe Gly Asp
225                 230                 235                 240

Ser Leu Tyr Leu Lys Phe Arg Leu Leu Leu Thr Leu Leu Ser Pro Phe
                245                 250                 255

Arg Ile Pro Phe Asn Arg Phe Thr Pro Lys Ser Val Glu Asp Tyr Ile
            260                 265                 270

Met Lys Leu Ile Ser Asp Thr Val Glu Tyr Arg Glu Lys Asn Lys Ile
        275                 280                 285

Thr Arg Asn Asp Phe Leu Glu Leu Leu Ile Gln Leu Lys Asn Lys Gly
    290                 295                 300

Ser Leu Lys Asp Glu Arg Lys Glu Glu Val Glu Glu Asn Phe Glu Ile
305                 310                 315                 320

Asn Leu Asp Val Met Ala Ala Gln Ser Phe Leu Phe Phe Ala Gly
                325                 330                 335

Tyr Glu Thr Ser Ser Ser Val Gln Thr Phe Cys Leu Tyr Glu Leu Ala
            340                 345                 350

```
Leu Asn Gln Asp Ile Gln Gln Lys Leu Arg Asn Glu Ile Gln Glu Val
        355                 360                 365

Ile Lys Ile His Gly Glu Val Thr Tyr Gln Ala Val Asn Asp Met Lys
    370                 375                 380

Tyr Leu His Met Val Val Ser Glu Thr Met Arg Lys Tyr Pro Thr Leu
385                 390                 395                 400

Pro Ala Leu Met Arg Arg Cys Val Ile Pro Phe Thr Met Pro Asp Gly
                405                 410                 415

Gly Lys Ile Gln Lys Gly Asp Gln Ile Phe Ile Pro Ile Trp Ser Leu
            420                 425                 430

Gln His Asp Pro Gln Tyr Phe Pro Asp Pro Glu Lys Phe Asp Pro Glu
        435                 440                 445

Arg Phe Ser Gln Glu Asn Glu Arg Asn Ile Ile Pro Tyr Thr Tyr Leu
    450                 455                 460

Pro Phe Gly Gly Gly Pro Arg Met Cys Ile Gly Asn Arg Phe Gly Leu
465                 470                 475                 480

Leu Gln Thr Lys Val Gly Leu Ile Thr Val Ile Arg Asn Phe Gln Val
                485                 490                 495

Leu Pro Cys Asp Lys Thr Ser Ile Pro Leu Lys Leu Val Lys Asn Ser
            500                 505                 510

Asn Asn Ile Thr Ala Cys Glu Gly Pro Ile Ile Leu Lys Leu Ile Pro
        515                 520                 525

Thr Ala Pro Glu Asn
    530
```

<210> SEQ ID NO 35
<211> LENGTH: 451
<212> TYPE: PRT
<213> ORGANISM: Nezara viridula

<400> SEQUENCE: 35

```
Met Leu Phe Val Val Phe Leu Leu Ala Val Val Leu Phe Leu Val Tyr
1               5                   10                  15

Lys Trp Trp Thr Ser Val Tyr Ser Val Trp Asp Arg Arg Gly Val Gln
            20                  25                  30

Asn Val Pro Ala Arg Thr Pro Leu Gly Ser Asp Gly Arg Phe Thr Leu
        35                  40                  45

Leu Thr Lys Tyr Gln Gly Tyr Thr Leu Asn Glu Met Tyr Gln Lys Phe
    50                  55                  60

Ser Ser Pro Tyr Phe Gly Ile Tyr Leu Ile Arg Ser Pro Phe Leu Val
65                  70                  75                  80

Ile Lys Asn Pro Glu Ile Ile Ser Ile Ile Leu Thr Lys Glu Phe Ser
                85                  90                  95

His Phe Arg Asn Arg Gln Phe Leu Lys Ile His Gln Asn Asp Phe Ile
            100                 105                 110

Phe Gln His Leu Phe Asn Leu Gly Asp Asp Lys Trp Lys Thr Thr Arg
        115                 120                 125

Gly Lys Met Gln Ser Thr Phe Ser Ser Ser Lys Leu Arg Thr Met Phe
    130                 135                 140

Pro Leu Phe Val Lys Cys Thr Glu Asn Leu Met Ser Ala Leu Leu Glu
145                 150                 155                 160

Lys Glu Gly Asp Thr Ile Asn Met Lys Gln Ala Leu Ala Ser Phe Thr
                165                 170                 175

Thr Asp Leu Thr Cys Lys Thr Leu Phe Gly Leu Glu Ala Asp Thr Asn
```

```
            180                 185                 190
Cys Asp Ser Glu Val Thr Arg Ile Gly Lys Ile Ala Thr Asp Phe Asn
        195                 200                 205

Leu Met Ile Leu Leu Lys Ile Ala Val Lys Leu Ala Phe Pro Glu Ile
    210                 215                 220

Ala Gln Asn Ile Pro Ile Lys Val Phe Ser Thr Asp Ile Asp Lys Phe
225                 230                 235                 240
Phe Leu Lys Leu Val Thr Glu Ile Val Asp Tyr Arg Glu Lys Asn Asn
                245                 250                 255

Val Lys Val His Asp Phe Met Asp Leu Leu Ile Gln Leu Lys Asn Arg
            260                 265                 270
Ser Lys Asn Gly Glu Glu Lys Lys Phe Glu Asn Gly Asn Ile Asn Ile
        275                 280                 285

Gln Ser Gln Asp Ile Thr Leu Glu Val Met Ala Ala Gln Cys Phe Phe
    290                 295                 300

Leu Phe Asn Ala Gly Phe Glu Asn Ser Ser Ser Ile Gln Thr Tyr Cys
305                 310                 315                 320
Leu Tyr Glu Leu Ala Leu Lys Pro Glu Ile Gln Lys Thr Leu Gln Asp
                325                 330                 335

Glu Ile Asp Lys Cys Leu Lys Lys His Gly Glu Met Thr Tyr Glu Ala
            340                 345                 350

Leu Lys Glu Met Asn Tyr Leu Asn Met Val Ile Ser Glu Thr Met Arg
        355                 360                 365

Lys Tyr Pro Ile Leu Pro Phe Val Thr Arg Val Cys Thr Ser Pro Leu
    370                 375                 380

Thr Phe Pro Asp Gly Phe Gln Val Glu Lys Gly Asp Gln Met Ile Leu
385                 390                 395                 400
Pro Thr Trp Ser Leu Gln His Asp Pro Gln Tyr Phe Pro Asp Pro Glu
                405                 410                 415

Lys Phe Asp Pro Glu Arg Phe Ser Glu Gln Asn Lys Asp Ser Ile Val
            420                 425                 430
Pro Tyr Thr Tyr Leu Pro Phe Gly Glu Gly Pro Arg Met Cys Leu Gly
        435                 440                 445

Met Arg Phe
    450

<210> SEQ ID NO 36
<211> LENGTH: 441
<212> TYPE: PRT
<213> ORGANISM: Nezara viridula

<400> SEQUENCE: 36

Lys His Lys Tyr Phe Gly Tyr Tyr Glu Met Arg Arg Pro Leu Leu Val
1               5                   10                  15

Val Lys Asp Pro Glu Val Leu Lys Leu Val Leu Thr Lys Glu Phe Ser
            20                  25                  30

His Phe Arg Asp Arg Phe Thr Arg Pro Met Pro Lys Thr Asp Pro Leu
        35                  40                  45

Leu His Tyr Gln Leu Phe Ile Leu Gly Gly Asp Lys Trp Arg Ala Leu
    50                  55                  60

Arg Thr Lys Leu Thr Pro Thr Phe Thr Ser Gly Arg Met Lys Ala Met
65                  70                  75                  80

Phe Pro Leu Phe Val Asp Cys Ala Gln Ala Leu Asn Thr Leu Leu Trp
                85                  90                  95
```

```
Ser Gln Val Gly Ser Ala Val Asp Val Lys Asp Val Ile Ser Arg Phe
                100                 105                 110

Thr Thr Asp Ile Ile Cys Ser Cys Ala Phe Gly Leu Gln Thr Asn Thr
            115                 120                 125

Ile Ala Glu Pro Asp His Pro Leu Arg Lys Ala Thr Ala Asp Phe Leu
        130                 135                 140

Ser Asn Gly Asp Ser Leu Phe Phe Lys Ile Lys Phe Ile Val Ser Met
145                 150                 155                 160

Leu Val Pro Phe Ile Leu Pro Leu Ser Arg Phe Thr Pro Gln Glu Val
                165                 170                 175

Glu Asp Tyr Ile Met Lys Leu Ile Ser Asp Thr Val Glu Tyr Arg Glu
            180                 185                 190

Lys Asn Gln Val Thr Arg Asn Asp Phe Leu Asp Leu Ile Gln Leu
        195                 200                 205

Lys Asn Lys Gly Ser Leu Arg Glu Glu Gly Ile Ala Glu Thr Glu Glu
        210                 215                 220

Ser Phe Glu Val Thr Leu Glu Val Met Ala Ala Gln Cys Phe Leu Phe
225                 230                 235                 240

Phe Phe Ala Gly Asn Glu Thr Ser Ser Val Gln Ser Phe Cys Leu
                245                 250                 255

Tyr Glu Leu Ala Leu His Pro Glu Ile Gln Gln Lys Leu Arg Glu Glu
            260                 265                 270

Ile Gln Glu Val Ile Arg Ile His Gly Val Thr Tyr Gln Ser Val
        275                 280                 285

Asn Glu Met Lys Tyr Leu His Met Val Val Ser Glu Thr Met Arg Lys
            290                 295                 300

Tyr Pro Thr Leu Pro Gln Leu Val Arg Ser Cys Val Glu Pro Ile Val
305                 310                 315                 320

Met Pro Asp Gly Gly Arg Val Glu Lys Gly Asp Gln Ile Ala Ile Pro
                325                 330                 335

Val Trp Ser Leu Gln His Asp Pro Gln Tyr Phe Pro Asp Pro Asp Lys
            340                 345                 350

Phe Asn Pro Asp Arg Phe Ala Pro Glu Asn Glu Gly Asn Ile Lys Pro
        355                 360                 365

Tyr Thr Tyr Leu Pro Phe Gly Glu Gly Pro Arg Met Cys Ile Gly Asn
        370                 375                 380

Arg Phe Gly Leu Leu Gln Thr Lys Val Gly Leu Ile Thr Ile Ile Arg
385                 390                 395                 400

Asn Phe Gln Val Leu Pro Cys Gly Lys Thr Ser Ile Pro Leu Lys Leu
                405                 410                 415

Val Arg Thr Asn Asn Ser Leu Thr Thr Cys Glu Gly Pro Ile Leu Leu
            420                 425                 430

Lys Leu Thr Ser Ile Glu Glu Arg Ser
        435                 440

<210> SEQ ID NO 37
<211> LENGTH: 392
<212> TYPE: PRT
<213> ORGANISM: Nezara viridula

<400> SEQUENCE: 37

Ser Lys Met Arg Gly Met Phe Thr Phe Met Ser Glu Cys Ala Lys Asp
1               5                   10                  15

Phe Ala Ser Tyr Phe Leu Glu Glu Ala Asn Gly Lys Pro Ile Glu Val
            20                  25                  30
```

```
Asp Met Lys Asp Leu Phe Thr Arg Tyr Thr Asn Asp Val Ile Ala Thr
         35                  40                  45

Ser Ser Leu Gly Ile Arg Cys Asp Ser Leu Arg Glu Arg Glu Asn Ser
 50                  55                  60

Phe Tyr Thr Met Gly Lys Lys Met Thr Thr Phe Ser Ser Leu Thr Ala
 65                  70                  75                  80

Gly Ile Lys Met Met Val Ala Thr Val Leu Pro Lys Leu Leu Glu Ile
                 85                  90                  95

Thr Lys Ile Gly Phe Leu Pro Lys Asp Cys Ala Asn Tyr Phe Thr Gln
                100                 105                 110

Ile Ile Phe Glu Thr Ile Gln Arg Arg Thr Lys Glu Asn Ile Ile Arg
             115                 120                 125

Pro Asp Met Ile His Leu Leu Leu Glu Ala Arg Lys Gly Asn Leu Lys
         130                 135                 140

His Glu Ser Lys Ala Asp Glu Ser Ser Gly Phe Ala Thr Val Glu Glu
145                 150                 155                 160

Ser Asp Ile Gly Lys Ser Gln Lys Ser Arg Ser Val Glu Leu Thr Asp
                165                 170                 175

Glu Val Ile Ala Ala Gln Ala Met Ile Phe Phe Phe Ala Gly Phe Glu
            180                 185                 190

Thr Ser Ser Thr Val Met Ser Phe Met Ser Leu Glu Leu Ala Ile Asn
            195                 200                 205

Thr Asp Val Gln Gln Arg Leu Leu Glu Glu Ile Asp Glu Val Tyr Lys
        210                 215                 220

Gln Tyr Gly Asp Asn Val Ser Tyr Asp Ala Ile Met Lys Met Gln Tyr
225                 230                 235                 240

Leu Asp Gln Val Ile Ser Glu Thr Leu Arg Lys Trp Thr Pro Gly Phe
                245                 250                 255

Gln Thr Asp Arg Val Cys Val Lys Asp Tyr Val Ile Glu Pro Thr Lys
            260                 265                 270

Glu Gly Glu His Pro Leu His Ile Glu Lys Gly Leu Leu Leu Leu Val
        275                 280                 285

Pro Thr Ala Gly Phe His Tyr Asp Pro Lys Tyr Phe Pro Asn Pro Glu
    290                 295                 300

Lys Phe Asp Pro Asp Arg Phe Ser Glu Glu Asn Arg Ser Ser Ile Val
305                 310                 315                 320

Pro Gly Ser Tyr Met Pro Phe Gly Leu Gly Pro Arg Asn Cys Ile Gly
                325                 330                 335

Ser Arg Phe Ala Leu Leu Glu Ile Lys Val Leu Phe Tyr His Ile Leu
            340                 345                 350

Ser Lys Phe Glu Leu Thr Val Val Lys Arg Ser Cys Val Pro Ile Lys
        355                 360                 365

Leu Ser Thr Glu Phe Asn Leu Thr Val Glu Gly Gly Phe Trp Leu Gly
    370                 375                 380

Leu Lys Pro Arg Asn Ile Ser Val
385                 390

<210> SEQ ID NO 38
<211> LENGTH: 490
<212> TYPE: PRT
<213> ORGANISM: Nezara viridula

<400> SEQUENCE: 38

Arg Met Trp Phe Leu Ile Leu Leu Ala Val Leu Leu Ala Leu Leu Ile
```

```
  1               5                  10                  15
Leu Glu Ser Thr Pro Pro Ser Arg Phe Pro Gly Pro Arg Trp Ile
             20                  25                  30
Pro Phe Leu Gly Asn Tyr Leu Leu Phe Tyr Lys Leu Arg Gln Lys Leu
             35                  40                  45
Gly Phe Thr His Leu Val Trp Glu Trp Leu Ser Lys Arg Tyr Gly Pro
             50                  55                  60
Leu Val Gly Val Arg Leu Gly Asn Asp Lys Leu Val Ile Gly Thr Asn
65                  70                  75                  80
Leu Ala Val Val Lys Glu Leu Leu Thr Lys Glu Gln Phe Glu Ala Arg
             85                  90                  95
Pro Asp Gly Phe Phe Gln Phe Arg Ala Phe Gly Glu Arg Tyr Gly
             100                 105                 110
Leu Val Phe Val Asp Gly Glu Phe Asn Glu Gln Lys Arg Phe Val
             115                 120                 125
Met Lys His Leu Lys Ser Phe Gly Leu Asn Arg Ser Ile Met Glu Gly
             130                 135                 140
Arg Ile Ser Gly Glu Ala Glu Asp Leu Val Gln His Ile Leu Lys Asn
145                 150                 155                 160
Gln Lys Asp Gly Val Val Phe Ser Glu Ile Val Glu Ile Ser Val Met
             165                 170                 175
Asn Ile Leu Trp Ser Ile Val Ala Gly Gly Arg Phe Gln Leu Asp Asp
             180                 185                 190
Lys Lys Ala Arg Val Leu Ile Asp His Ile His Thr Ser Phe Arg Leu
             195                 200                 205
Gln Asp Met Ser Gly Gly Ile Leu Asn Gln Met Pro Phe Leu Arg Phe
             210                 215                 220
Ile Cys Pro Glu Leu Thr Ser Phe Asn Lys Leu Lys Asp Val Leu Gly
225                 230                 235                 240
Asn Leu Thr Thr Phe Val Lys Gln Ile Ile Asp Glu His Arg Glu Thr
             245                 250                 255
Val Ser Ser Tyr Glu Asn Arg Asp Leu Val Asp Ala Phe Leu Asn Glu
             260                 265                 270
Met Lys Lys His Glu Ala Ser Lys Ser Thr Phe Thr Glu Lys Gln Leu
             275                 280                 285
Ile Ile Leu Leu Leu Asp Leu Phe Leu Ala Gly Pro Glu Thr Thr Ser
             290                 295                 300
Ala Thr Leu Gly Phe Ala Ile Leu His Leu Leu His Tyr Pro His Ile
305                 310                 315                 320
Gln Asn Asn Leu His Asn Glu Leu Asp Thr Val Ile Gly Lys Gly Lys
             325                 330                 335
Arg Pro Cys Met Lys Asp Lys Pro Asn Leu Val Tyr Met Glu Ala Phe
             340                 345                 350
Thr Met Glu Leu Leu Arg Ser Val Asn Val Thr Pro Thr Thr Val Ser
             355                 360                 365
His Arg Ala Lys Glu Asp Ala Glu Val Met Gly Tyr Ile Ile Pro Lys
             370                 375                 380
Asp Thr Ile Val Leu Ala Asn Leu Tyr Ser Leu His Met Asn Lys Asp
385                 390                 395                 400
His Trp Ile Asp Pro Glu Lys Phe Arg Pro Glu Arg Phe Ile Asp Glu
             405                 410                 415
Asn Gly Ala Ile Ile Gln Asn Asp Phe Phe Ile Pro Phe Gly Leu Gly
             420                 425                 430
```

```
Lys Arg Arg Cys Met Gly Glu Ala Leu Ala Lys Thr Ser Ile Phe Leu
            435                 440                 445

Phe Leu Thr Thr Ile Leu Gln Asn Phe Lys Val Arg Pro Val Ser Gln
    450                 455                 460

Glu Leu Pro Pro Met Lys Ser Leu Asp Gly Ala Thr Ile Ser Pro Ala
465                 470                 475                 480

Ser Phe Arg Cys Phe Phe Glu Pro Arg Glu
            485                 490

<210> SEQ ID NO 39
<211> LENGTH: 526
<212> TYPE: PRT
<213> ORGANISM: Nezara viridula

<400> SEQUENCE: 39

Met Tyr His Val Lys Met Leu Leu Glu Leu Arg Ser Leu Ala Val Phe
1               5                   10                  15

Phe Ile Val Phe Phe Gly Arg Arg Leu Trp Ala Leu Leu Ser Arg
            20                  25                  30

Ile Arg Thr Leu Pro Pro Gly Pro Trp Gly Leu Pro Leu Leu Gly Tyr
            35                  40                  45

Leu Pro Phe Leu Lys Pro Glu Ala His Val His Phe Ala Gln Met Ala
    50                  55                  60

Lys Lys Tyr Gly Gly Ile Phe Ser Leu Ser Leu Gly Asn Gln Phe Val
65                  70                  75                  80

Val Ile Leu Ser Asp Tyr Lys Leu Ile Arg Glu Ala Phe Arg Arg Glu
                85                  90                  95

Asp Phe Thr Gly Arg Pro Asp Thr Glu Phe Thr Asn Ile Leu Gly Gly
            100                 105                 110

Tyr Gly Ile Ile Asn Ser Asp Gly Arg Leu Trp Lys Glu Gln Arg Lys
            115                 120                 125

Phe Leu His Asp Lys Leu Arg Arg Leu Gly Met Thr Tyr Ser Gly Gln
    130                 135                 140

Gly Lys His Glu Met Glu Ala Arg Ile Met Lys Glu Val Glu Val Phe
145                 150                 155                 160

Leu His Thr Leu Ser Lys Glu Arg Asn Asn Ser Thr Asp Leu Asn Pro
                165                 170                 175

Ile Leu Cys Thr Ser Ile Ser Asn Val Ile Cys Ser Leu Val Met Ser
            180                 185                 190

Val Arg Phe Lys Gln Lys Asp Ala Lys Phe Thr Arg Phe Met Asn Leu
    195                 200                 205

Ile Ala Glu Gly Phe Arg Leu Phe Gly Ser Leu Asn Tyr Ala Asn Phe
    210                 215                 220

Phe Pro Ile Met Arg Tyr Leu Pro Gly Leu Gln Glu Val Ile Lys Lys
225                 230                 235                 240

Ile Ala Lys Asn Arg Thr Glu Met Ala Ala Phe Phe Gln Glu Thr Val
                245                 250                 255

Asp Asp His Arg Ala Thr Phe Asp Ser His Asn Met Arg Asp Leu Ile
            260                 265                 270

Asp Asn Tyr Leu Met Glu Ile Glu Asp Ala Lys Ala Thr Gly Arg Ser
            275                 280                 285

Glu Glu Leu Phe Gln Gly Lys Glu His Asp Arg Gln Met Gln Gln Ile
    290                 295                 300

Ile Gly Asp Leu Phe Ser Ala Gly Met Glu Thr Ile Lys Thr Thr Leu
```

305                 310                 315                 320
Leu Trp Ala Val Leu Tyr Met Ile His Glu Pro Glu Val Ala Ser Lys
                325                 330                 335

Ile Gln Glu Glu Leu Asp Arg Val Val Gly Arg Asn Arg Leu Pro Lys
                340                 345                 350

Leu Glu Asp Arg Pro Tyr Leu Pro Tyr Thr Glu Ala Val Ile Leu Glu
                355                 360                 365

Val Leu Arg Ile Ser Ser Val Val Pro Leu Gly Thr Thr His Ser Ile
                370                 375                 380

His Gln Glu Thr Lys Leu Gly Gly Tyr Thr Ile Pro Glu Asn Ala His
385                 390                 395                 400

Val Val Pro Leu Leu His Ala Val His Met Asp Pro Asn Leu Trp Asp
                405                 410                 415

Glu Pro Lys Ala Phe Lys Pro Glu Arg Phe Leu Asn Gln Glu Gly Lys
                420                 425                 430

Val Cys Lys Pro Glu Tyr Phe Met Pro Phe Gly Val Gly Arg Arg Met
                435                 440                 445

Cys Leu Gly Asp Val Leu Ala Arg Met Glu Leu Phe Glu Phe Phe Ser
                450                 455                 460

Ser Leu Met His Thr Phe His Leu Arg Lys Ala Gly Glu Asp Ser Gly
465                 470                 475                 480

Leu Pro Thr Leu Glu Ala Thr Thr Gly Ala Thr Leu Thr Pro Leu Pro
                485                 490                 495

Phe Glu Val Ser Leu Val Gln Arg Pro Leu Gln Asp Ser Pro His Glu
                500                 505                 510

Phe Leu Asn Thr Cys Gln Gly Leu Arg Pro Ala Gly Ser Leu
                515                 520                 525

<210> SEQ ID NO 40
<211> LENGTH: 539
<212> TYPE: PRT
<213> ORGANISM: Nezara viridula

<400> SEQUENCE: 40

Cys Val Pro Cys Trp Glu Val Leu Gln Arg Cys Glu Ser Ser Ser Leu
1               5                   10                  15

Ser Ile Gln Val Ile Phe Lys Leu Ile Phe Leu Tyr Pro Gly Tyr Leu
                20                  25                  30

Ser Glu His Thr Met Gln Arg Trp Ser Gly Leu Gly Arg Arg Leu Ser
                35                  40                  45

Gln Leu Ala Ala Cys Pro Ser Glu Val Val Arg Pro Tyr Gln Glu Val
                50                  55                  60

Pro Gly Pro Arg Pro Leu Pro Ile Gly Asn Thr Trp Arg Phe Leu
65                  70                  75                  80

Pro Val Val Gly Asp Ile Glu Val Ser Asp Val Ala Ala Val Ser Gln
                85                  90                  95

Lys Leu Tyr Asp Val Tyr Gly Lys Ile Val Arg Leu Ser Gly Leu Thr
                100                 105                 110

Gly Arg Pro Asp Leu Val Phe Val Phe Asp Pro Asp Glu Ala Glu Lys
                115                 120                 125

Val Tyr Arg Ala Glu Gly Asp Thr Pro Tyr Arg Pro Ser Met Pro Cys
                130                 135                 140

Ile Val Lys Tyr Lys Thr Glu Val Arg Lys Glu Phe Phe Gly Glu Leu
145                 150                 155                 160

```
Pro Gly Val Ile Gly Val His Gly Glu Pro Trp Arg Thr Phe Arg Thr
                165                 170                 175
Arg Val Gln Lys Pro Ile Leu Gln Pro Arg Val Val Lys Gln Tyr Ile
            180                 185                 190
Ala Pro Ile Gln Thr Val Thr Glu Leu Phe Ile Glu Arg Met Leu Glu
        195                 200                 205
Met Lys Asp Glu Asn Asp Glu Met Pro Asp Asp Phe Asp Asn Glu Val
    210                 215                 220
His Lys Trp Ser Leu Glu Cys Ile Gly Arg Ile Ala Leu Asp Val Arg
225                 230                 235                 240
Leu Gly Cys Leu Asp Arg Asn Leu Pro Asn Asn Ser Glu Pro Gln Lys
                245                 250                 255
Ile Ile Asp Ala Ala Lys Phe Ala Leu Arg Lys Ile Ala Ile Leu Glu
            260                 265                 270
Leu Lys Ala Pro Tyr Trp Arg Tyr Phe Pro Thr Thr Thr Trp Arg Lys
        275                 280                 285
Tyr Ile Glu Asn Met Asp Tyr Phe Arg Ser Val Cys Met Lys Tyr Ile
    290                 295                 300
Gln Met Ala Leu Glu Asn Leu Lys Lys Lys Asp Asn Lys Gln Glu Leu
305                 310                 315                 320
Ser Leu Leu Glu Arg Ile Leu Glu Thr Glu Lys Asp Pro Lys Ile Ala
                325                 330                 335
Cys Ile Leu Ala Leu Asp Leu Ile Leu Val Gly Ile Asp Thr Ile Ser
            340                 345                 350
Met Ala Val Cys Ser Val Leu Tyr Gln Leu Ala Thr Arg Pro Glu Glu
        355                 360                 365
Gln Gln Lys Met His Glu Glu Leu Val Arg Ile Met Pro Asp Pro Asn
    370                 375                 380
Cys Gln Leu Thr Ser Glu Met Leu Asp Lys Met Val Tyr Leu Lys Ser
385                 390                 395                 400
Phe Ile Lys Glu Val Leu Arg Met Tyr Ser Thr Val Ile Gly Ile Gly
                405                 410                 415
Arg Val Leu Gln Glu Asp Thr Val Leu Cys Gly Tyr Arg Ile Pro Ser
            420                 425                 430
Gly Thr Gln Leu Val Phe Pro Ser Ile Val Met Gly Ser Ile Glu Gly
        435                 440                 445
Tyr Val Ser Glu Pro His Arg Phe Leu Pro Glu Arg Trp Met Lys Cys
    450                 455                 460
Asp Arg Asp Asn His Tyr Ile His Pro Phe Ala Ser Leu Pro Tyr Gly
465                 470                 475                 480
Phe Gly Ala Arg Met Cys Leu Gly Arg Arg Phe Ala Asp Leu Glu Met
                485                 490                 495
Gln Ile Leu Leu Ala Lys Leu Ile Arg Thr Tyr Arg Ile Glu Tyr Phe
            500                 505                 510
His Glu Pro Leu Glu Tyr Lys Val Thr Phe Met Tyr Ala Pro Asp Gly
        515                 520                 525
Asn Leu Lys Leu Lys Met Ser Lys Arg Lys Glu
    530                 535
```

<210> SEQ ID NO 41
<211> LENGTH: 524
<212> TYPE: PRT
<213> ORGANISM: Nezara viridula

<400> SEQUENCE: 41

-continued

```
Met Glu Pro Ala Ala Gly Gly Glu Glu Leu Gly Gln Ala Ser Gln Ser
1               5                   10                  15

Pro Gln Leu Ser Leu His Leu Asn Met Ile Met Arg Arg Thr Leu Cys
            20                  25                  30

Ser Ala Val Ser Asp Ile Gly Ala Val Leu Pro Lys Ser Tyr Gln Lys
            35                  40                  45

Val Pro Gly Pro Arg Pro Leu Pro Leu Gly Asn Asn Trp Arg Phe
50                  55                  60

Leu Pro Tyr Ile Gly Gln Tyr Lys Leu Glu Glu Ile Asp Lys Leu Ser
65                  70                  75                  80

Leu Met Leu Arg Ser Arg Tyr Gly Arg Ile Val Arg Ile Ser Asn Leu
                85                  90                  95

Leu Gly Arg Pro Asp Met Val Phe Leu Tyr Asp Pro Asn Glu Ile Glu
            100                 105                 110

Lys Val Phe Arg Gly Glu Asp Thr Leu Pro Tyr Arg Pro Ser Met Pro
            115                 120                 125

Ser Leu Asp Tyr Tyr Lys His Gln Leu Arg Lys Asp Phe Phe Ser Asp
            130                 135                 140

Ile Gly Gly Val Ile Ala Thr His Gly Glu Lys Trp His Gln Phe Arg
145                 150                 155                 160

Thr Lys Val Gln His Ala Leu Leu Gln Pro Arg Ile Ala Gln Leu Tyr
                165                 170                 175

Leu Lys Pro Ile Glu Glu Thr Ala Asn Glu Phe Val Asn Arg Ile Arg
            180                 185                 190

Asp Ile Arg Asn Glu Asn Asn Glu Val Pro Asp Asp Phe Leu Asn Glu
            195                 200                 205

Ile His Lys Trp Ser Leu Glu Ser Ile Ala Lys Ile Ala Leu Asp Ala
            210                 215                 220

Arg Leu Gly Cys Leu Thr Pro Asp Gly Ser Gln Glu Thr Gln Glu Leu
225                 230                 235                 240

Ile Asp Ala Val Asn Thr Phe Phe Lys Asn Val Val Ile Leu Glu Leu
            245                 250                 255

Lys Ile Pro Phe Trp Arg Val Ile Ser Thr Arg Thr Trp Lys Glu Tyr
            260                 265                 270

Val Glu Ala Leu Asp Thr Ile Met Arg Ile Val Tyr Lys Phe Val Ser
            275                 280                 285

Lys Thr Leu Asp Glu Leu Lys Asn Lys Asn Asn Glu Cys Lys Glu Asp
            290                 295                 300

Ser Ser Leu Leu Gln Arg Val Leu Tyr Glu Asn Leu Asp Asn Pro Lys
305                 310                 315                 320

Val Ala Val Ile Leu Ala Leu Asp Leu Phe Leu Val Gly Ile Asp Thr
            325                 330                 335

Thr Ser Ala Ala Val Ser Ser Ile Leu Tyr Gln Leu Ser Leu His Gln
            340                 345                 350

Glu Ile Gln Asn Met Leu Tyr Glu Glu Ile Asn Arg Val Leu Gln Asn
            355                 360                 365

Gly Pro Ile Asp Met Lys Lys Leu Asp Gln Met Val Tyr Leu Lys Ala
370                 375                 380

Cys Ile Lys Glu Thr Leu Arg Met Tyr Pro Val Val Ile Gly Asn Gly
385                 390                 395                 400

Arg Cys Leu Lys Lys Asp Thr Val Cys Gly Tyr Thr Ile Pro Lys
                405                 410                 415
```

```
Gly Thr Gln Ile Val Phe Gln His His Ala Ile Ser Asn Ser Glu Glu
                420                 425                 430

Tyr Phe Asp Asp Pro Asn Val Tyr Lys Pro Glu Arg Trp Leu Lys Lys
            435                 440                 445

Gln Lys Lys Lys Gln Tyr His Pro Phe Ala Thr Leu Pro Phe Gly Tyr
    450                 455                 460

Gly Lys Arg Met Cys Leu Gly Lys Arg Phe Ala Asp Leu Glu Leu Gln
465                 470                 475                 480

Cys Leu Ile Ala Lys Ile Glu Thr Tyr Lys Val Glu Phe Lys Arg
                485                 490                 495

Lys Leu Leu Asp Tyr Ser Val His Pro Met Tyr Met Pro His Gly Pro
                500                 505                 510

Leu Asn Phe Lys Tyr Thr Glu Arg Lys Lys Lys Thr
            515                 520

<210> SEQ ID NO 42
<211> LENGTH: 512
<212> TYPE: PRT
<213> ORGANISM: Nezara viridula

<400> SEQUENCE: 42

Met Ala Phe Ile Gln Arg Ile Leu Ser Lys Arg Asn Val Cys Ser Asn
1               5                   10                  15

Ala Leu Arg Lys Lys Asp Val Pro Lys Pro Phe Asn Gln Ile Pro Gly
            20                  25                  30

Pro Arg Ser Leu Pro Ile Ile Gly Ser Trp Lys Tyr Ile Pro Phe
        35                  40                  45

Met Gly Asp Trp Asp Val Ser Lys Leu His Ile Val Gly Thr Lys Arg
50                  55                  60

Phe Glu Gln Tyr Gly Gly Leu Val Arg Glu Val Ser Pro Gly Ile
65                  70                  75                  80

Asn Phe Val His Val Tyr Ser Ala Gln Asp Ile Glu Lys Ile Tyr Lys
                85                  90                  95

Asn Glu Gly Lys Tyr Pro Glu Arg Leu Gly His Leu Ala Leu Met His
            100                 105                 110

Tyr Arg Leu Cys Arg Pro His Leu Tyr Asn Ser Gly Gly Leu Leu Pro
        115                 120                 125

Thr Asn Gly Ser Glu Trp Trp Arg Leu Arg Ser Thr Phe Gln Lys His
    130                 135                 140

Ile Ala Arg Val Gln Asp Ala Arg Ser Phe Leu Ser Lys Gly Glu Asp
145                 150                 155                 160

Ile Ile Asn Asp Phe Val Thr Thr Ile Leu Phe Asn Asn Tyr Thr Cys
                165                 170                 175

Glu Asp Phe Leu Pro Leu Leu Ser Arg Leu Tyr Leu Glu Leu Met Trp
            180                 185                 190

Met Phe Ile Phe Gly Lys Arg Leu Asn Ser Phe Asp Ser Ile Asn Ile
        195                 200                 205

Ser Glu Asn Ser Ile Pro Ser Lys Leu Met Lys Ala Ala Glu Asp Ile
    210                 215                 220

Thr His Thr Thr Met Ile Thr Asp Ser Ser Glu Lys Ile Trp Lys Val
225                 230                 235                 240

Ile Lys Thr Pro Ser Tyr Ile Lys Ile Glu Lys Asn Phe Glu Tyr Ile
                245                 250                 255

Glu Lys Ile Val Leu Ser Ala Leu Lys Glu Ala Glu Thr Glu Asn Ser
            260                 265                 270
```

```
Lys Asn Arg Lys His Ser Asp Glu Asn Ser Lys Ile Cys Leu Ile Asp
            275                 280                 285

Lys Phe Phe Gln Thr Pro Glu Met Ser Ser Lys Asp Ile Asn Ala Met
290                 295                 300

Thr Ala Asp Leu Val Leu Gly Gly Val Asp Thr Thr Ala Tyr Thr Thr
305                 310                 315                 320

Ala Phe Leu Met Tyr Asn Leu Ser Arg Asn Lys Ala Val Gln Glu Lys
            325                 330                 335

Leu Tyr Ser Glu Ala Val Lys Leu Leu Pro Ser Pro Asp Thr Arg Ile
            340                 345                 350

Thr Ser Asp Ile Leu Asn Ser Ala Ile Tyr Ala Arg Ala Val Leu Lys
            355                 360                 365

Glu Ser Leu Arg Leu Asn Pro Val Ser Val Gly Val Ser Arg Ile Leu
            370                 375                 380

Gln Gln Asp Thr Val Phe Ser Gly Tyr Leu Val Pro Lys Gly Thr Leu
385                 390                 395                 400

Met Leu Thr Gln Asn Leu Val Ala Cys Arg Asn Glu Asp Asn Phe Lys
            405                 410                 415

Asn Ala Leu Glu Phe Ile Pro Glu Arg Trp Ile Arg Gly Ser Pro Ala
            420                 425                 430

Tyr Gln Glu Val Ser Pro Tyr Leu Val Leu Pro Phe Ser His Gly Pro
            435                 440                 445

Arg Thr Cys Ile Ala Arg Arg Leu Ala Glu Gln Asn Met Leu Thr Leu
            450                 455                 460

Leu Leu Ser Ile Ile Arg Lys Tyr Ser Ile Ser Trp Met Gly Glu Val
465                 470                 475                 480

Met Asp Ile Glu Thr Pro Leu Thr Cys Lys Pro Asp Lys Ala Val Lys
            485                 490                 495

Leu Ser Phe His Asn Trp Val Val Lys Asn Lys Val Leu Asn Ile Ser
            500                 505                 510

<210> SEQ ID NO 43
<211> LENGTH: 502
<212> TYPE: PRT
<213> ORGANISM: Nezara viridula

<400> SEQUENCE: 43

Leu Lys Leu Gly Ile His Arg Glu Leu Thr Lys Met Ser Leu Leu Val
1               5                   10                  15

Phe Ile Ser Val Ile Val Leu Ile Val Leu Phe Tyr Tyr Asn Leu Lys
            20                  25                  30

Ser Val Lys Tyr Pro Pro Gly Pro Ile Ala Leu Pro Tyr Phe Gly Asn
            35                  40                  45

Ile Ile Thr Ile Lys Lys Leu Ser Lys Phe Asn Gly Leu Gln Gly
    50                  55                  60

Ala Phe Ile Glu Leu Ser Lys Gln Tyr Arg Thr Asp Val Leu Ser Val
65                  70                  75                  80

Ser Met Ser Gly Glu Tyr Ser Val Val Gln Gly Lys Glu Leu Ile
            85                  90                  95

Asp Glu Val Leu Arg Gly Asp Glu Phe Gln Gly Arg Pro Asn Asn Phe
            100                 105                 110

Phe Ile Lys Leu Arg Ser Met Gly Ala Arg Arg Gly Ile Thr Met Thr
            115                 120                 125

Asp Gly Pro Leu Trp Lys Glu Gln Arg Ala Phe Ala Phe Lys His Leu
```

```
            130                 135                 140
His Glu His Gly Leu Gly Thr Gln Lys Met Asp Asp Met Leu Gln Arg
145                 150                 155                 160

Gln Leu Gln Glu Met Leu Ser Lys Leu Asn Glu Gly Val Leu Ser Asn
                165                 170                 175

Leu Val Leu Lys Gln Tyr Val Ser Lys Cys Val Leu Asn Val Leu Trp
            180                 185                 190

Glu Met Val Thr Gly Ser Ser Phe Gln Asp Glu Glu Thr Met Thr Ser
                195                 200                 205

Leu Ile Ser Leu Met Glu Ala Arg Ser Lys Ala Phe Asp Ile Ser Gly
            210                 215                 220

Gly Leu Leu Ser Gln Phe Pro Trp Ile Arg Tyr Ile Phe Pro Lys Tyr
225                 230                 235                 240

Ser Gly Tyr Asn Leu Ile Gln Thr Leu Asn Arg Lys Phe Lys Glu Met
                245                 250                 255

Ile Met Gly Ile Ile Glu His His Lys Lys Thr Ile Val Lys Gly His
            260                 265                 270

Ser Arg Asp Phe Ile Asp Ala Phe Leu His Glu Met Asn Glu Asn Pro
                275                 280                 285

Thr Ser Ser Ser Phe Thr Asp Glu Gln Leu Val Met Val Cys Leu Asp
290                 295                 300

Phe Phe Ile Gly Gly Ser Gln Thr Ile Ser Gly Thr Leu Asp Tyr Cys
305                 310                 315                 320

Phe Leu Tyr Met Thr Met Tyr Lys Asp Val Gln Glu Lys Val Gln Lys
                325                 330                 335

Glu Leu Asp Asp Ile Leu Leu Pro Gly Gln Ser Pro Ser Arg Asn Asn
            340                 345                 350

Lys Asn Lys Cys Pro Phe Val Glu Ala Val Ile Ser Glu Val Leu Arg
                355                 360                 365

Ile Ser Pro Ile Ile Ser Leu Leu Gly Pro Arg Arg Thr Thr Cys Asp
            370                 375                 380

Thr Phe Leu Ser Gly Tyr Phe Ile Pro Lys Asp Thr Thr Val Tyr Leu
385                 390                 395                 400

Asn Phe Lys Thr Val His Asp Ser Ser Lys His Trp Glu Asp Pro Gly
                405                 410                 415

Lys Phe Lys Pro Glu Arg Phe Leu Asn Glu Glu Gly Thr Val Lys Gln
            420                 425                 430

Glu Gln Thr Leu Tyr Asn Phe Gly Arg Gly Lys Arg Arg Cys Pro Ala
                435                 440                 445

Glu Val Leu Ala Arg Thr Ala Leu Phe Ile Leu Phe Ser Gly Val Leu
            450                 455                 460

His Asn Leu Lys Leu Glu Pro Ala Asp Glu Lys Asp Pro Leu Ser Leu
465                 470                 475                 480

Arg Gln Val Pro Gly Ile Thr Thr Ser Ala Ala Glu Tyr Tyr Ile Lys
                485                 490                 495

Leu Thr Arg Arg His Lys
            500
```

<210> SEQ ID NO 44
<211> LENGTH: 558
<212> TYPE: PRT
<213> ORGANISM: Nezara viridula

<400> SEQUENCE: 44

-continued

```
Ala Val Ser Gln Leu Ile Thr Val Gln Tyr Leu Val Lys Cys Phe Thr
 1               5                  10                  15

Ile Leu Gln Ser Cys Leu Gln Val Met Tyr Glu Glu Asp Ala Arg Gly
                20                  25                  30

Gly Tyr Ile Ser Gly Val Leu Thr Lys Val Ala Val Arg Phe Ser Pro
                35                  40                  45

Leu Gln Ser Thr Ile Ala Met Leu Pro His His Asp Thr His Ser Thr
         50                  55                  60

Ser Tyr Gly Leu Asp Cys Ser Leu Ile Phe Lys Asp Leu Ser Glu Ile
 65                  70                  75                  80

Leu Ile Ala Ser Leu Val Leu Leu Cys Val Thr Val Phe Phe Tyr Tyr
                85                  90                  95

Leu Trp Arg Thr Arg Gly Met Pro Pro Gly Pro Trp Gly Leu Pro Leu
                100                 105                 110

Val Gly Tyr Leu Pro Trp Ile Asp Lys Asp Lys Pro Tyr Val Ser Met
                115                 120                 125

Met Glu Leu Tyr Gln Asp Tyr Gly Gly Ile Cys Thr Ile Arg Leu Gly
        130                 135                 140

Glu Val Ala Ile Val Val Ser Glu Pro His Tyr Val Lys Glu Ala
145                 150                 155                 160

Leu Ser Gln Glu Ser Leu Thr Gly Arg Ala Pro Leu Trp Leu Thr His
                165                 170                 175

Gly Leu Met Asn Asn Asn Gly Leu Ile Ala Val Glu Gly Pro Lys Trp
                180                 185                 190

Arg Glu Gln Arg Lys Phe Val Ile Asn Cys Leu Lys Asn Leu Gly Ala
                195                 200                 205

Val Lys Val Gly Glu Lys Arg Ala Val Met Glu Lys Arg Ile Leu Gly
        210                 215                 220

Gly Ile Arg Ile Thr Phe Gln Met Ile Asp Glu Arg Arg Glu Asp Gly
225                 230                 235                 240

Pro Phe Asp Pro Lys Gln Ile Leu Ser His Thr Ile Gly Asn Ile Met
                245                 250                 255

Asn Thr Ile Val Phe Gly Lys Ser Phe Asp Leu Asp Asp His Thr Trp
                260                 265                 270

Val Trp Leu Gln His Met Ala Glu Glu Gly Val Lys Leu Val Gly Val
                275                 280                 285

Ala Gly Pro Leu Asn Phe Met Pro Tyr Leu Arg Ile Leu Pro Gln Tyr
        290                 295                 300

Arg Lys Leu Leu Asp Phe Ile Lys Asn Gly Gln Lys Arg Thr His Asp
305                 310                 315                 320

Val Tyr Arg Ser Ile Ala Asn Glu Gln Arg Thr Lys Asp Asn Ile Leu
                325                 330                 335

Ser Tyr Tyr Leu Glu Ala Ile Ala Ser Gly Lys Gly Glu Tyr Phe Asp
                340                 345                 350

Glu Ala Gln Met Leu His Leu Leu Ala Asp Met Phe Gly Ala Gly Val
        355                 360                 365

Asp Ser Thr Leu Ala Thr Tyr Arg Trp Val Leu Leu Tyr Leu Ala Leu
        370                 375                 380

His Pro Glu Val Gln Glu Arg Val Tyr Glu Val Ser Ser Val Ile
385                 390                 395                 400

Gly Lys Gly Lys Glu Pro Asn Met Asp His Phe Ser Met Cys Pro Tyr
                405                 410                 415

Thr Glu Ala Thr Ile Leu Glu Thr Met Arg Ile Arg Pro Val Val Pro
```

```
            420                 425                 430
Leu Gly Ile Pro His Gly Ala Thr Lys Asp Thr Gln Ile Ala Gly Phe
            435                 440                 445

Arg Val Pro Glu Gly Thr Met Ile Val Asn Gln Trp Thr Leu His
    450                 455                 460

His Asn Pro Lys Tyr Trp Ile Asn Pro Glu Glu Phe Glu Pro Lys Arg
465                 470                 475                 480

Phe Ile Asp Ser Asp Gly Cys Val Arg Arg Lys Asp Ser Phe Asn Pro
                485                 490                 495

Phe Gln Thr Gly Lys Arg Ser Cys Phe Gly Glu Glu Leu Ala Lys Met
                500                 505                 510

Val Leu Phe Leu Phe Thr Ser Met Val Leu Arg Tyr Arg Leu Gln
                515                 520                 525

Leu Glu Gly Ser Ser Ser Ala Gly Leu Gly Gly Glu Cys Gly Ile Thr
                530                 535                 540

Leu Ser Pro Gly Gln His Ser Ile Ser Phe Val Leu Arg Gln
545                 550                 555
```

<210> SEQ ID NO 45
<211> LENGTH: 477
<212> TYPE: PRT
<213> ORGANISM: Nezara viridula

<400> SEQUENCE: 45

```
Met Glu Gly Ile Tyr Leu Ser Ser Ala Ser Tyr Leu Leu Phe Gly
1               5                   10                  15

Leu Ala Ile Leu Trp Ala Val Leu Ser Val Leu Lys Arg Pro Lys Gly
                20                  25                  30

Ser Ala Pro Gly Pro Thr Pro Leu Pro Val Leu Gly Ser Leu His Leu
            35                  40                  45

Leu Gly Gly Tyr Glu Leu Pro Tyr Gln Ala Phe Asp Lys Leu Ser Ser
        50                  55                  60

Lys Tyr Gly Pro Val Phe Gly Ile Arg Leu Gly Ser Val Glu Cys Leu
65                  70                  75                  80

Val Val Ser Ser Leu Glu Thr Val Lys Glu Ile Leu Ile Asn Lys Gly
                85                  90                  95

Glu His Phe Asp Ser Arg Pro Asn Phe Ser Arg Tyr Leu Asn Ile Phe
            100                 105                 110

Gly Gly Asp Lys Asp Asn Ser Leu Ala Phe Cys Asp Trp Ser Glu Leu
        115                 120                 125

Gln Lys Thr Arg Arg Glu Met Ile Arg Asp His Thr Phe Pro Lys Ala
130                 135                 140

Phe Ser Ser Lys Phe His Gln Leu Glu Ser Leu Leu Asn Arg Glu Leu
145                 150                 155                 160

Val Val Leu Cys Asp Gln Leu Ser Lys Gly Val Thr Asn Ile Lys Pro
                165                 170                 175

Ile Met Leu His Thr Cys Ala Asn Val Phe Met Ser Phe Phe Thr Asn
            180                 185                 190

Thr Arg Phe Gln Leu Glu Asp Pro Val Tyr Ser Lys Ile Leu Met Tyr
        195                 200                 205

Phe Asp Ile Ile Phe Tyr Glu Val Asn Gln Gly Tyr Ala Ala Asp Phe
    210                 215                 220

Met Pro Trp Leu Asn Pro Met Leu Met Asn Asn Met Lys Lys Met Arg
225                 230                 235                 240
```

```
Lys Leu Gly Lys Ile Ile Arg Glu Phe Met Asp Glu Arg Val Val Ser
                245                 250                 255

Asn Gly Gly Gln Glu Gly Asp Leu Leu His Met Leu Leu Glu Ser Val
            260                 265                 270

Glu Ser Gly Lys Met Asn Arg Glu Asn Ala Met Phe Ala Leu Glu Asp
        275                 280                 285

Ile Ile Gly Gly His Thr Ala Ile Ala Asn Leu Ile Ile Lys Ile Leu
    290                 295                 300

Gly Phe Ile Ser Asn Gln Pro Glu Val Gln Lys Met Gln Glu Glu
305                 310                 315                 320

Val Asp Ala Val Thr Cys Gly Lys Asn Ile Lys Leu Glu Asp Arg Leu
                325                 330                 335

Met Met Pro Tyr Thr Glu Ala Val Ile Leu Glu Ser Ile Arg His Ile
            340                 345                 350

Cys Ser Pro Ile Val Pro His Val Ala Ser Gln Asp Thr Thr Val Asn
        355                 360                 365

Asp Tyr His Val Glu Lys Gly Thr Leu Ile Phe Leu Asn Asn Tyr Thr
    370                 375                 380

Leu Asn Met Ser Pro Glu Leu Trp Thr Glu Pro Glu Lys Phe Ser Pro
385                 390                 395                 400

Glu Arg Phe Leu Thr Glu Asp Gly Arg Leu Ile Lys Pro Glu His Phe
                405                 410                 415

Leu Pro Phe Gly Gly Arg Arg Ser Cys Met Gly Tyr Lys Met Thr
            420                 425                 430

Gln Tyr Val Ser Phe Ser Val Leu Ala Thr Met Met Gln Lys Tyr Ser
        435                 440                 445

Ile Ala Pro His Pro Thr Asn Gly Lys Val Pro Arg Gly Asp Leu Ala
    450                 455                 460

Leu Pro Phe Asp Thr Leu Lys Phe Ile Phe Asn Pro Arg
465                 470                 475

<210> SEQ ID NO 46
<211> LENGTH: 511
<212> TYPE: PRT
<213> ORGANISM: Nezara viridula

<400> SEQUENCE: 46

Met Gln Pro Pro Leu Glu Trp Ser Ile Pro Asn Phe Thr Ala Val Phe
1               5                   10                  15

Leu Phe Ile Ala Ile Leu Leu Leu Lys Glu Leu Arg Pro Ile Phe Lys
            20                  25                  30

Lys Thr Arg Tyr Leu Thr Arg Pro Val Thr Thr Lys Lys Ile Pro
        35                  40                  45

Thr Val Asn Gln Ile Pro Gly Pro Leu Gln Leu Pro Val Ile Gly Thr
    50                  55                  60

Arg Trp Ile Tyr Tyr Thr Lys Tyr Thr Leu Glu Lys Leu His Glu Ala
65                  70                  75                  80

His Lys Asp Met Tyr Arg Thr Tyr Gly Pro Ile Val Lys Glu Glu Ala
            85                  90                  95

Leu Trp Asn Ile Pro Ile Asn Ile Phe Ser Lys Asn Glu Ile Glu
            100                 105                 110

Lys Ile Leu Arg His Pro Ser Lys Tyr Pro Leu Arg Pro Pro Thr Glu
        115                 120                 125

Val Thr Ala Tyr Tyr Arg Ala Thr Arg Pro Asp Arg Tyr Ala Ser Leu
    130                 135                 140
```

Gly Leu Ile Asn Glu Gln Gly Glu Thr Trp His Thr Leu Arg Ser His
145                 150                 155                 160

Leu Thr Pro Glu Leu Thr Ser Ala Lys Thr Met Ser Ser Phe Phe Pro
            165                 170                 175

Glu Leu Leu Ser Val Thr Glu Asp Phe Ile Arg Leu Leu Gln Val Ser
            180                 185                 190

Lys Asp Ala Asn Gly Ile Val Glu His Phe Asp Asp Leu Ala Cys Arg
            195                 200                 205

Met Gly Leu Glu Ser Thr Cys Cys Leu Ile Leu Gly Lys Arg Leu Gly
            210                 215                 220

Val Leu Glu Asp Glu Ala Ser Glu Val Ser Leu Arg Leu Ala Asn Ala
225                 230                 235                 240

Val Lys Glu Gln Phe Cys Ala Ser Arg Asp Thr Tyr Phe Gly Leu Pro
                245                 250                 255

Phe Tyr Lys Leu Tyr Pro Thr Lys Ala Tyr Lys Arg Phe Val Asn Ala
            260                 265                 270

Glu Glu Ile Ile Tyr Asp Val Ile Ser Glu Met Val Glu Asn Ala Glu
            275                 280                 285

Asn Leu Glu Asn Asp Thr Tyr Leu Glu Asp Ser Pro Ser Val Phe Gln
290                 295                 300

Ser Ile Leu Asn Asn Pro Gly Leu Asp Ile Arg Glu Lys Lys Ala Gly
305                 310                 315                 320

Ile Ile Asp Phe Ile Ala Ala Gly Ile Lys Thr Leu Gly Asn Thr Leu
                325                 330                 335

Val Phe Leu Leu Tyr Leu Met Ala Lys Asn Pro Glu Cys Gln Glu Lys
            340                 345                 350

Ile Val Asp Glu Ile Asp Ser Leu Thr Ser Gly Lys Glu Leu Thr Leu
            355                 360                 365

Gln Ala Leu Gly Lys Ala Asn Tyr Leu Lys Ala Cys Ile Ala Glu Ser
370                 375                 380

Tyr Arg Met Leu Pro Thr Ala Pro Cys Leu Ala Arg Ile Leu Glu Thr
385                 390                 395                 400

Asp Met Glu Leu Asn Gly Phe His Leu Pro Ser Gly Thr Val Val Leu
                405                 410                 415

Cys His Thr Trp Gln Ala Ser Leu Met Glu Glu Asn Phe Gln Asn Ala
            420                 425                 430

Asp Gln Phe Ile Pro Glu Arg Trp Leu Gly Lys Glu Arg Met Pro Trp
            435                 440                 445

Leu Val Ala Pro Phe Gly Ala Gly Arg Arg Leu Cys Pro Gly Lys Arg
450                 455                 460

Phe Val Glu Leu Glu Leu Gln Val Leu Leu Ala Gln Ile Val Arg Lys
465                 470                 475                 480

Phe Lys Leu Glu Cys Ala Gly Glu Leu Glu Ile Gln Phe Glu Phe Leu
                485                 490                 495

Met Ala Pro Ala Ser Pro Ser Ser Leu Lys Leu Val Glu Arg Thr
            500                 505                 510

<210> SEQ ID NO 47
<211> LENGTH: 443
<212> TYPE: PRT
<213> ORGANISM: Nezara viridula

<400> SEQUENCE: 47

Met Met Lys Met Ile Pro Tyr Val Lys Gly Leu Pro Ile Ile Gly Thr

-continued

```
  1               5                   10                  15
Ser Leu Ser Ile Leu Ala Ala Gly Ser Ser Pro Lys Leu His Leu Tyr
                 20                  25                  30
Ile Asp Arg Arg His Lys Lys Leu Gly Pro Ile Phe Lys Glu Asn Met
                 35                  40                  45
Gly Thr Ile Cys Gly Thr Phe Val Ala Asp Pro Leu Ala Ala Arg Thr
 50                  55                  60
Val Phe Ser Ala Glu Gly Arg Tyr Pro Lys His Met Val Pro Asp Ala
 65                  70                  75                  80
Trp Lys Val Tyr Asn Lys Met Tyr Asn Cys Asn Arg Gly Leu Phe Phe
                 85                  90                  95
Met Glu Gly Glu Glu Trp Leu Lys Tyr Arg His Ile Met Asn Lys Leu
                100                 105                 110
Ile Leu Lys Arg Asn Leu Pro Asn Gln Gln Val Gln Glu Tyr Ile Ile
                115                 120                 125
Ser Ser Phe Met Glu Ser Met Asp Asn Phe Val Gly Lys Gln Met His
130                 135                 140
Asn Ile Glu His Lys Phe Tyr Gln Leu Ser Ile Ser Phe Phe Ile Gly
145                 150                 155                 160
Thr Leu Met Gly Thr Ala Ile Ile Asn Lys Met Glu Tyr Phe Asn Lys
                165                 170                 175
Asp Ile Asp Asn Leu Ala Leu Val Val Asn Ser Ile Phe Ser Thr Thr
                180                 185                 190
Thr Asn Leu Met Asn Ile Pro Ile Ser Leu Ala Thr Ser Leu Asn Met
                195                 200                 205
Lys Ile Trp Lys Glu Phe Thr Glu Ser Val Glu Tyr Thr Leu Lys Ala
210                 215                 220
Gly Arg Val Leu Leu Glu Lys Ile Lys Gly Phe Pro Leu Asn Asp Gly
225                 230                 235                 240
Leu Leu Lys Asp Leu Leu Glu Glu Asp Leu Asp Asp Glu Val Ile Thr
                245                 250                 255
Gly Leu Val Met Asp Met Ile Leu Ala Ala Gly Asp Thr Ser Ala Tyr
                260                 265                 270
Thr Ser Gln Trp Ala Leu Tyr Leu Leu Ser Arg Glu Pro Glu Val Ala
                275                 280                 285
Asp Lys Val Arg Ser Asn Asp Gln Leu Val Ser Gly Val Val Lys Glu
                290                 295                 300
Val Leu Arg Leu Tyr Pro Ala Ala Ile Phe Ile Ser Arg Tyr Leu Asp
305                 310                 315                 320
Arg Asp Leu Ile Leu Pro Thr Leu Asp Cys Gln Leu Ser Lys Gly Glu
                325                 330                 335
Leu Val Met Leu Ser Leu Tyr Thr Ile Gly Arg Leu Glu Ser Ala Tyr
                340                 345                 350
Thr Glu Pro Leu Lys Phe Lys Pro Glu Arg Trp Met Arg His Val Asp
                355                 360                 365
Ser Asn Ser Arg His Tyr Leu Gly Val Lys Glu Pro Met Ala Trp Leu
                370                 375                 380
Pro Phe Gly Val Gly Ser Arg Ser Cys Ile Gly Arg Arg Leu Ala Glu
385                 390                 395                 400
Ala Gln Leu His Leu Thr Ile Ser Lys Ile Leu Ser Lys Tyr Arg Leu
                405                 410                 415
His Leu Val Glu Pro Val Asp Met Glu Leu Arg Met Val Pro Val Pro
                420                 425                 430
```

```
Thr Lys Pro Ile Lys Ile Lys Val Asp Arg Leu
        435                 440
```

<210> SEQ ID NO 48
<211> LENGTH: 516
<212> TYPE: PRT
<213> ORGANISM: Nezara viridula

<400> SEQUENCE: 48

```
Met Ile Thr Ile Ala Leu Leu Ile Val Ile Ser Leu Leu Ala Tyr
1               5                   10                  15

Val Tyr Asn Trp Ala Asn Asn Ile Asn Gln Thr Trp Lys Arg Arg Gly
            20                  25                  30

Val Lys His Arg Lys Pro Ala Leu Ile Phe Gly Asn Val Thr Ile Leu
        35                  40                  45

Val Pro Arg Lys Asp Gln Lys His Leu Ser Val Leu Cys Ala Asp Ile
    50                  55                  60

Cys Arg Glu Phe Pro Asp Glu Pro Leu Val Gly Phe Tyr Asp Phe Thr
65                  70                  75                  80

Gln Pro Trp Leu Leu Leu Gln Asp Ala Glu Tyr Ile Glu Lys Val Leu
                85                  90                  95

Ile Lys Asp Phe Val His Phe Thr Asp His Gly Phe Ala Ile Asn Glu
            100                 105                 110

Glu Lys Asn Pro Ile Asp Ala Gln Leu Phe Asn Met Val Gly Lys Arg
        115                 120                 125

Trp Arg Ala Phe Arg Tyr Lys Leu Ser Pro Ile Phe Thr Ser Gly Lys
130                 135                 140

Leu Lys Ser Met Tyr Glu Pro Met Ser Asp Cys Gly Val Asp Leu Asp
145                 150                 155                 160

Asn Val Leu Lys Thr Ser Asn Lys Glu Gly Leu Asp Phe Lys Gln Leu
                165                 170                 175

Met Thr His Phe Ala Val Asp Val Val Gly Ser Ser Val Phe Gly Ile
            180                 185                 190

His Pro Lys Ala Ile Gln Asn Pro Asn Thr Lys Phe Cys Ser Leu Ala
        195                 200                 205

Thr Asp Leu Phe Thr Phe Gly Phe Phe Asp Thr Ile Lys Phe Leu Ile
    210                 215                 220

Met Phe Ile Phe Pro Lys Leu Ser Ile Lys Leu Gly Ile Ser Phe Asn
225                 230                 235                 240

Asn Gln Asn Ala Val Asn Tyr Tyr Ser Lys Ile Leu Lys Glu Thr Phe
                245                 250                 255

Glu Tyr Arg Thr Lys Asn Lys Val Glu Arg Asn Asp Phe Val Gln Leu
            260                 265                 270

Leu Leu Thr Leu Lys Glu Lys Lys Ile Asp Val Gln Asn Trp Asp
        275                 280                 285

Ser Asn Asp Asp Tyr Leu Lys Asp Gly Glu Ala Pro Ala Glu Leu Glu
290                 295                 300

Ser Tyr Glu Ile Thr Glu Asn Ile Leu Met Ala Gln Ala Tyr Ala Phe
305                 310                 315                 320

Leu Val Asn Gly Ile Asp Val Leu Ala Leu Ser Gln Val Tyr Ala Leu
                325                 330                 335

Tyr Glu Leu Ser Leu Glu Pro Glu Ile Gln Glu Lys Ala Gln Asn Glu
            340                 345                 350

Ile Arg Glu Gln Met Lys Leu His Asn Gly Ile Thr Tyr Thr Ala Leu
```

```
                355                 360                 365
Lys Asn Met Thr Tyr Leu Glu Lys Val Val Lys Glu Thr Leu Arg Leu
    370                 375                 380

His Pro Ala Gly Gly Thr Leu Phe Arg Thr Cys Thr Lys Asp Tyr Val
385                 390                 395                 400

Phe Pro Asn Gly Thr Val Ile Lys Glu Gly Glu Met Leu Val Ile Pro
                405                 410                 415

Met Ser Ala Val His Leu Asn Pro Asn Tyr Tyr Pro Glu Pro Asp Val
            420                 425                 430

Phe Lys Pro Glu Arg Phe Asp Leu Pro Met Lys Pro Gly Thr Phe Leu
        435                 440                 445

Thr Phe Gly Asp Gly Pro Arg Val Cys Ile Ala Met Arg Tyr Ala Ile
    450                 455                 460

Leu Leu Ile Lys Tyr Gly Ile Val Lys Ile Leu Ser Asn Tyr Lys Val
465                 470                 475                 480

Thr Leu Asn Thr Lys Thr Glu Leu Pro Ile Lys Leu Lys Pro Asn Ala
                485                 490                 495

Ala Ile Gly Thr Pro Thr Ser Pro Leu Leu Phe Asp Leu Glu Ala Ile
            500                 505                 510

Asn Lys Asp Tyr
            515

<210> SEQ ID NO 49
<211> LENGTH: 512
<212> TYPE: PRT
<213> ORGANISM: Nezara viridula

<400> SEQUENCE: 49

Met Leu Thr Leu Cys Leu Ile Ile Leu Val Leu Thr Leu Val Gly Phe
1               5                   10                  15

Ile Val Asn Trp Ile Arg Lys Val His Leu Phe Trp Glu Lys Lys Gly
            20                  25                  30

Ile Lys His Leu Lys Pro Ser Phe Leu Phe Gly Asn Ser Leu Pro Val
        35                  40                  45

Leu Leu Asn Lys Lys Ser Ile Ser Glu Gln Phe Ile Asp Leu Cys Lys
    50                  55                  60

Thr Tyr Pro Asn Glu Pro Leu Leu Gly His Tyr Asp Phe Leu Lys Pro
65                  70                  75                  80

Ser Leu Ile Val Gln Asp Ala Asp Tyr Ala Glu Lys Ile Leu Ile Lys
                85                  90                  95

Asp Phe Leu His Phe Thr Asp His Gly Met Glu Val Asn Glu Asp Lys
            100                 105                 110

Asn Pro Ile Asp Ala Gln Leu Phe Thr Met Cys Gly Lys Lys Trp Arg
        115                 120                 125

Ala Phe Arg Tyr Lys Leu Ser Pro Ile Phe Thr Ser Gly Lys Leu Lys
    130                 135                 140

Asn Met Phe Asp Thr Met Ala Val Phe Gly Asp Arg Leu Val Asn Leu
145                 150                 155                 160

Leu Ser Thr Lys Lys Glu Tyr Lys Lys Val Asn Leu Arg Glu Ala Met
                165                 170                 175

Ser Ser Leu Ser Met Asp Ile Ile Ala Ser Thr Val Phe Gly Ile Glu
            180                 185                 190

Thr Asn Val Leu Glu Asn Pro Asp Ser Glu Phe Arg Lys Met Gly Lys
        195                 200                 205
```

Lys Val Phe Asp Phe Gly Ile Val Gly Phe Ile Lys Ile Trp Ile Ile
            210                 215                 220

Met Ser Phe Pro Gly Leu Gly Lys Lys Leu Gly Val Ser Ile Asn Asn
225                 230                 235                 240

Lys Asp Val Val Gln Tyr Phe Thr Asp Ile Ile Lys Lys Thr Phe Ser
                245                 250                 255

His Arg Arg Lys Asn Asn Ile His Arg Asn Asp Phe Val Gln Met Met
            260                 265                 270

Ile Gln Leu Gln Asp Lys Gly His Ile Glu Val Arg Asn Trp Asp Ala
        275                 280                 285

Asn Asp Asp Tyr Leu Lys Thr Asp Glu Asp Ser Asn Met Asn Val Asp
290                 295                 300

Ser Tyr Glu Ile Thr Glu Asn Val Val Ile Ala Gln Ala Phe Thr Phe
305                 310                 315                 320

Leu Thr Thr Gly Leu Asp Thr Ile Gly Ile Gly Gln Thr Tyr Leu Leu
                325                 330                 335

Tyr Glu Leu Ala Leu Gln Ala Asp Ile Gln Asp Arg Val Arg Glu Glu
            340                 345                 350

Ile Phe Glu Gln Cys Lys Ile His Gly Gly Leu Asn Tyr Asp Ser Leu
        355                 360                 365

Lys Ala Met Thr Tyr Leu Glu Lys Cys Leu Lys Glu Ser Leu Arg Leu
370                 375                 380

His Ser Thr Pro Gln Leu Phe Arg Ile Cys Asn Lys Asn Tyr Thr Phe
385                 390                 395                 400

Pro Asn Gly Tyr Thr Ile Lys Lys Gly Glu Thr Ile Gln Ile Ala Val
                405                 410                 415

Ser Ala Ile His Arg Asn Pro Asp Tyr His Pro Asp Pro Glu Val Phe
            420                 425                 430

Lys Pro Glu Arg Phe Asp Asn Leu Met Arg Pro Gly Val Trp Leu Ser
        435                 440                 445

Phe Gly Glu Gly Pro Arg Val Cys Ile Ala Met Arg Phe Ala Leu Leu
450                 455                 460

Gln Val Lys Phe Gly Val Ala Arg Met Leu Met Lys Tyr Arg Leu Ser
465                 470                 475                 480

Ile Asn Pro Glu Thr Lys Leu Pro Val Glu Val Leu Pro Gln Ser Val
                485                 490                 495

Val Leu Glu Pro Lys Tyr Pro Ile Tyr Phe Asp Leu Glu Val Ser
            500                 505                 510

<210> SEQ ID NO 50
<211> LENGTH: 512
<212> TYPE: PRT
<213> ORGANISM: Nezara viridula

<400> SEQUENCE: 50

Met Leu Ala Val Gly Phe Gly Val Leu Phe Ile Val Leu Leu Leu Leu
1               5                   10                  15

Ile Leu Met Trp Ile Ser Ser Met Asn Arg His Trp Glu Lys Lys Gly
            20                  25                  30

Ile Lys Phe Ser Lys Pro Phe Pro Leu Leu Gly Asn Cys Leu Pro Met
        35                  40                  45

Ile Leu Ser Lys Lys Ser Phe Thr Asp Ile Ile Asp Asp Leu Tyr Asn
    50                  55                  60

Ala His Pro Asn Glu Leu Val Ile Gly Tyr Tyr Glu Phe Val Ser Pro
65                  70                  75                  80

```
Lys Leu Ile Val Arg Asp Leu Glu Leu Ala Arg Lys Val Leu Ile Lys
                85                  90                  95

Asp Phe Ser Tyr Phe Val Asp His Val Ser Glu Met Asp Asn Val Ala
            100                 105                 110

Trp Asp Ser Gln Leu Phe Met Leu Ser Gly Asn Lys Trp Lys Ala Leu
        115                 120                 125

Arg Leu Gln Met Ala Ser Ile Phe Thr Thr Gly Lys Leu Arg Thr Met
    130                 135                 140

Tyr Asp Ser Met Pro Asp Ile Gly Lys Asn Leu Leu Gln His Leu Asp
145                 150                 155                 160

Asn Lys Val Gly Asn Asp Ile Asp Ile His Glu Leu Met Ile Leu Phe
                165                 170                 175

Ser Met Asp Met Ile Gly Ser Thr Ala Phe Gly Ile Asp Val Gly Ser
            180                 185                 190

Leu Asn Asn Pro Asn Ser Glu Ile Met Gln Met Gly Lys Lys Ile Ile
        195                 200                 205

Asp Val Gly Phe Leu Ser Val Met His Phe Trp Leu Tyr Leu Leu Tyr
    210                 215                 220

Pro Lys Leu Gly Asn Lys Ile Gly Ile Pro His Val Tyr Arg Glu Val
225                 230                 235                 240

Asn Asn Tyr Tyr Ser Glu Ile Leu Lys Asn Thr Ile Asn Tyr Arg Lys
                245                 250                 255

Ala Asn Lys Ile Gln Arg Asn Asp Phe Ile Glu Met Met Ile Gln Leu
            260                 265                 270

Arg Glu Lys Gly Lys Leu Glu Leu Lys Asn Leu Asp Pro Ala Asn Asp
        275                 280                 285

Tyr Leu Thr Ser Glu Leu Val Leu Asn Ser Pro Glu Met Leu Asn Ile
    290                 295                 300

Thr Asp Asp Leu Leu Met Ala Gln Ala His Ala Val Leu Thr Ala Gly
305                 310                 315                 320

Phe Glu Ser Thr Ser Leu Leu Thr Tyr Thr Met Val Glu Leu Cys
                325                 330                 335

Lys Asn Thr Asp Ile Gln Asp Ile Ala Arg Arg Glu Ile Met Leu Gln
            340                 345                 350

Val Lys Leu Asn Gly Gly Leu Thr Tyr Asp Ala Leu Lys Asn Met Lys
        355                 360                 365

Tyr Leu Asp Gln Val Ile Lys Glu Thr Gln Arg Phe Tyr Pro Phe Thr
    370                 375                 380

Pro Val Leu Met Arg Ile Cys Thr Lys Asp Tyr Thr Leu Ala Asp Gly
385                 390                 395                 400

Tyr Val Leu Lys Lys Gly Asp Pro Leu Tyr Ile Pro Val Ala Ser Ile
                405                 410                 415

His Lys Asp Pro Ser Ile Phe Pro Glu Pro Asp Ser Phe Lys Pro Glu
            420                 425                 430

Arg Phe Glu Asp Ser Gln Gln Pro Thr Ala Phe Met Ala Phe Gly Ala
        435                 440                 445

Gly Pro Arg Met Cys Ile Ala Val Lys Tyr Thr Leu Leu Ile Met Lys
    450                 455                 460

Tyr Gly Leu Ala Leu Leu Leu Met Asn Tyr Glu Val Lys Leu Ser Pro
465                 470                 475                 480

Leu Thr Lys Leu Pro Ile Lys Phe Thr Asn Lys Lys Phe Gly Asn Cys
                485                 490                 495
```

```
Glu Thr Glu Lys Ile Leu Phe Ser Phe Glu Lys Leu Val Lys Glu His
            500                 505                 510

<210> SEQ ID NO 51
<211> LENGTH: 548
<212> TYPE: PRT
<213> ORGANISM: Nezara viridula

<400> SEQUENCE: 51

Arg Thr Val Glu Ile Ile Gln Tyr Arg Val Arg Thr Lys Phe Gly Leu
1               5                   10                  15

Asn Gln Arg Leu Leu Ala Ala Asn Gln Phe Gly Ser Gln Cys Ala
            20                  25                  30

Thr Asp Arg Met Ile Gly Ile Ala Leu Leu Val Leu Ala Ile Thr Ala
            35                  40                  45

Leu Ala Tyr Ala Phe Asn Trp Ile Lys Tyr Trp Thr Lys Tyr Trp Glu
        50                  55                  60

Asn Lys Gly Val Lys Cys Leu Pro Ala Val Pro Ile Phe Gly Asn Cys
65                  70                  75                  80

Leu Pro Met Val Leu Asn Lys Lys Asn Val Ser Glu Ile Met Glu Asp
                85                  90                  95

Ile Tyr Asn Ala Phe Pro Asp Glu Pro Val Ala Gly Tyr Tyr Glu Phe
            100                 105                 110

Leu Thr Pro Arg Leu Leu Ile Arg Asp Asn Glu Leu Val Gln Lys Val
        115                 120                 125

Leu Val Lys Asp Phe Gly His Phe Val Asp His Gly Phe Glu Val Asp
    130                 135                 140

Glu Lys Lys Asn Pro Leu Asp Asn Gln Leu Phe Leu Met Thr Gly Asn
145                 150                 155                 160

Lys Trp Arg Ala Phe Arg Thr Lys Met Ala Pro Leu Phe Thr Ser Gly
                165                 170                 175

Lys Leu Lys Thr Met Tyr Asp Val Met Asn Glu Val Gly Asn Gly Leu
            180                 185                 190

Leu Glu Tyr Met Asp Lys Asn Lys Ala Asn Asp Ile Asp Ile Arg Glu
        195                 200                 205

Ala Met Gly Leu Phe Ser Met Asp Ile Ile Gly Ser Ala Ala Phe Gly
    210                 215                 220

Ile Asn Pro Gly Val Leu Lys Asn Pro Asp Ser Glu Phe Arg Val Lys
225                 230                 235                 240

Gly Lys Gln Ile Asn Asp Pro Asn Trp Arg Asn Leu Ile Arg Ile Trp
                245                 250                 255

Phe Phe Phe Ala Phe Pro Lys Phe Ser Lys Lys Leu Gly Phe Ser Phe
            260                 265                 270

Gln Pro Arg Ala Val Thr Ser Tyr Phe Cys Asn Ile Ile Arg Asn Ala
        275                 280                 285

Ile Asp Tyr Arg Lys Lys Asn Lys Ile Gln Arg Asn Asp Phe Val Gln
    290                 295                 300

Met Met Met Gln Leu Lys Glu Lys Gly Asn Ile Glu Leu Lys Thr Leu
305                 310                 315                 320

Asp Ala Thr Asp Asp Tyr Leu Lys Asn Glu Leu Asn Glu Ala Ser Thr
                325                 330                 335

Glu Ile Phe Glu Ile Thr Asp Asp Val Leu Met Ala Gln Ala Gln Ser
            340                 345                 350

Phe Leu Ile Ala Gly Phe Glu Ala Thr Ala Leu Leu Leu Thr Tyr Ala
        355                 360                 365
```

```
Met Leu Glu Ile Cys Gln Lys Pro Glu Ile Gln Asp Ala Leu Arg Lys
    370                 375                 380

Glu Val Leu Glu Gln Val Lys Leu Asn Gly Gly Leu Thr Tyr Glu Ala
385                 390                 395                 400

Leu Arg Asn Met Lys Tyr Leu Glu Gln Ala Ile Lys Glu Thr Gln Arg
                405                 410                 415

Ile Tyr Pro Leu Ile Pro Phe Leu Thr Arg Val Cys Thr Lys Ser Tyr
            420                 425                 430

Thr Leu Ser Asn Gly Phe Thr Ile Glu Lys Gly Glu Tyr Ile Tyr Ile
        435                 440                 445

Pro Ala Ala Ile His Met Asp Pro Thr Phe Tyr Pro Asp Pro Lys
    450                 455                 460

Thr Phe Lys Pro Glu Arg Phe Ala Glu Gln Pro Lys Pro Gly Thr Phe
465                 470                 475                 480

Leu Pro Phe Gly Glu Gly Pro Arg Met Cys Ile Ala Met Arg Tyr Ala
                485                 490                 495

Met Leu Val Val Lys Tyr Gly Leu Ala Leu Phe Leu Leu Asn Tyr Arg
                500                 505                 510

Ala Lys Leu Ser Pro Ser Thr Lys Leu Pro Val Gln Phe Leu Asn Arg
            515                 520                 525

Ala Phe Gly Asn Ile Pro Thr Glu Lys Ile Leu Phe Asn Val Glu Lys
        530                 535                 540

Tyr Asn Glu Lys
545

<210> SEQ ID NO 52
<211> LENGTH: 388
<212> TYPE: PRT
<213> ORGANISM: Nezara viridula

<400> SEQUENCE: 52

Met Cys Gly Asn Gln Trp Arg Val Tyr Arg Gln Lys Leu Ser Pro Ala
1               5                   10                  15

Phe Thr Thr Gly Lys Leu Lys Tyr Met Leu Asp Pro Leu Ala Glu Cys
                20                  25                  30

Val Asn Asn Leu Leu Thr Leu Leu Glu Ser His Ala Gly Glu Glu Val
            35                  40                  45

Asp Met Lys Glu Thr Met Glu Leu Phe Ser Met Asp Val Ile Gly Ser
        50                  55                  60

Cys Val Phe Gly Ile Asp Pro Gly Val Thr Lys Asn Pro Asn Ser Glu
65                  70                  75                  80

Phe Arg Thr Ile Gly Lys Thr Ile Phe Glu Phe Thr Ala Ile Gln Gln
                85                  90                  95

Phe Arg Phe Ala Val Leu Thr Met Leu Pro Lys Leu Ala Lys Lys Leu
                100                 105                 110

Asn Phe Thr Phe Phe Arg Pro Glu Val Val Thr Tyr Tyr Cys Asn Ile
            115                 120                 125

Ile Leu Asn Thr Leu Glu Tyr Arg Lys Lys Asn Gly Ile Glu Arg His
        130                 135                 140

Asp Phe Ile Gln Met Met Leu Gln Leu Gln Ser Lys Gly Lys Leu Asp
145                 150                 155                 160

Ser Gln Ser Thr Asp Pro Ala Asp Asp Leu Lys Thr Asp Lys Thr
            165                 170                 175

Leu Glu Gly Asp Asp Val Gln Ile Thr Asp Glu Leu Leu Ile Gly Thr
```

```
                180                 185                 190
Ala Phe Gly Phe Leu Thr Ala Gly Phe His Thr Thr Ala Ser Ser Met
            195                 200                 205

Thr Tyr Ala Leu Tyr Glu Leu Ser Arg Asn Pro Glu Ala Leu Glu Lys
        210                 215                 220

Thr Lys Arg Glu Ile Lys Glu Gln Val Ala Val His Gly Asp Ile Thr
225                 230                 235                 240

Tyr Asp Ser Leu Lys Ser Met Thr Tyr Leu Glu Lys Val Leu Lys Glu
                245                 250                 255

Ala Leu Arg Leu His Pro Gly Ser Pro Ser Thr Met Arg Val Cys Thr
            260                 265                 270

Lys Glu Tyr Lys Phe Pro Asn Gly Leu Thr Met Leu Pro Gly Asp Ser
        275                 280                 285

Ile Asn Ile Pro Ile Tyr Ala Leu His Arg Asp Pro Asn Asn Phe Pro
    290                 295                 300

Asp Pro Leu Ser Phe Asn Pro Asp Arg Phe Asp Glu Thr Pro Thr Pro
305                 310                 315                 320

Gly Thr Tyr Leu Pro Phe Gly Asp Gly Pro Arg Met Cys Ile Gly Met
                325                 330                 335

Arg Phe Ala Met Thr Ala Met Lys Tyr Ala Leu Ser Lys Val Leu Leu
            340                 345                 350

Asn Tyr Asp Ile Gln Leu Gly Lys Thr Asn Glu Thr Pro Ile Arg Met
        355                 360                 365

Ala Pro Arg Gly Phe Leu Asn Val Pro Lys Lys Glu Val Asn Ile Lys
    370                 375                 380

Ile Ile Lys Val
385

<210> SEQ ID NO 53
<211> LENGTH: 520
<212> TYPE: PRT
<213> ORGANISM: Nezara viridula

<400> SEQUENCE: 53

Met Ser Trp Gln Asp Trp Leu Met Leu Ala Thr Ile Ala Ala Leu Ser
1               5                   10                  15

Leu Leu Gly Leu Ala Tyr Tyr Thr Ile Lys Lys Leu Tyr Arg His Phe
            20                  25                  30

Glu Asp Arg Asn Ile Pro Tyr Ile Lys Pro Lys Phe Leu Leu Gly Ser
        35                  40                  45

Asp Pro Asp Gly Val Leu Phe Arg Leu His Val Cys Asp Ser Trp Asp
    50                  55                  60

Asn Ile Tyr Lys Lys Leu Glu Gly Lys Pro Ile Gly Gly Phe Phe Gln
65                  70                  75                  80

Thr Val Leu Pro Phe Leu Met Val Arg Asp Pro Glu Tyr Ile His Gln
                85                  90                  95

Val Leu Ile Ser Ser Phe Asp His Phe Phe Asp Arg Asn Phe Leu Ile
            100                 105                 110

Asp Glu Glu Val Asn Pro Leu Asp Ala His Leu Phe Leu Leu Arg Gly
        115                 120                 125

Asn Lys Trp Arg Tyr Leu Arg Asn Lys Leu Ser Pro Ile Phe Ser Ser
    130                 135                 140

Gly Lys Leu Arg Trp Met Phe Asp Glu Met Asp His Cys Gly Asp Ile
145                 150                 155                 160
```

Phe Leu Glu Cys Ile Asp Lys Leu Ala Asp Gly Lys Asp Arg Asp Ile
                165                 170                 175

Leu Asp Glu Leu Ala Arg Tyr Ala Thr Asp Val Ile Glu Ser Cys Ala
            180                 185                 190

Phe Gly Leu Glu Gly Asp Ser Ile Lys Asn Pro Asn Ser Lys Met Arg
        195                 200                 205

Gln Val Gly Arg Asp Leu Phe Asp Thr Ser Lys Phe Asn Leu Ser Gln
    210                 215                 220

Phe Phe Phe Leu Leu Arg Phe Ser Ile Pro Arg Leu Leu Ile Trp Leu
225                 230                 235                 240

Lys Val Pro Ser Val Pro Ser His Ala Lys Asn Phe Phe Cys Thr Thr
                245                 250                 255

Met Ser Asp Val Leu Glu Tyr Arg Arg Lys Thr Gly Phe Gln Arg Lys
            260                 265                 270

Asp Phe Val Gln Leu Leu Leu Gln Leu Lys Asp Lys Glu Ile Val Glu
        275                 280                 285

Ile Asn Ser Asn Tyr Asp Val Gly Asp Glu Lys Gly Lys His Glu Glu
    290                 295                 300

Thr Val Thr Glu Lys Ile Glu Ile Thr Asp Leu Leu Val Ala Gln
305                 310                 315                 320

Ser Phe Val Phe Phe Val Ala Gly Phe Glu Thr Thr Ser Arg Thr Leu
                325                 330                 335

His Phe Leu Ile His Gln Leu Ala Glu His Gln Phe Gln Lys Arg
            340                 345                 350

Ala Arg Lys Glu Val Leu Asp Ile Lys Ala Lys His Gly Arg Phe Ser
        355                 360                 365

Tyr Asp Ala Leu Lys Asp Met Lys Phe Leu Asn Lys Cys Ile Ala Glu
    370                 375                 380

Thr Leu Arg Met Tyr Pro Pro Val Ala Met Leu Asn Arg Glu Cys Thr
385                 390                 395                 400

Lys Asp Phe Thr Phe Gln Asp Gly Thr Leu Ile Lys Lys Gly Glu Gln
                405                 410                 415

Ile Val Ile Pro Ile Tyr Ser Ile His Arg Asp Pro Arg Tyr Phe Pro
            420                 425                 430

Asp Pro Leu Lys Tyr Asn Pro Asp Arg Phe Glu Val Asp Pro Gln Asn
        435                 440                 445

Gly Thr Tyr Leu Pro Phe Gly Asp Gly Pro Arg Ile Cys Ile Gly Lys
    450                 455                 460

Arg Phe Ala Ile Val Glu Ile Lys Ile Ile Met Ala Arg Leu Leu Glu
465                 470                 475                 480

Arg Tyr Trp Phe Glu Leu Ser Pro Leu Asn Gly Glu Lys Ile Glu Ile
                485                 490                 495

Asp Pro Trp Ser Leu Ile Val Ser Ser Lys Lys Gly Leu Trp Val Lys
            500                 505                 510

Ile His Lys Leu Thr Asp Leu Lys
        515                 520

<210> SEQ ID NO 54
<211> LENGTH: 509
<212> TYPE: PRT
<213> ORGANISM: Nezara viridula

<400> SEQUENCE: 54

Ile Ala Ala Phe Ser Leu Leu Ala Leu Ala Tyr Tyr Lys Ile Lys Lys
1               5                   10                  15

Thr Phe Arg His Phe Lys Asp Arg Asn Ile Pro Tyr Val Glu Pro Thr
             20                  25                  30

Phe Pro Leu Gly Ser Glu Pro Gln Gly Val Leu Phe Arg Lys His Ile
             35                  40                  45

Val Asp Ser Phe Gly Glu Ile Tyr Asn Gln Leu Glu Gly Lys Pro Val
 50                  55                  60

Gly Gly Phe Phe Gln Thr Val Leu Pro Phe Leu Met Ile Arg Asp Pro
 65                      70                  75                  80

Glu Tyr Val His Gln Val Leu Ile Ser Ser Phe Asp His Phe Phe Asp
                 85                  90                  95

Arg Asn Phe Leu Val Asp Glu Lys Val Asn Pro Leu Asp Ala His Leu
                100                 105                 110

Phe Phe Leu Arg Gly Asn Lys Trp Arg Tyr Leu Arg Asn Lys Leu Ser
            115                 120                 125

Pro Ile Phe Ser Gly Val Lys Leu Arg Trp Met Phe Glu Glu Met Glu
            130                 135                 140

Lys Cys Gly Glu Ser Phe Val Glu Cys Phe Asp Lys Leu Ala Asp Gly
145                 150                 155                 160

Lys Asp Arg Asp Val Leu Asp Glu Leu Ala Arg Tyr Ala Thr Asp Val
                165                 170                 175

Ile Gly Ser Cys Ala Phe Gly Leu Glu Gly Asp Ser Leu Lys Asn Pro
            180                 185                 190

Asn Ser Pro Met Arg Gln Met Gly Lys Asp Leu Phe Asp Thr Ser Ser
            195                 200                 205

Ile Asn Arg Thr Gln Ile Thr Phe Leu Leu Arg Phe Ser Val Pro Arg
            210                 215                 220

Leu Leu Leu Trp Phe Lys Val Arg Ser Leu Pro Ser Ala Ile Glu Glu
225                 230                 235                 240

Tyr Phe Cys Ser Thr Ile Ser Ser Val Leu Glu Arg Arg Lys Thr
            245                 250                 255

Gly Leu Lys Arg Arg Asp Phe Val Gln Leu Leu Leu Gln Leu Lys Glu
            260                 265                 270

Lys Asp Val Val Asn Ile Asp Ala Asn Asp Val Asp Glu Lys Glu Asp
            275                 280                 285

Lys Ser Gln Gln Asn Asn Asp Ile Glu Lys Phe Glu Ile Thr Asp Arg
            290                 295                 300

Leu Leu Met Ala Gln Ser Phe Val Phe Phe Val Gly Gly Phe Glu Thr
305                 310                 315                 320

Thr Ser Arg Thr Leu His Tyr Leu Ile Tyr Gln Leu Ala Gln His Pro
                325                 330                 335

Glu Ile Gln Glu Arg Ala Arg Gln Glu Val Leu Arg Ile Lys Glu Lys
            340                 345                 350

His Ser Gln Phe Ser Tyr Asp Ala Leu Lys Asp Leu Lys Phe Leu Asp
            355                 360                 365

Asn Cys Ile Ser Glu Thr Leu Arg Leu Asn Pro Pro Val Ser Met Leu
            370                 375                 380

Asn Arg Glu Cys Thr Lys Asp Phe Thr Phe Pro Asp Gly Thr Ser Ile
385                 390                 395                 400

Glu Lys Gly Glu Gln Ile Val Ile Pro Ile Tyr Ser Ile His Arg Asp
                405                 410                 415

Pro Lys Tyr Phe Pro Glu Pro Thr Lys Phe Asn Pro Asp Arg Phe Leu
            420                 425                 430

Ser Asp Pro Gln Arg Gly Thr Tyr Leu Pro Phe Gly Asp Gly Pro Arg
        435                 440                 445

Ile Cys Ile Gly Lys Arg Phe Ala Leu Val Glu Ile Lys Ile Val Met
450                 455                 460

Ala Arg Leu Leu Glu Arg Tyr Ser Phe Glu Pro Ser Ser Leu Asn Lys
465                 470                 475                 480

Glu Pro Ile Glu Leu Asn Pro Trp Ile Asn Val Leu Cys Ala Lys Asn
            485                 490                 495

Gly Leu Phe Val Lys Ile Gln Lys Leu Asn Asn Ser Lys
        500                 505

<210> SEQ ID NO 55
<211> LENGTH: 486
<212> TYPE: PRT
<213> ORGANISM: Nezara viridula

<400> SEQUENCE: 55

Phe Phe Glu Lys Arg Asn Ile Lys Tyr Val Lys Pro Lys Phe Leu Leu
1               5                   10                  15

Gly Ser Glu Pro Asp Gly Val Leu Phe Lys Ile His Ile Thr Glu Ser
            20                  25                  30

Trp Glu Arg Ile Tyr Lys Lys Leu Glu His Glu Lys Tyr Gly Gly Phe
        35                  40                  45

Phe His Ala Ile Leu Pro Thr Leu Met Ile Arg Asp Pro Glu Tyr Ile
    50                  55                  60

Glu Asp Ile Leu Lys Thr Ser Phe Asp His Phe Val Asp Arg Ser Phe
65                  70                  75                  80

Leu Val Asp Val Lys Thr Asn Pro Leu Asp Glu Asn Leu Phe Phe Met
                85                  90                  95

Arg Gly Asn Lys Trp Lys Tyr Leu Arg Cys Lys Met Ala Ser Leu Phe
            100                 105                 110

Ser Gln Ile Lys Leu Lys Trp Met Tyr Glu Glu Ile Glu Lys Cys Ser
        115                 120                 125

Asn Thr Phe Asp Glu Cys Leu Ser Glu Phe Ala Asp Gly Lys Asp Ala
    130                 135                 140

Asp Ile Lys Asp Leu Leu Ala Arg Phe Val Thr Asp Val Val Ala Ser
145                 150                 155                 160

Cys Gly Phe Gly Val Glu Pro Gln Ala Leu Lys Asn Pro Asp Trp Ile
                165                 170                 175

Phe Arg Asp Ile Gly Arg Glu Ile Val Asp Pro Glu Asn Ile Asn Met
            180                 185                 190

Pro Leu Phe Leu Leu Arg Phe Ser Ile Pro Arg Leu Leu Ile Trp Phe
        195                 200                 205

Lys Ile Lys Thr Leu Thr Lys Lys Leu Arg Asn Phe Phe Leu Ser Thr
    210                 215                 220

Thr Lys Arg Ile Leu His His Arg Arg Ser Thr Gly Ile Ile Arg Lys
225                 230                 235                 240

Asp Phe Val Gln Leu Phe Leu Glu Leu Lys Glu Lys Gly Thr Val Gly
                245                 250                 255

Ile Asp Ser Arg Asn Ile Asp Thr Asn Lys Thr Asn Thr Glu Ser Asn
            260                 265                 270

Asn Glu Ile Ile Glu Leu Thr Asp Asn Leu Leu Ala Ala Asn Ser Phe
        275                 280                 285

Leu Phe Phe Leu Ala Gly Phe Glu Thr Thr Ser Thr Thr Leu Tyr Tyr
    290                 295                 300

-continued

```
Thr Tyr Tyr Phe Leu Ala Lys His Gln Glu Ile Gln Glu Arg Ala Arg
305                 310                 315                 320

Lys Glu Val Gln Glu Val Lys Ala Lys Tyr Gly His Phe Thr Phe Asp
                325                 330                 335

Ser Leu Lys Glu Leu Lys Phe Leu Ile Asn Cys Ile Ser Glu Thr Met
            340                 345                 350

Arg Ile Tyr Pro Pro Ile Ala Val Val Ile Arg Glu Cys Thr Lys Asp
        355                 360                 365

Tyr Asn Leu Leu Asp Gly Thr Leu Ile Asp Lys Gly Met Arg Ile Ile
    370                 375                 380

Val Pro Ile Met Ser Ile His Arg Asp Pro Lys Asn Phe Ala Glu Pro
385                 390                 395                 400

Met Glu Tyr Lys Pro Glu Arg Phe Glu Asn Pro Pro Ala Ser Gly Thr
                405                 410                 415

Tyr Leu Pro Phe Gly Asp Gly Pro Arg Ile Cys Ile Gly Lys Arg Phe
            420                 425                 430

Ala Glu Ile Ile Met Tyr Ser Thr Leu Ala Arg Thr Leu Asp Lys Tyr
        435                 440                 445

Lys Leu Glu Leu Ser Pro Lys Cys Asp His Glu Ile Lys Leu Asn Pro
    450                 455                 460

Lys Val Ile Ser Thr Thr Pro Val His Gly Leu Phe Arg Ile His
465                 470                 475                 480

Lys Leu Asn Asp Thr Asn
                485

<210> SEQ ID NO 56
<211> LENGTH: 483
<212> TYPE: PRT
<213> ORGANISM: Nezara viridula

<400> SEQUENCE: 56

Phe Phe Glu Lys Arg Asn Ile Lys Tyr Val Lys Pro Lys Phe Leu Leu
1               5                   10                  15

Gly Ser Asp Pro Asp Gly Val Leu Phe Lys Ile His Val Thr Glu Ser
                20                  25                  30

Trp Asp Arg Ile Tyr Lys Gln Leu Glu Asn Glu Lys Cys Gly Gly Phe
            35                  40                  45

Tyr Gln Ala Ile Val Pro Thr Leu Met Ile Arg Asp Pro Glu Tyr Val
        50                  55                  60

Asn Ile Val Leu Lys Ser Ser Phe Asp His Phe Ser Asp Arg Ile Phe
65                  70                  75                  80

Leu Val Asp Glu Lys Thr Asn Pro Leu Asp Glu His Leu Phe Phe Leu
                85                  90                  95

Arg Gly Asn Lys Trp Arg Tyr Leu Arg Asn Lys Ile Ser Pro Leu Phe
            100                 105                 110

Ser Gln Val Lys Leu Lys Trp Met Tyr Glu Ile Asp Lys Cys Val
        115                 120                 125

Asn Leu Phe Asp Glu Cys Leu Ala Glu Leu Ser Asp Gly Lys Asp Leu
    130                 135                 140

Asp Ile Lys Glu Leu Leu Ala Arg Tyr Thr Thr Asp Val Val Ala Ser
145                 150                 155                 160

Cys Gly Phe Gly Ile Glu Pro Gln Cys Leu Lys Asn Pro Ser Ser Glu
                165                 170                 175

Phe Arg Lys Ile Gly Arg Glu Tyr Phe Asp Pro Asn Lys Ile Asn Met
```

```
                180                 185                 190
Arg Met Leu Phe Leu Arg Leu Ser Ile Pro Arg Leu Leu Met Trp Phe
            195                 200                 205

Lys Ile Lys Thr Val Ser Ala Lys Ile Asn Asn Phe Phe Leu Thr Thr
            210                 215                 220

Thr Lys Asn Ile Leu His His Arg Arg Ser Thr Gly Val Val Arg Lys
225                 230                 235                 240

Asp Phe Val Gln Leu Leu Glu Leu Lys Glu Lys Gly Thr Val Glu
                245                 250                 255

Ile Asp Thr Thr Glu Ile Glu Lys Asp Glu Thr Tyr Lys Glu Ser Pro
            260                 265                 270

Asn Glu Lys Ile Glu Leu Thr Asp Asn Leu Leu Ala Ala Gln Ser Phe
            275                 280                 285

Val Phe Phe Leu Ala Gly Phe Glu Thr Thr Ala Ser Val Leu Asn Phe
            290                 295                 300

Thr Phe Tyr Phe Trp Ala Lys His Gln Glu Ile Gln Glu Arg Ala Arg
305                 310                 315                 320

Lys Glu Val Leu Glu Val Lys Glu Lys Tyr Gly Gln Phe Thr Phe Asp
            325                 330                 335

Ser Leu Lys Glu Leu Lys Phe Leu Lys Asn Cys Ile Ala Glu Thr Leu
            340                 345                 350

Arg Ile Tyr Pro Ser Val Pro Ala Leu Asn Arg Glu Cys Met Lys Asp
            355                 360                 365

Phe Thr Leu Pro Asp Gly Thr Val Ile Glu Lys Gly Leu His Val Leu
            370                 375                 380

Val Pro Ile Leu Ser Leu His Arg Asp Pro Lys Tyr Phe Pro Glu Pro
385                 390                 395                 400

Leu Glu Tyr Lys Pro Asp Arg Phe Glu Asn Pro Val Asn Gly Thr
            405                 410                 415

Tyr Met Pro Phe Gly Asp Gly Pro Arg Thr Cys Ile Gly Lys Arg Phe
            420                 425                 430

Ala Glu Ala Ala Met Thr Ser Val Leu Ala Arg Ser Leu Glu Lys Tyr
            435                 440                 445

Lys Phe Glu Leu Ser Pro Met Asn Asn Cys Gly Asp Ile Lys Leu Asn
            450                 455                 460

Pro Lys Val Ile Thr Ser Ser Pro Leu His Gly Ile Phe Leu Arg Ile
465                 470                 475                 480

His Lys Leu

<210> SEQ ID NO 57
<211> LENGTH: 497
<212> TYPE: PRT
<213> ORGANISM: Nezara viridula

<400> SEQUENCE: 57

Met Met Glu Met Ile Leu Tyr Ala Ala Leu Ile Ile Ala Leu Thr Asn
1               5                   10                  15

Leu Ala Leu Gly Ile Ile Ile Trp Phe Arg Val Arg Lys Leu Tyr Ala
            20                  25                  30

Tyr Pro Gly Leu Leu Gly Phe Pro Val Phe Gly Asn Leu Tyr Tyr Phe
            35                  40                  45

Tyr Lys Asn Leu Phe Leu Gly Ser Phe Glu Ser Ile Arg Val Tyr Leu
        50                  55                  60

Phe Glu Ile Val Lys Gln His Gly Lys Asn Gly Ile Cys Phe His Ile
```

```
                65                  70                  75                  80
Ala Tyr Gly Phe Arg Lys Leu Val Ile Ile Ser Ser Pro Gln Val Val
                        85                  90                  95
Lys Gln Leu Gly Phe His Pro His Leu Lys Asp Lys Pro Val Tyr Gly
                100                 105                 110
Phe Gln Gly Phe Arg Arg Tyr Met Asn Gly Pro Phe Ser Arg Pro Arg
                115                 120                 125
Ser Asp Asp Ser Trp Lys Met Arg Arg Lys Glu Tyr Asn Cys Leu Leu
130                 135                 140
Lys Lys Ser Ser Val Glu Asn Asn Phe Tyr Tyr Asn Phe Leu Lys Ser
145                 150                 155                 160
Ala Asp Lys Met Val Glu Leu Met Leu Lys Ser Pro Ser Ala Leu Asp
                165                 170                 175
Ile His Arg Ala Val Leu Gly Val Thr Gln Ser Val Thr Met Glu Thr
                180                 185                 190
Leu Phe Gly Val Glu Ser Ser Leu Ala Phe His Pro Asp Val Leu Gln
                195                 200                 205
Tyr Met His Ser Ile Lys Asp Ile Ala Ser Arg Ile Ala Ser Pro
                210                 215                 220
Gly Ile Ala Arg Thr Ile Leu Ser Ile Leu Arg Pro Tyr Asp Glu Ile
225                 230                 235                 240
Tyr Ile Arg Lys Ile Gly Thr Leu Arg Arg Met Val Leu Lys Glu Leu
                245                 250                 255
Tyr Arg Lys Met Asn Asn Asn Gln Cys Phe Pro Ser Glu Asn Thr Gln
                260                 265                 270
Ser Phe Asn His Leu Pro Met Tyr Ile Ala Ser Arg Thr Glu Lys Ser
                275                 280                 285
Lys Lys Phe Asn Arg Arg Val Val Thr Glu Leu Gln Glu Val Phe Ile
                290                 295                 300
Thr Ser Ser His Thr Val Ala Ser Thr Met Ser Ser Thr Ile Thr Cys
305                 310                 315                 320
Leu Ala Val Leu Pro Glu Ile Gln Glu Arg Ala Trp Lys Glu Gln Tyr
                325                 330                 335
Glu Ile Phe Gly Asp Asp Asn Arg Glu Pro Thr Leu Gln Asp Leu Glu
                340                 345                 350
Gln Met Thr Tyr Leu Glu Arg Phe Ile Lys Glu Ser Leu Arg Phe Cys
                355                 360                 365
Gly Pro Pro Leu Val Gly Lys Gln Ala Thr Asp Ile Glu Val Asp
                370                 375                 380
Gly Ile Thr Ile Pro Lys Asp Thr Ile Val Val Tyr Leu Leu Asp Phe
385                 390                 395                 400
Met Arg Lys Asp Pro Asn Tyr Trp Lys Asp Pro Glu Leu Phe Asn Pro
                405                 410                 415
Asp Arg Phe Leu Glu Gly Gly Glu Glu Leu Lys Tyr Ser Phe Ala Pro
                420                 425                 430
Phe Gly Ile Gly Val Arg Asn Cys Pro Gly Met Thr Tyr Ala Met Thr
                435                 440                 445
Glu Met Lys Ile Ile Leu Ser Lys Val Leu Arg Arg Thr Lys Leu Ser
                450                 455                 460
Leu Val Asn Lys Asp Leu Lys Phe Glu Asp Leu Glu Phe Glu Ala Gln
465                 470                 475                 480
Ile Leu Met Glu Leu Lys Asn Pro Pro Leu Leu Gln Val Glu Glu Arg
                485                 490                 495
```

Val

<210> SEQ ID NO 58
<211> LENGTH: 510
<212> TYPE: PRT
<213> ORGANISM: Nezara viridula

<400> SEQUENCE: 58

```
Met Phe Asn Val Glu Tyr Ile Phe Arg Lys Met Glu Lys Phe Ala Thr
1               5                   10                  15

Thr Ala Phe Ile Ile Ala Val Ala His Leu Val Leu Gly Leu Leu Leu
            20                  25                  30

Trp Phe Arg Val Arg Lys Leu Tyr Ser Tyr Pro Gly Leu Leu Gly Phe
        35                  40                  45

Pro Val Phe Gly Asn Leu Tyr Tyr Phe Tyr Lys Thr Met Leu Ile Ala
    50                  55                  60

Ser Phe Glu Asn Met Arg Ile His Leu Val Gln Val Ala Glu Gln Tyr
65                  70                  75                  80

Gly Lys Asn Gly Ile Cys Phe Cys Ile Leu Phe Cys Phe Arg Lys Val
                85                  90                  95

Val Ile Ile Ser Ser Pro Gln Val Met Lys Gln Ile Gly Phe His Pro
            100                 105                 110

Asn Leu Lys Asp Lys Pro Pro Tyr Val Phe Glu Ser Phe Leu Lys Tyr
        115                 120                 125

Thr Asp Gly Pro Phe Thr Thr Pro Ser Ser Asp Asp Val Trp Lys Met
    130                 135                 140

Lys Arg Lys Glu Tyr Asn Asn Leu Leu Lys Lys Ser Ser Val Glu Asn
145                 150                 155                 160

Asn Phe Tyr Asn Ile Phe Leu Lys Ser Ala Asp Lys Leu Val Glu Leu
                165                 170                 175

Met Leu Ala Thr Pro Ser Thr Leu Asp Ile Glu Lys Ala Val Leu Gly
            180                 185                 190

Val Thr Gln Ser Val Thr Met Glu Ala Leu Phe Gly Val Asp Gly Arg
        195                 200                 205

Pro Ala Phe Asp Pro Glu Ile Ile Asp His Met Tyr Thr Leu Lys Asn
    210                 215                 220

Ile Ile Thr Leu Ile Ile Gly Asn Pro Gly Ile Ala Lys Thr Ile Leu
225                 230                 235                 240

Asn Gly Leu Gly Pro Phe Asp Gly Leu Leu Ile Arg Gln Ala Gly Ala
                245                 250                 255

Leu Lys Lys Leu Ser Ser Gln Ile Met Lys Gln Val His Val Lys Leu
            260                 265                 270

Lys Ser Ser Gln His Phe Pro Ser Glu Asn Thr Lys Ser Asn Tyr Ser
        275                 280                 285

Leu Ser Met Tyr Ile Ala Ser Arg Thr Glu Lys Ser Lys Lys Phe Asp
    290                 295                 300

Gln Asn Val Leu Thr Glu Leu Gln Glu Leu Phe Ile Thr Ser Ser Ser
305                 310                 315                 320

Thr Val Ser Ser Thr Met Ser Cys Thr Ile Cys Leu Ala Val Leu
                325                 330                 335

Pro Glu Met Gln Glu Lys Ala Trp Lys Glu Gln Asn Glu Ile Phe Gly
            340                 345                 350

Asp Asp Thr Arg Glu Pro Ser Leu Glu Asp Leu Glu Arg Met Ile Phe
        355                 360                 365
```

Leu Glu Arg Phe Ile Lys Glu Ser Leu Arg Phe Cys Gly Pro Leu
    370                 375                 380

Ile Ala Lys His Ala Ala Glu Asp Ile Lys Val Asp Gly Val Ile Ile
385                 390                 395                 400

Pro Lys Glu Ala Ile Val Val Tyr Met Leu Asp Phe Met Arg Lys Asp
                405                 410                 415

Pro Lys Tyr Trp Lys Asp Pro Lys Leu Phe Asp Pro Asp Arg Phe Leu
            420                 425                 430

Glu Glu Asn Glu Cys Ser Asn Tyr Thr Tyr Ala Pro Phe Gly Ile Gly
                435                 440                 445

Val Arg Thr Cys Pro Gly Met Asn Phe Ala Met Thr Gln Met Lys Ile
        450                 455                 460

Thr Leu Ser Lys Val Leu Arg Arg Val Lys Leu Ser Thr Val Lys Lys
465                 470                 475                 480

Asp Leu Lys Phe Glu Asn Leu Glu Phe Glu Ala Met Leu Leu Met Glu
                485                 490                 495

Leu Lys Asn Pro Pro Phe Leu Lys Val Glu Glu Arg Ile Met
                500                 505                 510

<210> SEQ ID NO 59
<211> LENGTH: 382
<212> TYPE: PRT
<213> ORGANISM: Nezara viridula

<400> SEQUENCE: 59

Gly Ile Tyr Ala Tyr Ala Lys Gly Pro Phe Thr Gln Ile Arg Ser Asp
1               5                   10                  15

Asp Leu Trp Lys Gln Lys Arg Lys Glu Tyr Asn Ile Gly Leu Lys Arg
                20                  25                  30

Ser His Ile Asp Asn Val Phe Cys Asn Ile Phe Asn Lys Ser Ala Asp
            35                  40                  45

Lys Leu Ile Asp Leu Met Val Ala Ser Ala Ser Val Asp Ala Leu
50                  55                  60

His Ala Thr Met Gly Ile Val Arg Asn Val Thr Leu Glu Thr Leu Phe
65                  70                  75                  80

Asn Val Asp Ser Ser Leu Ala Tyr Asp Pro Gln Leu Ile Thr Leu Met
                85                  90                  95

Lys Lys His Arg Tyr Leu Ala Ser Phe Ile Val Ala Asn Pro Asn Leu
                100                 105                 110

Ser Gly Ile Ile Leu Asn Ile Leu Arg Pro Leu Asp Glu Ile Leu Phe
            115                 120                 125

Arg Lys Leu Gly Glu Phe Arg Lys Val Ile Ser Glu Glu Ile Asp Lys
130                 135                 140

Thr Leu Leu Ser Glu Gln Cys Pro Leu Pro Glu Gln Tyr Leu Thr Met
145                 150                 155                 160

Gln Ile Val Ser Arg Thr Ile Lys Cys Asn Gly Asn Asn Asn Trp Asn
                165                 170                 175

Thr Thr Lys Leu Gln Asp Glu Leu Met Glu Leu Tyr Phe Thr Ala Thr
            180                 185                 190

Leu Thr Val Ser Ser Val Leu Ser Asn Thr Ile Ile Leu Ala Leu
                195                 200                 205

Leu Pro Asp Ile Gln Glu Arg Val Trp Gln Glu Gln Tyr Arg Ile Phe
210                 215                 220

Gly Asn Asp Asn Arg Asp Pro Ser Ile Asp Asp Leu Lys Glu Met Gln

```
            225                 230                 235                 240
        Phe Leu Asp Arg Cys Ile Lys Glu Ser Leu Arg Phe Leu Gly Pro Pro
                        245                 250                 255
        Phe Val Ala Lys Ser Val Ser His Asp Ile Asp Ile Asn Gly Ile Thr
                        260                 265                 270
        Ile Pro Arg Gly Thr Asn Val Leu Tyr Leu Thr Gly Tyr Leu Arg Met
                        275                 280                 285
        Asp Pro Thr His Trp Lys Asn Pro Lys Val Phe Asp Pro Asp Arg Phe
                        290                 295                 300
        Leu Glu Glu Ser Glu Thr Leu Lys His Ser Tyr Ser Pro Phe Gly Ile
        305                 310                 315                 320
        Gly Val Arg Gly Cys Pro Gly Ser Tyr Phe Ala Pro Thr Leu Met Lys
                        325                 330                 335
        Ile Thr Leu Ser Lys Leu Leu Arg Arg Leu Lys Leu Arg Pro Val Gln
                        340                 345                 350
        Lys Asp Phe Arg Phe Glu Asp Ile Lys Phe Lys Val Ser Leu Met Thr
                        355                 360                 365
        Glu Ile Glu Asp Pro Pro Ala Leu Gln Val Glu Glu Arg Thr
                        370                 375                 380

<210> SEQ ID NO 60
<211> LENGTH: 503
<212> TYPE: PRT
<213> ORGANISM: Nezara viridula

<400> SEQUENCE: 60

Met Glu Lys Phe Ala Thr Thr Ala Phe Ile Ile Ala Val Ala His Leu
        1               5                   10                  15
        Val Leu Gly Leu Leu Leu Trp Phe Arg Val Arg Lys Leu Tyr Ser Tyr
                        20                  25                  30
        Pro Gly Leu Leu Gly Phe Pro Val Phe Gly Asn Leu Tyr Tyr Phe Tyr
                        35                  40                  45
        Arg Thr Leu Phe Leu Val Thr Met Asp Ser Met Glu Lys Tyr Met Ile
                        50                  55                  60
        Arg Ile Ser Glu Thr Tyr Gly Lys Asp Gly Leu Cys Phe His Trp Ile
        65                  70                  75                  80
        Tyr Gly Phe Arg Thr Leu Val Thr Val Thr Asn Pro His Ile Val Lys
                        85                  90                  95
        Glu Ile Gly Phe His Pro Asn Val Thr His Lys Pro Asn Phe Ile Phe
                        100                 105                 110
        Ser Ala Phe His Ser Tyr Phe Ser Gly Pro Phe Val Ser Ser Arg Ser
                        115                 120                 125
        Asp Asp Leu Trp Lys Ile Gln Arg Lys Glu Tyr Asp Lys Leu Tyr Ala
                        130                 135                 140
        Val Phe Thr Phe His Ser Arg Phe Leu Lys Lys Ser Arg Val Glu Ser
        145                 150                 155                 160
        Glu His Ser Asn Thr Phe Ser Lys Tyr Ala Asp Gln Met Ile Glu Leu
                        165                 170                 175
        Met Leu Ala Ser Pro Ser Ala Asp Ile Leu Arg Ala Val Thr Leu Glu
                        180                 185                 190
        Phe Thr His Asn Ser Thr Met Glu Thr Leu Phe Gly Val Asp Ser Ser
                        195                 200                 205
        Ile Val Tyr Asn Pro Gln Val Ile Gly Phe Met Ser Val Ile Pro Val
                        210                 215                 220
```

Leu Gly Thr Leu Ser Val Ala Asn Pro Lys Leu Ala Gly Thr Ile Phe
225                 230                 235                 240

Gly Ile Phe Lys Lys Met Glu Ser Phe Phe Leu Arg Thr Ile Glu Lys
            245                 250                 255

Thr Arg Arg Leu Ile Leu Glu Asp Ile Tyr Ser Lys Ile Leu Thr Ser
                260                 265                 270

Ser Pro Val Ala Ala Asn Lys Lys Ala Leu Leu Ser Arg Gln Ile Thr
        275                 280                 285

Ser Arg Met Arg Lys Cys Asn Glu Asp Glu Asp Lys Leu Ile Asn Glu
    290                 295                 300

Leu Met Glu Leu Phe Val Thr Ser Ser Gly Thr Thr His Ala Leu Leu
305                 310                 315                 320

Ser Ser Ser Leu Ile Phe Leu Ala Leu Leu Pro Asp Ile Gln Glu Arg
                325                 330                 335

Ala Trp Gln Glu Gln Tyr Glu Ile Phe Asp Asn Asp Lys Arg Asp Ala
                340                 345                 350

Thr Phe Asp Asp Leu Ser Gln Met Arg Phe Leu Asp Arg Phe Ile Lys
        355                 360                 365

Glu Ala Leu Arg Phe Val Ala Pro Pro Phe Tyr Phe Lys Ser Val Thr
370                 375                 380

Gly Asp Thr Thr Ile Asn Gly Ile Thr Ile Pro Lys Gly Ser Asn Leu
385                 390                 395                 400

Val Tyr Leu Thr Gly Tyr Met Arg Met Asp Pro Lys Tyr Trp Lys Asn
                405                 410                 415

Pro Lys Val Phe Asp Pro Asp Arg Phe Leu Glu Glu Ser Glu Thr Leu
        420                 425                 430

Lys His Ser Tyr Thr Pro Phe Gly Ile Gly Val Arg Asn Cys Pro Gly
    435                 440                 445

Met His Tyr Thr Thr Thr Leu Met Lys Val Ala Leu Ser Lys Ile Ile
    450                 455                 460

Arg Arg Leu Lys Leu Arg Pro Val Gln Lys Asp Phe Arg Phe Glu Asp
465                 470                 475                 480

Ile Gln Phe Glu Thr Phe Ile Met Arg Glu Leu Ala Asn Pro Pro Val
                485                 490                 495

Leu Gln Val Glu Gln Arg Glu
            500

<210> SEQ ID NO 61
<211> LENGTH: 488
<212> TYPE: PRT
<213> ORGANISM: Nezara viridula

<400> SEQUENCE: 61

Met Asp Gly Ile Tyr Lys Val Leu Leu Thr Ile Leu Leu Ala Asn Leu
1               5                   10                  15

Val Phe Gly Val Ile Leu Trp Leu Arg Val Arg Lys Leu Cys Ser Phe
            20                  25                  30

Pro Gly Phe Leu Gly Val Pro Val Ile Gly Asn Leu Phe Tyr Phe Tyr
        35                  40                  45

Lys Thr Leu Phe Leu Ile Thr Ala Asp Ser Leu Glu Asn His Leu Lys
    50                  55                  60

Glu Val Thr Glu Lys His Gly Lys Asn Gly Phe Cys Phe His Ile Ser
65                  70                  75                  80

Tyr Gly Tyr Lys Ile Thr Ala Ile Ile Thr Asn Pro Glu Ile Ile Lys
                85                  90                  95

Lys Ile Ser Phe His Pro Asn Leu Ile Asp Lys Ser Tyr Glu Met Tyr
            100                 105                 110

Gly Gly Phe Leu Asp Tyr Met Arg Gly Pro Phe Ser Arg Pro Arg Ser
            115                 120                 125

Asp Glu Lys Trp Lys Met Trp Arg Lys Glu Tyr Asn Ile Phe Leu Lys
130                 135                 140

Arg Ser Cys Val Asp Asn Asp Tyr Phe Asn Thr Tyr Ile Thr Ser Ala
145                 150                 155                 160

Glu Thr Leu Val Asn Met Met Leu Asp Ser Thr Ser Ala Tyr Gly Ala
            165                 170                 175

Ser Ile Ala Leu Thr Gln Asn Val Thr Met Arg Thr Leu Phe Gly Val
            180                 185                 190

Glu Thr Asp Leu Val Tyr Asn Lys Glu Ile Ile Lys Val Leu Thr Arg
            195                 200                 205

Leu Ile Glu Met Gly Ala Met Leu Gly Ala Asn Thr Asn Ile Ala Arg
210                 215                 220

Ala Ile Ala Pro Ile Val Arg Pro Ile Ala Glu Lys Val Ser Gly Lys
225                 230                 235                 240

Ala Val Val Ile Arg Lys Thr Ile Phe Gln Lys Ile Tyr Lys Thr Ile
            245                 250                 255

Val Ser Lys Lys Glu Pro Leu Ser Glu Pro Arg Leu Ala Met Asn Val
            260                 265                 270

Ala Ala Lys Ser Ile Glu Ser Asn Glu Ser Lys Arg Thr Leu Leu Gln
            275                 280                 285

Leu Met Gln Glu Val Leu Phe Thr Ser Ala His Thr Val Ala Ser Ala
290                 295                 300

Leu Ser Asn Thr Ile Ile Leu Ala Val Gln Pro Asp Met Gln Glu
305                 310                 315                 320

Arg Ala Phe Lys Glu Gln Cys Glu Ile Phe Gly Asn Asp Ser Arg Asp
            325                 330                 335

Pro Thr Ile Glu Asp Val Glu Arg Met Glu Phe Leu Gly Arg Phe Ile
            340                 345                 350

Lys Glu Cys Leu Arg Phe Leu Gly Pro Pro Phe Ser Arg Lys Ala
            355                 360                 365

Thr Ala Asp Ile Asn Leu Asp Gly Thr Ile Ile Pro Lys Gly Ser Ile
370                 375                 380

Val Val Tyr Leu Phe Asn Ser Ile Thr Met Asp Ser Lys Tyr Trp Gln
385                 390                 395                 400

Asn Pro Asn Val Phe Glu Pro Asp Arg Phe Leu Glu Glu Ser Asp Leu
            405                 410                 415

Met Lys Tyr Thr Phe Thr Pro Phe Gly Val Gly Val Arg Ser Cys Pro
            420                 425                 430

Gly Met Tyr Phe Ala Thr Thr Leu Ile Lys Ile Thr Leu Ser Lys Ile
            435                 440                 445

Leu Arg Thr Val Lys Leu Arg Pro Val Asp Lys Asp Phe Arg Phe Glu
            450                 455                 460

Ser Leu Lys Tyr Arg Ser Ser Leu Leu Thr Glu Ile Ala Asn His Pro
465                 470                 475                 480

Lys Leu His Val Glu Arg Arg Ala
            485

<210> SEQ ID NO 62
<211> LENGTH: 517

<212> TYPE: PRT
<213> ORGANISM: Nezara viridula

<400> SEQUENCE: 62

```
Ala Leu Ser Val Gly Trp Pro Thr His Phe Leu Trp Tyr Gln Lys Phe
1               5                   10                  15

His Leu Arg Arg Thr Gln Thr Val Arg Met Ile Glu Thr Ile Leu Tyr
            20                  25                  30

Ala Ala Leu Ala Ile Leu Met Ala His Leu Leu Phe Gly Val Val Leu
        35                  40                  45

Trp Phe Arg Val Arg Lys Phe Tyr Ser Tyr Pro Asn Val Leu Gly Phe
    50                  55                  60

Pro Val Ile Gly Asn Leu Tyr Tyr Phe Tyr Arg Thr Leu Phe Leu Phe
65                  70                  75                  80

Thr Ala Asp Arg Thr Leu Lys Tyr Val Ile Pro Val Ala Glu Glu His
                85                  90                  95

Gly Lys Asp Gly Leu Phe Phe His Trp Met Phe Gly Ser Ser Val Ala
            100                 105                 110

Ala Val Ile Thr Cys Pro His Leu Leu Lys Lys Leu Ser Phe His Pro
        115                 120                 125

Asn Leu Val Asp Lys Pro Tyr Ala Ala Tyr Lys Gly Phe Gln Ile Phe
    130                 135                 140

Met Glu Gly Pro Phe Ser Ala Leu Arg Ser Asp Asp Val Trp Lys Gln
145                 150                 155                 160

His Arg Lys Asp Tyr Asn Asn Tyr Leu Lys Lys Ser Arg Val Asp Lys
                165                 170                 175

Asp Tyr Phe Lys Thr Phe Thr Lys Ser Ala Asp Lys Leu Val Asp Ile
            180                 185                 190

Met Leu Glu Thr Pro Ser Ser Leu Asp Ala Asn Ala Ala Cys Thr Ala
        195                 200                 205

Val Ala His Asp Ile Ser Met Lys Thr Met Phe Ser Val Glu Thr Ser
    210                 215                 220

Leu Val Tyr Arg Pro Glu Cys Leu Arg Tyr Ile Tyr Arg Ile Lys Asp
225                 230                 235                 240

Ile Ser Ser Ile Leu Phe Leu Asn Val Leu Ile Ser Pro Leu Phe
                245                 250                 255

His Ile Leu Gln Pro Leu Ser Asp Leu Thr Ile Gly Lys Leu Thr Glu
            260                 265                 270

Leu Arg Lys Leu Ile Leu Glu Asn Ile Asp Asn Gln Leu Lys Ser Asn
        275                 280                 285

Gln Thr Pro Leu His Glu Leu Pro Phe Ser Thr Tyr Leu Ala Leu Lys
    290                 295                 300

Asn Arg Lys Asp Asn Gly Ser Lys Arg Gln Leu Tyr Asn Lys Ile His
305                 310                 315                 320

Glu Leu Phe Leu Thr Ser Gly His Thr Ile Ser Val Gln Leu Glu Asn
                325                 330                 335

Met Ile Cys Phe Leu Ala Val Leu Pro Asp Ile Gln Glu Arg Ala Trp
            340                 345                 350

Gln Glu Gln Tyr Glu Ile Phe Gly Asn Asp Ile Arg Asp Pro Thr Ile
        355                 360                 365

Asp Asp Leu Asn Gln Met Asn Tyr Leu Asp Arg Phe Leu Lys Glu Ser
    370                 375                 380

Tyr Arg Phe Leu Lys Val Pro Leu Leu Ala Arg Met Ala Thr Ala Asp
385                 390                 395                 400
```

```
Ile Asn Val Asp Gly Ile Thr Ile Pro Ser Gly Thr Val Ile Tyr
                405                 410                 415

Leu Met Gly Tyr Met Lys Phe Leu Pro Lys Tyr Trp Glu Asn Pro Tyr
            420                 425                 430

Ile Phe Asp Pro Asp Arg Phe Leu Glu Glu Ser Asp Leu Leu Lys Cys
        435                 440                 445

Ile Ser Ser Pro Phe Gly Phe Gly Ile Arg Asn Cys Pro Gly Glu Tyr
    450                 455                 460

Tyr Ala Thr Ile Leu Ile Lys Ile Ile Leu Ser Lys Val Leu Arg Lys
465                 470                 475                 480

Leu Lys Phe Arg Pro Val Gln Lys Asp Phe Arg Phe Glu Asp Ile Lys
                485                 490                 495

Phe Lys Ser Tyr Ile Phe Thr Glu Ala Glu Asn Pro Pro Asn Leu Gln
            500                 505                 510

Val Glu Glu Arg Thr
            515

<210> SEQ ID NO 63
<211> LENGTH: 493
<212> TYPE: PRT
<213> ORGANISM: Nezara viridula

<400> SEQUENCE: 63

Met Leu Ile Glu Ala Ile Ile Leu Val Ala Thr Leu Cys Ala Ser
1               5                   10                  15

Tyr Tyr Trp Leu Phe Gly Phe Trp Asn Arg Arg Asn Val Phe Asn Val
                20                  25                  30

Lys Phe Gln Ile Thr Phe Leu Thr Phe Ile Lys Val Leu Ile Lys Asn
            35                  40                  45

Glu His Leu Gly Asn Ile Phe Ala Asp Ile Tyr Lys Lys Tyr Lys Ser
        50                  55                  60

His Gly Met Val Gly Phe Tyr Ile Leu Phe Asp Pro Met Leu Leu Val
65                  70                  75                  80

Thr Asn Pro Lys Leu Val Glu Glu Val Ile Val Lys Glu Phe Asn Lys
                85                  90                  95

Phe His Asp Thr Pro Thr Glu Met Lys Lys Gly Ile Asn Pro Leu Phe
            100                 105                 110

Ala Leu Asn Pro Phe Ala Ala Lys Gly Thr Glu Lys Trp Lys Glu Leu
        115                 120                 125

Arg Ser Ile Gln Ala Ser Asn Met Thr Thr Phe Arg Phe Lys Glu Ile
    130                 135                 140

Leu Pro Ile Ile Tyr Cys Val Ala Glu Asn Met Val Asn Tyr Leu Thr
145                 150                 155                 160

Glu Met Lys Met Glu Pro Ile Ala Ala Lys Glu Leu Ser Phe Leu Phe
                165                 170                 175

Ser Val Glu Ser Ser Cys Leu Cys Gly Phe Gly Val Gln Pro Asn Ala
            180                 185                 190

Phe Thr Asp Ser Glu Asn Ser Phe Ile Glu Tyr Ser Glu Asn Ile Phe
        195                 200                 205

Lys Pro Ser Pro Phe Thr Met Phe Cys His Phe Leu Leu Pro Trp Ile
    210                 215                 220

Gly Asn Leu Leu Lys Leu Arg Ile Leu Ser Lys Asp Ala Glu Glu Ser
225                 230                 235                 240

Phe Ile Leu Phe Val Lys Thr Ile Phe Glu Tyr Arg Ser Arg Ser Asn
```

```
            245                 250                 255
Val Thr Lys Asn Asp Phe Ile Tyr Tyr Leu Met Lys Leu Asn Gln Lys
        260                 265                 270

Leu Lys Glu Gly Asn Lys Pro Glu Tyr Ser Asn Val Glu Leu Ala Gly
            275                 280                 285

His Cys Leu Thr Tyr Tyr Leu Asp Ser Thr Gln Thr Ser Asn Gln
        290                 295                 300

Leu Ala Phe Phe Leu Leu Asp Leu Ala Asn His Gln His Val Gln Asp
305                 310                 315                 320

Lys Leu Arg Lys Glu Ile Ser Ser Ile Ser Asn Ser Pro Arg Asp Phe
            325                 330                 335

Asp Leu Glu Lys Val Asn Ser Ile Arg Tyr Leu Asn Met Ala Ile Asn
        340                 345                 350

Glu Ser Leu Arg Met His Thr Gln Gly Thr Trp Ile Ser Arg Thr Cys
            355                 360                 365

Thr Gln Asp Ala Val Ile Gly Asn Thr Pro Ile Pro Lys Gly Thr Lys
        370                 375                 380

Val Phe Val Pro Val Glu Ala Phe His Asn Asp Pro Glu Trp Phe Pro
385                 390                 395                 400

Ser Pro Glu Lys Phe Asp Pro Glu Arg Phe Ser Glu Arg Lys Asp
            405                 410                 415

Ser Ile Pro Lys Tyr Thr Phe Leu Pro Phe Gly Glu Gly Pro Arg Ile
        420                 425                 430

Cys Val Gly Tyr Lys Leu Ala Leu Leu Gln Ile Arg Met Ala Val Ile
            435                 440                 445

Phe Leu Val Leu Asn Phe Thr Ile Leu Pro Ser Ser Lys Val Asp Arg
450                 455                 460

Glu Glu Ile Val Leu Glu Asn Ala Leu Leu Pro Thr Pro Gly His Asn
465                 470                 475                 480

Ala Lys Leu Lys Phe Lys Pro Met Lys Cys Ile Asp Gln
            485                 490

<210> SEQ ID NO 64
<211> LENGTH: 496
<212> TYPE: PRT
<213> ORGANISM: Nezara viridula

<400> SEQUENCE: 64

Met Ile Ala Glu Ala Ile Val Val Leu Ile Ile Thr Ser Tyr Leu Ser
1               5                   10                  15

Tyr Ile Trp Leu Phe Gly Phe Trp Asp Arg Arg Asn Val Phe Asn Ile
            20                  25                  30

Lys Phe Gly Phe Thr Leu Gln Thr Phe Pro Lys Ile Leu Ile Arg Asn
        35                  40                  45

Glu His Ile Gln Asp Phe Phe Val Asp Leu Tyr Thr Lys Tyr Lys Ser
    50                  55                  60

His Gly Ile Val Gly Phe Tyr Ala Met Phe Thr Pro Met Leu Leu Val
65                  70                  75                  80

Thr Asp Pro Glu Ile Val Lys Thr Val Met Val Lys Asp Phe Asn Lys
            85                  90                  95

Phe Thr Asp Thr Gly Ile Glu Ile Arg Lys Asp Val Asp Pro Leu Phe
        100                 105                 110

Ala Ile Asn Pro Phe Val Ala Lys Gly Ile Glu Lys Trp Lys Glu Leu
    115                 120                 125
```

Arg Ser Ile Gln Ala Ala Asn Leu Thr Ala Val Arg Phe Lys Glu Ile
    130                 135                 140

Ile Pro Thr Ile His Arg Val Ala Glu Ser Met Val Asp Tyr Val Arg
145                 150                 155                 160

Glu Lys Lys Met Glu Pro Ile Thr Ala Gln Lys Leu Ser Phe Met Tyr
                165                 170                 175

Thr Val Asp Asn Ala Cys Ser Cys Gly Phe Gly Ile Glu Pro Ser Ala
            180                 185                 190

Phe Thr Asp Thr Glu Asn Asn Phe Ile Lys Tyr Ala Asn Ser Asp Lys
        195                 200                 205

Leu Phe Asn Pro Ser Pro Leu Thr Met Tyr Cys His Leu Phe Ile Pro
210                 215                 220

Ala Met Thr Ser Val Leu Lys Leu Arg Ile Leu Ser Glu Glu Ala Gly
225                 230                 235                 240

Asp Phe Phe Asp Ser Phe Val Lys Lys Met Ile Glu Tyr Arg Thr Ser
                245                 250                 255

Ser Asn Ile Thr Lys Asn Asp Leu Ile Asn His Ile Met Lys Ile Asn
            260                 265                 270

Gln Lys Leu Lys Glu Glu Asn Lys Pro Ala Tyr Thr Asn Leu Glu Leu
        275                 280                 285

Ala Gly His Cys Met Thr Phe Tyr Val Asp Ser Thr Ala Thr Ser Ala
290                 295                 300

Ser Gln Leu Thr Phe Phe Leu Phe Asp Leu Ala Asp Asn Pro Glu Val
305                 310                 315                 320

Gln Glu Lys Leu Arg Lys Glu Ile Ser Ser Ile Ser Lys Cys Pro Ser
                325                 330                 335

Asp Phe Asp Ile Glu Lys Ile Asn Ser Ile Asn Tyr Leu Asn Met Ala
            340                 345                 350

Ile Asn Glu Ser Ile Arg Ile His Thr Gln Ala Thr Trp Ile Ser Arg
        355                 360                 365

Thr Cys Thr Gln Asp Ser Val Ile Ala Asn Thr Pro Ile Pro Lys Gly
370                 375                 380

Thr Lys Val Phe Ile Pro Ile Gly Gln Phe His Lys Asp Pro Glu Tyr
385                 390                 395                 400

Phe Pro Asp Pro Asn Lys Phe Asp Pro Glu Arg Phe Ser Glu Glu Asn
                405                 410                 415

Lys Asp Ser Ile Pro Lys Tyr Thr Phe Leu Pro Phe Gly Glu Gly Pro
            420                 425                 430

Arg Ile Cys Val Gly Phe Lys Phe Ala Leu Leu Gln Ile Lys Leu Ala
        435                 440                 445

Val Ile Phe Leu Leu Leu Asn Phe Thr Ile Leu Pro Ser Asn Gln Glu
450                 455                 460

Gly Lys Glu Gly Ile Val Ile Asp Asn Thr Ala Phe Val Thr Pro Gly
465                 470                 475                 480

Ser Ser Ser Lys Leu Lys Phe Lys Pro Ile Ile Gln Asp Ile Ser Gln
                485                 490                 495

<210> SEQ ID NO 65
<211> LENGTH: 493
<212> TYPE: PRT
<213> ORGANISM: Nezara viridula

<400> SEQUENCE: 65

Met Leu Val Glu Ala Ile Val Val Leu Phe Ile Ala Leu Cys Leu Ser
1               5                   10                  15

```
Tyr Ser Trp Phe Phe Gly Phe Trp Asp Arg Arg Lys Val Val Asn Val
         20                  25                  30

Lys Phe Glu Phe Thr Tyr Leu Thr Phe Ser Arg Ala Phe Ile Lys Asn
         35                  40                  45

Glu His Leu His Asp Ile Phe Ala Asp Ile Tyr Arg Lys Tyr Lys Ser
         50                  55                  60

Tyr Gly Thr Val Gly Phe Tyr Thr Ile Leu Ser Pro Met Leu Leu Val
65                   70                  75                  80

Thr Asp Pro Glu Leu Val Lys Asp Val Leu Val Lys Glu Phe Asn Lys
             85                  90                  95

Phe His Asp Thr Val Met Glu Met Lys Lys Glu Val Asp Pro Leu Leu
             100                 105                 110

Ala Leu Asn Pro Phe Val Ala Lys Gly Met Glu Lys Trp Lys Glu Leu
             115                 120                 125

Arg Ser Ile Gln Ala Ser Asn Met Thr Thr Val Arg Phe Lys Glu Val
130                 135                 140

Ile Pro Ile Met Tyr Arg Val Ala Glu Asn Met Val Asn Tyr Leu Ala
145                 150                 155                 160

Glu Lys Lys Met Glu Pro Ile Gly Ala Lys Glu Leu Ser Phe Leu Tyr
             165                 170                 175

Thr Val Asp Asn Ser Cys Ser Cys Gly Phe Gly Val Glu Pro Ser Ala
             180                 185                 190

Phe Thr Asp Pro Glu Asn Asn Phe Val Lys Tyr Ala Asn Ser Asp Lys
             195                 200                 205

Ile Phe Lys Pro Ser Pro Tyr Thr Met Leu Phe His Phe Leu Leu Pro
210                 215                 220

Arg Met Ala Asn Ile Leu Lys Leu Arg Ile Ser Ser Glu Asp Ala Glu
225                 230                 235                 240

Glu Phe Phe Lys Ser Phe Val Gln Lys Met Ile Glu Tyr Arg Thr Ser
             245                 250                 255

Ser Asn Ile Thr Lys Asn Asp Phe Ile Asn Tyr Ile Met Lys Leu Asn
             260                 265                 270

Gln Lys Leu Lys Glu Glu Asn Lys Pro Val Tyr Ser Lys Leu Glu Leu
             275                 280                 285

Ala Ala His Cys Leu Thr Phe Tyr Ala Asp Ser Thr Glu Thr Ser Ser
290                 295                 300

Asn Gln Leu Ala Phe Phe Leu Leu Asp Leu Ala Asn His Gln Asp Val
305                 310                 315                 320

Gln Asp Lys Leu Arg Lys Glu Ile Ser Ser Ile Ser Lys Ser Pro Ile
             325                 330                 335

Asp Phe Asp Leu Glu Lys Val Asn Ser Ile Asn Tyr Leu Asn Met Ala
             340                 345                 350

Leu Asn Glu Ser Leu Arg Leu His Thr Gln Gly Asn Trp Leu Ser Arg
             355                 360                 365

Thr Cys Thr Gln Asp Thr Val Ile Gly Asn Ala Pro Ile Pro Lys Gly
             370                 375                 380

Thr Lys Val Phe Val Pro Ile Gly Gln Phe His Lys Asp Pro Glu Tyr
385                 390                 395                 400

Phe Pro Asp Pro Glu Lys Phe Asp Pro Glu Arg Phe Ser Glu Glu Asn
             405                 410                 415

Lys Asp Ser Ile Pro Lys Tyr Thr Phe Leu Pro Phe Gly Glu Gly Pro
             420                 425                 430
```

```
Arg Ile Cys Val Gly Phe Lys Phe Ala Leu Leu Gln Ile Arg Leu Ala
            435                 440                 445

Val Ile Phe Leu Val Leu Asn Phe Thr Ile Leu Pro Ser Asn Glu Asp
450                 455                 460

Gly Lys Glu Glu Ile Val Leu Glu Asn Ala Pro Leu Pro Thr Pro Ala
465                 470                 475                 480

Pro Thr Ser Lys Leu Lys Phe Lys Pro Ile Asn Thr Tyr
                485                 490

<210> SEQ ID NO 66
<211> LENGTH: 491
<212> TYPE: PRT
<213> ORGANISM: Nezara viridula

<400> SEQUENCE: 66

Met Leu Leu Glu Ile Phe Ile Ile Ala Leu Ser Ala Leu Tyr Leu Phe
1               5                   10                  15

Asn Trp Trp Ala His Gly Tyr Trp Lys Arg Lys Asn Val Phe Ser Val
                20                  25                  30

Pro Thr Glu Phe Leu Phe Gly Asn Val Arg Leu Leu Leu Gln Gln Lys
            35                  40                  45

Ile Thr Met Tyr Gly Met Tyr Arg Asn Phe Tyr Gln Lys Tyr Lys Glu
        50                  55                  60

His Lys Ile Ile Gly Phe Tyr Ser Phe Tyr His Pro Ala Leu Leu Val
65                  70                  75                  80

Thr Asp Pro Glu Ile Ile Lys Arg Ile Leu Val Thr Asp Phe Asn Ser
                85                  90                  95

Phe Ser Asn Ser Gly Ser Asp Met Asn Lys Thr Leu Asp Pro Ile Phe
            100                 105                 110

Gly Leu Asn Pro Phe Leu Leu Lys Ser Ile Pro Glu Trp Lys Glu Ser
        115                 120                 125

Arg Ser Val Gln Ala Ala His Gln Thr Gln Val Lys Leu Arg Glu Leu
    130                 135                 140

Val Pro Gly Phe Ile Lys Val Ala Asp Phe Met Phe Asp Phe Ile Lys
145                 150                 155                 160

Asn Gln Lys Asn Gln Thr Ile Lys Val Leu Asp Leu Ala Thr Arg Ile
                165                 170                 175

Met Val Asp Phe Ser Val Leu Ser Ala Phe Gly Leu Glu Pro Lys Ser
            180                 185                 190

Phe Thr Asp Pro Asp Phe Gly Phe Leu Lys His Ala Cys Ser Glu Lys
        195                 200                 205

Val Phe Ala Ser Ser Arg Trp Asn Thr Ile Gly Ser Ile Phe His Pro
    210                 215                 220

Leu Leu Ile Arg Ile Phe Ser Leu Arg Phe Val Thr Lys Glu Ala Glu
225                 230                 235                 240

Asp Phe Phe Leu His Ile Ser Lys Thr Asn Leu Glu His Arg Leu Ser
                245                 250                 255

Ala Lys Ile Thr Arg Asn Asp Leu Phe Asp Thr Ile Met Lys Ser Gln
            260                 265                 270

Lys Lys Asn Glu Gly Gln Asn Lys Glu Lys Ile Gln Ala Glu Met
        275                 280                 285

Val Ile Ala Ala Asn Cys Ala Thr Phe Tyr Met Asp Ala Thr Ile Thr
    290                 295                 300

Ser Ser Ser Val Leu Cys Phe Ile Leu Leu Glu Leu Ala Ser His Gln
305                 310                 315                 320
```

```
Asp Ile Gln Glu Lys Leu Arg Glu Glu Ile Leu Ser Val Gly Lys Lys
            325                 330                 335

Pro Glu Asp Phe Asp Phe Glu Lys Ile Asn Thr Met Thr Tyr Leu Gln
        340                 345                 350

Met Val Phe Asp Glu Cys Met Arg Leu His Pro Val Pro Ser Leu
    355                 360                 365

Ser Arg Thr Cys Thr Lys Asp Ile Val Ile Asn Asp Ile Lys Ile Ser
370                 375                 380

Lys Gly Thr Lys Val Phe Ile Ser Ala Leu Ala Leu His Gln Asp Pro
385                 390                 395                 400

Val Tyr Tyr Pro Glu Pro Met Lys Phe Asp Pro Glu Arg Phe Ser Glu
                405                 410                 415

Val Asn Lys Ser Ser Arg Val Lys Tyr Thr Tyr Leu Pro Phe Gly Glu
                420                 425                 430

Gly Pro Arg Ile Cys Val Gly Phe Lys Tyr Gly Thr Leu Val Val Lys
            435                 440                 445

Thr Ala Thr Ile Phe Ile Leu Leu Lys Tyr Arg Ile Leu Ala Ser Asn
        450                 455                 460

Asn Ala Lys Gly Ser Leu His Asp Pro Phe Glu Phe Leu Ser Pro
465                 470                 475                 480

Lys Pro Asp Ala Thr Ile Ile Phe Gln Glu Leu
                485                 490

<210> SEQ ID NO 67
<211> LENGTH: 508
<212> TYPE: PRT
<213> ORGANISM: Nezara viridula

<400> SEQUENCE: 67

Leu Ser Ser Trp Leu Lys Lys Thr Ser Thr Thr Ser Trp Phe Asn Phe
1               5                   10                  15

Tyr Asn Asn Met Leu Leu Glu Thr Ile Ile Val Leu Ser Ser Val Leu
                20                  25                  30

Phe Ile Phe Asn Trp Trp Ala Tyr Gly Tyr Trp Arg Arg Arg Asn Val
            35                  40                  45

Tyr Ser Leu Pro Thr Glu Phe Leu Phe Gly Asn Ile Lys Glu Ile Ile
        50                  55                  60

Met Asn Gln Lys Val Met Cys Leu Lys Phe Arg Asp Ile Tyr Glu Gln
65                  70                  75                  80

Tyr Lys Gln His Arg Met Val Gly Phe Tyr Ser Phe Tyr Lys Pro Met
                85                  90                  95

Leu Phe Val Ser Asp Pro Glu Ile Ile Lys Arg Val Leu Ala Thr Asp
                100                 105                 110

Phe Asn Ser Phe Ser Ser Asn Gly Phe Thr Met Asp Lys Asp Ile Asp
            115                 120                 125

Pro Ile Met Gly Phe Asn Pro Phe Thr Ala Lys Thr Val Pro Leu Trp
        130                 135                 140

Lys Glu Leu Arg Ser Ile Gln Ala Ser Asn Leu Thr Ala Leu Lys Leu
145                 150                 155                 160

Lys Glu Val Val Pro Gly Met Val Lys Ile Gly Glu Phe Met Lys Asp
                165                 170                 175

Tyr Ile Lys Asn Lys Lys Ser Gln Pro Val Ser Val Phe Asp Ile Thr
                180                 185                 190

Thr Arg Ala Ala Val Asp Ser Ala Ile Leu Phe Gly Phe Gly Ile Glu
```

```
            195                 200                 205
Pro Lys Ser Phe Thr Asp Ser Glu Phe Ser Phe Met Lys Tyr Gly Thr
210                 215                 220

Val Glu His Leu Phe Ser Thr Asn Tyr Met Asn Thr Ile Ser Ser Phe
225                 230                 235                 240

Phe Leu Pro Ser Leu Ser Lys Ile Phe Asn Ser Arg Ile Thr Ser Lys
                245                 250                 255

Ala Ala Glu Asp Phe Phe Ile Ser Met Thr Lys Thr Asn Ile Glu His
                260                 265                 270

Arg Lys Thr Thr Lys Ile Thr Arg Gly Asp Leu Phe Asp Thr Ile Leu
                275                 280                 285

Lys Leu Asn Lys Lys Leu Glu Gln Gly Asp Lys Ala Tyr Ser Asn
290                 295                 300

Leu Glu Met Ser Ala His Cys Ala Thr Phe Tyr Leu Asp Ala Thr Val
305                 310                 315                 320

Thr Ser Ala Thr Val Ser Thr Phe Leu Leu Leu Glu Leu Ala Thr His
                325                 330                 335

Gln Asp Ile Gln Glu Lys Leu Arg Arg Glu Ile Phe Leu Val Gly Lys
                340                 345                 350

Lys Pro Glu Asp Phe Asp Phe Asp Lys Ile Asn Gly Ile Pro Tyr Leu
                355                 360                 365

Gln Met Val Phe Asp Glu Ser Ile Arg Ile His Ser Pro Val Thr Val
                370                 375                 380

Leu Thr Arg Ser Cys Thr Lys Asp Thr Val Ile Glu Asp Val Lys Ile
385                 390                 395                 400

Ser Lys Gly Thr Lys Val Phe Ile Ser Ser Leu Ala Leu His Tyr Asp
                405                 410                 415

Pro Glu Tyr Tyr Pro Glu Pro Glu Lys Phe Asp Pro Glu Arg Phe Ser
                420                 425                 430

Glu Asn Asn Lys Glu Ser Met Thr Lys Tyr Thr Phe Leu Pro Phe Gly
                435                 440                 445

Glu Gly Pro Arg Ile Cys Val Gly Leu Lys Tyr Gly Asn Leu Phe Val
450                 455                 460

Lys Thr Leu Ile Ala Phe Ile Leu Leu Lys Tyr Arg Ile Leu Pro Thr
465                 470                 475                 480

Tyr Asp Gln Asn Lys Val Leu His Asp Tyr Glu Asn Phe Leu Leu Val
                485                 490                 495

Pro Lys Ser Asp Ala Thr Ile Lys Phe Glu Glu Leu
                500                 505

<210> SEQ ID NO 68
<211> LENGTH: 489
<212> TYPE: PRT
<213> ORGANISM: Nezara viridula

<400> SEQUENCE: 68

Met Leu Leu Glu Ile Ile Ile Leu Leu Leu Ser Ala Ile Phe Ile Phe
1               5                   10                  15

Asn Trp Trp Ala His Gly Tyr Trp Lys Lys Arg Asn Val Phe Ser Ile
                20                  25                  30

Pro Thr Glu Phe Leu Phe Gly Asn Thr Arg Glu Leu Val Met Gly Gln
            35                  40                  45

Thr Leu Met Ala Leu Met Phe Glu Asp Ile Tyr Lys Lys Tyr Lys Lys
50                  55                  60
```

His Arg Met Ile Gly Phe Tyr Cys Phe Tyr Lys Pro Met Leu Phe Ile
65                  70                  75                  80

Thr Asp Pro Asp Ile Val Lys Lys Ile Phe Val Thr Glu Phe Asn Asn
                85                  90                  95

Phe Ser Asn Asn Gly Phe Thr Val Ser Lys Glu Val Asp Pro Leu Leu
            100                 105                 110

Gly Phe Asn Pro Phe Thr Ala Lys Asn Ser Ile Gln Trp Lys Glu Leu
        115                 120                 125

Arg Ser Ile Gln Ala Leu Asn Gln Thr Pro Leu Lys Leu Arg Glu Val
    130                 135                 140

Val Ser Ser Leu Ala Lys Ile Gly Glu Phe Met Tyr Asp Phe Ile Lys
145                 150                 155                 160

Asn Gln Lys Gly Glu Ser Ile Ala Val Leu Asp Leu Thr Thr Arg Ala
                165                 170                 175

Ala Ile Asp Ser Ala Val Leu His Gly Phe Gly Ile Glu Pro Lys Ser
            180                 185                 190

Phe Thr Asp Ser Glu Phe Gly Phe Met Lys His Ala Ser Gly Asp Lys
        195                 200                 205

Phe Phe Glu Thr Ser Ser Trp Asn Ile Phe Ala Ala Leu Phe Phe Pro
    210                 215                 220

Ser Leu Asn Lys Leu His Asn Phe Arg Ile Thr Ser Lys Glu Ala Glu
225                 230                 235                 240

Asp Phe Phe Lys Cys Val Thr Lys Thr Asn Ile Asp His Arg Gln Ser
                245                 250                 255

Ala Asn Ile Thr Arg Gly Asp Ile Val Asp Thr Ile Ile Lys Leu Asn
            260                 265                 270

Lys Lys Lys Leu Glu Gln Thr Asn Lys Ala Tyr Thr Asp Leu Glu Met
        275                 280                 285

Thr Ala His Cys Ala Thr Phe Tyr Leu Asp Ala Thr Val Thr Ala Ser
    290                 295                 300

Met Val Leu Ala Phe Phe Leu Leu Glu Leu Ala Asn His Ile Asp Val
305                 310                 315                 320

Gln Glu Lys Leu Arg Ser Glu Ile Lys Ser Val Gly Asn Lys Pro Glu
                325                 330                 335

Asp Phe Asp Tyr Asp Lys Ile Asn Ser Ile Pro Tyr Leu Gln Met Val
            340                 345                 350

Leu Asp Glu Thr Leu Arg Met His Thr Pro Leu Thr Val Met Ser Arg
        355                 360                 365

Ile Cys Thr Arg Asp Thr Val Leu Glu Asp Val Lys Ile Cys Lys Gly
    370                 375                 380

Thr Arg Ile Phe Ile Ser Ser Ile Ala Leu His Asn Asp Pro Glu Tyr
385                 390                 395                 400

Phe Pro Asp Pro Glu Lys Phe Glu Pro Glu Arg Phe Ser Glu Ser Asn
                405                 410                 415

Lys Glu Leu Met Thr Lys Tyr Thr Phe Leu Pro Phe Gly Glu Gly Pro
            420                 425                 430

Arg Ile Cys Val Gly Met Lys Tyr Ala Thr Ile Phe Val Lys Thr Ile
        435                 440                 445

Ile Ala Phe Ile Leu Leu Lys Tyr Arg Ile Leu Pro Ser Gly Asp Lys
    450                 455                 460

Asn Thr Ser Leu Asn Glu Tyr Asp Ser Phe Leu Leu Ile Val Lys Pro
465                 470                 475                 480

Asp Ala Ala Val Lys Leu Glu Glu Leu

-continued

```
<210> SEQ ID NO 69
<211> LENGTH: 488
<212> TYPE: PRT
<213> ORGANISM: Nezara viridula

<400> SEQUENCE: 69

Met Leu Leu Glu Ile Ile Val Leu Leu Ala Ser Phe Leu Leu Ile Phe
1               5                   10                  15

Asn Trp Trp Gly His Gly Tyr Trp Lys Arg Arg Asn Val Phe Ser Ile
            20                  25                  30

Pro Lys Leu Phe Leu Phe Gly Asn Phe Trp Gln Leu Val Met Gly Gln
        35                  40                  45

Lys Val Ser Leu Met Phe Cys Asp Ile Tyr Lys Lys Tyr Lys Lys His
    50                  55                  60

Arg Val Val Gly Phe Tyr Cys Phe Tyr Lys Pro Met Leu Leu Ile Ser
65                  70                  75                  80

Asp Pro Glu Ile Ile Lys Arg Val Leu Val Ile Asp Phe Asn Ser Phe
                85                  90                  95

Ser Asp Asn Gly Phe Val Val Asp Lys Asp Ile Asp Pro Leu Phe Gly
            100                 105                 110

Tyr Asn Pro Phe Thr Ala Lys Thr Ile Pro Leu Trp Lys Glu Leu Arg
        115                 120                 125

Ser Ile Gln Ala Ala Asn Gln Thr Pro Leu Lys Leu Lys Glu Val Val
    130                 135                 140

Pro Ser Leu Ala Asn Ile Lys Glu Phe Met Tyr Asp Phe Ile Lys Asn
145                 150                 155                 160

Gln Lys Asn Gln Pro Ile Glu Val Ser Asp Leu Thr Leu Arg Ala Ala
                165                 170                 175

Ile Asp Ser Ala Val Leu Asn Gly Phe Gly Ile Glu Pro Lys Ser Phe
            180                 185                 190

Thr Asp Pro Glu Phe Ser Phe Met Thr His Ala Ser Gly Glu Lys Leu
        195                 200                 205

Phe Glu Ala Thr Phe Val Thr Met Ile Ser Ala Phe Phe Pro Leu
    210                 215                 220

Ile Asn Arg Leu Phe Ser Leu Arg Met Thr Ser Lys Glu Ala Glu Glu
225                 230                 235                 240

Phe Phe Val Ser Met Ala Lys Thr Asn Ile Asp Tyr Arg Gln Ser Ala
                245                 250                 255

Lys Ile Thr Arg Ser Asp Leu Phe Asp Thr Ile Met Lys Leu Asn Gln
            260                 265                 270

Lys Lys Leu Glu Gln Gly Asn Lys Ala Tyr Ser Ala Leu Glu Met Ser
        275                 280                 285

Ser His Cys Ala Ser Phe Tyr Met Asp Ala Thr Ile Thr Ser Ser Ala
    290                 295                 300

Val Leu Ser Phe Ile Leu Leu Glu Leu Ala Tyr His Gln Asp Val Gln
305                 310                 315                 320

Asp Lys Leu Arg Arg Glu Ile Phe Leu Ile Gly Lys Lys Pro Glu Asp
                325                 330                 335

Leu Asp Phe Asp Lys Ile Asn Ser Met Thr Tyr Leu Gln Met Val Phe
            340                 345                 350

Asp Glu Thr Leu Arg Met His Pro Pro Val Met Ile Val Ser Arg Leu
        355                 360                 365
```

```
Cys Thr Lys Asp Thr Glu Ile Glu Asp Val Lys Ile Ser Lys Gly Thr
    370                 375                 380

Lys Val Phe Ile Ser Pro Phe Ala Leu His Tyr Asp Pro Glu Tyr Phe
385                 390                 395                 400

Pro Asn Pro Glu Lys Phe Asp Pro Asp Arg Phe Ser Asp Ile Asn Lys
                405                 410                 415

Glu Ser Met Thr Lys Tyr Ser Phe Leu Pro Phe Gly Glu Gly Pro Arg
            420                 425                 430

Ile Cys Val Gly Met Lys Tyr Ala Asn Ile Phe Val Lys Thr Ser Ile
                435                 440                 445

Ala Leu Ile Leu Leu Lys Tyr Lys Ile Leu Pro Ala Tyr Asp Gln Asn
450                 455                 460

Glu Ser Leu His Asp Ile Asp His Phe Leu Leu Gly Pro Lys Pro Asn
465                 470                 475                 480

Ala Ala Val Lys Phe Glu Glu Phe
                485
```

<210> SEQ ID NO 70
<211> LENGTH: 513
<212> TYPE: PRT
<213> ORGANISM: Nezara viridula

<400> SEQUENCE: 70

```
Leu Ile Pro Cys Thr Ile Lys Leu Gln Glu Val Gln Glu Leu Gln Ile
1               5                   10                  15

Ile Met Leu Gly Leu Ile Thr Ser Leu Ile Cys Leu Val Phe Val Ala
                20                  25                  30

Ala Tyr Ile Phe Leu Lys Arg Arg Tyr Thr Tyr Trp Lys Met Leu Gly
            35                  40                  45

Val Ala Gly Pro Glu Pro Thr Met Val Val Gly Asn Met Lys His Ile
50                  55                  60

Ile Ser Leu Lys Phe Ser Glu Pro Asp Met Met Asn Gly Trp Tyr Lys
65                  70                  75                  80

Glu Tyr Lys Asn Glu Pro Tyr Ile Gly Tyr Tyr Asn Phe Trp Lys Pro
                85                  90                  95

Thr Leu Phe Val Ile Asp Pro Glu Leu Ile Lys Ala Ile Thr Glu Thr
                100                 105                 110

Asp Phe Asn His Phe Thr Asp His Pro Asn Phe Thr Thr Glu Thr Glu
            115                 120                 125

Thr Asp Ala Ile Leu Asp Ser Leu Phe Asp Met Lys Gly Ala Arg Trp
130                 135                 140

Lys Ala Lys Arg Gln Ile Phe Thr Lys Leu Phe Ser Pro Lys Lys Leu
145                 150                 155                 160

Arg Glu Leu Ser Asn Ile Leu Glu Glu Gln Gln Asp Ser Leu Leu Gly
                165                 170                 175

Glu Phe Glu Lys Leu Leu Lys Ser Thr Asp Glu Val Glu Leu Met Arg
            180                 185                 190

Ile Met Glu Arg His Val Leu Lys Ile Leu Thr Ser Phe Met Tyr Ser
            195                 200                 205

Ile Asp Ser Ser Gln Asn Gln Glu Ser His Ser Lys Leu Ser Glu Leu
210                 215                 220

Ser Glu Ile Phe Ala Arg Pro Pro Gly Ser Ser Val Arg Arg Phe Leu
225                 230                 235                 240

Phe Phe Val Val Phe Pro Ser Leu Tyr His Lys Leu Lys Leu Ser Ala
                245                 250                 255
```

Phe Pro Arg Val Phe Trp Asn Tyr Phe Asn Asn Phe Thr Asn Glu Leu
260 265 270

Leu Gln Ser Arg Asn Asp Gln Asn Val Asn Arg Glu Asp Leu Val Ala
275 280 285

Leu Ile Gly Lys Met Gln Lys Glu Gly Leu Leu Glu Thr Asp Arg Ile
290 295 300

Gly His Asn Glu Ala Val Gly His Val Phe Gly Phe Leu Ile Ala Gly
305 310 315 320

His His Thr Thr Met Thr Thr Val Ser His Ala Ile Tyr Gln Leu Ser
325 330 335

Leu His Pro Gln Ile Gln Glu Lys Leu Arg Thr Glu Val Asp Ser Val
340 345 350

Leu Lys Gly Lys Asp Asn Ile Thr Tyr Asp Ser Ile Lys Gln Met Thr
355 360 365

Tyr Leu Asp Gly Val Ile Asn Glu Thr Leu Arg Leu Phe Pro Leu Leu
370 375 380

Gly Val Leu Lys Arg Thr Cys Thr Gln Thr Tyr Lys Ile Asn Asp Lys
385 390 395 400

Leu Thr Ile Pro Lys Gly Met Asp Ile Ser Ile Pro Ala Tyr Ser Ile
405 410 415

His Thr Asp Pro Glu Tyr Phe Pro Glu Pro Glu Lys Phe Ile Pro Glu
420 425 430

Arg Phe Thr Asp Ala Glu Thr Pro Pro Ser Leu Phe Met Ser Phe Gly
435 440 445

Lys Gly Pro Arg Met Cys Ile Gly Lys Arg Phe Ala Tyr Ile Ser Met
450 455 460

Lys Ser Ile Ile Ala Lys Ile Ile Ser Glu Tyr Ile Ile Leu Pro Gly
465 470 475 480

Thr Lys Thr Arg Lys Pro Leu Gln Phe Asp Thr Ser Thr Phe Phe Ile
485 490 495

Thr Val His Pro Val Gly Gly Leu His Val Arg Leu Gln Lys Arg Ile
500 505 510

Lys

<210> SEQ ID NO 71
<211> LENGTH: 523
<212> TYPE: PRT
<213> ORGANISM: Nezara viridula

<400> SEQUENCE: 71

Met His Leu Trp Tyr Phe Arg Thr Val Gln Phe Pro Tyr Ser Ile Gly
1 5 10 15

Glu Met Phe Glu Gln Ser Thr Ile Ile Phe Ile Leu Phe Phe Ile Thr
20 25 30

Ala Val Phe Cys Ser Phe Leu Gly Val Cys Tyr Glu Tyr Met Lys Arg
35 40 45

Arg Tyr Arg Tyr Trp Ser Asp Ile Gly Ile Pro Gly Pro Lys Pro Glu
50 55 60

Phe Ile Ile Gly Asn Met Lys Glu Ser Leu Phe Met Lys Cys Thr Glu
65 70 75 80

Pro Glu Met Thr Asp Val Trp Tyr Lys Asp Tyr Arg Gly Asn Pro Tyr
85 90 95

Ile Gly Phe Tyr Asn Leu Leu Lys Pro Ser Leu Phe Ile Met Asp Pro
100 105 110

-continued

Glu Leu Ile Arg Lys Val Thr Glu Val Asp Phe Asn His Phe Ile Asp
            115                 120                 125

His Pro Ser Phe Ser Glu His Ser Gly Ser Asp Val Ile Ile Tyr Ser
    130                 135                 140

Leu Phe Ala Met Lys Asp Gln Val Trp Lys Val Lys Arg Pro Ile Phe
145                 150                 155                 160

Ser Arg Leu Phe Thr Pro Lys Lys Leu Arg Glu Gln Ile Glu Ile Phe
                165                 170                 175

Asn Asn Arg Tyr Ser Leu Leu Lys Glu Glu Ile Glu Asn Lys Ser Glu
            180                 185                 190

Leu Arg Lys Asp Thr Glu Leu Leu Lys Phe Ile Gly Arg Tyr Ile Leu
        195                 200                 205

Ile Ser Phe Ser Thr Ile Leu Tyr Gly Leu Asp Leu Met Lys Asp Glu
    210                 215                 220

Lys Leu Phe Glu Asp Leu Glu Gly His Ser Glu Lys Phe Phe His Pro
225                 230                 235                 240

Gly Leu His Gln Ala Leu Met Phe Leu Phe Tyr Thr Ala Ser Pro Asp
                245                 250                 255

Leu Phe Asn Phe Leu Arg Met Lys Thr Phe Pro Arg Asp Ile Trp Lys
            260                 265                 270

Tyr Phe Ser Pro Phe Thr Lys Glu Leu Gln Glu His Asn Lys Arg Leu
        275                 280                 285

Val Asn Thr Asn Gly Cys Asn Leu Val Ser Leu Leu Asn Gln Tyr Gln
    290                 295                 300

Asp Ser Glu Pro Ala Ser Ala Ile Asp His Pro Glu Ala Val Gly His
305                 310                 315                 320

Ile Phe Ser Phe Ser Ala Ser Asn His Thr Thr Ile Thr Thr Val
                325                 330                 335

Ser Tyr Gly Leu Phe Leu Leu Gly Gln His Pro Glu Val Gln Asp Met
            340                 345                 350

Leu Arg Glu Glu Val Asp Arg Val Leu Lys Arg Asn Gln Asn Ile Thr
        355                 360                 365

Ser Glu Asn Ile Asn Asp Met Val Tyr Leu Asp Ala Val Leu Asn Glu
    370                 375                 380

Thr Met Arg Leu Tyr Pro Leu Leu Gly Val Leu Lys Arg Val Cys Thr
385                 390                 395                 400

Lys Lys Tyr Tyr Val Asp Glu Leu Leu Thr Ile Pro Glu Gly Met Asp
                405                 410                 415

Val Phe Ile Pro Val Gln Ala Leu His Met Asp Pro Glu Tyr Phe Pro
            420                 425                 430

Glu Pro Glu Lys Phe His Pro Glu Arg Phe Leu Gly Leu Glu Lys Leu
        435                 440                 445

Pro Ser Ile Phe Met Pro Phe Gly Arg Gly Pro Arg Asn Cys Ile Gly
    450                 455                 460

Leu Arg Met Ala Glu Ile Ala Phe Lys Ile Ala Val Ala Arg Leu Ile
465                 470                 475                 480

Ser Asp Tyr Val Ile Leu Pro Asn Pro Lys Ser Thr Leu Pro Ile Lys
                485                 490                 495

Phe Asp Pro Arg Ser Leu Phe Ile Thr Cys Met Pro Glu Asn Gly Leu
            500                 505                 510

Trp Val Lys Leu Gln Lys Arg Glu Thr His Gln
        515                 520

<210> SEQ ID NO 72
<211> LENGTH: 442
<212> TYPE: PRT
<213> ORGANISM: Nezara viridula

<400> SEQUENCE: 72

Met Leu Asp Gln Ser Thr Ser Ile Leu Ile Ser Ile Thr Ala Val Phe
1 5 10 15

Phe Val Phe Leu Gly Val Cys Tyr Glu Tyr Leu Lys Arg Arg Tyr Arg
20 25 30

Tyr Trp Ser Asp Lys Gly Ile Pro Gly Pro Lys Pro Ile Val Phe Ile
35 40 45

Gly Asn Met Lys Glu Ser Leu Phe Arg Lys Cys Thr Glu Pro Gln Met
50 55 60

Thr Asp Val Trp Tyr Gln Asn Tyr Arg Gly Ser Pro Tyr Ile Gly Phe
65 70 75 80

Tyr Asn Leu Leu Lys Pro Ser Val Phe Leu Ile Asp Pro Glu Leu Ile
85 90 95

Arg Lys Val Thr Glu Val Asp Phe Asn His Phe Val Asp His Pro Pro
100 105 110

Leu Ser Gly His Ser Gly Ser Asp Ala Ile Ile Asp Ser Leu Phe Thr
115 120 125

Met Asn Gly Gln His Trp Lys Asp Lys Arg Ser Ile Phe Ser Arg Met
130 135 140

Phe Thr Pro Lys Arg Leu Arg Glu Gln Ile Glu Ile Phe Asn Asn Arg
145 150 155 160

Tyr Ser Phe Leu Lys Glu Glu Ile Glu Lys Gln Pro Gly Leu Asn Lys
165 170 175

Asp Ala Asp Leu Phe Lys Phe Ile Gly Arg Tyr Ile Leu Ile Gly Phe
180 185 190

Ser Thr Ile Leu Tyr Gly Leu Asp Leu Thr Lys Asp Glu Lys Leu Phe
195 200 205

Glu Asp Phe Glu Arg His Ser Glu Ile Phe Leu His Pro Gly Leu His
210 215 220

Thr Ser Leu Met Phe Leu Phe Tyr Ser Ala Ser Pro Asn Leu Phe Asn
225 230 235 240

Leu Leu Ser Met Lys Thr Phe Pro Arg Asp Ile Tyr His Tyr Phe Ser
245 250 255

Pro Leu Thr Lys Gly Leu Leu Glu Gln Asn Lys Lys Leu Gly Tyr Thr
260 265 270

Asn Ser Ser Asp Leu Pro Ser Leu Leu Asn Gln Tyr Gln Asp Ser Asn
275 280 285

Pro Ala Ser Ala Ile Asp His Pro Glu Ser Val Gly His Ile Phe Ser
290 295 300

Phe Leu Ser Ala Ser Asn His Thr Thr Ile Thr Thr Ile Ser Tyr Gly
305 310 315 320

Leu Phe Leu Leu Gly Gln His Pro Glu Val Gln Asp Lys Leu Arg Asp
325 330 335

Glu Val Asp Arg Val Leu Lys Asp Asn Gln Asp Ile Thr Ser Glu Asn
340 345 350

Ile Asn Glu Met Val Tyr Leu Asp Ala Val Leu Tyr Glu Thr Met Arg
355 360 365

Met Tyr Thr Leu Leu Gly Val Leu Lys Arg Ile Cys Thr Lys Lys Tyr
370 375 380

```
Tyr Val Asp Glu Arg Leu Thr Ile Pro Glu Gly Met Glu Val Phe Ile
385                 390                 395                 400

Pro Ala Gln Ser Leu His Met Asp Pro Glu Tyr Phe Pro Glu Pro Glu
            405                 410                 415

Lys Phe Asn Pro Glu Arg Phe Leu Gly Leu Glu Lys Leu Pro Ser Ile
            420                 425                 430

Phe Met Pro Phe Gly Arg Gly Pro Arg Asn
            435                 440

<210> SEQ ID NO 73
<211> LENGTH: 495
<212> TYPE: PRT
<213> ORGANISM: Nezara viridula

<400> SEQUENCE: 73

Met Ala Ile Val Glu Leu Ile Phe Val Ala Phe Leu Leu Ser Ile Ile
1               5                   10                  15

His Ile Val Gln His Phe Arg Lys Thr Met Ser Tyr Trp Lys Val Arg
            20                  25                  30

Gly Val Lys His Ile Pro Pro Leu Pro Val Val Gly Asn Met Leu Arg
            35                  40                  45

Ala Phe Lys Phe Asp Arg His Phe His Val Tyr Asn Lys Met Tyr
50                  55                  60

His Ala Phe Pro Glu Glu Arg Met Val Gly Met Tyr Glu Phe Thr Thr
65                  70                  75                  80

Ala Thr Leu Ile Leu Arg Asp Pro Glu Leu Ile Lys Thr Val Leu Val
            85                  90                  95

Ser Glu Phe Ser Thr Phe Pro Asp Arg Gly Pro Ile Met Phe Asn Pro
            100                 105                 110

Gly Cys Ile Leu Tyr Trp Ser Ile Phe Ser Leu Gly Gly Asn Lys Trp
            115                 120                 125

Arg Ala Ile Arg Ser Lys Leu Leu Thr Pro Phe Thr Thr Gly Arg Leu
    130                 135                 140

Lys Leu Ile Leu Pro Ser Val Thr Arg Ser Cys Leu Glu Phe Leu Glu
145                 150                 155                 160

Ser Gly Pro Lys Glu Leu Thr Leu Asp Ile Leu Arg Gln Leu Thr Leu
            165                 170                 175

Arg Ile Phe Ser Gln Thr Met Phe Gly Ile Asp Ile Lys Ser Glu Glu
            180                 185                 190

Ala Glu Phe Leu Glu Asn Tyr Arg Gly Met Leu Ser Val Ser Lys Ser
            195                 200                 205

Lys Val Val Gln Gln Val Gly Leu Thr Phe Phe Pro Arg Phe Ser Asp
    210                 215                 220

Phe Met Ser Phe Lys Phe Met Pro Ile His Leu Glu Lys Tyr Phe Arg
225                 230                 235                 240

Ser Phe Leu Asn Ala Ile Leu Asn Lys Lys Met Asp Asp Ser Ser Trp
            245                 250                 255

Arg Asp Asp Ala Ile Thr Ile Leu Asn Glu Met Arg Lys Arg Gly Lys
            260                 265                 270

Val His Phe His Asp Lys Glu Lys Asp Met Glu Leu Phe Asp Phe
            275                 280                 285

Asn Asp Glu Leu Ala Gln Ala Gln Ala Phe Leu Leu Leu Phe Ala Ala
    290                 295                 300

Leu Glu Pro Ser Ser Ile Thr Leu Met His Leu Ala Tyr Asp Leu Ala
```

```
              305                 310                 315                 320
        Gln Ser Pro Asp Ser Gln Asn Lys Ala Arg Gln Glu Ile Lys Ala Leu
                        325                 330                 335

Leu Gln Lys Tyr Gly Gly Tyr Ser Trp Glu Cys Val Lys Glu Met Lys
                        340                 345                 350

Tyr Leu Asn Cys Cys Leu Lys Glu Thr Leu Arg Leu His Pro Pro Leu
                        355                 360                 365

Gln Phe Leu Asn Arg Val Cys Asn Lys Asp Thr Glu Leu Gly Gly Val
                370                 375                 380

Lys Leu Asp Lys Gly Thr Arg Ile Val Val Pro Leu Gln Asn Leu His
        385                 390                 395                 400

Leu Asp Pro Asn Tyr Phe Ser Asp Pro Lys Lys Tyr Lys Pro Glu Arg
                        405                 410                 415

Phe Leu Asp Glu Lys Ile His Gln Phe Ile Tyr Leu Pro Phe Ser Asp
                        420                 425                 430

Gly Pro Arg Ile Cys Leu Gly Ser Arg Phe Phe Ile Met Glu Ala Leu
                        435                 440                 445

Thr Leu Phe Ala His Ile Leu Glu Lys Phe Glu Leu Ser Ile Ser Lys
                        450                 455                 460

Glu Met Lys Leu Pro Leu Lys Tyr Glu Pro Ile Thr Val Phe Leu Thr
        465                 470                 475                 480

Pro Lys Ile Asn Asn Pro Val Ile Ile His Leu Lys Lys Ile Asn
                        485                 490                 495

<210> SEQ ID NO 74
<211> LENGTH: 502
<212> TYPE: PRT
<213> ORGANISM: Nezara viridula

<400> SEQUENCE: 74

Met Tyr Gln Ile Pro Leu Ala Leu Phe Ile Ile Thr Ala Ile Cys Gly
1               5                   10                  15

Leu Leu Tyr Phe Phe Ile Ser Val Trp Ser Ala Met Ile Tyr Trp Lys
                20                  25                  30

Val Arg Gly Val Lys His Leu Ala Pro Trp Pro Ile Val Gly Asn Leu
            35                  40                  45

Gly Ala Leu Leu Arg Leu Asp Lys His Val Ser Tyr Tyr Tyr Asp Lys
        50                  55                  60

Ile Tyr His Ala Phe Pro Asn Glu Arg Met Ile Gly Met Tyr Glu Phe
65                  70                  75                  80

Met Thr Pro Thr Leu Val Leu Arg Asp Pro Glu Leu Ile Glu Gln Val
                85                  90                  95

Leu Val Arg Glu Phe Ser Thr Phe Pro Asp His Gly Pro Leu Leu Ile
            100                 105                 110

Glu Asp Asp Ser Leu Ile Ser Glu Ser Val Phe Ala Leu Thr Gly Ser
        115                 120                 125

Gly Ala Lys Trp Arg Ala Val Arg Asn Lys Leu Leu Thr Thr Phe Thr
    130                 135                 140

Thr Gly Lys Met Arg Ala Ile Phe Pro Glu Leu Val Ala Ser Cys Gln
145                 150                 155                 160

Ala Leu Val Asp Lys Arg Pro Lys Thr Leu Ile Lys Glu Asp Phe Thr
                165                 170                 175

Ala Phe Ala Val Glu Ser Phe Met Asn Ser Met Phe Gly Thr Ala Ile
            180                 185                 190
```

```
Leu Pro Ala Gly Lys Glu Glu Leu Val Leu Asn Cys Lys Thr Val Phe
            195                 200                 205

Glu Gly Ser Arg Tyr Arg Met Phe Gln Gln Tyr Gly Leu Thr Tyr Phe
            210                 215                 220

Thr Lys Leu Ser Gln Phe Phe Asn Met Thr Phe Met Ala Asn Glu Leu
225                 230                 235                 240

His Asn Tyr Phe Ser Ser Leu Met His Thr Leu Leu Asn Gln Arg Ser
            245                 250                 255

Glu Leu Asp Cys Gly Arg Asn Asp Tyr Ala Gln Val Leu Val Asp Met
            260                 265                 270

Lys Arg Leu Lys Lys Met Val Ile Phe Ser Arg Glu Asn Ser Arg Glu
            275                 280                 285

Asn Gln Glu Phe Asp Ile Thr Asp Asp Leu Val Ile Ala Gln Ala Phe
            290                 295                 300

Met Phe Phe Phe Ala Gly Leu Asp Thr Thr Thr Leu Val Met Leu His
305                 310                 315                 320

Leu Ala Phe Asp Leu Ser Gln Ala Lys Asp Cys Gln Glu Thr Ala Arg
            325                 330                 335

Gln Glu Val Arg Asn Val Leu Lys Lys Tyr Gly Gly Tyr Ser Trp Asp
            340                 345                 350

Ser Val Arg Asp Met Lys Tyr Leu Asp Ala Cys Ile Gln Glu Thr Leu
            355                 360                 365

Arg Leu His Pro Ser Leu Gln Phe Val Arg Val Asn Asp Lys Pro
            370                 375                 380

Thr Asp Val Ala Gly Val Lys Ile Asp Lys Gly Thr Arg Ile Val Ile
385                 390                 395                 400

Pro Leu Gln Thr Ile His Met Asp Pro Asn Asn Phe Pro Lys Pro Glu
            405                 410                 415

Lys Tyr Asp Pro Gly Arg Trp Leu Asp Glu Ser Thr Arg Pro Asn Lys
            420                 425                 430

Phe Thr His Leu Pro Phe Ser Glu Gly Pro Arg Val Cys Leu Gly Lys
            435                 440                 445

Arg Phe Ala Leu Met Glu Ile Ala Thr Leu Phe Ala His Ile Leu Asp
450                 455                 460

Asn Phe Glu Leu Thr Leu Ser Pro Glu Thr Lys Val Pro Leu Ile Tyr
465                 470                 475                 480

Glu Pro Asn Val Phe Phe His Ser Pro Ile Ser Lys Asn Pro Ile Arg
            485                 490                 495

Val Asp Leu Met Lys Ile
            500

<210> SEQ ID NO 75
<211> LENGTH: 513
<212> TYPE: PRT
<213> ORGANISM: Nezara viridula

<400> SEQUENCE: 75

Ser Gly Pro Pro Thr Leu Gln Gly Gly Lys Ser Ser Ile Gln Gln Lys
1               5                   10                  15

Met Leu Thr Leu Glu Leu Leu Thr Leu Ala Val Val Gly Leu Ile
            20                  25                  30

His Phe Ser Ile Ile Ile Trp Lys Ser Met Thr Tyr Trp Lys Glu Arg
            35                  40                  45

Gly Val Lys His His Thr Pro Val Pro Ile Phe Gly Asn Phe Leu Ser
50                  55                  60
```

```
Val Ile Ser Phe Arg Lys His Phe His Tyr Tyr Asp Lys Val Tyr
65                  70                  75                  80

Lys Ala Phe Pro Asn Glu Arg Met Val Gly Leu Tyr Glu Phe Met Thr
                85                  90                  95

Pro Thr Leu Val Leu Arg Asp Thr Gln Leu Ile Glu His Val Leu Ile
                100                 105                 110

Arg Glu Phe Ser Thr Phe Pro Asp His Gly Ser Phe Leu Phe Glu Pro
                115                 120                 125

Ser Ser Val Met Tyr Asp Ser Ile Phe Asn Met Ser Gly Ile Arg Trp
            130                 135                 140

Arg Ala Leu Arg Asn Lys Leu Leu Ile Thr Phe Thr Thr Gly Lys Met
145                 150                 155                 160

Arg Ser Val Phe Pro Ser Leu Ser Glu Ser Cys Leu Gln Leu Leu Asn
                165                 170                 175

Ser Asn Pro Lys Thr Leu Glu Arg Glu Met Leu Ser Asp Leu Ala Ile
                180                 185                 190

Arg Thr Phe Met Glu Ser Met Phe Gly Thr Lys Ile Leu Lys Ser Ala
            195                 200                 205

Glu Ala Glu Ile Tyr Thr Lys Ala Arg Lys Ile Phe Glu Pro Thr Trp
210                 215                 220

Trp Arg Tyr Thr Gln Gln Thr Leu Leu Thr Tyr Phe Pro Lys Leu Ala
225                 230                 235                 240

Asp Phe Leu His Leu Thr Phe Met Pro Lys His Leu Asp Asn Tyr Phe
                245                 250                 255

Arg Ser Ile Met Asn Thr Ile Leu Asn Gln Arg Val Asp Ser Met Glu
                260                 265                 270

Asp Arg Asn Asp Tyr Ala Gln Val Leu Val Gln Met Arg Glu Gln Lys
            275                 280                 285

Lys Leu Asn Ile Tyr Asn Arg Glu Asn Lys Lys Val Asp Gln Thr Phe
            290                 295                 300

Asp Val Thr Asn Asp Leu Ala Ile Ala Gln Ala Phe Met Phe Phe Phe
305                 310                 315                 320

Ala Gly Met Asp Ala Thr Ser Leu Leu Met Leu Tyr Thr Ala Ala Asn
                325                 330                 335

Leu Ala Gln Ser Lys Asn Cys Gln Ala Lys Ala Arg Glu Glu Ile Lys
                340                 345                 350

Thr Val Leu His Lys Tyr Gly Gly Tyr Ser Trp Glu Ala Val Arg Asp
            355                 360                 365

Met Lys Tyr Ile Asp Ser Cys Val Gln Glu Thr Leu Arg Met Gln Pro
            370                 375                 380

Ser Leu Gln Phe Leu Asn Arg Val Cys Asp Lys Asp Thr Ser Ile Asp
385                 390                 395                 400

Gly Val Lys Leu Val Lys Gly Thr Arg Ile Ile Ile Pro Ile His Thr
                405                 410                 415

Ile Gln Met Asp Pro Lys Asn Phe Pro Asn Pro Glu Lys Phe Asp Pro
                420                 425                 430

Glu Arg Phe Met Glu Gly Ile Asn Asp Lys Phe Ala His Leu Pro Phe
                435                 440                 445

Ser Asp Gly Pro Arg Val Cys Leu Gly Lys Arg Phe Ala Thr Met Glu
            450                 455                 460

Thr Thr Thr Phe Met Ala His Leu Leu Glu Asn Phe Glu Leu Ser Leu
465                 470                 475                 480
```

Ser Pro Glu Thr Lys Leu Pro Leu Lys Tyr Gln Pro Thr Ala Leu Phe
                485                 490                 495

Leu Thr Pro Lys Ala Thr Asn Pro Ile Lys Ile Asp Leu Lys Arg Ile
                500                 505                 510

Asn

<210> SEQ ID NO 76
<211> LENGTH: 539
<212> TYPE: PRT
<213> ORGANISM: Nezara viridula

<400> SEQUENCE: 76

Met Met Ser Glu Ser Ile Thr Ser Met Phe Phe Lys Ser Trp Glu Phe
1               5                   10                  15

Ile Gln Asp Leu Ile Lys Ser Asp Ser Phe Gly Tyr Thr Thr Ile Ile
                20                  25                  30

Ile Ser Leu Leu Val Ser Arg Met Leu Leu Thr Ser Glu Phe Val Ala
            35                  40                  45

Phe Thr Ala Leu Trp Gly Leu Leu Tyr Leu Cys Leu Asn Ile Tyr Trp
        50                  55                  60

Ala Met Asn Tyr Trp Lys Ile Arg Gly Val Lys His Phe Lys Pro Trp
65                  70                  75                  80

Pro Ile Val Gly Asn Met Ala Arg Val Leu Lys Leu Glu Tyr His Leu
                85                  90                  95

Ala Tyr Tyr Tyr Asp Glu Ile Tyr Asn Ala Phe Pro Gly Glu Arg Met
                100                 105                 110

Val Gly Met Tyr Glu Phe Met Thr Pro Ser Leu Val Leu Arg Asp Thr
            115                 120                 125

Glu Leu Ile Glu Gln Val Leu Val Lys Asp Phe Ser Thr Tyr Pro Asp
130                 135                 140

His Gly Pro Phe Leu Met Glu Pro Lys Ser Ile Leu Phe Glu Ser Val
145                 150                 155                 160

Phe Ala Met Ser Gly Ile Arg Trp Arg Ala Ile Arg Asn Arg Leu Leu
                165                 170                 175

Thr Thr Phe Thr Thr Gly Lys Met Arg Val Ile Phe Pro Gln Ile Leu
            180                 185                 190

Ala Pro Cys Gln Ser Phe Val Lys Gly Lys Pro Lys Cys Leu Asn Val
        195                 200                 205

Glu Ile Ile Asn Glu Leu Ala Val Lys Ile Phe Met Thr Ala Met Phe
210                 215                 220

Gly Ile Asn Ile Leu Pro Thr Gly Glu Glu Leu Met Ile Asn Cys
225                 230                 235                 240

Lys Arg Ile Phe Glu Pro Lys Ala Thr Arg Ile Leu Gln Leu Ile Phe
                245                 250                 255

Leu Thr Tyr Phe Pro Lys Leu Ser Asn Val Leu Asn Leu Lys Phe Met
            260                 265                 270

Pro Arg Asp Leu Asp Asp Tyr Phe Arg Ser Leu Met Asn Thr Ile Leu
        275                 280                 285

Asp Gln Arg Glu Asn Ile Asp Phe Glu Arg Asn Asp Tyr Thr Lys Val
290                 295                 300

Leu Val Glu Met Arg Lys Gln Glu Lys Met Asn Ile Tyr Asn Met Arg
305                 310                 315                 320

Asn Asp Lys Val Ser Gln Thr Phe Asp Met Thr Asn Glu Ile Ala Leu
                325                 330                 335

-continued

```
Ser Gln Ala Phe Met Phe Phe Ala Gly Leu Asp Thr Val Ser Leu
            340             345                 350

Leu Ile Leu His Leu Ala Phe Glu Phe Ser Lys Ser Lys Tyr Cys Gln
        355                 360                 365

Asp Lys Ala Arg Gln Glu Val Arg Ser Val Leu Lys Lys Phe Asn Gly
        370                 375                 380

Tyr Ser Trp Glu Ala Val Arg Glu Met Lys Tyr Leu Glu Gln Cys Ile
385                 390                 395                 400

Leu Glu Thr Leu Arg Leu His Pro Ser Leu Gln Phe Leu Val Arg Ile
                405                 410                 415

Thr Asp Lys Asp Thr Glu Leu Gly Gly Val Lys Ile Lys Lys Asn Thr
            420                 425                 430

Arg Ile Val Ile Pro Ile His Ser Ile Gln Met Asp Pro Lys Asn Phe
        435                 440                 445

Thr Asp Pro Asn Lys Phe Asp Pro Glu Arg Phe Asn Val Glu Asn Gln
    450                 455                 460

Gln Asn Lys Phe Ala His Leu Pro Phe Ser Asp Gly Pro Arg Val Cys
465                 470                 475                 480

Leu Gly Lys Arg Phe Ala Ile Met Glu Thr Ala Thr Phe Phe Ala His
                485                 490                 495

Ile Leu Asp Asn Tyr Glu Leu Ser Leu Ser Pro Gln Thr Arg Leu Pro
            500                 505                 510

Leu Gln Tyr Glu Pro Lys Thr Leu Phe His Thr Pro Lys Val Gln Thr
        515                 520                 525

Ser Ile His Val Thr Leu Asn Glu Ile Arg Lys
    530                 535

<210> SEQ ID NO 77
<211> LENGTH: 497
<212> TYPE: PRT
<213> ORGANISM: Nezara viridula

<400> SEQUENCE: 77

Met Thr Thr Leu Thr Leu Leu Val Ala Val Val Cys Cys Phe Leu
1               5                   10                  15

Tyr Leu Gly Leu Ile Leu Trp Lys Ala Asn Thr Tyr Trp Glu Val Arg
            20                  25                  30

Gly Val Lys His Phe Lys Pro Trp Pro Leu Val Gly Asn Leu Ala Arg
        35                  40                  45

Ala Leu Lys Phe Asn Arg His Val Ser Phe Phe Tyr Asp Glu Ile Tyr
    50                  55                  60

Lys Ala Phe Pro Thr Glu Arg Met Val Gly Met Tyr Glu Phe Leu Thr
65                  70                  75                  80

Pro Thr Leu Ile Ile Arg Asp Pro Thr Leu Val Glu Asn Val Leu Val
                85                  90                  95

Arg Glu Phe Ser Thr Tyr Pro Asp His Gly Pro Leu Phe Phe Glu Pro
            100                 105                 110

Ser Ser Ile Ser Tyr Glu Ser Ile Phe Thr Ile Thr Gly Ile Arg Trp
        115                 120                 125

Arg Ala Leu Arg Asn Lys Leu Leu Thr Ser Phe Ser Thr Gly Lys Met
    130                 135                 140

Lys Ala Ile Phe Pro Asp Ile Val Arg Ser Cys Gln Ser Val Val Asp
145                 150                 155                 160

Ser Asp Pro Lys Arg Leu His Lys Asp Met Leu His Glu Phe Ala Val
                165                 170                 175
```

```
Lys Ser Phe Leu Asn Ser Met Phe Gly Thr Asn Ile Leu Pro Glu Gly
            180                 185                 190

Glu Glu Glu Leu Met Ala Lys Ser Lys Glu Val Phe Gln Gly Lys Pro
            195                 200                 205

Gln Arg Ile Ile Gln Ile Met Leu Thr Phe Pro Lys Leu Gly
210                 215                 220

Asp Phe Leu Asn Met Lys Phe Met Pro Lys Thr Leu Asp Asn Tyr Phe
225                 230                 235                 240

Arg Asn Leu Leu Asn Thr Leu Val Glu Gln Arg Ala Ser Ala Asn Ile
            245                 250                 255

Lys Arg Asp Asp Tyr Ala Lys Val Leu Cys Asp Met Asn Lys Met Gly
            260                 265                 270

Lys Met Asp Val Tyr Asn Arg Glu Asn Lys Arg Ile Asp Glu Thr Phe
            275                 280                 285

Asp Val Thr Asn Asp Leu Val Leu Ala Gln Ala Phe Met Phe Phe Phe
            290                 295                 300

Ala Gly Leu Asp Thr Thr Val Leu Val Met Leu His Thr Ala Leu Glu
305                 310                 315                 320

Leu Ser Leu Ala Lys Ser Cys Gln Glu Lys Ala Arg Gln Glu Val Arg
            325                 330                 335

Ser Val Leu Lys Lys Tyr Gly Gly Tyr Ser Trp Glu Ala Val Arg Asp
            340                 345                 350

Met Lys Tyr Leu Asp Gln Cys Ile Gln Glu Thr Leu Arg Met His Pro
            355                 360                 365

Ser Leu Gln Phe Ile Val Arg Met Ser Asp Lys Asp Thr Val Ile Asp
370                 375                 380

Gly Val Lys Ile Lys Lys Asn Thr Arg Ile Ile Ile Pro Leu His Ser
385                 390                 395                 400

Ile Gln Met Asp Pro Asn His Phe Pro Asn Pro His Ile Phe Asp Pro
                405                 410                 415

Glu Arg Phe Ser Val Pro Leu Ser Ser Lys Phe Thr His Leu Pro Phe
            420                 425                 430

Ser Glu Gly Pro Arg Val Cys Leu Gly Lys Arg Phe Ala Thr Leu Glu
            435                 440                 445

Thr Ala Thr Ile Ile Ala His Ile Leu Asp Asn Phe Glu Leu His Pro
450                 455                 460

Ser Pro Glu Leu Lys Phe Pro Leu Lys Tyr Glu Pro Asn Ala Leu Phe
465                 470                 475                 480

His Ser Pro Ile Ser Asn Asp Glu Ile Ser Ile Ile Leu Lys Arg Ile
                485                 490                 495

Met

<210> SEQ ID NO 78
<211> LENGTH: 514
<212> TYPE: PRT
<213> ORGANISM: Nezara viridula

<400> SEQUENCE: 78

Met Val Asp Leu Asn Gln Phe Trp Ile Ser Leu Ile Ser Ile Gly Ile
1               5                   10                  15

Pro Leu Leu Ile Pro Ile Ile Phe Tyr Leu Met Val Gln Asn Tyr Lys
            20                  25                  30

Arg Thr Ser Tyr Trp Lys Lys Arg Asn Ile Val Tyr Leu Pro Ala Thr
        35                  40                  45
```

```
Pro Leu Phe Ser Lys Asn Ile Phe Asp Ser Phe Leu Ile Arg Tyr Ser
    50                  55                  60

Leu Leu Ser Thr Val Tyr Lys His Gly Lys Gly Asn Val Cys Cys Gly
65                  70                  75                  80

Phe Phe Gln Phe Arg Lys Pro Ala Leu Leu Ile Arg Ser Pro His Val
            85                  90                  95

Ile Asn Leu Val Leu Asn Gln Glu Phe Arg Ile Phe Gln Asn Lys Arg
                100                 105                 110

Gln Ser Asp Tyr Thr Glu Gly Asn Lys Asp Pro Leu Ser Gln His Leu
            115                 120                 125

Leu Ala Leu Asn Gly Tyr Lys Trp Lys Phe Leu Arg Ala Lys Leu Thr
    130                 135                 140

Pro Thr Phe Thr Ser Glu Lys Leu Lys Ser Met Phe Ser Leu Leu Glu
145                 150                 155                 160

Ile Cys Val Gln Asn Phe Leu Ser Tyr Ile Asp Glu Ser Lys Asp Ser
                165                 170                 175

Pro Ile Asp Ile Met Glu Ile Cys Gly Lys Leu Ser Ile Asp Ala Ile
            180                 185                 190

Ala Ser Cys Ala Phe Gly Leu Glu Leu Gln Cys Leu Lys Asn Arg Asn
    195                 200                 205

His Asp Phe Ile Lys Met Gly Lys Ala Ala Phe Arg Pro Gly Asn Trp
210                 215                 220

His Met Phe Lys Ala His Leu Arg Thr Leu Tyr Pro Gln Leu Phe Lys
225                 230                 235                 240

Lys Phe Asn Ile Arg Ala Tyr Gly Lys Asp Val Asn Asp Phe Phe Cys
                245                 250                 255

Ser Leu Val Ser Glu Thr Ile Arg Arg Arg Met Ser Gly Glu Lys
            260                 265                 270

Arg Val Asp Phe Ile Tyr Leu Leu Met Lys Met Leu Glu Glu Asp Glu
    275                 280                 285

Ala Thr Val Thr Glu Phe Asn Arg Thr Ser Thr Ile Lys Phe Thr Asp
290                 295                 300

Asp Leu Ile Ala Ala Gln Ala Phe Ser Phe Ile Gly Gly Tyr Glu
305                 310                 315                 320

Thr Thr Ser Ile Thr Met Ser Cys Ile Phe Tyr Glu Leu Ala Cys His
                325                 330                 335

Asp Glu Ile Arg Gln Lys Val Gln Asn Glu Ile Asp Ser Asn Leu Ser
            340                 345                 350

Ser Glu Ser Glu Ile Ser Tyr Asn Asp Leu Lys Ser Leu Glu Tyr Leu
    355                 360                 365

Asp Met Val Ile Lys Glu Val Leu Arg Leu His Pro Pro Ala Phe Tyr
370                 375                 380

Thr Gln Arg Ile Cys Ser Glu Asp Phe Lys Ile Pro Gly Ser Asp Val
385                 390                 395                 400

Thr Ile Val Lys Asp Met Glu Val Tyr Ile Pro Ile Leu Glu Leu His
                405                 410                 415

Ser Asp Glu Glu Asn Phe Pro Arg Pro Leu Glu Phe Ile Pro Glu Arg
            420                 425                 430

Phe Ser Arg Glu Asn Lys Ser Arg Ile Pro Lys Gly Ser Tyr Leu Pro
    435                 440                 445

Phe Gly Asp Gly Pro Arg Lys Cys Ile Gly Met Arg Phe Ser Leu Met
450                 455                 460
```

```
Glu Leu Lys Leu Val Met Ala Ile Thr Met Leu Lys Tyr Asp Phe His
465                 470                 475                 480

Leu Glu Lys Lys Thr Pro Glu His Ile Asn Leu Glu Glu Tyr Ser Arg
            485                 490                 495

Ile Tyr Lys Ile Lys Asn Lys Ile Phe Leu Lys Phe Thr Lys Arg Val
            500                 505                 510

Ile Ser

<210> SEQ ID NO 79
<211> LENGTH: 488
<212> TYPE: PRT
<213> ORGANISM: Nezara viridula

<400> SEQUENCE: 79

Met Val Cys Leu Ile Arg Asn Ile Trp Asn Ser Val Leu Arg Arg Lys
1               5                   10                  15

Phe Tyr Ile Met Ala Pro Ser Val Lys Lys Asn Met Ile Thr Ala Leu
                20                  25                  30

Leu Leu Phe Thr Leu Phe Phe Leu Cys Phe Gln Leu Thr Lys Lys
            35                  40                  45

Ser Leu Trp Ser Gln Leu Arg Ile Pro Glu Val His Gly Ile Pro Ile
50                  55                  60

Val Gly Asn Leu Leu Pro Val Val Leu Lys Lys Ser Tyr Phe Glu
65                  70                  75                  80

Thr Ile Glu Asp Leu Tyr Lys Leu Gly Glu Gly Lys Asp Tyr Ile Gly
                85                  90                  95

Ile Tyr Asn Gly Thr Gln Pro Thr Leu Leu Ile Arg Asn Pro Asp Leu
                100                 105                 110

Val Glu Ile Leu Ile Lys Glu Glu Ala Lys Asn Phe Glu Asp Arg Gly
            115                 120                 125

Leu Cys Ser Asp Leu Ser Asp Pro Leu Ser Leu Asn Leu Phe Phe Leu
130                 135                 140

Lys Gly Lys Leu Trp Lys Trp Thr Arg Ala Lys Leu Arg Pro Ala Phe
145                 150                 155                 160

Ser Asn Ile Arg Leu Lys Thr Val Phe Asn Gly Ile Glu Leu Cys Thr
                165                 170                 175

Ala Asp Cys Val Asn Ser Phe Gly Ser Ser Val Asp Ile Lys Glu Val
            180                 185                 190

Met Asp Glu Tyr Thr Cys Asn Val Ile Ala Lys Asn Val Phe Cys Val
            195                 200                 205

Gln Asp Asn Thr Gly Phe Ile Glu Asn Ser Leu Lys Val Phe Ser Leu
210                 215                 220

Ser Gly Leu Ser Gly Ile Ala Val Leu Leu Arg Val Phe Ile Pro Asn
225                 230                 235                 240

Phe Ala Leu Ser Ile Gly Ile Lys Thr Val Pro Gln Glu Ile Glu Thr
                245                 250                 255

Phe Tyr Arg Asn Ala Ile Ala Lys Ser Thr Arg Val Pro Gly Ser Phe
            260                 265                 270

Leu Asp Leu Met Leu His Leu Lys Glu Thr Glu Pro Asp Phe Ser Asp
            275                 280                 285

Asp Leu Met Val Ala Gln Phe Phe Ile Phe Ile Leu Ala Gly Phe Glu
            290                 295                 300

Thr Thr Ser Ser Ala Leu Thr Tyr Ala Leu Tyr Leu Leu Ser Lys Asn
305                 310                 315                 320
```

Pro Asp Ala Gln Asn Lys Ala Arg Phe Glu Ala Gln Lys Val Phe Lys
            325                 330                 335

Glu His Gly Arg Ser Ile Asp Ser Leu Lys Lys Leu Thr Tyr Leu Glu
        340                 345                 350

Ser Ile Ile Asn Glu Thr Leu Arg Leu Tyr Pro Ser Val Thr Gly Met
    355                 360                 365

Phe Arg Val Ala Glu Lys Pro Phe Lys Leu Pro Cys Gly Ala Val Leu
370                 375                 380

Pro Pro Gly Thr Ala Ile Ser Val Pro Ile Tyr Cys Leu His Arg Asp
385                 390                 395                 400

Ser Arg Phe Tyr Glu Asp Pro Leu Lys Phe Ile Pro Glu Arg Trp Glu
            405                 410                 415

Met Pro Gln Lys Val Phe Tyr Pro Phe Gly Leu Gly Pro Arg Leu Cys
        420                 425                 430

Ile Gly Met Lys Phe Ala Leu Leu Glu Met Lys Ile Phe Leu Ser Ser
    435                 440                 445

Val Ile Leu Lys Tyr Asn Ile Lys Leu Asn Tyr Ala Thr Val Glu Pro
450                 455                 460

Leu Ser Phe Asp Pro Thr Ser Phe Phe Tyr Lys Ala Ile Asn Pro Ile
465                 470                 475                 480

Leu Leu Asp Phe Glu Lys Thr Val
            485

<210> SEQ ID NO 80
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 80
atggcagcaa gggcacccgt aca                                         23

<210> SEQ ID NO 81
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 81
ttagttattt aatacgcttt cagcttct                                    28

<210> SEQ ID NO 82
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 82
gtttgggctt ccgtgtgtg                                              19

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83

```
taccgaagtg gcgcttaacc                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
atgccacttg caaaactgtg                                              20

<210> SEQ ID NO 85
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 85
ctactgcttt ctgccatatg ttttatg                                      27

<210> SEQ ID NO 86
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 86
atggcagcaa gggcatc                                                 17

<210> SEQ ID NO 87
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 87
ttaaacatac acttttattc tttcaatttg                                   30

<210> SEQ ID NO 88
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 88
gctcgtggtc ccaaaaagc                                               19

<210> SEQ ID NO 89
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 89
gacctgagct gggccttg                                                18

<210> SEQ ID NO 90
<211> LENGTH: 42
<212> TYPE: PRT
<213> ORGANISM: Nezara viridula
```

<400> SEQUENCE: 90

Asn Lys Met Tyr Ile Ile Arg Ala Ser Met Asp Leu Leu Phe Thr Met
1               5                   10                  15

Ser Ala Val Leu Asp Asp Ile Ser Asp Lys Ser Asp Ser Arg Arg Gly
            20                  25                  30

Lys Lys Ser Trp His Ile Ile Cys Gln Gly
        35                  40

<210> SEQ ID NO 91
<211> LENGTH: 42
<212> TYPE: PRT
<213> ORGANISM: Nezara viridula

<400> SEQUENCE: 91

Thr Lys Met Tyr Leu Ile Arg Ala Thr Met Asp Leu Leu Phe Thr Met
1               5                   10                  15

Ser Ala Val Leu Asp Asp Ile Ser Asp Arg Ser Glu Phe Arg Lys Gly
            20                  25                  30

Lys Lys Gly Trp His Met Ile Cys Gln Gly
        35                  40

<210> SEQ ID NO 92
<211> LENGTH: 42
<212> TYPE: PRT
<213> ORGANISM: Nezara viridula

<400> SEQUENCE: 92

Glu Lys Cys Arg Ile Ile Arg Ala Leu Met Asp Met Ser Tyr Ala Met
1               5                   10                  15

Ala Gly Ile Leu Asp Asp Tyr Val Asp Lys Gly Glu Phe Arg Arg Gly
            20                  25                  30

Lys Lys Val Trp Ala Ser Val Cys Glu Gly
        35                  40

<210> SEQ ID NO 93
<211> LENGTH: 42
<212> TYPE: PRT
<213> ORGANISM: Nezara viridula

<400> SEQUENCE: 93

Arg Leu Ala Gln Ile Leu Gly Trp Cys Val Glu Met Leu Gln Gly Phe
1               5                   10                  15

Phe Val Ile Asp Asp Leu Thr Asp Gln Ser Val Thr Arg Arg Gly
            20                  25                  30

Arg Pro Cys Trp Tyr Arg Leu Pro Gly Ile
        35                  40

<210> SEQ ID NO 94
<211> LENGTH: 42
<212> TYPE: PRT
<213> ORGANISM: Nezara viridula

<400> SEQUENCE: 94

Arg Leu Ala Gln Ile Leu Gly Trp Cys Val Glu Met Leu Gln Gly Phe
1               5                   10                  15

Phe Leu Val Ile Asp Asp Leu Ala Asp Gln Ser Ile Thr Arg Arg Gly
            20                  25                  30

Arg Pro Cys Trp Tyr Arg Asn Pro Asp Val
        35                  40

```
<210> SEQ ID NO 95
<211> LENGTH: 42
<212> TYPE: PRT
<213> ORGANISM: Nezara viridula

<400> SEQUENCE: 95

Arg Leu Ala Gln Ile Leu Gly Trp Cys Val Glu Met Leu Gln Gly Phe
1               5                   10                  15

Phe Val Val Ile Asp Asp Leu Ala Asp Gln Ser Val Thr Arg Arg Gly
            20                  25                  30

Arg Pro Cys Trp Tyr Arg Leu Pro Gly Val
        35                  40

<210> SEQ ID NO 96
<211> LENGTH: 42
<212> TYPE: PRT
<213> ORGANISM: Nezara viridula

<400> SEQUENCE: 96

Asp Leu Ile Glu Lys Thr Val Glu Ile Phe Thr Ile Ala Gly Arg Met
1               5                   10                  15

Ile Gln Thr Trp Asp Asp Phe Asn Asp Tyr Tyr Ser Ser Asp Gln
            20                  25                  30

Asn Gly Lys Pro Ser Cys Asp Leu Ile Asn
        35                  40

<210> SEQ ID NO 97
<211> LENGTH: 42
<212> TYPE: PRT
<213> ORGANISM: Nezara viridula

<400> SEQUENCE: 97

Asp Leu Ile Asp Lys Thr Val Glu Ile Phe Thr Ile Ala Gly Gln Ile
1               5                   10                  15

Ile Gln Thr Trp Asp Asp Phe Asn Asp Tyr Tyr Ser Ser Glu Gln
            20                  25                  30

Asn Gly Lys Leu Ser Cys Asp Phe Met Asn
        35                  40

<210> SEQ ID NO 98
<211> LENGTH: 42
<212> TYPE: PRT
<213> ORGANISM: Nezara viridula

<400> SEQUENCE: 98

Asp Leu Leu Asp Arg Thr Ser Glu Val Phe Gly Tyr Thr Gly His Leu
1               5                   10                  15

Phe Gln Val Trp Asp Asp Phe Met Glu His Tyr Ala Val Lys Glu Gln
            20                  25                  30

Ser Gly Lys Gly Ala Pro Asp Thr Lys Tyr
        35                  40

<210> SEQ ID NO 99
<211> LENGTH: 42
<212> TYPE: PRT
<213> ORGANISM: Nezara viridula

<400> SEQUENCE: 99

Glu Leu His Arg Gln Ala Lys Ser Val Leu Leu Glu Met Gly His Tyr
1               5                   10                  15
```

```
Phe Gln Val Gln Asp Asp Tyr Leu Asp Val Phe Ser Asp Glu Glu Val
             20                  25                  30

Ser Gly Lys Lys Gly Thr Asp Ile Gln Glu
         35                  40

<210> SEQ ID NO 100
<211> LENGTH: 42
<212> TYPE: PRT
<213> ORGANISM: Nezara viridula

<400> SEQUENCE: 100

Glu Leu His Arg Gln Ala Lys Ser Val Leu Leu Glu Met Gly His Tyr
1               5                   10                  15

Phe Gln Val Gln Asp Asp Tyr Leu Asp Val Phe Gly Asp Glu Glu Val
             20                  25                  30

Ile Gly Lys Ile Gly Thr Asp Ile Gln Glu
         35                  40

<210> SEQ ID NO 101
<211> LENGTH: 42
<212> TYPE: PRT
<213> ORGANISM: Nezara viridula

<400> SEQUENCE: 101

Glu Leu His Arg Gln Ala Lys Ser Val Leu Leu Glu Met Gly His Tyr
1               5                   10                  15

Phe Gln Val Gln Asp Asp Tyr Leu Asp Val Phe Gly Asp Glu Glu Met
             20                  25                  30

Ile Gly Lys Lys Gly Thr Asp Ile Gln Glu
         35                  40
```

SOUTHERN GREEN STINK BUG PHEROMONE SYNTHESIS ENZYMES AND USES THEREOF

CROSS-REFERENCE TO RELATED APPLICATIONS

This application is the U.S. National Stage Application under 35 U.S.C. § 371 of Patent Cooperation Treaty Application No.: PCT/US2019/053708, filed on Sep. 28, 2019, entitled "SOUTHERN GREEN STINK BUG PHEROMONE SYNTHESIS ENZYMES AND USES THEREOF," which claims the benefit of and priority to U.S. Provisional Patent Application No. 62/756,392, filed on Nov. 6, 2018, entitled "Production of Stink Bug Pest Aggregation Pheromone Precursors" the contents of which are incorporated by reference herein in their entireties.

STATEMENT REGARDING FEDERALLY SPONSORED RESEARCH

This invention was made with Government support 2016-67013-24579 awarded by the USDA National Institute of Food and Agriculture. The Government has certain rights in the invention.

SEQUENCE LISTING

This application contains a sequence listing filed in electronic form as an ASCll.txt file entitled VTIP-0225WP_ST25.txt, created on Sep. 27, 2019. The content of the sequence listing is incorporated herein in its entirety.

TECHNICAL FIELD

The subject matter disclosed herein is generally directed to engineered terpene synthesis enzymes, and more particularly those related to those present in insects.

BACKGROUND

The southern green stink bug poses a threat to many agriculturally important corps grown throughout the tropical and subtropical regions of the world. Current methods to control southern green stink bug populations include biological control (e.g., wasps and flies that transmit parasites to the southern green stink bug) and chemical control. Given the need to find alternatives to chemical control of pests in agriculture, there exists a need for alternative methods for control of pests, such as the southern green stink bug, in agriculture.

SUMMARY

Described herein are aspects of an engineered polynucleotide that includes one or more polynucleotides that each have a sequence that is 69-100% identical to SEQ ID NO: 1.

Described herein are aspects of an engineered polynucleotide that includes one or more polynucleotides that each have a sequence that is 90-100% identical to SEQ ID NO: 2.

Described herein are aspects of an engineered polynucleotide that encodes a polypeptide having a sequence that is about 55-100% identical to SEQ ID NO: 4. In some aspects, the polypeptide has a sequence that is 69-100% identical to SEQ ID NO: 1.

Described herein are aspects of an engineered polynucleotide that encodes a polypeptide having a sequence that is about 93-100% identical to SEQ ID NO: 5. In some aspects, the engineered polynucleotide of claim 5, wherein the polypeptide has a sequence that is 69-100% identical to SEQ ID NO: 2.

Described herein are aspects of an engineered polynucleotide that encodes 2 or more of the following: (a) a polypeptide having a sequence that is about 55-100% identical to SEQ ID NO: 4; (b) a polypeptide having a sequence that is about 93-100% identical to SEQ ID NO: 5; and (c) a polypeptide having a sequence that is 70-100% identical to any one of SEQ ID NOs: 6-79.

Described herein are aspects of an engineered polynucleotide that includes an engineered polynucleotide of claim 1, an engineered polynucleotide of claim 2, or both; and an engineered polynucleotide that encodes a polypeptide having a sequence that is 70-100% identical to any one of SEQ ID NOs: 6-79.

Described are aspects of a vector that includes one or more engineered polynucleotides described herein. The one or more engineered polynucleotides can be operably coupled to a regulatory element.

Described herein are aspects of a cell that includes an engineered polynucleotide as described herein, a vector, wherein the vector includes an engineered polynucleotide as described herein; or both. The cell can be a plant cell. The cell can be a plant cell that is from a plant species suitable for use as a trap crop for management of the southern green stink bug. The cell can be capable of producing a southern green stink bug pheromone, a southern green stink bug pheromone intermediate, or both.

Described herein are aspects of a cell that can include a vector as described herein. The cell can be a plant cell. The cell can be a plant cell that is from a plant species suitable for use as a trap crop for management of the southern green stink bug. The cell can be capable of producing a southern green stink bug pheromone, a southern green stink bug pheromone intermediate, or both.

Described herein are aspects of a genetically modified plant that includes (a) an engineered polynucleotide as described herein, (b) a vector as described herein, (c) a cellas described herein, (d) an enzyme having a sequence that is 55-100% identical to SEQ ID NO: 4, (e) an enzyme having a sequence that is 93-100% identical to SEQ ID NO: 5, (f) an enzyme having a sequence that is 70-100% identical to any one of SEQ ID NOs: 6-79; or (g) any combination thereof. The plant can be a species suitable for use as a trap crop for management of the southern green stink bug.

Described herein are aspects of a method of managing southern green stink bug infestation of a desired crop, the method including: planting a genetically modified plant as described herein. The genetically modified plant is planted in a location next to or near the desired crop.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 2A) Recombinant NvTPS was expressed in *E. coli* and purified by affinity chromatography. Protein was incubated with 50 μM of different FPP isomers in the presence of Mg2+ and products were analyzed by GC-MS. (FIG. 2B) LC-MS analysis of the prenyl diphosphate product from functional assays of recombinant NvFPPS. Fifty μM IPP and 50 μM DMAPP were provided as substrates. 1, α-(Z)-bisabolene, 2,(E,E)-FPP, 3, (Z,E)-FPP, 4, (Z,Z)-FPP. (FIG. 2C) Proposed pathway for the biosynthesis of the *N. viridula* pheromone.

FIG. 3 can demonstrate determination of the absolute configuration of the NvTPS enzymatic product. GC-MS chromatograms of (+)-(S,Z)-α-bisabolene produced by NvTPS (top), a mixture of (+)-(S,Z)-α-bisabolene and (−)-(R,Z)-α-bisabolene standards (middle), and a mixture of the NvTPS product and bisabolene standards (bottom). Compounds were separated on a chiral Hydrodex-β-6TBDM column as described under Methods and Materials in Example 1.

FIGS. 4A-4B can demonstrate transcript abundance of NvTPS in (FIG. 4A) mature *N. viridula* male (MM) and female (MF) whole bug and (FIG. 4B) cuticle-associated tissue rela-tive to that of ribosomal protein S4 (n=3, ±SD). Abundance in the mature female is set to 1. *p <0.05, ** p<0.01.

FIG. 8 can demonstrate transcript abundance of NvTPS and NvFPPS in mature male and female *N. viridula* determined by RT-PCR. Ribosomal binding protein 4 (RpS4) was used as an expression control.

FIG. 11 shows a table showing BLAST query sequences.

FIG. 12 shows an identity matrix table of pentatomid IDS and TPS proteins developed from the alignment of proteins listed in FIG. 11.

FIG. 14B harlequin stink bug; FIG. 14C Southern green stink bug).

DETAILED DESCRIPTION

Figure 1:
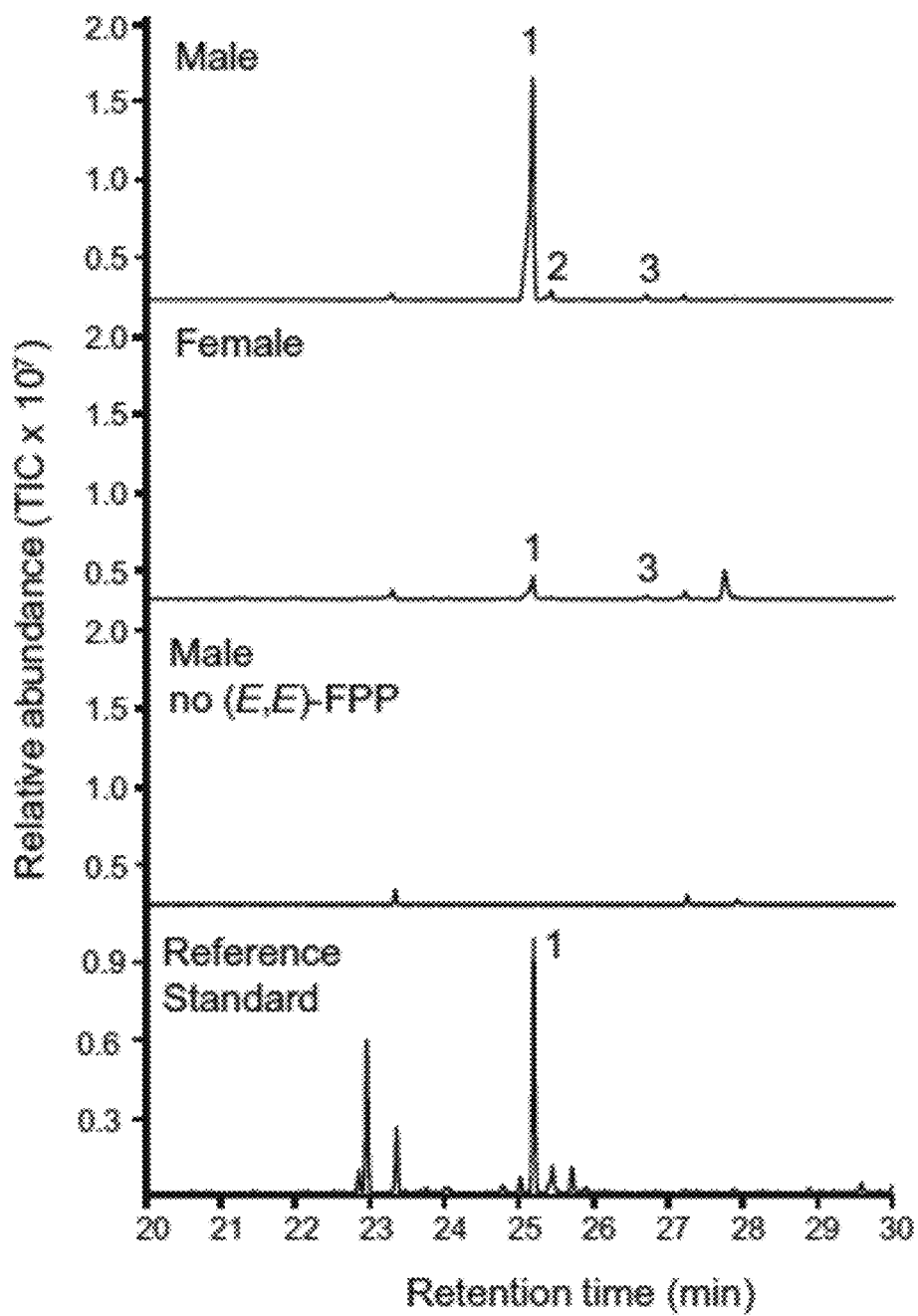
FIG. 1 can demonstrate terpene synthase activity in crude protein extracts from tissues of the abdominal cuticle of mature male and female *N. viridula*. Tissue was homogenized in assay buffer and assayed with 50 µM (E,E)-FPP. Volatile products were extracted with an equal volume of hexane and analyzed by GC-MS. Chromatograms from top to bottom show products extracted from assays with male-derived protein extract, female-derived protein extract, and male-derived protein extract without (E,E)-FPP. Opoponax oil was used as a reference standard for (Z)-α-bisabolene. Similar results were obtained in several independent experiments. 1, (Z)-α-bisabolene, 2, β-bisabolene, 3, nerolidol isomer.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g., the phrase "x to y" includes the range from 'x' to 'y' as well as the range greater than 'x' and less than 'y'. The range can also be expressed as an upper limit, e.g., 'about x, y, z, or less' and should be interpreted to include the specific ranges of 'about x', 'about y', and 'about z' as well as the ranges of 'less than x', 'less than y', and 'less than z'. Likewise, the phrase 'about x, y, z, or greater' should be interpreted to include the specific ranges of 'about x', 'about y', and 'about z' as well as the ranges of 'greater than x', 'greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

Embodiments of the present disclosure will employ, unless otherwise indicated, techniques of molecular biology, microbiology, organic chemistry, biochemistry, physiology, cell biology, plant biology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary.

It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-r interactions, anion-r interactions, polar r-interactions, and hydrophobic effects.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein with reference to the relationship between DNA, cDNA, cRNA, RNA, protein/peptides, and the like "corresponding to" or "encoding" (used interchangeably herein) refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "deoxyribonucleic acid (DNA)" and "ribonucleic acid (RNA)" can generally refer to any polyribonucleotide or polydeoxyribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins. In some instances, "expression" can also be a reflection of the stability of a given RNA. For example, when one measures RNA, depending on the method of detection and/or quantification of the RNA as well as other techniques used in conjunction with RNA detection and/or quantification, it can be that increased/decreased RNA transcript levels are the result of increased/decreased transcription and/or increased/decreased stability and/or degradation of the RNA transcript. One of ordinary skill in the art will appreciate these techniques and the relation "expression" in these various contexts to the underlying biological mechanisms.

As used herein, "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA.

As used herein, "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, in aspects modulation may encompass an increase in the value of the measured variable by about 10 to 500 percent or more. In aspects, modulation can encompass an increase in the value of at least 10%, 20%, 30%, 40%, 50%, 75%, 100%, 150%, 200%, 250%, 300%, 400% to 500% or more, compared to a reference situation or suitable control without said modulation. In aspects, modulation may encompass a decrease or reduction in the value of the measured variable by about 5 to about 100%. In some aspects, the decrease can be about 5%, 10%, 20%, 30%, 40%, 50%, 60%, 70%, 80%, 90%, 95%, 96%, 97%, 98%, 99% to about 100%, compared to a reference situation or suitable control without said modulation. In aspects, modulation may be specific or selective, hence, one or more desired phenotypic aspects of a cell or cell population may be modulated without substantially altering other (unintended, undesired) phenotypic aspect(s).

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

The term "nanoparticle" as used herein includes a nanoscale deposit of a homogenous or heterogeneous material. Nanoparticles may be regular or irregular in shape and may be formed from a plurality of co-deposited particles that form a composite nanoscale particle. Nanoparticles may be generally spherical in shape or have a composite shape formed from a plurality of co-deposited generally spherical particles. Exemplary shapes for the nanoparticles include, but are not limited to, spherical, rod, elliptical, cylindrical, disc, and the like. In some embodiments, the nanoparticles have a substantially spherical shape.

As used herein, "nucleic acid," "nucleotide sequence," and "polynucleotide" can be used interchangeably herein and can generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used interchangeably herein, "operatively linked" and "operably linked" in the context of recombinant or engineered polynucleotide molecules (e.g., DNA and RNA) vectors, and the like refers to the regulatory and other sequences useful for expression, stabilization, replication, and the like of the coding and transcribed non-coding sequences of a nucleic acid that are placed in the nucleic acid molecule in the appropriate positions relative to the coding sequence so as to effect expression or other characteristic of the coding sequence or transcribed non-coding sequence. This same term can be applied to the arrangement of coding sequences, non-coding and/or transcription control elements (e.g., promoters, enhancers, and termination elements), and/or selectable markers in an expression vector. "Operatively linked" can also refer to an indirect attachment (i.e. not a direct fusion) of two or more polynucleotide sequences or polypeptides to each other via a linking molecule (also referred to herein as a linker).

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, "overexpressed" or "overexpression" refers to an increased expression level of an RNA and/or protein product encoded by a gene as compared to the level of expression of the RNA or protein product in a normal or control cell. The amount of increased expression as compared to a normal or control cell can be about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.2, 2.4, 2.6, 2.8, 3.0, 3.3, 3.6, 3.9, 4.0, 4.4, 4.8, 5.0, 5.5, 6, 6.5, 7, 7.5, 8.0, 8.5, 9, 9.5, 10, 11, 12, 13, 14, 15, 16, 17, 18, 19, 20, 25, 30, 35, 40, 45, 50, 60, 70, 80, 90, 100 fold or more greater than the normal or control cell.

As used herein, "polypeptides" or "proteins" refers to amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). "Protein" and "Polypeptide" can refer to a molecule composed of one or more chains of amino acids in a specific order. The term protein is used interchangeable with "polypeptide." The order is determined by the base sequence of nucleotides in the gene coding for the protein. Proteins can be required for the structure, function, and regulation of the body's cells, tissues, and organs.

As used herein, "promoter" includes all sequences capable of driving transcription of a coding or a non-coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, the term "recombinant" or "engineered" can generally refer to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc. Recombinant or engineered can also refer to the polypeptide encoded by the recombinant nucleic acid. Non-naturally occurring nucleic acids or polypeptides include nucleic acids and polypeptides modified by man.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

DISCUSSION

The southern green stink bug poses a threat to many agriculturally important corps grown throughout the tropical and subtropical regions of the world. Stink bugs are in the family Pentatomidae and adults can be recognized by their shield-shape, five-segmented antennae, and their malodorous scent. The southern green stink bug, Nezara viridula (not to be confused with the green stink bug, Chinavia halaris) is a highly polyphagous feeder and attacks many important food crops. Generally, the southern green stink bug can be found in the tropical and subtropical regions of Europe, Asia, Africa, and the Americas. In South America, it has expanded its range to Paraguay, south Argentina, and into Brazil, tracking the expanding soybean and other agriculture production in these regions. In North America, the Southern Green stink bug can be found in the southeastern United States, from Virginia to Florida in the east, Ohio and Arkansas in the Midwest, and to Texas in the Southwest. It has also established in Hawaii and California.

The southern green stink bug is most prevalent during the periods of October through December and again in March through April. The southern green stink bug has piercing-sucking mouthparts that help it feed on all plant parts. However, the southern green stink bug appears to prefer growing shoots and developing fruits. Attacked shoots usually wither, or in extreme cases, may die. The damage on fruit from the punctures is hard brownish or black spots, which affect the fruit's edible qualities and market value. Growth of attacked young fruit may be slowed and/or the young fruit may wither and be dropped from the plant. In addition to the physical damage caused directly by the southern green stink bug to the plant, the southern green stink bug can also facilitate the transmission of various diseases between plants, such as tomato bacterial spot.

The southern green stink bug poses a threat to many agriculturally important corps grown throughout the tropical and subtropical regions of the world. Current methods to control southern green stink bug populations include biological control (e.g., wasps and flies that transmit parasites to the southern green stink bug) and chemical control. The southern green stink bug is also developing resistance to insecticides used to control them. Given the need to find alternatives to chemical control of pests in agriculture, there exists a need for alternative methods for control of pests, such as the southern green stink bug, in agriculture.

Trap crops are crops that are planted to attract insect pests from another crop, especially one in which the pest fail to survive or reproduce or can be sacrificed to destroy the pests and/or offspring to reduce the population. Trap crops can be planted in an area, usually a small area, adjacent to the cash crops. Trap crops must be intercepted by the stink bug prior to their movement to the cash crop. Currently, the use of trap crops is not widely used or accepted for control of the southern green stink bug, which may be due to a variety of reasons such as a strong "edge effect" behavior when moving through landscape, a dislike of crossing open areas where they are more exposed to natural enemies, and a preference for type of plant and plant part that varies with life stage. Further, trap crops are not effective if planted interspersed as it will draw the southern green stink bug to the center of the field where they would not naturally bother. In short, correctly placing the trap crop for optimal stink bug control is challenging. As such there exists a need to improve trap crops, particularly for control of the southern green stink bug.

Insects communicate with pheromones of diverse chemical structure and composition (Müller and Buchbauer. 2011. Flavour Frag J 26:357-377; Stokl and Steiger. 2017. Curr Opp Insct Sci 24:36-42). Many insect pheromones are derived from fatty acids while others arise from terpene (isoprenoid), amino acid, or alkaloid precursors (Blomquist and Vogt. 2003. PNAS 113:2922-2927; Jurenka. 2004. Insect pheromone biosynthesis. In: Schulz (ed.) Chemistry of pheromones and other Semiochemicals I, Vol. 239. Topics in current Chemistry. pp 97-131; Tillman et al. 1999; Yew and Chung. 2015. Prog Lipid Res. 59:88-105). Several studies over the past decades have investigated whether the biosynthesis of insect pheromones depends on the sequestration and conversion of dietary host plant precursors or may occur de novo (Blomquist and Vogt. 2003. PNAS 113:2922-2927; Tillman et al. 1999. Insect Biochem Mol Biol. 29:481-514). Terpenes are released by insects for attraction, aggregation, dispersal, or as trail pheromones (Bartelt et al. 2001. J. Chem Ecol. 27:2397-2423; Brown et al. 2006. J. Chem Ecol. 32:2489-2499; Dewhirst et al. 2010. Aphid pheromones. In: Litwack G. (ed) Vitamins and hormones: pheromones, vol 83. Academic Press, pp 551-574; Sillam-Dusses et al. 2009. J. Insct Physiol 55:751-757). All terpene specialized metabolites are derived from the 5-carbon diphosphate building block isopentenyl diphosphate (IPP) and its allylic isomer dimethylallyl diphosphate (DMAPP) (Tholl. 2015. Adv. Biochem Eng-Biotechnol. 148:63-106). Conjugation of DMAPP with one or several units of IPP by enzymes called isoprenyl diphosphate synthases (IDSs) results in the formation of cis- or trans-isoprenyl diphosphate intermediates such as medium size 10-carbon geranyl diphosphate (GPP) or 15-carbon (E,E)-farnesyl diphosphate (FPP). In plants and microbes these di-phosphates are converted by terpene synthases (TPSs) to monoterpenes (C10) or sesquiterpenes (C15), respectively, in a carbocation-dependent reaction (Chen et al. 2011. Plant J. 66:212-229; Christianson. 2017. Chem Rev. 117:11570-11648; Degenhardt et al. 2009. Phytochemistry. 70:1621-1637; Dickschat. 2016. Nat Prod Rep. 33:87-110). Insects synthesize isoprenyl diphosphates such as (E,E)-FPP as a precursor of juvenile hormones (Noriega. 2014. Juvenile hormone biosynthesis in insects: what is new, what do we know, and what questions remain? ISRN Zoology 967361). Consequently, FPP synthases or bi-functional GPP/FPP synthases have been identified from a larger number of insects (e.g., Cusson et al. 2006. Proteins. 65:742-758; Ma et al. 2010. Insect Biochem. Mol. Biol. 40:552-561; Sen et al. 2007. Insect Biochem Mol. Biol. 37:819-828; Taban et al. 2009. Arch Insect Biochem Physiol. 71:88-104; Vandermoten et al. 2008. FEBS Lett. 582:1928-1934). Moreover, GPP and FPP synthases have been implicated with providing the pre-cursors of defensive monoterpenoids in leaf beetles and alarm pheromones in aphids (Frick et al. 2013. PNAS. 110:56-61; Lewis et al. 2008. Insect Mol Biol. 17:437-443). However, in most cases insects have been assumed to lack the ability to convert prenyl diphosphate intermediates to terpenes by activity of TPS enzymes because of the absence of plant or microbial type TPS genes in insect genomes.

Only a single study of the bark beetle Ips pini (Coleoptera: Curculionidae) by Gilg and co-workers (Gilg et al. 2009.

Naturwissenschaften 96:731-735) suggested that the monoterpene myrcene, a precursor of the aggregation pheromone ipsdienol, is synthesized de novo from IPP and DMAPP in a reaction catalyzed by a bi-functional IDS/TPS enzyme. This enzyme first produces GPP as an enzymatic intermediate and subsequently converts it to the monoterpene product (Gilg et al. 2005. PNAS 102:9769-9765 and Gilg et al. 2009. Naturwissenschaften 96:731-735). Recently, a similar biosynthetic route has been detected for the formation of sesquiterpene aggregation pheromones in the striped flea beetle Phyllotreta striolata (Coleoptera: Chrysomelidae) (Beran et al. 2016. PNAS. 113:2922-2927) supporting the notion of a TPS-mediated biosynthesis of terpene pheromones in beetles. A family of nine P. striolata IDS-type genes was found, of which four encode functionally active recombinant sesqui-TPSs. Of those, PsTPS1 produces a blend of sesquiterpene olefins similar to that released by male P. striolata with (6R,7S)-himachala-9,11-diene as a main compound (Beran et al. 2016. PNAS. 113:2922-2927 and Beran et al. 2016. J Chem Ecol. 42:748-755). Interestingly, PsTPS1 requires a (Z,E)-FPP isomer as substrate, which is made from GPP and IPP by an enzyme with cis-IDS activity.

Whether the ability of IDS proteins to function as TPS enzymes has emerged throughout insect evolution is largely unknown despite the common occurrence of terpenes as pheromones or defensive compounds in different insect lineages. Among the true bugs (Hemiptera), stink bugs (Pentatomidae) release sesquiterpene sex or aggregation pheromones with a bisabolane chemical backbone (Weber et al. 2018. CRC Press, Boca Raton, pp 677-725). For example, the harlequin bug M. histrionica, a crucifer specialist, re-leases a mixture of (3S,6S,7R,10S) and (3S,6S,7R,10R) stereo-isomers of 10,11-epoxy-1-bisabolen-3-ol as a male-specific aggregation pheromone named murgantiol (Khrimian et al. 2014. J Chem Ecol 40:1260-1268; Weber et al. 2014. J Chem Ecol. 40:1251-1259; Zahn et al. 2008. J Chem Ecol 34:238-251). An IDS-type TPS, which produces (1S,6S,7R)-1,10-bisabolardien-1-ol (sesquipiperitol) from (E,E)-FPP as the presumed natural precursor of murgantiol in harlequin bugs has been described (Lancaster et al. 2018. PNAS 1150: 115: E8534-E8641).

The Southern green stink bug Nezara viridula is a generalist crop pest worldwide that attacks over 30 plant families (Capinera. 2001. Handbook of vegetable pests. Academic Press. San Diego) and can cause heavy crop damage on cotton, soybean, tomato, and other vegetable crops (Esquivel et al. 2018. In: McPherson (ed) Invasive stink bugs and related species (Pentatomoidea): biology, higher systematics, Semiochemistry, and management. CRC Press, Boca Raton. pp 351-423; Greene et al. 1999. J Econ Entomol 92:941-944). The sex pheromone of N. viridula was first identified in 1987 as a mixture of trans-/cis-(Z)-α-bisabolene epoxides (Aldrich et al. 1987. J Exp. Zool. 244:171-175 and Harris and Todd. 1980. Entomol Exp Appl. 27:117-126), which is released from unicellular glands at the ventral abdomen of mature males (Cribb et al. 2006. J Morphol 267: 831-840). Several ecotypes producing different ratios of the two pheromone isomers have been described (Aldrich et al. 1987. J Exp. Zool. 244:171-175; Baker et al. 1987. J Chem Soc Chem Commun: 414-416; Brezot et al. 1993. J Chem Ecol. 20:3133-3147). Since N. viridula feeds on a variety of different host plants, several of which are not known to accumulate bisabolenes, it was hypothesized that it produces its pheromone de novo, similar to M. histrionica (the harlequin stink bug). However, there is no significant homology with the IDS-type TPS identified in harlequin bugs to known enzymes in the known pheromone pathway of the southern green stink bug.

With that said, described herein are engineered Southern green stink bug pheromone synthesis enzymes and systems thereof that can be capable of producing (E,E)-FPP and converting (E,E)-FPP to (Z)-alpha-bisabolene, which can serve as a precursor of trans-/cis-(Z)-alpha-bisabolene epoxide. Also described herein are engineered polynucleotides and vectors capable of expressing one or more of the engineered Southern green stink bug pheromones described herein. Also described herein are genetically modified cells and/or plants that can express one or more of these engineered Southern green stink bug pheromone synthesis enzymes, polynucleotides, enzymes, and/or vectors. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Figures 14A, 14B, 14C:
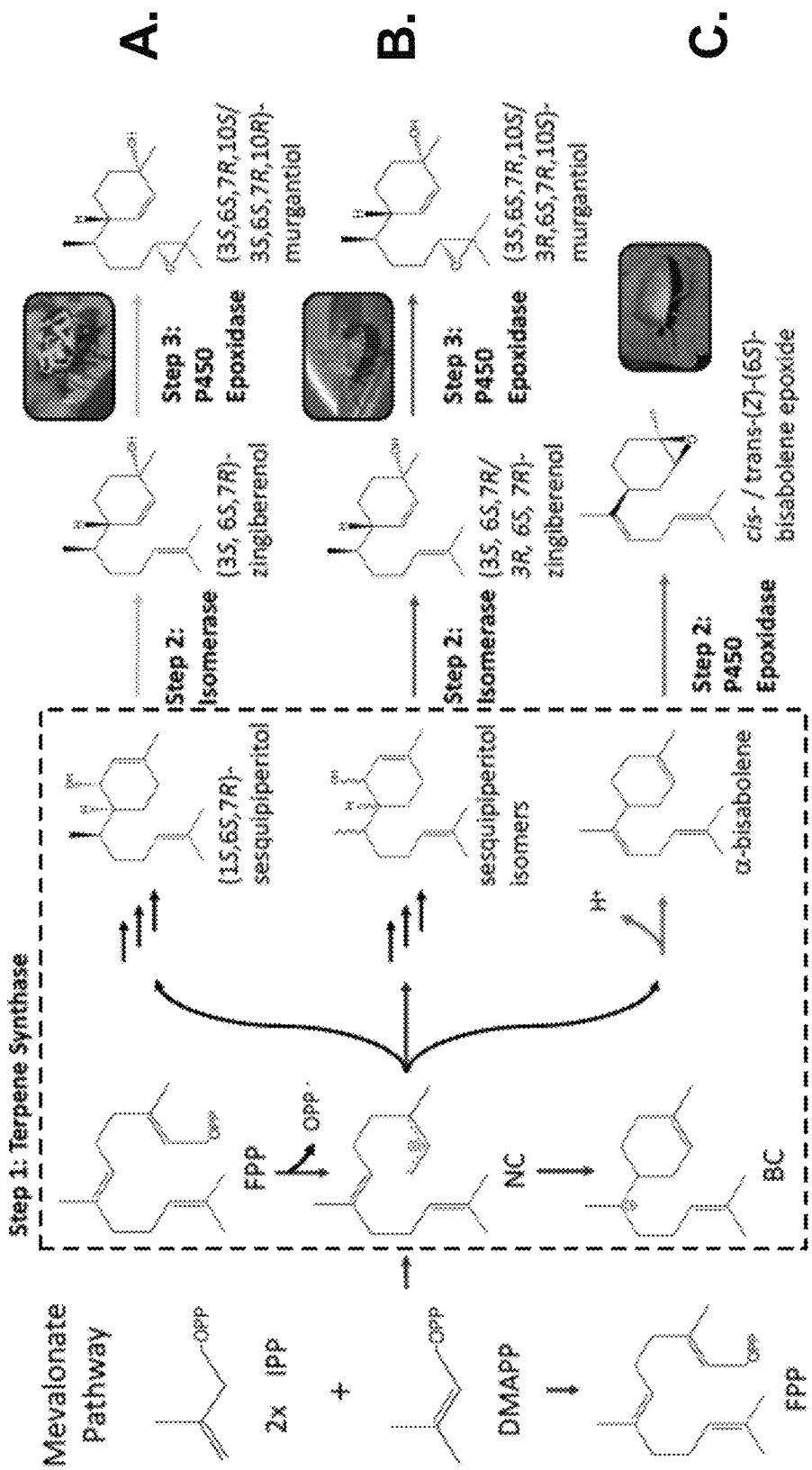
FIGS. 14A-14C show a comparison of different stink bug terpene pheromone synthetic pathways (FIG. 14A, brown marmorated stink bug.

Engineered N. viridula Terpene Pheromone Synthesis Polynucleotides, Vectors, Enzymes, and Systems Thereof All pentatomid pheromones are produced by the male stink bug and are either sex or aggregation pheromones. Many are terpenes with a bisabolene-based chemical backbone. Since the pheromone of N. viridula was first identified as a mixture of trans/-cis-(Z)-alpha-bisabolene epoxide, several ecotypes producing different ratios of these two components have been identified. The production of the N. viridula terpene pheromones relies on a linear reaction scheme involving multiple enzymes which produce various intermediates (see e.g., FIG. 14C and FIG. 2C). The pheromone composition and the production pathways between different species are quite different (see e.g., FIGS. 14A-14C).

Isoprenyl diphosphate synthases (IDS) are enzymes that combine two or more C5 isoprenyl diphosphate subunits in a head-to-tail condensation reaction to form the diphosphate precursors used by terpene synthase (TPS) to form over 55,000 terpenes known to date. With respect to terpene pheromones, a common question in this area is whether the insect (e.g., southern green stink bug) derives the precursors to the pheromones from the host plants on which they feed or if they are made by the insect de novo. As is discussed and demonstrated elsewhere herein, the Southern green stink bug produces them de novo. Also described and demonstrated herein are various aspects of engineered N. viridula enzymes and polypeptides that can be involved and capable of producing terpene pheromones of N. viridula. In some aspects, at least one of the enzymes is an IDS-like TPS N. viridula protein that can be capable of synthesizing the precursor (Z)-alpha-bisabolene (see e.g., FIGS. 14C and 15). In some aspects, at least one of the enzymes is a trans-IDS protein (NvFPPS) that is capable of synthesizing (E,E-FPP) (see e.g., FIG. 14C). As is discussed elsewhere herein, although these proteins may have evolved from a common ancestor they are now quite divergent from each other and across species of stink bugs.

The engineered Southern green stink bug pheromone synthesis enzymes, polypeptides, and vectors described herein can be used to produce N. viridula terpene pheromones in a variety of contexts including but not limited to in vitro production (such as in a cell-based production system) and in vivo production (such as in a transgenic plant). Further aspects, features, and advantages are discussed elsewhere herein.

Enzymes and Systems Thereof

Figure 2A:
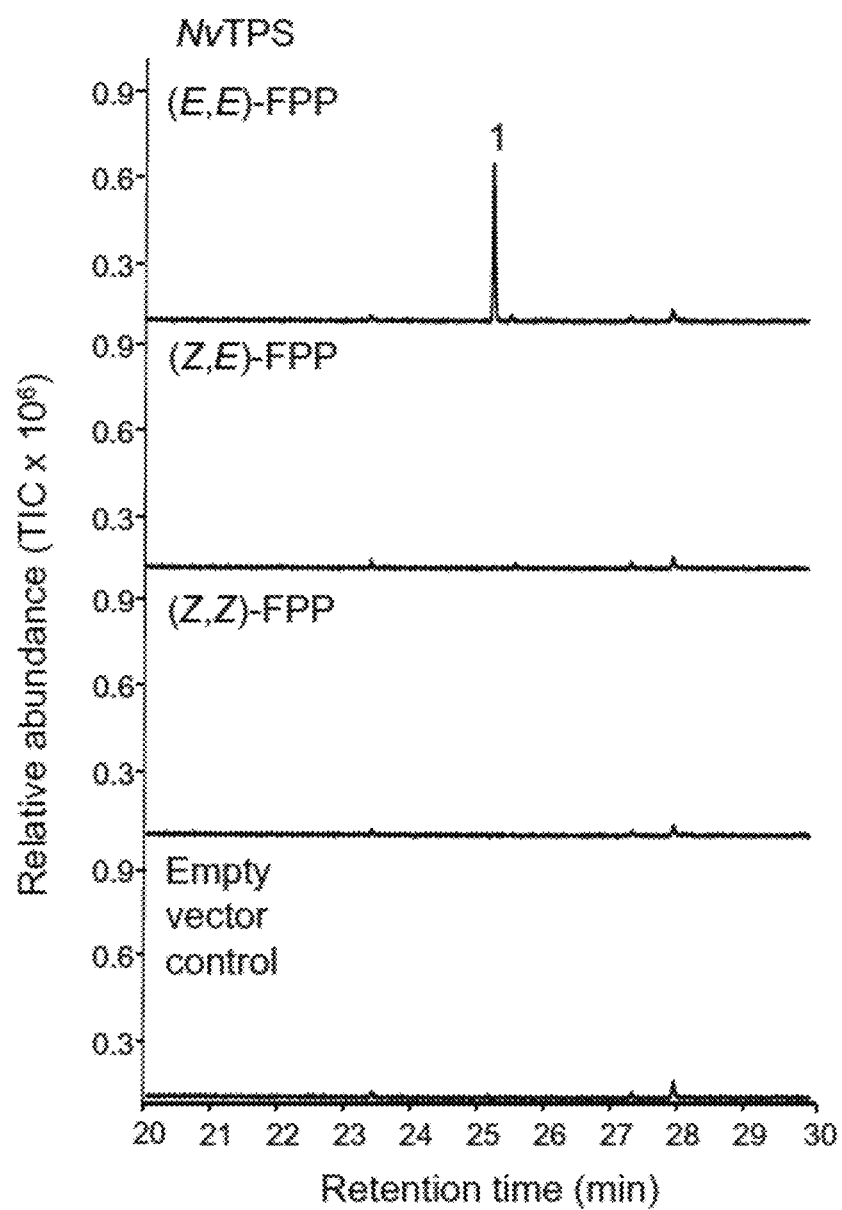
FIGS. 2A-2C can demonstrate functional characterization of NvTPS and NvFPPS from *N. viridula*.
Figure 2B:
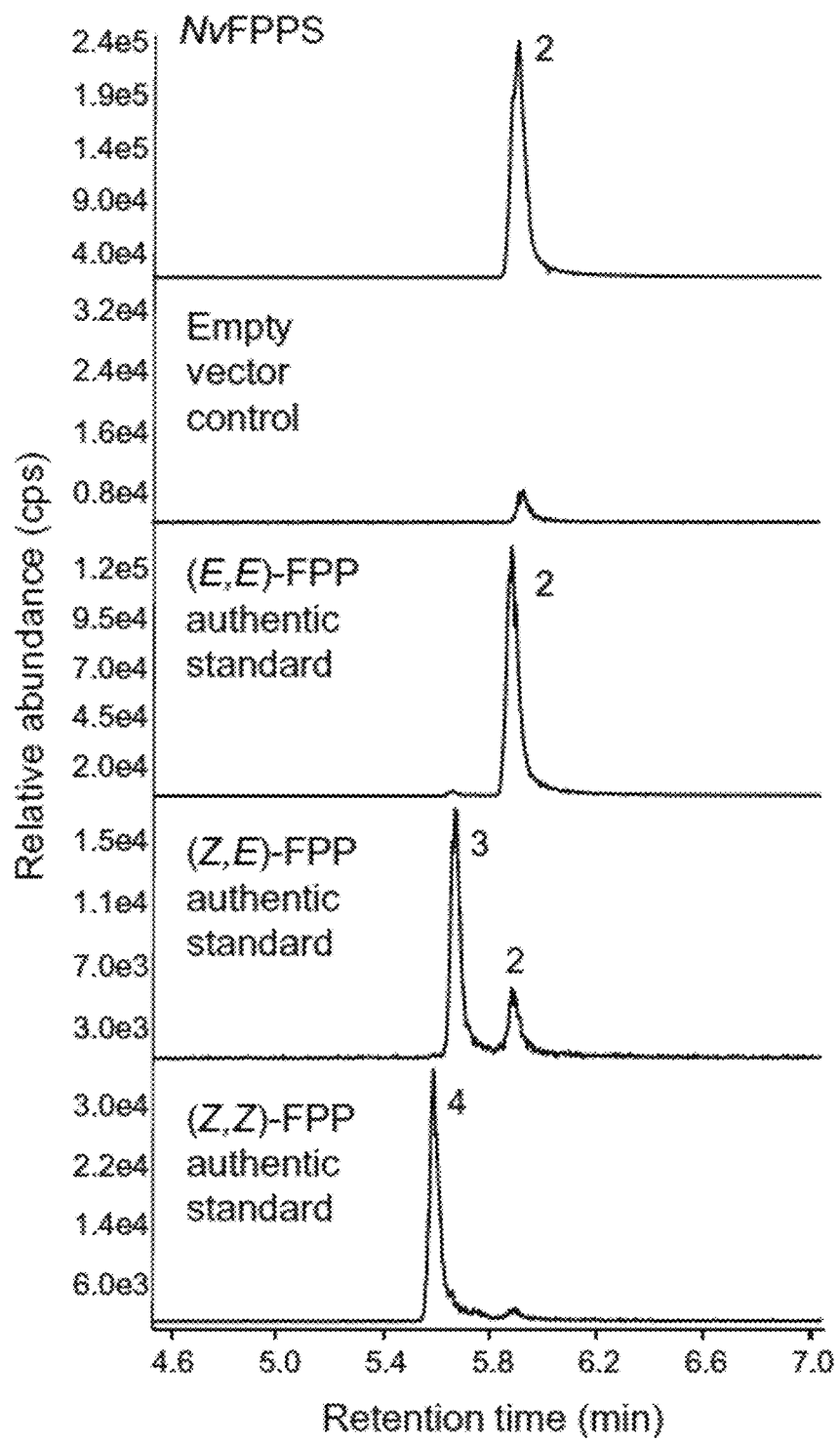
Figure 2C:
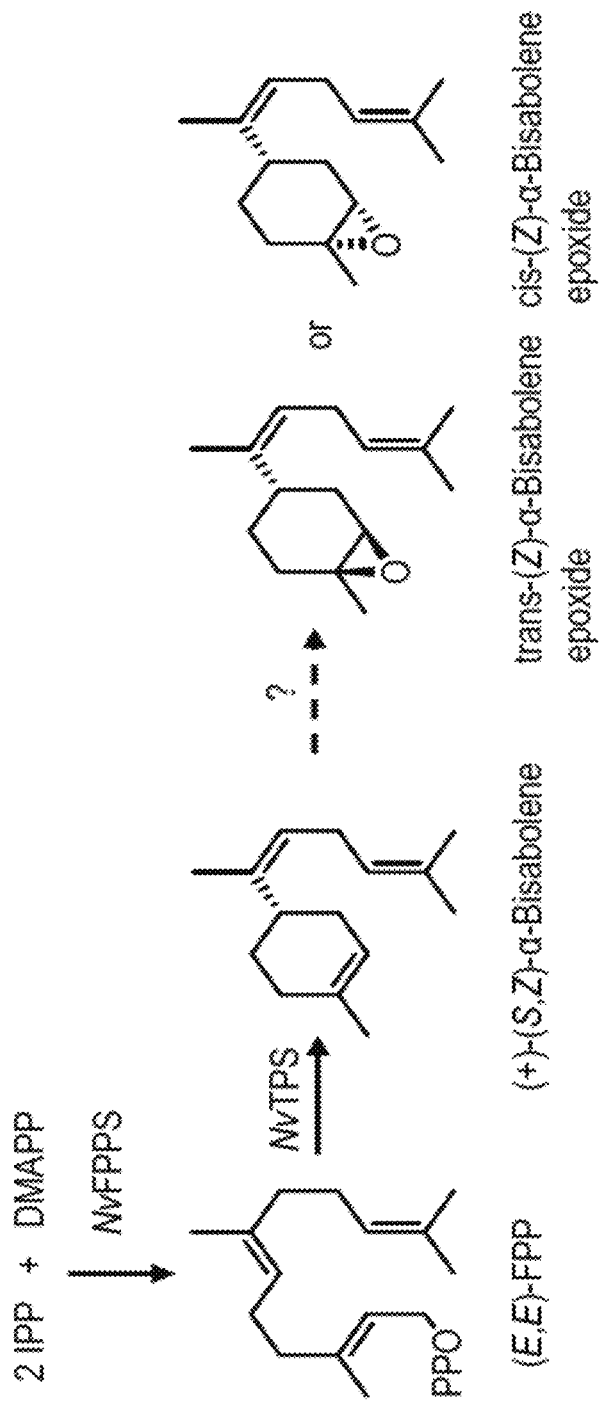

As shown in e.g., FIG. 2C, the engineered Southern green stink bug terpene pheromone synthetic pathway can include an FPPS enzyme (NvFPPS) that is capable of converting the precursors IPP and DMAPP into (E,E)-FPP. In some aspects, the NvFPPS enzyme can have an amino sequence that is about 93-100% identical to SEQ ID NO: 5. As shown in e.g., FIG. 2C, the engineered Southern green stink bug terpene pheromone synthetic pathway can include a TPS (NvTPS) enzyme that is capable of converting (E,E)-FPP into (Z)-alpha-Bisabolene. In some aspects, the NvTPS enzyme can have an amino sequence that is about 55-100% identical to SEQ ID NO: 4. As shown in e.g., FIG. 2C, the engineered Southern green stink bug terpene pheromone synthetic pathway can include an enzyme capable of converting (Z)-alpha-Bisabolene into the cis-(Z)-alpha-bisabolene epoxide isomer, the trans-(Z)-alpha-bisabolene epoxide isomer, or both. In some aspects, enzyme capable of converting (Z)-alpha-Bisabolene into the cis-(Z)-alpha-bisabolene epoxide isomer, the trans-(Z)-alpha-bisabolene epoxide isomer, or both can be a P450 enzyme. In some aspects, the P450 enzyme is a member of the cytochrome P450 enzyme superfamily. Southern green stink bug P450 family members have been identified and characterized. See e.g., Denecke et al. Epigenetics and Genomics. DOI 10.21203 (2019). In some aspects, the P450 enzyme can be a CYP9, CYP6, CYP4, CYP395, CYP3230, CYP3231, CRP322, CYP3226, CYP3225, CYP3224, CYP315, CYP314, CYP3092, CYP307, CYP306, CYP305, CYP302, CYP301, CYP18, CYP15. In some aspects, the P450 enzyme(s) can be selected from the group of CYP9, CYP6, CYP4, CYP395, CYP3230, CYP3231, CRP322, CYP3226, CYP3225, CYP3224, CYP315, CYP314, CYP3092, CYP307, CYP306, CYP305, CYP302, CYP301, CYP18, CYP15 and combinations thereof. In some aspects, the P450 enzyme can have or include a sequence that is about 70% to 100% identical to any one of SEQ ID NOs: 6-79. In some aspects, the P450 enzyme can be selected from a polynucleotide having or including a sequence that is about 70% to 100% identical to any one of SEQ ID NOs: 6-79 and combinations thereof.

The enzymes can be used alone to catalyze a step in the process of southern green stink bug pheromone productions. Where an intermediate is produced, the intermediate can then be supplied to a new reaction with an enzyme present in the following step of the process. In some aspects, one or more of the NvFPPS, NvTPS, and P450 enzymes can be included in a reaction to produce the southern green stink bug pheromones or an intermediate in the synthesis scheme. Where two or more enzymes of different types (e.g., NvFPPS., NvTPS and/or, P450) are included, an enzyme system is created. An enzyme system can include (a) one or more (e.g., 1, 2, 3, 4, 5, 6, 7, 8, 9, 10 etc.) different NvFPPS enzymes, with enzymes having different polypeptide sequences being considered different enzymes in this context; (b) one or more (e.g., 1, 2, 3, 4, 5, 6, 7, 8, 9, 10 etc.) different NvTPS enzymes, with enzymes having different polypeptide sequences being considered different enzymes in this context; and/or (c) one or more (e.g., 1, 2, 3, 4, 5, 6, 7, 8, 9, 10 etc.) different P450 enzymes, with enzymes having different polypeptide sequences being considered different enzymes in this context.

One or more of the enzyme(s) described herein can be contained in, expressed in, and/or otherwise produced by a cell. In some aspects, one or more enzymes can be produced by a cell and subsequently harvested by a suitable technique. Suitable cell-based protein production techniques are generally known in the art. Various vectors to facilitate cell-based expression are discussed in greater detail elsewhere herein. The enzymes described herein can also be made in a cell-free system. See e.g., Lee and Kim. 2018. FEMS Microbiol. Lett. 1:365(17). As described in greater detail elsewhere herein, the enzymes can be used to produce southern green stink bug pheromones, in vivo, ex vivo, and in vitro.

```
>NezVir_CYP4G227/1-562
                                                          SEQ ID NO: 6
MSISAATPVISVPSAVLSATSVFYFLLVPALVLWYVYWRMSRRHMIELASKIPGPPGLPILGN

ALQFTGSSHDIFERVYSYSFEYKDVTRVWIGPRLVIFLVDPRDVELILSSHVYIDKSREYRFF

RPWLGNGLLISSGPKWRAHRKLIAPTFHLNVLKSFIDLFNANSRHVIKKLEKELGKEFDCHD

YMSEATVEILLETAMGVSKKTQDQSGYDYAMAVMKMCDILHLRHTKFWLRPDSIFNLTKYG

KIQENLLATIHGLTRKVIKRKKADFAKGIRGSTAEVPKELQTKNYESKVEQKATVEGLSYGQS

AGLKDDLDVDDNDIGEKKRMAFLDLMIEASQNGVVINDEEIKEQVDTIMFEGHDTTAAGSSF

FLCMMGVHQHIQDRVIQELDEIFGDSDRPATFADTLEMKYLERCLMETLRLYPPVPIIAREM

KEDLKLASGDYTIPAGATVVIGTFKLHRKPEIYPNPNKFDPDNFLPERTANRHYYAFVPFSA

GPRSCVGRKYAMLKLKILLSTILRNYRVYSDVKEEDFKLQADIILKRSDGFRIRLEPRKRAAK

A

>NezVir_CYP4G228/1-554
                                                          SEQ ID NO: 7
FGSSVNNKKMIAVFTFLIVTAATLYYIKWRSERKRLYELAEKIPGPELLPLASKAFSILKNHNT

LLKYIYDLSFIPEYQNVAKLWLGSRLVVGLVHPKDVEIILSSNVHLKKSQEYKLFEPWFGNGL

LISSGETWRHQRKMIAPTFHLNILKRFMDEFNRNSQRVIERMRKENGKMFDCHDYMSEIMV

ETLIETVMGVKQESQNRECFSYAHSVMDLCDILHTRHTRPWYRPEYLFKLTNMSKEWDRN
```

-continued

LQNIFNLTNRVFNTKKEDCIKNKSKESTMTKEDVKEETKVETKIETHSDEKFSYGQAAGLKD

DLDDDNEIGEKKRLPFLESLIDRSQNGDKLTDQDIIDQVNTIMFEGHDTTAAGSSFFLCVMG

DRQDIQAKCIEEIDSIFGDSDRPVTFQDTIEMKYLERCIMETLRLFPPVPLIARELEQDVQLMS

ENILLPKGCAVVIGTFKLHRRADIYVDPDNFDPDRFLPENAVNRHYYSFVPFSAGPRSCVGR

KYAMLKLKILLANILRNFRVKQGKPMKDWQLQADIILKRSDKFEITLEPRRVQKVC--------

>NezVir_CYP4G229/1-550
SEQ ID NO: 8

MDSQELDHSELRSRLYSISSLILPIFILLYVGWRLANKRFIELAEKIPGPPGLPIIGNALELRGT

PNEIFENLYSKSEIYPDVARVWAGPRLLVFLTNPADIEIVLSSHDHLDKSAEYDFLRPWLGN

GLLVSTGEKWRSHRKIIAPTFHLNVLRSFMERFNRNSKKTLERLAKEGDNEFDIHDYMSEFT

VEVLIETVMGVKKENEGRSCFDYAQAVMKLCDIVHLRHTKFYLRPDLVFYSSKYGSEQKSL

LSVIHGLTEKVLKVKKAQFENKIQDKHQETAEKEVLKETSESKEGFSYGQASGLKDDLDVED

IGEKKRNAFLESILERAANNDSINDKEVKEQLDTIMFEGHDTTAAASSFFLCMMAAHPDIQQ

KCYEEIMRVLGDSDRDITFNDILEMKYLERCLMETLRLYPPVPIIARQPKKEFKLASKNLIIPA

NCTVVIGIIKLHRRADIYPNPEKFDPDNFLPEKSASRHYYSFIPFSAGPRSCVGRKYAMLKLK

TILASTLRAFYVKPGYTEEEWKLKADIILKRADGFRIKLEPRKETNTKN------------

>NezVir_CYP4G230/1-532
SEQ ID NO: 9

MDLLTFFGAVLTAAIAGYGAFWYSRRRLYELAAKIPGPTSLPLLGTLSEFSGGAHMVFENMV

KKCHEYGDVIKFWIGPRLLVFLADPADIELILSSHVHIDKAPEYQFFQPWLGDGLLISTGNKW

RNHRKLIAPTFHLNILKSFIPLFNSNSRGVATKLKKEVGKEFDCHDYMSEATVEILLETAMGV

NKKTQESGYEYAMAVMKMCDILHLRQTKLWLRPNIIFYLTSLGKLQDKLLNIIHSLTKKVLKIR

MEEYKNNGSKLPGNVTFVTGDDGKIQVEGDFSFGHSKGIKDDLDEDIGEKKRLAFLDLLIDA

SQGGKLTDEEIQNQVDTIMFEGHDTTAAASSFFLCEMAARPDIQEKCIEELNKIFGDSDRPV

TFEDTLEMKYIERCLMETLRMYPPVPVIARELQHELKLASRDLVIPAKCTVIVATFKLHRKENI

YPNPNVFDPDNFLPERSASRHYYSYVPFSAGPRSCVGRKYAMLKLKVLIATILRKYKVLPGK

KEADWKLQGDIILKRTDGFGIRVEPRTSSV-------------------------------

>NezVir_CYP4G231/1-551
SEQ ID NO: 10

STIKSSLDRRQEQHSEGGMDILGIDSILVAGLTAAIAAYGYFWFSRRRLYELASKIPGPAGYP

FIGNALRFIGGADTLFKNVFSRTLEYGDWKMWVGPRLLVFLTNPADIELILSSHVHIDKAPE

YRLFEPWLGDGLLISTGEKWRNHRKLIAPTFHLNVLKSFIPTFNSNSVDVVKKLKQDVGREF

DAHDYMSEATVEILLETAMGVNKKTQKNGYEYAMAVMGLSNILHLRHTKLWLRPDFIFNMT

SLSKLQEKLLNVIHSLTRKVFNIRMDEYKKNGSKIISTTPEDNAKVQAEGDYAFGHSKGIKDD

LDDEIGEKKRMAFLDLLIDASQGGGKLTSEEIQHQIDTIMFEGHDTTAAGSSFFLAMMAARP

DIQEKCVEEVKRIFGDSNRPVTFQDTLEMKYIERCLMETLRMYPPVPIIARELKQELKLASCD

LTIPAHCTVVVNTFMLHRKPDIYSSPNYFDPDNFLPEKSASRHYYSYIPFSAGPRSCVGRKY

AVLKLKVMLATILRNYRILPGKKEKDWKLQGDIILKRADGFPLVMEPRAIKV-----------

>NezVir_CYP4EK4/1-537
SEQ ID NO: 11

MAEVTSFDVFSSSYLPQSKRVYKSPCRNLLPVNSEMVRLFKLQKVLSSAISALSDVISCLYS

WTRFYWMVSRLPGLPLTHSYKQWEGFQSKYNALNTLVKWREKYKTFHKVYISFLPVIFAYS

PELIQELLSKKQKHNDKGKVYHTLLPLLGDGLITSKGEKWFAHRRMLTPAFHSNILESFFETF

KSETNTYINSLKDSELTKGYGDICPHTRRLTLKFICETAMGFSELADCKEAEAVIKSMHKLEEI

```
ATLRVIHPWLLSDSIFKMSALYKELNENKKILHNFSNTLIKRRKSILKKRLRNPYLEVHKRKEIF

LDQLILQQLQGIKITDEDIRDQVNTFMFAGHNTTQLAINYCIYLFGRYKDVQETAHNELEEIFN

DSNREPTLDDLRNMEYLDRCIKEALRLYPSVPIIARKLTEDQPIGKHILPKDTDCFIIPYVTHR

NPEQFPNPEVFDPDNFLPERINNRHPYSYIPFSAGPRNCIGKRFANIAEKTVLSWILREFKIE

SKLKQEDLKLIPSTVLIPSGGLQVKLTPRKC------------------------
```

>NezVir_CYP4GW2/1-528                                            SEQ ID NO: 12

```
MMDKPSVMEELLAECIIYWLFILGIIVSSVVALHYYLSKRRYYQLARKIPAPPGLPIIGHAFNIL

MGTEEAFRNVWNTMSDCDVCKLWLGTRLFVFIKNPADIELVLNSRIHLCKPSESNLLKTCLG

DGINTVSGCQWKSYRQLIAPMFQWSQTFQPILRNYSRILDDRLLKNVGKDIDCYNYMSDAV

MELLLISIFGENTDTEESKKYFEAIQKLKEIIRYRQNKFWLHPDLIFNLTKYSKLQKDLLRIINRF

TRQAIKNRKRALMEQGYGWPKNGYFEDQNGNIEHNNNITTCLKEGDRSPSLLELMMEVSH

NGTTLMDSEIQNQVDALVLEGLDTTALTGSFFLGVMADRPDIQERCAIELSQIFGDSDRQVT

FEDTLQMKYLERCLMETLRIHPPVPFITRELQQELRLASTCLTIPANSTLMVDVKKLHMNEEL

YSSPDVFDPDNFLLEKCVSRHYYSFIPFSAGPRSCVGTKYSMLSLKVLLSSILRKYKIFPSSG

QESASMMTKDTRRTERFVIKMEHRKR--------------------------------
```

>NezVir_CYP4GX1/1-546                                            SEQ ID NO: 13

```
MFRMTDWTSDLQTVAFFAAVVPLLYYVYWRIANRRLLQLAAKIPGPPGLPLLGNLLEFTGSP

TEIFEKLVEKSYQYEDVIKVWFGPRLFVFLTNPVDIEVLLTSTEHIEKSVEYDFMKPWLGDGL

LISSGQKWFTHRKVIAQTFHLNILRSFLGKFNENAKKLVKYFEDETGNEFDCRRYMCKYTAE

TLIDTVMGADKDQLGFESPVYSGATTKLCELVHLRHTKLHFRSDLLFNSTKHGFEHKKFVSL

VHDFSAKVIKFKKSQRELLKPSPFIEKFDDIRKEDKSLTHYEKSTGISYGQSSGLKDDLDNEV

IGRKKKCAFLDTLLEKEANREVFSMKDVQDQIDTLMFEGHDTTAGVSSMFLCLMATNLDVQ

AKCVEELEKIFGDSDRDVTFEDTYEMKYLERCVMETLRIYSPVPVIARNLKKELTLVTNNITL

PVSTTVIVAIFKLHRREDLYPNSEKFNPDNFIQEKTAARSFYSFIPFSAGPRSCVGRKYAILKL

KVVLSTILRNYQITTSCPMESWKLQADITLKRTDGFKIKLIPRKNA
```

>NezVir_CYP4GY1/1-494                                            SEQ ID NO: 14

```
AAIAIVLILLSIIITLLISRVIRDLFKLKGIPGPWELPFLAELRMILLPFTVLYPVLQKYIEDYGGVC

AIYRTGRVYVMLSEPETVEPVLSSYNHIKKGDYDYAFLRPWLRDGLLLSDGSKWRNRRKLL

TPAFHFKILEDGMKCLTEKSEEITEKLLATKGEPTDLEDIIRSSTLGAILETAMGVPSSDANGY

QQHQQEYQSKIKGITESIMRRYYRLWKHIESLYRLSSEGKEFFNDVNRLQLFTKKVIKDRKQ

LYLIERDSKPGDKKSKIKPFLDCLIELNVSTPGAISEDGIAEEVDTFMFEGHDTTASALNSALF

LLANNPIEQEKAAEEQMEIFGDDNRVPSTHDLNKMEYLDMVIKEVLRLYPSVPIITRSLTEDL

KINESITVPAGCIAAIMPYFVHRSAKHWDNPEEFRPERFDTGISRHPFSFIPFSAGPRNCIGQ

KFAMMEMKTMLSAILRKCKLEPVTTSFEIIPTWLKSDQPILIKVLPRK
```

>NezVir_CYP4GY2/1-483                                            SEQ ID NO: 15

```
MFEALYAVVVVFLVGLILKKWWDQKIPGPRGLPIMGIALELAQIPPRDIFAKIDSLRQTYSGIF

EMKIMTDSYVMLTDPESVEPLLSSSKHIKKGIFDYKFWRLFLGDGLLLSDGAKWHHRRKVLT

PTFHFKILEDAMTSLVKNAQSLTEQFLDTEGKPTDVGNIIRSSTLKVICETAMGVKLNTDDET

QNKYVEAVKRIPEAIILRYLKFWLHSDFVYNLTKDGRNFKKDLNLAHSFTKKIISERRMLYKN

QKADNSENKSKKKAFLDCLLEMGEALTDQDICEEVDTFMFEGHDTTSANLVFSLFLLANHP

EEQEKVVEELIEIFGETDRPPTLSDLAKMNYLEMVIKESLRLYPSVPLISRSLTEDLKLGADVII
```

-continued

PAGYTAVVAPFLVHRSKTHWENPEEFRPERFMPGTPRHPFAFIPFSAGPRNCIGQKFAMM

ELKTMLSSVLRKCKLEAVTKEVNILPTGIIKSEETILMKIYKRNL

>NezVir_CYP4GZ9/1-458

SEQ ID NO: 16

MWMMVAVILCLICVLLVLFVGYLAIYWKPSRLPGPRGLPYFGIAFSMIGITSKDIIHHLMKWFE

EYGDIFEFQILGQKYVFVTDPQLLQPILSSNTNITKGRFEYSFFRPMFNDGLIISDGDKWRTR

RKLLTPSFHFKILETSIESVGRNTEEFVSHLLKSNGKATEIEDHIYLLTFKIICETAMGVKLNTV

DNQQNEYIKASKICHDSTVYRYLRIWLFPDFIYRLCKVGKTFFKCLDVIHNFADQVIKSRKEL

FIAEKNDFTNKDSKRKAKNTFLDNLLELDDSNPGLFTKSDIREEVDTFMIAGHNPTAAALKFL

HFLLANHPDVQEKVHDEQVEIYGDDKRTPTAQDLHKMIYLEMVIKETLRLYPSIPLYSRLLDK

DLQIDEKTIIPAGCNVAVFNYCVHRSKKHWDNPEEFVPERFVPGIERHPYSFIPFSAGPRNCI

GQKYAMMELKTIMP

>NezVir_CYP4GZ10/1-502

SEQ ID NO: 17

MIVIWGLSCVLMVVFVRFLVKNWKPSMLPGPRGFPYFGAAFSVVGISSKDIIPLIIKWCDEYG

KMFGVKMLGANYVFVSEPELVKPLLTSSINITKGRFEYSFLKLIFNDGLIVSDGEKWRSNRRL

LTPSFHNKILKSSVETVGRNAEEFVSQLLASDGKPIDIEDTTHLLTLKIICETAMGVKLNTKDK

QQNEYVKASRICHDTLVYRYLRFWLFPDFIFRRSDVGKRFIKSLKLIHEVADQVIKKRKELYIA

EKNESKNEDSRKKERNAFLDNLLELVDSNPDLFNESNIREEVDTFLIAGHNPSAATLKFLHFI

LANRPDVQEKLYDEQVDIFGDSKRMTTAQDLEKMTYLKMVINETLRLYPTIPLYSRCLKEDL

LIDEKTIIPAGHTVAVFTYAVHRSKKHWDNPEEFIPERFAPGIEIHPFSFLPFSAGPRNCIGQK

YAMMELKIIISTLVRQCWLEPVTTSVSLDYGITLNPVEPIIVKAIPRNGTRRMIPERNS

>NezVir_CYP4GZ11/1-501

SEQ ID NO: 18

MMSITLGLICVLLLVLASFYRKPSTLPGPRGLPYFGNVWLYMIGRSSKDIIPFLKYFVNYYGNI

FELQIFGMNYVFGSEAELVKPILTSHTNITKGRFEWSFFKPMFRDGVIISEGEKWRTRRKILE

PSFHFKILKRSIESVARYAEEYVSNLLNSEGKPTEIEDMIYLLTLKIICETAMGVKLNTEDRQQ

NEYVKASKLCHDGAVYRFFKLWLYPDFIYRRSNAGKTFFRSVDIIHDFATQVIRNRKELFIAE

KTGSNNQDSTKKEKNAFLDNLLELDDSNPGLFTESDIEEEVSTFMIAGHNPSAATLKFLHFV

LANRPDVQEKLYDEQMEIFGNDKRIPTGQDLQKMIYLEMVIKETLRLYPIVPFQSRLLEEDLQ

IDENTIIPAGHHFVVVSFSIHRSKKHWDNPEEFIPERFAPGNIINPFSFIPFSAGPRSCIGQKY

AMMEMKTIMSTVVRQCWLEPVTTSITLDYGIILKSAEPIIVKAFPRNENQRINYKRNN

>NezVir_CYP4GZ12/1-490

SEQ ID NO: 19

MMLMCLLAALCGFLTLRLWRRRPRGPPGPPAIPYFGQAFRLLSIAERDILPLFKEWFDTYGS

VVQVEMLGNVYVLLSEPESLEPVLSSSVHISKGYWEYLFFRPWLNDGLLLSTGDKWRLRRK

LLTPSFHFKILESFLGGISKNSETYVESILESGGKPLDIQEPIRMATLKIICETAMGVTLSTDNE

EQNAFITAIKDASEGIVLRYLTFWLYSDFIYRRSEFGKKFYNSIDTLQSFSKKVIRRRKQLYQS

EKSDVGEGNKSRRKAFLDLLLEVEDSNPGLFTEADIQEEVDTFMFEGHDTVSAAIIFSHFLLA

NHPNVQEKAFKEQDGIFGNDDRPASMQDLQRMTYLEMVIKETLRLYPSVPFHSRKLYQDL

RIDDNTWPAGQSVGILTFYIHRSTRHWDDPELFIPERFDPEISRHPFSYIPFSAGPRNCIGQ

KLAMMEIKTLLSTVLRNCILEPVTKSVDPVASVIIRNLDPIILKVVPRPRAA

-continued

>NezVir_CYP4HB9/1-489
SEQ ID NO: 20
MLLLLLSLALLFIVWWKSIPSSKFREAGSTIPGPKAYPVVGNLFNFKLTGPSALKHWERYTKI

YGNTFRIWIGPHLQIFTIEPDDIQTIFSSKMSTKSNSYKALESWLGTGLLISNGNLWHQRRKAI

TPTFHFKILESFVPIFYKCGIILVNCLKEKVGKVPFDITPYMSNCALDVVAETAMGTEVKAQTN

PHDEYPKSVLRMTKLLADKMYNPYWNLLEPIYTLLGKKKEETDLLKLLSTFPLELLKRKENE

KNNHPSSRENGENKNIAFLELLVRIKETKNPAFKSEQDIKDEVVTFMFEGHDTSSMALVYTF

WLLGLHSEIQEALFQEVSQTLVGKIPSMEDYHKMDLLNRVLKESLRLYSPVPLVSRMITEEIV

LPGSGYRLPAGTQVVVSMYSLHRRADLFPEPEKFNPDRFLEPIKHPFAYVPFAAGPRNCIG

QKFVMLELKVIVSLVVLNFEIHSSNKNLKLTRDILLRCLNGPNVSLTLRK

>NezVir_CYP4HB10/1-493
SEQ ID NO: 21
MDFFLYLSAILAVLLIWLLFPNRMSRMARKIPGPRALPIFGNIFNFIVIGPKAPECWKKQMETY

GNTFRVWLGPQLHVFMVDPEDIKAILSSQSLLTKSESYKTLVPWLKTGLLVSTGKLWQMRR

KAITPTFHFKILDEFVPIFYKCSKILLDCIKDKVGQEPFLITGFMSNCALDTIAETAMGTELKAQ

TNPQSEYPTSILRMTTVLVERVANPLLGMEPLYTLSGRRKVESDLLKILFSLPREVIRGKKYF

KSNRKNITPSDEAFGIKKKTAFLELLLEMKENNAPAFQTDKDVQDEVITFMFEGHDTTTMAL

TYTTWLLGMHPDEQEKLYQEVSSILEGKAEPSMEDYSKMEYLERVIKESLRLYPPVPIIGRE

AIEDVLLPSSGFLIPKGTQITIIIYALHRREDLFPDAEKFNPDRFLEQQKHPYAFLPFSAGPRN

CIGQKFAMLELKVMISNLVLHYKIKSKKDMILNPEMLLRSENGPYISITPRN

>NezVir_CYP4HB11/1-477
SEQ ID NO: 22
WLLTPEKRLREMGNKIPGPTPYPLVGNIFNFNIFGIKALDDWKYCMNKYGRTFRFWLGPQL

HIFITEPEDIQMLLSSQTLITKSEAYYTLESWLGSGLLVSTGELWQRRRKAITPTFHFKILDEF

VPTFNKCANTLVKILKDKVSKGFFPLTDFMSHCALDAVAETAMGTEIKAQTNPIGEYPSSVV

KMTTTLMEKIGNPLLGMEPLYTMSGRRTREDHLLNILFSLPLEVIRKKENEKNSPTDSSPTE

EAFGVKKKTAFLEYLLKMKRDNVPAFQTEKDIKDEVMTFMFEGHDTTTMALTFAVWLLGLH

QDIQEELYREVSGILVGQEPTMEDYQKMTYLERVLKETIRLYPSVPIVARKATQDVVLPSCG

YTVPKGAHLDVIILALQRREDLFTDPDKFNPDRYFEPQKHPYAYIPFSAGPRNCIGQKFAML

DMKVIVSNLVLNYKIESDEDIIVSPEMILRTKKGPNIRLISRN

>NezVir_CYP4HB12/1-494
SEQ ID NO: 23
MYMILITLALGAFMIWWLFRPEKRLREMGNKIPGPKAYPIVGNIFNFNLYGINGPKDWKECIE

KYGPTFRVWLGPQLHIIIAEPEDIQALSSKTLITKSDAYSALQPWLGTGLLLSTGELWQRRRK

AITPTFHFKILDQFVPTFSKCANTLLKVLKDKVGKGFFPLTHIISDCALDSVAETVMGTELNAM

TNPIGEYPTAIERMTLLLMEKIKNPLLGMEPHYTLSGRRKKEKHLLNILFSLPLEVIRKKEIENI

DVRDDSDASGDAVLGVKRKAALLELLLKMKRDKVPAFQTEKDVKDEVITFMFEGHDTTTSS

LTFAIWILGKHQDVQEEVYREVSEILVGQEPTYEDFQKMTYLDRVLKESMRLYPAVPIVARQ

ATHDWLPHNGYTIPKGAYLNVMIYPLHRREDLFPDSEKFNPDRHLKPHKHAYAYIPFSAGP

RNCIGQKFAMLNMKVIISSLLLSYKIESNDDLIVYPELLLRTKKGPYIRLTPRN

>NezVir_CYP4HB13/1-518
SEQ ID NO: 24
PLLKQCSIFILARDHYISHSKSRMEFLLLSLALGAFILWWMFSSPKRLRELGNRFPGPRTYPI

VGNIFNFQIIGPNAPQCWSNFSKKYGYTMRFWLGPELHIFVSEPDDMQMILSSQTLITKSTS

YKLLDSWLGMGLLLSTGNLWQMRRKAITPTFHFKILEKFIPTFNKCANTLVNCLKDKADKGY

-continued

FNIIDYMSNCALDAIAETAMGTEIKAQTNPLEKYPRSLSRMTKYLIERVRNPLLSMEPIYTLSG

RRKEEAKHLDVLFSLPLEVLEKKKNEKINTLNETEPLEEDYGAKKKTAFLEMLLEMKQKNIP

GFRSDKDIKDEVMTFMFEGHDTTTTVLSYTIWLIGMHPDIQEELYKDLKEITEDSELTIDVYH

KMHYLERIIKESLRLYPPVPAFGRLATQDIVLPTSGYVIPAGAQVDLVVYLLHRREDLFPEPE

KFNPDRFLEPAKHPFAYIPFSAGPRNCIGQKFAMLDLKAIISHVVLNYKIESDSNLEVNPEML

LRTSKGPNVKLTARNQ

>NezVir_CYP4HC1/1-511
SEQ ID NO: 25

MDMSVVIWIIVMGVGWAWPYLLLGIVLLLIYKFYNSRSFKLLSAIPSTNAPRFIGHTLDFLTMH

PSNILSFMLQLFDKNKTNKNVMAIWTGPFCFVYLRTLPDIEKLLSDNQQLRKSINYIYLEPWL

GQGLINSDGTIWQRHRKMITPSFHFKILEGFLEIMNSKLDIFSEVLEKKVGNGYFDIEPLIANY

SLDVITETAMSTNVDAQRTNSEFIDCIKSLTEVIIRSVRIMYFFQPIFNLSPYKNQESKSINYV

NKYIAKILENKRTEAKNIKKDENVENDIGAKEKLALLDMLLQLQFSNAKITDKEIYDEVNTFMF

AGHDTVSSALSFVIYNLAVHQDVQEKVYAEVMEVLGDSKPTYQSLMNFKYLERVIKETMRL

YPSVPYIGRRLKKDMPITDGHIVPKDSDVAVFIYDHHRNPENFPDPEKFDPDRFLPENIAKR

HPYAYIPFSAGSRNCIGQKFAMMEQLATVSHLLRQFRISIEPGFVMKPISHIVLRPNVEGVRI

KLTKR

>NezVir_CYP4HD1/1-469
SEQ ID NO: 26

MLILFGILLTALFLLRFFCRHFNYYKLALRLPYAKKAPLIGHALNLWVDKDELLDKILEIIGEPD

NKRSIQEHGVLAVWIGPMAIVLVHDLQDIEQILTSRDLTRKSYQYKFFEPWLGQGLFTASGP

HWYSHRKLITPAFHFKILEKFIPIFNANIDIYLRKLDEKVGKGSFNIENYIAYLSLDIIAETAMDA

KINAQKEESPYAQKVKDMTETILLRGCRLLYYSDVIFSLSSLGRRQKRSKRFIDNFINDLVKR

KKEERNRIQLTKNNKNNSEIDEKERVALMDVLLETQNRSSHFTDKDILDEVNTFMFGGHDTI

TSCINFTLYLLSKHPTIQEEVLREIESVIGEEKFTLSNLQQLKYLERVIKESLRILPVGPFMQRA

AEKDIKLRSGYVLPAGCTIIMMIYALHRNPEYFPNPEQFDPDRFLPENCLNRHPYAYLPFSA

GPRNCIGQKFALLEMKAIIAATIR

>NezVir_CYP4KC1/1-522
SEQ ID NO: 27

GQNDRGAPTLYRPPAAQSFATSLPEDMIILVLLAIVVVLFVYLLSPDAKTRKCGQQIPGPKP

WPLIGNLFDMELGHKGVKTYNGFQAKYGHVIRYWLGSKLAVLLSDADDAEVLFRDTQNLG

KADVYKFMHPWLGTGLLTSTGHKWFQRRKAITPTFHFKVLDQFIEVFERKSTILVECLKSMA

NGQSFDIHPFVSRYSLDVICETAMGTSVDAQNNIESEYFNAIRTVADCIVTRILKFWLHPNFIY

RFSRLSKQHDAALRWHGFSKKVISEQDRLNNKEQLHNDKESDTGMKKRTAFLKLLIEMKR

QQNGAFTSEDDIREEVDTFMFEGFDTTASAISFAIYEFGRHPNIQETAYHEVRDAFAGETAL

TIECLNNLKYLERFIKEVLRLYPSVPMIAREICKDIKIPSGYLIPAGSIATVVIGGIHRNKKYYKN

PDKFDPDRFLPENMVNRHPYSYVPFSAGSRNCIGQKFAMLEMKASLSHILLNYEIGTTEESK

YGMLLTLQSFNGQNVWLKPRRTA

>NezVir_CYP6HK6/1-496
SEQ ID NO: 28

MLAIILVVLAAYAFYQYSVWTFDYWKKRKVPHPPPVPLFGNIKEVVLMKQYPGHCHQQIYK

MYPNEKFVGLYQLRMPSLLIRDPSLVKQCLIKDFDHFFDRGFHTDEEREPLTGHLVSLTGTR

WKLLRTKLTPVFSSGKIKQMFPLLLDCSDQLRDFIKTQMGGKEGVLEMREVTARFTTDVIGT

VAFGLQPESMSGDSVFRQMGKRALQPTVAGALAKAMRCFTPKLFDLLKMRTFPEEINSFFT

NVVSETMKQRTEANYGRNDFLQLMMQLRDASGADIAKNDIELNDQVIAAQAFVFFLAGFET

```
SSTTLSYCLYELAKNRQCQEAVFNEIQEVMKKHGELSYEAVSDMIYLEQVLLETMRMYPPV

GNLCRVCTKPYRIPGTDIQLDEGVSLVIPVFALHHDPELYPDPESFIPERFTDKELQKAPYYL

PFGGGPRICIGQRFAMIEMKLALLRLLENYTFSLSSKTPPELPVEPKSFIMAPIGGIWLNLNA

RS

>NezVir_CYP6LV26/1-492
                                                     SEQ ID NO: 29
KYYVSVYDLWEKRGIPYYPSTFPFGCSYQILTHSRFPGYIHDEMYKKLAPNPMFGLFVMRV

PMLQIRDPDLIQLILTKEFSHFRERMFIKISEKDVLNQHLFNLDGERWRALRLKLTPTFTSGK

MKAMFPLFLNCAEAFDSLILSKIGCDVDVKDLIGRLMTDIICSCAFGLDSNTIKEPDHKLRQIG

AQVFKMNFMDKVKIAILQAMPKLANKIEARFTPKETEDYIVKLVENTIEYREKNNIKRNDFLDL

LIQLKNKGTVGDDLKDEIEEQKCQPFELTIGLMAAQCFVFLVAGFETSSSVQSFCLYELAINQ

DIQTRVKKEIDEKIEKHGGLTYQAVKEMEYLDMVISETMRKYPTLPILMRYCSKSITTPYGYKI

EAGDTIIIPVWSLHHDPEYYPNPEKFDPERFSPQNMESINPYTYLPFGEGPRMCIGMRFGKL

QTKVGLITILRNCRVEPCAATKIPLVIGPSPMLTIPKDPIELKLVPRSSSS

>NezVir_CYP6LV27/1-510
                                                     SEQ ID NO: 30
MLTILIGLLIPLWLFYKYYVSVYNFWESRGIASEPGRFPFGNKLQLVTMNKSQALVIDKMYKK

FESQPYFGFYVLRSALLVVKDPEIIRLIMAKDFSHFRDRFPARVFTSKEDKLQHHLFNLGGE

KWRALRIKLTPTFTSGKLKGMFPLFIACAEDLSKMLISQIDKPVNVKDITACYTTDTVCNCVF

GWENNSINEKENKMRKLGQTVLEISKTVLLKRMLRNIFPGIAKLLKLRIVSNEIEDSLIKMVGD

TIAYREANGIKRNDFLDLLIQLKNKGSVEDDVKKNGNDTTAEPVEMDLGMLTAQCFVFFVAG

FETSSSVQSYCLYELALNPEIQKKLREEINATINKHGGITYQAIQEMEYLDMWSETMRMYPT

LPALNRHCTKDYTTPSGQKIKKGDDIIIPLYSLQRDEKYFPEPKKFDPERFSKTNKYKINPFTY

MPFGEGPRNCIGSRFGLIQTKVGLITILKNYEVCKTEETQVPLEFRGSGVIAMTKGPITLKLS

PKPSDY

>NezVir_CYP6LV28/1-500
                                                     SEQ ID NO: 31
MLVGWIIVGLLWLFYKHWISNYSYWKKRGIPFYPAEFPYGSDPNFVKLKKFKGYTMDKMY

HEFAPHPMFGIWLRKPMLIVKDPELIQMVLTKEFSHFRDRGIFKLPKRDTINHHLFNLEGEK

WKAIRMKLTPTFTSGKLKTMFPLIISCAENFSSLLLSMADSKVDIKELAGRFTADVISSCAFGL

EIDIMNNPDNKLRRIGIERVKVKTLKKLKNTLTQIFPALSTILPARSNESEEQNYVINLVKSIIEQ

RENNGIVRNDFIDVLIKLKNKGNLGDDAQETEEPFEMTIELMAAQCFVFFIAGFETSSSVQSF

CLYELALHQDIQSRLIKEIDETIEKNGSLTYKAVQEMEYLDMVISETSRKYPTVPTLVRQCTK

SVTLSTGQNIEKDTMIIIPVWSLHHDSQYFMDPDKFDPERFSKENRDSIVPYTYLPFGEGPR

MCIGMRFGLLQTKVGWTLLRKFRVEPCEETNIPLVIGGNSATTASDKPIIIKLIARY

>NezVir_CYP6LV29/1-514
                                                     SEQ ID NO: 32
ATSRRIVLLQLPYKMLFGVTIIAGLLWLFYKHWVSVYTHWKEKGIPFHPAKFPFGSHPNLVKL

KEYRGYTIDKMYHRFAPHPMFGIFFLRSPMLIVRDPETIQLILTKEFSHFRDRRILKISEKDVL

NHHLFYLQGEKWRDLRMKLTPTFTSGKLKAMFPLFISCAESFSSLLLSKSDSKIDIKELMSRF

TADVICSCAFGLELDVINHPDSKLRMIGIEKIKLQFLQKLKMAATILFPALSTLLNMRFTSLEDE

KYILNLVKKIVEQREKNGIVRNDFIDLLMQSKNKGNQGDNEQEFEKTFEITLELMAAQCYVFF

LAGFETSSSLQSFCLYELALHQDIQSRLIKEINEKIENNNGLTYKALHEMEYLDMIISETSRKY
```

PTLPMLYRSCTKPIILPSGHKIEQDTIISIPTWSLHHDPQYFPDPEKFDPQRFSQENRGSIVPY

TYLPFGEGPRMCIGMRFGLLQTKVGIVTLLQKCKVETCEDTKIPLVMGGISATTAPDEPIIIKLI

ARS

>NezVir_CYP6LV30/1-507

SEQ ID NO: 33

MFMTIYLVALAFFLLYKFWTSNYSYWKDRDIPHIPPVFPFGSSRDLALQRGFQGDIWSELYR

KCSSQPFFGVHIMRTPFLVMRDPEMIRFVLASSFFNFRDRQPFKRSREPLTHHLFNLEGEQ

WRALRTKLTATFTSGKLRGMFPLFLSCSESLDSILQTNVNKVIDVKDITARFSTDIIGSCAFG

MDMDSISNPNSEFRKIGIEIFKLKNSTRIKLALVNTFPDIMKLFSPRFTPKSVEKFILRAVSGTI

EHRLRYGIKRKDFIDLLMILKYMNGDKKKSDDIPKLNLNDMTMEMMAAQCFVFFTAGFETS

GSVQSCCLYELALNQNIQNRVQKEIDHMTEHYGGLTYEAVHKMVFLDMVIAETMRKYPTLP

SLTRFSTERTVLPSGHVIDKGVRVLIPVWALHRDPLLFPEPEKFDPERFSDDNMALIKPFSYL

PFGEGPRMCIGKRFGLLQTKMGLITVLKKYRVEPTSKTEIPLDFSPKCILITATEGPIHLRLVE

RTDHCPS

>NezVir_CYP6LV31/1-533

SEQ ID NO: 34

FDNWLYLNTLFFIQLFSLKQVHTFNEMFAIIISLVVIAAVVYYRRYRSFYSHWDKRGIPAIPGS

VPWGSYSSRSHMRQYQGFSLDKFYYKMTNHPYFGFYDMRSPILIAKDPEVIRLILTKEFSHF

IDRTYTGLPKTDPLLHYQLFSLSGNKWRALRTKLTPTFTSGRMKAMFPLFLDCAQGLNSLL

WSRVGSIVDVKDAVARFTTDVICSCAFGLQTNTVVEPNHPLRKAAADFLAFGDSLYLKFRLL

LTLLSPFRIPFNRFTPKSVEDYIMKLISDTVEYREKNKITRNDFLELLIQLKNKGSLKDERKEE

VEENFEINLDVMAAQSFLFFFAGYETSSSVQTFCLYELALNQDIQQKLRNEIQEVIKIHGEVT

YQAVNDMKYLHMVVSETMRKYPTLPALMRRCVIPFTMPDGGKIQKGDQIFIPIWSLQHDPQ

YFPDPEKFDPERFSQENERNIIPYTYLPFGGGPRMCIGNRFGLLQTKVGLITVIRNFQVLPCD

KTSIPLKLVKNSNNITACEGPIILKLIPTAPEN

>NezVir_CYP6LV32/1-451

SEQ ID NO: 35

MLFVVFLLAVVLFLVYKWWTSVYSVWDRRGVQNVPARTPLGSDGRFTLLTKYQGYTLNEM

YQKFSSPYFGIYLIRSPFLVIKNPEIISIILTKEFSHFRNRQFLKIHQNDFIFQHLFNLGDDKWKT

TRGKMQSTFSSSKLRTMFPLFVKCTENLMSALLEKEGDTINMKQALASFTTDLTCKTLFGLE

ADTNCDSEVTRIGKIATDFNLMILLKIAVKLAFPEIAQNIPIKVFSTDIDKFFLKLVTEIVDYREK

NNVKVHDFMDLLIQLKNRSKNGEEKKFENGNINIQSQDITLEVMAAQCFFLFNAGFENSSSI

QTYCLYELALKPEIQKTLQDEIDKCLKKHGEMTYEALKEMNYLNMVISETMRKYPILPFVTRV

CTSPLTFPDGFQVEKGDQMILPTWSLQHDPQYFPDPEKFDPERFSEQNKDSIVPYTYLPFG

EGPRMCLGMRF

>NezVir_CYP6LV33/1-441

SEQ ID NO: 36

KHKYFGYYEMRRPLLVVKDPEVLKLVLTKEFSHFRDRFTRPMPKTDPLLHYQLFILGGDKW

RALRTKLTPTFTSGRMKAMFPLFVDCAQALNTLLWSQVGSAVDVKDVISRFTTDIICSCAFG

LQTNTIAEPDHPLRKATADFLSNGDSLFFKIKFIVSMLVPFILPLSRFTPQEVEDYIMKLISDTV

EYREKNQVTRNDFLDLLIQLKNKGSLREEGIAETEESFEVTLEVMAAQCFLFFFAGNETSSS

VQSFCLYELALHPEIQQKLREEIQEVIRIHGGVTYQSVNEMKYLHMWSETMRKYPTLPQLV

RSCVEPIVMPDGGRVEKGDQIAIPVWSLQHDPQYFPDPDKFNPDRFAPENEGNIKPYTYLP

FGEGPRMCIGNRFGLLQTKVGLITIIRNFQVLPCEKTSIPLKLVRTNNSLTTCEGPILLKLTSIE

ERS

>NezVir_CYP9DS1/1-392 SEQ ID NO: 37
SKMRGMFTFMSECAKDFASYFLEEANGKPIEVDMKDLFTRYTNDVIATSSLGIRCDSLRER

ENSFYTMGKKMTTFSSLTAGIKMMVATVLPKLLEITKIGFLPKDCANYFTQIIFETIQRRTKENI

IRPDMIHLLLEARKGNLKHESKADESSGFATVEESDIGKSQKSRSVELTDEVIAAQAMIFFFA

GFETSSTVMSFMSLELAINTDVQQRLLEEIDEVYKQYGDNVSYDAIMKMQYLDQVISETLRK

WTPGFQTDRVCVKDYVIEPTKEGEHPLHIEKGLLLLVPTAGFHYDPKYFPNPEKFDPDRFS

EENRSSIVPGSYMPFGLGPRNCIGSRFALLEIKVLFYHILSKFELTVVKRSCVPIKLSTEFNLT

VEGGFWLGLKPRNISV

>NezVir_CYP15A1/1-490 SEQ ID NO: 38
RMWFLILLAVLLALLILESTPPSRFPPGPRWIPFLGNYLLFYKLRQKLGFTHLVWEWLSKRY

GPLVGVRLGNDKLVIGTNLAVVKELLTKEQFEARPDGFFFQFRAFGERYGLVFVDGEFFNE

QKRFVMKHLKSFGLNRSIMEGRISGEAEDLVQHILKNQKDGVVFSEIVEISVMNILWSIVAGG

RFQLDDKKARVLIDHIHTSFRLQDMSGGILNQMPFLRFICPELTSFNKLKDVLGNLTTFVKQII

DEHRETVSSYENRDLVDAFLNEMKKHEASKSTFTEKQLIILLLDLFLAGPETTSATLGFAILHL

LHYPHIQNNLHNELDTVIGKGKRPCMKDKPNLVYMEAFTMELLRSVNVTPTTVSHRAKEDA

EVMGYIIPKDTIVLANLYSLHMNKDHWIDPEKFRPERFIDENGAIIQNDFFIPFGLGKRRCMG

EALAKTSIFLFLTTILQNFKVRPVSQELPPMKSLDGATISPASFRCFFEPRE

>NezVir_CYP18A1/1-526 SEQ ID NO: 39
MYHVKMLLELRSLAVFFIVFFFGRRLWALLSRIRTLPPGPWGLPLLGYLPFLKPEAHVHFAQ

MAKKYGGIFSLSLGNQFVVILSDYKLIREAFRREDFTGRPDTEFTNILGGYGIINSDGRLWKE

QRKFLHDKLRRLGMTYSGQGKHEMEARIMKEVEVFLHTLSKERNNSTDLNPILCTSISNVIC

SLVMSVRFKQKDAKFTRFMNLIAEGFRLFGSLNYANFFPIMRYLPGLQEVIKKIAKNRTEMA

AFFQETVDDHRATFDSHNMRDLIDNYLMEIEDAKATGRSEELFQGKEHDRQMQQIIGDLFS

AGMETIKTTLLWAVLYMIHEPEVASKIQEELDRVVGRNRLPKLEDRPYLPYTEAVILEVLRISS

VVPLGTTHSIHQETKLGGYTIPENAHVVPLLHAVHMDPNLWDEPKAFKPERFLNQEGKVCK

PEYFMPFGVGRRMCLGDVLARMELFEFFSSLMHTFHLRKAGEDSGLPTLEATTGATLTPLP

FEVSLVQRPLQDSPHEFLNTCQGLRPAGSL

>NezVir_CYP301A1/1-539 SEQ ID NO: 40
CVPCWEVLQRCESSSLSIQVIFKLIFLYPGYLSEHTMQRWSGLGRRLSQLAACPSEVVRPY

QEVPGPRPLPIIGNTWRFLPVVGDIEVSDVAAVSQKLYDVYGKIVRLSGLTGRPDLVFVFDP

DEAEKVYRAEGDTPYRPSMPCIVKYKTEVRKEFFGELPGVIGVHGEPWRTFRTRVQKPILQ

PRVVKQYIAPIQTVTELFIERMLEMKDENDEMPDDFDNEVHKWSLECIGRIALDVRLGCLDR

NLPNNSEPQKIIDAAKFALRKIAILELKAPYWRYFPTTTWRKYIENMDYFRSVCMKYIQMALE

NLKKKDNKQELSLLERILETEKDPKIACILALDLILVGIDTISMAVCSVLYQLATRPEEQQKMH

EELVRIMPDPNCQLTSEMLDKMVYLKSFIKEVLRMYSTVIGIGRVLQEDTVLCGYRIPSGTQL

VFPSIVMGSIEGYVSEPHRFLPERWMKCDRDNHYIHPFASLPYGFGARMCLGRRFADLEM

QILLAKLIRTYRIEYFHEPLEYKVTFMYAPDGNLKLKMSKRKE

-continued

>NezVir_CYP301B1/1-524　　　　　　　　　　　　　　　　　　　　　　SEQ ID NO: 41

MEPAAGGEELGQASQSPQLSLHLNMIMRRTLCSAVSDIGAVLPKSYQKVPGPRPLPLLGNN

WRFLPYIGQYKLEEIDKLSLMLRSRYGRIVRISNLLGRPDMVFLYDPNEIEKVFRGEDTLPYR

PSMPSLDYYKHQLRKDFFSDIGGVIATHGEKWHQFRTKVQHALLQPRIAQLYLKPIEETANE

FVNRIRDIRNENNEVPDDFLNEIHKWSLESIAKIALDARLGCLTPDGSQETQELIDAVNTFFK

NVVILELKIPFWRVISTRTWKEYVEALDTIMRIVYKFVSKTLDELKNKNNECKEDSSLLQRVL

YENLDNPKVAVILALDLFLVGIDTTSAAVSSILYQLSLHQEIQNMLYEEINRVLQNGPIDMKKL

DQMVYLKACIKETLRMYPVVIGNGRCLKKDTVVCGYTIPKGTQIVFQHHAISNSEEYFDDPN

VYKPERWLKKQKKKQYHPFATLPFGYGKRMCLGKRFADLELQCLIAKIIETYKVEFKRKLLD

YSVHPMYMPHGPLNFKYTERKKKT

>NezVir_CYP302A1/1-512　　　　　　　　　　　　　　　　　　　　　　SEQ ID NO: 42

MAFIQRILSKRNVCSNALRKKDVPKPFNQIPGPRSLPIIGSSWKYIPFMGDWDVSKLHIVGTK

RFEQYGGLVREEVSPGINFVHVYSAQDIEKIYKNEGKYPERLGHLALMHYRLCRPHLYNSG

GLLPTNGSEWWRLRSTFQKHIARVQDARSFLSKGEDIINDFVTTILFNNYTCEDFLPLLSRLY

LELMWMFIFGKRLNSFDSINISENSIPSKLMKAAEDITHTTMITDSSEKIWKVIKTPSYIKIEKN

FEYIEKIVLSALKEAETENSKNRKHSDENSKICLIDKFFQTPEMSSKDINAMTADLVLGGVDT

TAYTTAFLMYNLSRNKAVQEKLYSEAVKLLPSPDTRITSDILNSAIYARAVLKESLRLNPVSV

GVSRILQQDTVFSGYLVPKGTLMLTQNLVACRNEDNFKNALEFIPERWIRGSPAYQEVSPY

LVLPFSHGPRTCIARRLAEQNMLTLLLSIIRKYSISWMGEVMDIETPLTCKPDKAVKLSFHNW

VVKNKVLNIS

>NezVir_CYP305L1/1-502　　　　　　　　　　　　　　　　　　　　　　SEQ ID NO: 43

LKLGIHRELTKMSLLVFISVIVLIVLFYYNLKSVKYPPGPIALPYFGNIITIKKLSKKFNGLQGAFI

ELSKQYRTDVLSVSMSGEYSVVVQGKELIDEVLRGDEFQGRPNNFFIKLRSMGARRGITMT

DGPLWKEQRAFAFKHLHEHGLGTQKMDDMLQRQLQEMLSKLNEGVLSNLVLKQYVSKCV

LNVLWEMVTGSSFQDEETMTSLISLMEARSKAFDISGGLLSQFPWIRYIFPKYSGYNLIQTLN

RKFKEMIMGIIEHHKKTIVKGHSRDFIDAFLHEMNENPTSSSFTDEQLVMVCLDFFIGGSQTI

SGTLDYCFLYMTMYKDVQEKVQKELDDILLPGQSPSRNNKNKCPFVEAVISEVLRISPIISLL

GPRRTTCDTFLSGYFIPKDTTVYLNFKTVHDSSKHWEDPGKFKPERFLNEEGTVKQEQTLY

NFGRGKRRCPAEVLARTALFILFSGVLHNLKLEPADEKDPLSLRQVPGITTSAAEYYIKLTRR

HK

>NezVir_CYP306A1/1-558　　　　　　　　　　　　　　　　　　　　　　SEQ ID NO: 44

AVSQLITVQYLVKCFTILQSCLQVMYEEDARGGYISGVLTKVAVRFSPLQSTIAMLPHHDTH

STSYGLDCSLIFKDLSEILIASLVLLCVTVFFYYLWRTRGMPPGPWGLPLVGYLPWIDKDKPY

VSMMELYQDYGGICTIRLGEVVAIVVSEPHYVKEALSQESLTGRAPLWLTHGLMNNNGLIAV

EGPKWREQRKFVINCLKNLGAVKVGEKRAVMEKRILGGIRITFQMIDERREDGPFDPKQILS

HTIGNIMNTIVFGKSFDLDDHTWVWLQHMAEEGVKLVGVAGPLNFMPYLRILPQYRKLLDFI

KNGQKRTHDVYRSIANEQRTKDNILSYYLEAIASGKGEYFDEAQMLHLLADMFGAGVDSTL

ATYRWVLLYLALHPEVQERVYEEVSSVIGKGKEPNMDHFSMCPYTEATILETMRIRPVVPLG

IPHGATKDTQIAGFRVPEGTMIIVNQWTLHHNPKYWINPEEFEPKRFIDSDGCVRRKDSFNP

FQTGKRSCFGEELAKMVLFLFTSSMVLRYRLQLEGSSSAGLGGECGITLSPGQHSISFVLR

Q

>NezVir_CYP307B1/1-477

SEQ ID NO: 45

MEGIYLSSASYLLLFGLAILWAVLSVLKRPKGSAPGPTPLPVLGSLHLLGGYELPYQAFDKLS

SKYGPVFGIRLGSVECLVVSSLETVKEILINKGEHFDSRPNFSRYLNIFGGDKDNSLAFCDW

SELQKTRREMIRDHTFPKAFSSKFHQLESLLNRELVVLCDQLSKGVTNIKPIMLHTCANVFM

SFFTNTRFQLEDPVYSKILMYFDIIFYEVNQGYAADFMPWLNPMLMNNMKKMRKLGKIIREF

MDERVVSNGGQEGDLLHMLLESVESGKMNRENAMFALEDIIGGHTAIANLIIKILGFISNQPE

VQKKMQEEVDAVTCGKNIKLEDRLMMPYTEAVILESIRHICSPIVPHVASQDTTVNDYHVEK

GTLIFLNNYTLNMSPELWTEPEKFSPERFLTEDGRLIKPEHFLPFGGGRRSCMGYKMTQYV

SFSVLATMMQKYSIAPHPTNGKVPRGDLALPFDTLKFIFNPR

>NezVir_CYP314A1/1-511

SEQ ID NO: 46

MQPPLEWSIPNFTAVFLFIAILLLKELRPIFKKTRYLTRPVTTKKKIPTVNQIPGPLQLPVIGTR

WIYYTKYTLEKLHEAHKDMYRTYGPIVKEEALWNIPIINIFSKNEIEKILRHPSKYPLRPPTEVT

AYYRATRPDRYASLGLINEQGETWHTLRSHLTPELTSAKTMSSFFPELLSVTEDFIRLLQVS

KDANGIVEHFDDLACRMGLESTCCLILGKRLGVLEDEASEVSLRLANAVKEQFCASRDTYF

GLPFYKLYPTKAYKRFVNAEEIIYDVISEMVENAENLENDTYLEDSPSVFQSILNNPGLDIREK

KAGIIDFIAAGIKTLGNTLVFLLYLMAKNPECQEKIVDEIDSLTSGKELTLQALGKANYLKACIA

ESYRMLPTAPCLARILETDMELNGFHLPSGTVVLCHTWQASLMEENFQNADQFIPERWLG

KERMPWLVAPFGAGRRLCPGKRFVELELQVLLAQIVRKFKLECAGELEIQFEFLMAPASPS

SLKLVERT

>NezVir_CYP315A1/1-443

SEQ ID NO: 47

MMKMIPYVKGLPIIGTSLSILAAGSSPKLHLYIDRRHKKLGPIFKENMGTICGTFVADPLAART

VFSAEGRYPKHMVPDAWKVYNKMYNCNRGLFFMEGEEWLKYRHIMNKLILKRNLPNQQV

QEYIISSFMESMDNFVGKQMHNIEHKFYQLSISFFIGTLMGTAIINKMEYFNKDIDNLALVVNS

IFSTTTNLMNIPISLATSLNMKIWKEFTESVEYTLKAGRVLLEKIKGFPLNDGLLKDLLEEDLD

DEVITGLVMDMILAAGDTSAYTSQWALYLLSREPEVADKVRSNDQLVSGVVKEVLRLYPAAI

FISRYLDRDLILPTLDCQLSKGELVMLSLYTIGRLESAYTEPLKFKPERWMRHVDSNSRHYL

GVKEPMAWLPFGVGSRSCIGRRLAEAQLHLTISKILSKYRLHLVEPVDMELRMVPVPTKPIKI

KVDRL

>NezVir_CYP395P1/1-516

SEQ ID NO: 48

MITIALLIVIVSLLAYVYNWANNINQTWKRRGVKHRKPALIFGNVTILVPRKDQKHLSVLCADI

CREFPDEPLVGFYDFTQPWLLLQDAEYIEKVLIKDFVHFTDHGFAINEEKNPIDAQLFNMVG

KRWRAFRYKLSPIFTSGKLKSMYEPMSDCGVDLDNVLKTSNKEGLDFKQLMTHFAVDVVG

SSVFGIHPKAIQNPNTKFCSLATDLFTFGFFDTIKFLIMFIFPKLSIKLGISFNNQNAVNYYSKIL

KETFEYRTKNKVERNDFVQLLLTLKEKKKIDVQNWDSNDDYLKDGEAPAELESYEITENILM

AQAYAFLVNGIDVLALSQVYALYELSLEPEIQEKAQNEIREQMKLHNGITYTALKNMTYLEKV

VKETLRLHPAGGTLFRTCTKDYVFPNGTVIKEGEMLVIPMSAVHLNPNYYPEPDVFKPERFD

LPMKPGTFLTFGDGPRVCIAMRYAILLIKYGIVKILSNYKVTLNTKTELPIKLKPNAAIGTPTSP

LLFDLEAINKDY

>NezVir_CYP395Q3/1-512

SEQ ID NO: 49

MLTLCLIILVLTLVGFIVNWIRKVHLFWEKKGIKHLKPSFLFGNSLPVLLNKKSISEQFIDLCKT

YPNEPLLGHYDFLKPSLIVQDADYAEKILIKDFLHFTDHGMEVNEDKNPIDAQLFTMCGKKW

RAFRYKLSPIFTSGKLKNMFDTMAVFGDRLVNLLSTKKEYKKVNLREAMSSLSMDIIASTVF

GIETNVLENPDSEFRKMGKKVFDFGIVGFIKIWIIMSFPGLGKKLGVSINNKDVVQYFTDIIKK

TFSHRRKNNIHRNDFVQMMIQLQDKGHIEVRNWDANDDYLKTDEDSNMNVDSYEITENVVI

AQAFTFLTTGLDTIGIGQTYLLYELALQADIQDRVREEIFEQCKIHGGLNYDSLKAMTYLEKCL

KESLRLHSTPQLFRICNKNYTFPNGYTIKKGETIQIAVSAIHRNPDYHPDPEVFKPERFDNLM

RPGVWLSFGEGPRVCIAMRFALLQVKFGVARMLMKYRLSINPETKLPVEVLPQSVVLEPKY

PIYFDLEEVS

>NezVir_CYP395R1/1-512

SEQ ID NO: 50

MLAVGFGVLFIVLLLLILMWISSMNRHWEKKGIKFSKPFPLLGNCLPMILSKKSFTDIIDDLYN

AHPNELVIGYYEFVSPKLIVRDLELARKVLIKDFSYFVDHVSEMDNVAWDSQLFMLSGNKW

KALRLQMASIFTTGKLRTMYDSMPDIGKNLLQHLDNKVGNDIDIHELMILFSMDMIGSTAFGI

DVGSLNNPNSEIMQMGKKIIDVGFLSVMHFWLYLLYPKLGNKIGIPHVYREVNNYYSEILKNT

INYRKANKIQRNDFIEMMIQLREKGKLELKNLDPANDYLTSELVLNSPEMLNITDDLLMAQAH

AVLTAGFESTSLLLTYTMVELCKNTDIQDIARREIMLQVKLNGGLTYDALKNMKYLDQVIKET

QRFYPFTPVLMRICTKDYTLADGYVLKKGDPLYIPVASIHKDPSIFPEPDSFKPERFEDSQQP

TAFMAFGAGPRMCIAVKYTLLIMKYGLALLLMNYEVKLSPLTKLPIKFTNKKFGNCETEKILFS

FEKLVKEH

>NezVir_CYP395S11/1-548

SEQ ID NO: 51

RTVEIIQYRVRTKFGLNQRLLAAANQFGSQCATDRMIGIALLVLAITALAYAFNWIKYWTKYW

ENKGVKCLPAVPIFGNCLPMVLNKKNVSEIMEDIYNAFPDEPVAGYYEFLTPRLLIRDNELVQ

KVLVKDFGHFVDHGFEVDEKKNPLDNQLFLMTGNKWRAFRTKMAPLFTSGKLKTMYDVM

NEVGNGLLEYMDKNKANDIDIREAMGLFSMDIIGSAAFGINPGVLKNPDSEFRVKGKQINDP

NWRNLIRIWFFFAFPKFSKKLGFSFQPRAVTSYFCNIIRNAIDYRKKNKIQRNDFVQMMMQL

KEKGNIELKTLDATDDYLKNELNEASTEIFEITDDVLMAQAQSFLIAGFEATALLLTYAMLEIC

QKPEIQDALRKEVLEQVKLNGGLTYEALRNMKYLEQAIKETQRIYPLIPFLTRVCTKSYTLSN

GFTIEKGEYIYIPAAAIHMDPTFYPDPKTFKPERFAEQPKPGTFLPFGEGPRMCIAMRYAML

VVKYGLALFLLNYRAKLSPSTKLPVQFLNRAFGNIPTEKILFNVEKYNEK

>NezVir_CYP395T3/1-388

SEQ ID NO: 52

MCGNQWRVYRQKLSPAFTTGKLKYMLDPLAECVNNLLTLLESHAGEEVDMKETMELFSMD

VIGSCVFGIDPGVTKNPNSEFRTIGKTIFEFTAIQQFRFAVLTMLPKLAKKLNFTFFRPEVVTY

YCNIILNTLEYRKKNGIERHDFIQMMLQLQSKGKLDSQSTDPADDDLKTDKTLEGDDVQITD

ELLIGTAFGFLTAGFHTTASSMTYALYELSRNPEALEKTKREIKEQVAVHGDITYDSLKSMTY

LEKVLKEALRLHPGSPSTMRVCTKEYKFPNGLTMLPGDSINIPIYALHRDPNNFPDPLSFNP

DRFDETPTPGTYLPFGDGPRMCIGMRFAMTAMKYALSKVLLNYDIQLGKTNETPIRMAPRG

FLNVPKKEVNIKIIKV

>NezVir_CYP3092D6/1-520
SEQ ID NO: 53
MSWQDWLMLATIAALSLLGLAYYTIKKLYRHFEDRNIPYIKPKFLLGSDPDGVLFRLHVCDS
WDNIYKKLEGKPIGGFFQTVLPFLMVRDPEYIHQVLISSFDHFFDRNFLIDEEVNPLDAHLFL
LRGNKWRYLRNKLSPIFSSGKLRWMFDEMDHCGDIFLECIDKLADGKDRDILDELARYATD
VIESCAFGLEGDSIKNPNSKMRQVGRDLFDTSKFNLSQFFFLLRFSIPRLLIWLKVPSVPSHA
KNFFCTTMSDVLEYRRKTGFQRKDFVQLLLQLKDKEIVEINSNYDVGDEKGKHEETVTEKIEI
TDLLLVAQSFVFFVAGFETTSRTLHFLIHQLAEHQEFQKRARKEVLDIKAKHGRFSYDALKD
MKFLNKCIAETLRMYPPVAMLNRECTKDFTFQDGTLIKKGEQIVIPIYSIHRDPRYFPDPLKY
NPDRFEVDPQNGTYLPFGDGPRICIGKRFAIVEIKIIMARLLERYWFELSPLNGEKIEIDPWSL
IVSSKKGLWVKIHKLTDLK

>NezVir_CYP3092D7/1-509
SEQ ID NO: 54
IAAFSLLALAYYKIKKTFRHFKDRNIPYVEPTFPLGSEPQGVLFRKHIVDSFGEIYNQLEGKPV
GGFFQTVLPFLMIRDPEYVHQVLISSFDHFFDRNFLVDEKVNPLDAHLFFLRGNKWRYLRN
KLSPIFSGVKLRWMFEEMEKCGESFVECFDKLADGKDRDVLDELARYATDVIGSCAFGLEG
DSLKNPNSPMRQMGKDLFDTSSINRTQITFLLRFSVPRLLLWFKVRSLPSAIEEYFCSTISSV
LERRRKTGLKRRDFVQLLLQLKEKDVVNIDANDVDEKEDKSQQNNDIEKFEITDRLLMAQSF
VPFVGGFETTSRTLHYLIYQLAQHPEIQERARQEVLRIKEKHSQFSYDALKDLKFLDNCISET
LRLNPPVSMLNRECTKDFTFPDGTSIEKGEQIVIPIYSIHRDPKYFPEPTKFNPDRFLSDPQR
GTYLPFGDGPRICIGKRFALVEIKIVMARLLERYSFEPSSLNKEPIELNPWINVLCAKNGLFVK
IQKLNNSK

>NezVir_CYP3092E6/1-486
SEQ ID NO: 55
FFEKRNIKYVKPKFLLGSEPDGVLFKIHITESWERIYKKLEHEKYGGFFHAILPTLMIRDPEYIE
DILKTSFDHFVDRSFLVDVKTNPLDENLFFMRGNKWKYLRCKMASLFSQIKLKWMYEEIEK
CSNTFDECLSEFADGKDADIKDLLARFVTDVVASCGFGVEPQALKNPDWIFRDIGREIVDPE
NINMPLFLLRFSIPRLLIWFKIKTLTKKLRNFFLSTTKRILHHRRSTGIIRKDFVQLFLELKEKGT
VGIDSRNIDTNKTNTESNNEIIELTDNLLAANSFLFFLAGFETTSTTLYYTYYFLAKHQEIQER
ARKEVQEVKAKYGHFTFDSLKELKFLINCISETMRIYPPIAVVIRECTKDYNLLDGTLIDKGMR
IIVPIMSIHRDPKNFAEPMEYKPERFENPPASGTYLPFGDGPRICIGKRFAEIIMYSTLARTLD
KYKLELSPKCDHEIKLNPKVISTTPVHGLFFRIHKLNDTN

>NezVir_CYP3092E7/1-483
SEQ ID NO: 56
FFEKRNIKYVKPKFLLGSDPDGVLFKIHVTESWDRIYKQLENEKCGGFYQAIVPTLMIRDPEY
VNIVLKSSFDHFSDRIFLVDEKTNPLDEHLFFLRGNKWRYLRNKISPLFSQVKLKWMYEEIDK
CVNLFDECLAELSDGKDLDIKELLARYTTDVVASCGFGIEPQCLKNPSSEFRKIGREYFDPN
KINMRMLFLRLSIPRLLMWFKIKTVSAKINNFFLTTTKNILHHRRSTGVVRKDFVQLLLELKEK
GTVEIDTTEIEKDETYKESPNEKIELTDNLLAAQSFVFFLAGFETTASVLNFTFYFWAKHQEIQ
ERARKEVLEVKEKYGQFTFDSLKELKFLKNCIAETLRIYPSVPALNRECMKDFTLPDGTVIEK
GLHVLVPILSLHRDPKYFPEPLEYKPDRFENPPVNGTYMPFGDGPRTCIGKRFAEAAMTSV
LARSLEKYKFELSPMNNCGDIKLNPKVITSSPLHGIFLRIHKL

>NezVir_CYP3224A4/1-497 SEQ ID NO: 57

MMEMILYAALIIALTNLALGIIIWFRVRKLYAYPGLLGFPVFGNLYYFKNLFLGSFESIRVYLF

EIVKQHGKNGICFHIAYGFRKLVIISSPQVVKQLGFHPHLKDKPVYGFQGFRRYMNGPFSRP

RSDDSWKMRRKEYNCLLKKSSVENNFYYNFLKSADKMVELMLKSPSALDIHRAVLGVTQS

VTMETLFGVESSLAFHPDVLQYMHSIKDIASRIIASPGIARTILSILRPYDEIYIRKIGTLRRMVL

KELYRKMNNNQCFPSENTQSFNHLPMYIASRTEKSKKFNRRVVTELQEVFITSSHTVASTM

SSTITCLAVLPEIQERAWKEQYEIFGDDNREPTLQDLEQMTYLERFIKESLRFCGPPLVGKQ

ATDDIEVDGITIPKDTIVVYLLDFMRKDPNYWKDPELFNPDRFLEGGEELKYSFAPFGIGVRN

CPGMTYAMTEMKIILSKVLRRTKLSLVNKDLKFEDLEFEAQILMELKNPPLLQVEERV

>NezVir_CYP3224A5/1-510 SEQ ID NO: 58

MFNVEYIFRKMEKFATTAFIIAVAHLVLGLLLWFRVRKLYSYPGLLGFPVFGNLYYFYKTMLIA

SFENMRIHLVQVAEQYGKNGICFCILFCFRKVVIISSPQVMKQIGFHPNLKDKPPYVFESFLK

YTDGPFTTPSSDDVWKMKRKEYNNLLKKSSVENNFYNIFLKSADKLVELMLATPSTLDIEKA

VLGVTQSVTMEALFGVDGRPAFDPEIIDHMYTLKNIITLIIGNPGIAKTILNGLGPFDGLLIRQA

GALKKLSSQIMKQVHVKLKSSQHFPSENTKSNYSLSMYIASRTEKSKKFDQNVLTELQELFI

TSSSTVSSTMSCTIICLAVLPEMQEKAWKEQNEIFGDDTREPSLEDLERMIFLERFIKESLRF

CGPPLIAKHAAEDIKVDGVIIPKEAIVVYMLDFMRKDPKYWKDPKLFDPDRFLEENECSNYT

YAPFGIGVRTCPGMNFAMTQMKITLSKVLRRVKLSTVKKDLKFENLEFEAMLLMELKNPPFL

KVEERIM

>NezVir_CYP3224B9/1-382 SEQ ID NO: 59

GIYAYAKGPFTQIRSDDLWKQKRKEYNIGLKRSHIDNVFCNIFNKSADKLIDLMVASASSVDA

LHATMGIVRNVTLETLFNVDSSLAYDPQLITLMKKHRYLASFIVANPNLSGIILNILRPLDEILF

RKLGEFRKVISEEIDKTLLSEQCPLPEQYLTMQIVSRTIKCNGNNNWNTTKLQDELMELYFT

ATLTVSSVLSNTIIILALLPDIQERVWQEQYRIFGNDNRDPSIDDLKEMQFLDRCIKESLRFLG

PPPFVAKSVSHDIDINCITIPRGTNVLYLTGYLRMDPTHWKNPKVFDPDRFLEESETLKHSYS

PFGIGVRGCPGSYFAPTLMKITLSKLLRRLKLRPVQKDFRFEDIKFKVSLMTEIEDPPALQVE

ERT

>NezVir_CYP3224B10/1-503 SEQ ID NO: 60

MEKFATTAFIIAVAHLVLGLLLWFRVRKLYSYPGLLGFPVFGNLYYFRTLFLVTMDSMEKY

MIRISETYGKDGLCFHWIYGFRTLVTVTNPHIVKEIGFHPNVTHKPNFIFSAFHSYFSGPFVS

SRSDDLWKIQRKEYDKLYAVFTFHSRFLKKSRVESEHSNTFSKYADQMIELMLASPSADILR

AVTLEFTHNSTMETLFGVDSSIVYNPQVIGFMSVIPVLGTLSVANPKLAGTIFGIFKKMESFFL

RTIEKTRRLILEDIYSKILTSSPVAANKKALLSRQITSRMRKCNEDEDKLINELMELFVTSSGTT

HALLSSSLIFLALLPDIQERAWQEQYEIFDNDKRDATFDDLSQMRFLDRFIKEALRFVAPPFY

FKSVTGDTTINGITIPKGSNLVYLTGYMRMDPKYWKNPKVFDPDRFLEESETLKHSYTPFGI

GVRNCPGMHYTTTLMKVALSKIIRRLKLRPVQKDFRFEDIQFETFIMRELANPPVLQVEQRE-

>NezVir_CYP3224C1/1-488 SEQ ID NO: 61

MDGIYKVLLTILLANLVFGVILWLRVRKLCSFPGFLGVPVIGNLFYFYKTLFLITADSLENHLKE

VTEKHGKNGFCFHISYGYKITAIITNPEIIKKISFHPNLIDKSYEMYGGFLDYMRGPFSRPRSD

EKWKMWRKEYNIFLKRSCVDNDYFNTYITSAETLVNMMLDSTSAYGASIALTQNVTMRTLF

```
GVETDLVYNKEIIKVLTRLIEMGAMLGANTNIARAIAPIVRPIAEKVSGKAVVIRKTIFQKIYKTIV

SKKEPLSEPRLAMNVAAKSIESNESKRTLLQLMQEVLFTSAHTVASALSNTIILLAVQPDMQE

RAFKEQCEIFGNDSRDPTIEDVERMEFLGRFIKECLRFLGPPFSGRKATADINLDGTIIPKGSI

VVYLFNSITMDSKYWQNPNVFEPDRFLEESDLMKYTFTPFGVGVRSCPGMYFATTLIKITLS

KILRTVKLRPVDKDFRFESLKYRSSLLTEIANHPKLHVERRA
```

>NezVir_CYP3224D1/1-517                                            SEQ ID NO: 62

```
ALSVGWPTHFLWYQKFHLRRTQTVRMIETILYAALAILMAHLLFGVVLWFRVRKFYSYPNVL

GFPVIGNLYYFYRTLFLFTADRTLKYVIPVAEEHGKDGLFFHWMFGSSVAAVITCPHLLKKLS

FHPNLVDKPYAAYKGFQIFMEGPFSALRSDDVWKQHRKDYNNYLKKSRVDKDYFKTFTKS

ADKLVDIMLETPSSLDANAACTAVAHDISMKTMFSVETSLVYRPECLRYIYRIKDISSILFLNV

LIISPLFHILQPLSDLTIGKLTELRKLILENIDNQLKSNQTPLHELPFSTYLALKNRKDNGSKRQ

LYNKIHELFLTSGHTISVQLENMICFLAVLPDIQERAWQEQYEIFGNDIRDPTIDDLNQMNYL

DRFLKESYRFLKVPLLARMATADINVDGITIPSGTVVIYLMGYMKFLPKYWENPYIFDPDRFL

EESDLLKCISSPFGFGIRNCPGEYYATILIKIILSKVLRKLKFRPVQKDFRFEDIKFKSYIFTEAE

NPPNLQVEERT
```

>NezVir_CYP3225A5/1-493                                            SEQ ID NO: 63

```
MLIEAIIILVATLCASYYWLFGFWNRRNVFNVKFQITFLTFIKVLIKNEHLGNIFADIYKKYKSHG

MVGFYILFDPMLLVTNPKLVEEVIVKEFNKFHDTPTEMKKGINPLFALNPFAAKGTEKWKEL

RSIQASNMTTFRFKEILPIIYCVAENMVNYLTEMKMEPIAAKELSFLFSVESSCLCGFGVQPN

AFTDSENSFIEYSENIFKPSPFTMFCHFLLPWIGNLLKLRILSKDAEESFILFVKTIFEYRSRSN

VTKNDFIYYLMKLNQKLKEGNKPEYSNVELAGHCLTYYLDSTQTTSNQLAFFLLDLANHQHV

QDKLRKEISSISNSPRDFDLEKVNSIRYLNMAINESLRMHTQGTWISRTCTQDAVIGNTPIPK

GTKVFVPVEAFHNDPEWFPSPEKFDPERFSEERKDSIPKYTFLPFGEGPRICVGYKLALLQI

RMAVIFLVLNFTILPSSKVDREEIVLENALLPTGHNAKLKFKPMKCIDQ
```

>NezVir_CYP3225A6/1-496                                            SEQ ID NO: 64

```
MIAEAIVVLIITSYLSYIWLFGFWDRRNVFNIKFGFTLQTFPKILIRNEHIQDFFVDLYTKYKSH

GIVGFYAMFTPMLLVTDPEIVKTVMVKDFNKFTDTGIEIRKDVDPLFAINPFVAKGIEKWKEL

RSIQAANLTAVRFKEIIPTIHRVAESMVDYVREKKMEPITAQKLSFMYTVDNACSCGFGIEPS

AFTDTENNFIKYANSDKLFNPSPLTMYCHLFIPAMTSVLKLRILSEEAGDFFDSFVKKMIEYR

TSSNITKNDLINHIMKINQKLKEENKPAYTNLELAGHCMTFYVDSTATSASQLTFFLFDLADN

PEVQEKLRKEISSISKCPSDFDIEKINSINYLNMAINESIRIHTQATWISRTCTQDSVIANTPIPK

GTKVFIPIGQFHKDPEYFPDPNKFDPERFSEENKDSIPKYTFLPFGEGPRICVGFKFALLQIK

LAVIFLLLNFTILPSNQEGKEGIVIDNTAFVTPGSSSKLKFKPIIQDISQ
```

>NezVir_CYP3225A7/1-493                                            SEQ ID NO: 65

```
MLVEAWLFIALCLSYSWFFGFWDRRKVVNVKFEFTYLTFSRAFIKNEHLHDIFADIYRKYKS

YGTVGFYTILSPMLLVTDPELVKDVLVKEFNKFHDTVMEMKKEVDPLLALNPFVAKGMEKW

KELRSIQASNMTTVRFKEVIPIMYRVAENMVNYLAEKKMEPIGAKELSFLYTVDNSCSCGFG

VEPSAFTDPENNFVKYANSDKIFKPSPYTMLFHFLLPRMANILKLRISSEDAEEFFKSFVQKM

IEYRTSSNITKNDFINYIMKLNQKLKEENKPVYSKLELAAHCLTFYADSTETSSNQLAFFLLDL
```

-continued

ANHQDVQDKLRKEISSISKSPIDFDLEKVNSINYLNMALNESLRLHTQGNWLSRTCTQDTVI

GNAPIPKGTKVFVPIGQFHKDPEYFPDPEKFDPERFSEENKDSIPKYTFLPFGEGPRICVGF

KFALLQIRLAVIFLVLNFTILPSNEDGKEEIVLENAPLPTPAPTSKLKFKPINTY

>NezVir_CYP3225B7/1-491

SEQ ID NO: 66

MLLEIFIIALSALYLFNWWAHGYWKRKNVFSVPTEFLFGNVRLLLQQKITMYGMYRNFYQKY

KEHKIIGFYSFYHPALLVTDPEIIKRILVTDFNSFSNSGSDMNKTLDPIFGLNPFLLKSIPEWKE

SRSVQAAHQTQVKLRELVPGFIKVADFMFDFIKNQKNQTIKVLDLATRIMVDFSVLSAFGLEP

KSFTDPDFGFLKHACSEKVFASSRWNTIGSIFHPLLIRIFSLRFVTKEAEDFFLHISKTNLEHR

LSAKITRNDLFDTIMKSQKKNEGQNNKEKIQAEMVIAANCATFYMDATITSSSVLCFILLELAS

HQDIQEKLREEILSVGKKPEDFDFEKINTMTYLQMVFDECMRLHPPVPSLSRTCTKDIVINDI

KISKGTKVFISALALHQDPVYYPEPMKFDPERFSEVNKSSRVKYTYLPFGEGPRICVGFKYG

TLVVKTATIFILLKYRILASNNAKGSLHDPFEFFLSPKPDATIIFQEL

>NezVir_CYP3225B8/1-508

SEQ ID NO: 67

LSSWLKKTSTTSWFNFYNNMLLETIIVLSSVLFIFNWWAYGYWRRRNVYSLPTEFLFGNIKEI

IMNQKVMCLKFRDIYEQYKQHRMVGFYSFYKPMLFVSDPEIIKRVLATDFNSFSSNGFTMD

KDIDPIMGFNPFTAKTVPLWKELRSIQASNLTALKLKEWPGMVKIGEFMKDYIKNKKSQPVS

VFDITTRAAVDSAILFGFGIEPKSFTDSEFSFMKYGTVEHLFSTNYMNTISSFFLPSLSKIFNS

RITSKAAEDFFISMTKTNIEHRKTTKITRGDLFDTILKLNKKKLEQGDKAYSNLEMSAHCATFY

LDATVTSATVSTFLLLELATHQDIQEKLRREIFLVGKKPEDFDFDKINGIPYLQMVFDESIRIHS

PVTVLTRSCTKDTVIEDVKISKGTKVFISSLALHYDPEYYPEPEKFDPERFSENNKESMTKYT

FLPFGEGPRICVGLKYGNLFVKTLIAFILLKYRILPTYDQNKVLHDYENFLLVPKSDATIKFEEL

>NezVir_CYP3225B9/1-489

SEQ ID NO: 68

MLLEIIILLLSAIFIFNWWAHGYWKKRNVFSIPTEFLFGNTRELVMGQTLMALMFEDIYKKYKK

HRMIGFYCFYKPMLFITDPDIVKKIFVTEFNNFSNNGFTVSKEVDPLLGFNPFTAKNSIQWKE

LRSIQALNQTPLKLREVVSSLAKIGEFMYDFIKNQKGESIAVLDLTTRAAIDSAVLHGFGIEPK

SFTDSEFGFMKHASGDKFFETSSWNIFAALFFPSLNKLHNFRITSKEAEDFFKCVTKTNIDH

RQSANITRGDIVDTIIKLNKKKLEQTNKAYTDLEMTAHCATFYLDATVTASMVLAFFLLELAN

HIDVQEKLRSEIKSVGNKPEDFDYDKINSIPYLQMVLDETLRMHTPLTVMSRICTRDTVLEDV

KICKGTRIFISSIALHNDPEYFPDPEKFEPERFSESNKELMTKYTFLPFGEGPRICVGMKYATI

FVKTIIAFILLKYRILPSGDKNTSLNEYDSFLLIVKPDAAVKLEEL

>NezVir_CYP3225B10/1-488

SEQ ID NO: 69

MLLEIIVLLASFLLIFNWWGHGYWKRRNVFSIPKLFLFGNFWQLVMGQKVSLMFCDIYKKYK

KHRVVGFYCFYKPMLLISDPEIIKRVLVIDFNSFSDNGFVVDKDIDPLFGYNPFTAKTIPLWKE

LRSIQAANQTPLKLKEVVPSLANIKEFMYDFIKNQKNQPIEVSDLTLRAAIDSAVLNGFGIEPK

SFTDPEFSFMTHASGEKLFEATFVTMISAFFFPLINRLFSLRMTSKEAEEFFVSMAKTNIDYR

QSAKITRSDLFDTIMKLNQKKLEQGNKAYSALEMSSHCASFYMDATITSSAVLSFILLELAYH

QDVQDKLRREIFLIGKKPEDLDFDKINSMTYLQMVFDETLRMHPPVMIVSRLCTKDTEIEDVK

ISKGTKVFISPFALHYDPEYFPNPEKFDPDRFSDINKESMTKYSFLPFGEGPRICVGMKYANI

FVKTSIALILLKYKILPAYDQNESLHDIDHFLLGPKPNAAVKFEEF

-continued

>NezVir_CYP3226A1/1-513
SEQ ID NO: 70
LIPCTIKLQEVQELQIIMLGLITSLICLVFVAAYIFLKRRYTYWKMLGVAGPEPTMVVGNMKHII

SLKFSEPDMMNGWYKEYKNEPYIGYYNFWKPTLFVIDPELIKAITETDFNHFTDHPNFTTET

ETDAILDSLFDMKGARWKAKRQIFTKLFSPKKLRELSNILEEQQDSLLGEFEKLLKSTDEVEL

MRIMERHVLKILTSFMYSIDSSQNQESHSKLSELSEIFARPPGSSVRRFLFFVVFPSLYHKLK

LSAFPRVFWNYFNNFTNELLQSRNDQNVNREDLVALIGKMQKEGLLETDRIGHNEAVGHVF

GFLIAGHHTTMTTVSHAIYQLSLHPQIQEKLRTEVDSVLKGKDNITYDSIKQMTYLDGVINETL

RLFPLLGVLKRTCTQTYKINDKLTIPKGMDISIPAYSIHTDPEYFPEPEKFIPERFTDAETPPSL

FMSFGKGPRMCIGKRFAYISMKSIIAKIISEYIILPGTKTRKPLQFDTSTFFITVHPVGGLHVRL

QKRIK

>NezVir_CYP3226B4/1-523
SEQ ID NO: 71
MHLWYFRTVQFPYSIGEMFEQSTIIFILFFITAVFCSFLGVCYEYMKRRYRYWSDIGIPGPKP

EFIIGNMKESLFMKCTEPEMTDVWYKDYRGNPYIGFYNLLKPSLFIMDPELIRKVTEVDFNHF

IDHPSFSEHSGSDVIIYSLFAMKDQVWKVKRPIFSRLFTPKKLREQIEIFNNRYSLLKEEIENK

SELRKDTELLKFIGRYILISFSTILYGLDLMKDEKLFEDLEGHSEKFFHPGLHQALMFLFYTAS

PDLFNFLRMKTFPRDIWKYFSPFTKELQEHNKRLVNTNGCNLVSLLNQYQDSEPASAIDHP

EAVGHIFSFFSASNHTTITTVSYGLFLLGQHPEVQDMLREEVDRVLKRNQNITSENINDMVY

LDAVLNETMRLYPLLGVLKRVCTKKYYVDELLTIPEGMDVFIPVQALHMDPEYFPEPEKFHP

ERFLGLEKLPSIFMPFGRGPRNCIGLRMAEIAFKIAVARLISDYVILPNPKSTLPIKFDPRSLFIT

CMPENGLWVKLQKRETHQ

>NezVir_CYP3226B5/1-442
SEQ ID NO: 72
MLDQSTSILISITAVFFVFLGVCYEYLKRRYRYWSDKGIPGPKPIVFIGNMKESLFRKCTEPQ

MTDVWYQNYRGSPYIGFYNLLKPSVFLIDPELIRKVTEVDFNHFVDHPPLSGHSGSDAIIDSL

FTMNGQHWKDKRSIFSRMFTPKRLREQIEIFNNRYSFLKEEIEKQPGLNKDADLFKFIGRYILI

GFSTILYGLDLTKDEKLFEDFERHSEIFLHPGLHTSLMFLFYSASPNLFNLLSMKTFPRDIYHY

FSPLTKGLLEQNKKLGYTNSSDLPSLLNQYQDSNPASAIDHPESVGHIFSFLSASNHTTITTI

SYGLFLLGQHPEVQDKLRDEVDRVLKDNQDITSENINEMVYLDAVLYETMRMYTLLGVLKRI

CTKKYYVDERLTIPEGMEVFIPAQSLHMDPEYFPEPEKFNPERFLGLEKLPSIFMPFGRGPR

N

>NezVir_CYP3227A1/1-495
SEQ ID NO: 73
MAIVELIFVAFLLSIIHIVQHFRKTMSYWKVRGVKHIPPLPVVGNMLRAFKFDRHFFHVYNKM

YHAFPEERMVGMYEFTTATLILRDPELIKTVLVSEFSTFPDRGPIMFNPGCILYWSIFSLGGN

KWRAIRSKLLTPFTTGRLKLILPSVTRSCLEFLESGPKELTLDILRQLTLRIFSQTMFGIDIKSE

EAEFLENYRGMLSVSKSKVVQQVGLTFFPRFSDFMSFKFMPIHLEKYFRSFLNAILNKKMD

DSSWRDDAITILNEMRKRGKVHFHDKEKDMEELFDFNDELAQAQAFLLLFAALEPSSITLMH

LAYDLAQSPDSQNKARQEIKALLQKYGGYSWECVKEMKYLNCCLKETLRLHPPLQFLNRV

CNKDTELGGVKLDKGTRIVVPLQNLHLDPNYFSDPKKYKPERFLDEKIHQFIYLPFSDGPRIC

LGSRFFIMEALTLFAHILEKFELSISKEMKLPLKYEPITVFLTPKINNPVIIHLKKIN

-continued

\>NezVir_CYP3227B1/1-502  
SEQ ID NO: 74  
MYQIPLALFIITAICGLLYFFISVWSAMIYWKVRGVKHLAPWPIVGNLGALLRLDKHVSYYYDK

IYHAFPNERMIGMYEFMTPTLVLRDPELIEQVLREFSTFPDHGPLLIEDDSLISESVFALTGS

GAKWRAVRNKLLTTFTTGKMRAIFPELVASCQALVDKRPKTLIKEDFTAFAVESFMNSMFG

TAILPAGKEELVLNCKTVFEGSRYRMFQQYGLTYFTKLSQFFNMTFMANELHNYFSSLMHT

LLNQRSELDCGRNDYAQVLVDMKRLKKMVIFSRENSRENQEFDITDDLVIAQAFMFFFAGL

DTTTLVMLHLAFDLSQAKDCQETARQEVRNVLKKYGGYSWDSVRDMKYLDACIQETLRLH

PSLQFVVRVNDKPTDVAGVKIDKGTRIVIPLQTIHMDPNNFPKPEKYDPGRWLDESTRPNKF

THLPFSEGPRVCLGKRFALMEIATLFAHILDNFELTLSPETKVPLIYEPNVFFHSPISKNPIRV

DLMKI

\>NezVir_CYP3227B2/1-513  
SEQ ID NO: 75  
SGPPTLQGGKSSIQQKMLTLELLTLAVVVGLIHFSIIIWKSMTYWKERGVKHHTPVPIFGNFL

SVISFRKHFFHYYDKVYKAFPNERMVGLYEFMTPTLVLRDTQLIEHVLIREFSTFPDHGSFLF

EPSSVMYDSIFNMSGIRWRALRNKLLITFTTGKMRSVFPSLSESCLQLLNSNPKTLEREMLS

DLAIRTFMESMFGTKILKSAEAEIYTKARKIFEPTWWRYTQQTLLTYFPKLADFLHLTFMPKH

LDNYFRSIMNTILNQRVDSMEDRNDYAQVLVQMREQKKLNIYNRENKKVDQTFDVTNDLAI

AQAFMFFFAGMDATSLLMLYTAANLAQSKNCQAKAREEIKTVLHKYGGYSWEAVRDMKYI

DSCVQETLRMQPSLQFLNRVCDKDTSIDGVKLVKGTRIIIPIHTIQMDPKNFPNPEKFDPERF

MEGINDKFAHLPFSDGPRVCLGKRFATMETTTFMAHLLENFELSLSPETKLPLKYQPTALFL

TPKATNPIKIDLKRIN

\>NezVir_CYP3227B3/1-539  
SEQ ID NO: 76  
MMSESITSMFFKSWEFIQDLIKSDSFGYTTIIISLLVSRMLLTSEFVAFTALWGLLYLCLNIYW

AMNYWKIRGVKHFKPWPIVGNMARVLKLEYHLAYYYDEIYNAFPGERMVGMYEFMTPSLV

LRDTELIEQVLVKDFSTYPDHGPFLMEPKSILFESVFAMSGIRWRAIRNRLLTFTTGKMRVI

FPQILAPCQSFVKGKPKCLNVEIINELAVKIFMTAMFGINILPTGEEELMINCKRIFEPKATRIL

QLIFLTYFPKLSNVLNLKFMPRDLDDYFRSLMNTILDQRENIDFERNDYTKVLVEMRKQEKM

NIYNMRNDKVSQTFDMTNEIALSQAFMFFFAGLDTVSLLILHLAFEFSKSKYCQDKARQEVR

SVLKKFNGYSWEAVREMKYLEQCILETLRLHPSLQFLVRITDKDTELGGVKIKKNTRIVIPIHS

IQMDPKNFTDPNKFDPERFNVENQQNKFAHLPFSDGPRVCLGKRFAIMETATFFAHILDNY

ELSLSPQTRLPLQYEPKTLFHTPKVQTSIHVTLNEIRK

\>NezVir_CYP3227B4/1-497  
SEQ ID NO: 77  
MTTLTLLVAVVVCCFLYLGLILWKANTYWEVRGVKHFKPWPLVGNLARALKFNRHVSFFYD

EIYKAFPTERMVGMYEFLTPTLIIRDPTLVENVLREFSTYPDHGPLFFEPSSISYESIFTITGI

RWRALRNKLLTSFSTGKMKAIFPDIVRSCQSVVDSDPKRLHKDMLHEFAVKSFLNSMFGTN

ILPEGEEELMAKSKEVFQGKPQRIIQQIMLTFFPKLGDFLNMKFMPKTLDNYFRNLLNTLVEQ

RASANIKRDDYAKVLCDMNKMGKMDVYNRENKRIDETFDVTNDLVLAQAFMFFFAGLDTTV

LVMLHTALELSLAKSCQEKARQEVRSVLKKYGGYSWEAVRDMKYLDQCIQETLRMHPSLQ

FIVRMSDKDTVIDGVKIKKNTRIIIPLHSIQMDPNHFPNPHIFDPERFSVPLSSKFTHLPFSEGP

RVCLGKRFATLETATIIAHILDNFELHPSPELKFPLKYEPNALFHSPISNDEISIILKRIM

-continued

>NezVir_CYP3230A1/1-514

SEQ ID NO: 78

MVDLNQFWISLISIGIPLLIPIIFYLMVQNYKRTSYWKKRNIVYLPATPLFSKNIFDSFLIRYSLL

STVYKHGKGNVCCGFFQFRKPALLIRSPHVINLVLNQEFRIFQNKRQSDYTEGNKDPLSQH

LLALNGYKWKFLRAKLTPTFTSEKLKSMFSLLEICVQNFLSYIDESKDSPIDIMEICGKLSIDAI

ASCAFGLELQCLKNRNHDFIKMGKAAFRPGNWHMFKAHLRTLYPQLFKKFNIRAYGKDVN

DFFCSLVSETIRRRRMSGEKRVDFIYLLMKMLEEDEATVTEFNRTSTIKFTDDLIAAQAFSFFI

GGYETTSITMSCIFYELACHDEIRQKVQNEIDSNLSSESEISYNDLKSLEYLDMVIKEVLRLHP

PAFYTQRICSEDFKIPGSDVTIVKDMEVYIPILELHSDEENFPRPLEFIPERFSRENKSRIPKG

SYLPFGDGPRKCIGMRFSLMELKLVMAITMLKYDFHLEKKTPEHINLEEYSRIYKIKNKIFLKF

TKRVIS

>NezVir_CYP3231A1/1-488

SEQ ID NO: 79

MVCLIRNIWNSVLRRKFYIMAPSVKKNMITALLLFTLFFLLCFQLTKKSLWSQLRIPEVHGIPIV

GNLLPVVLKKKSYFETIEDLYKLGEGKDYIGIYNGTQPTLLIRNPDLVEILIKEEAKNFEDRGL

CSDLSDPLSLNLFFLKGKLWKWTRAKLRPAFSNIRLKTVFNGIELCTADCVNSFGSSVDIKE

VMDEYTCNVIAKNVFCVQDNTGFIENSLKVFSLSGLSGIAVLLRVFIPNFALSIGIKTVPQEIET

FYRNAIAKSTRVPGSFLDLMLHLKETEPDFSDDLMVAQFFIFILAGFETTSSALTYALYLLSKN

PDAQNKARFEAQKVFKEHGRSIDSLKKLTYLESIINETLRLYPSVTGMFRVAEKPFKLPCGA

VLPPGTAISVPIYCLHRDSRFYEDPLKFIPERWEMPQKVFYPFGLGPRLCIGMKFALLEMKIF

LSSVILKYNIKLNYATVEPLSFDPTSFFYKAINPILLDFEKTV

Polynucleotides

The southern green stink bug pheromone enzyme polypeptides described herein (e.g., the NvFPPS, NvTPS, and cytochrome P450 enzymes) can be encoded by polynucleotides. In some aspects, the NvFPPS enzyme can be encoded by a polynucleotide that has or includes a sequence that is 90-100% identical to SEQ ID NO: 2. In some aspects, the NvTPS enzyme can be encoded by a polynucleotide that has or includes a sequence that is 69-100% identical to SEQ ID NO: 1. One of ordinary skill in the art, based upon at least the polypeptide sequence can generate appropriate polynucleotides capable of encoding said polypeptide sequences using commercially and other wise available software that is capable of determining reading frames, codons, and the like. In some aspects the polynucleotides can be codon optimized. Codon optimization is described in greater detail elsewhere herein. In some aspects, the polynucleotides are codon optimized for expression in a plant cell. The polynucleotides can be naked or included in a vector. Suitable vectors are discussed in greater detail elsewhere herein. The polynucleotide can include one or more modified bases. The modification can modulate (increase or decrease) stability, modulate transcription efficiency, and provide other functionalities. Such modifications that can be applied to the polynucleotides described herein will be appreciated by those of ordinary skill in the art.

Vectors

Also provided herein are vectors that can contain one or more of the southern green stink bug pheromone enzymes described herein. In aspects, the vector can contain one or more polynucleotides encoding one or more elements of a southern green stink bug pheromone enzyme or system thereof described herein. The vectors can be useful in producing bacterial, fungal, yeast, plant cells, animal cells, and transgenic animals that can express one or more southern green stink bug pheromone enzymes or systems thereof described herein. Within the scope of this disclosure are vectors containing one or more of the polynucleotide sequences described herein. One or more of the polynucleotides that are part of or can encode one or more of the southern green stink bug pheromone enzymes or systems thereof described herein can be included in a vector or vector system. The vectors and/or vector systems can be used, for example, to express one or more of the polynucleotides in a cell, such as a producer cell, to produce one or more engineered southern green stink bug pheromone enzymes or systems thereof described elsewhere herein. Other uses for the vectors and vector systems described herein are also within the scope of this disclosure. In general, and throughout this specification, the term "vector" refers to a tool that allows or facilitates the transfer of an entity from one environment to another. In some contexts which will be appreciated by those of ordinary skill in the art, "vector" can be a term of art to refer to a nucleic acid molecule capable of transporting another nucleic acid to which it has been linked. A vector can be a replicon, such as a plasmid, phage, or cosmid, into which another DNA segment may be inserted so as to bring about the replication of the inserted segment. Generally, a vector is capable of replication when associated with the proper control elements.

Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can be composed of a nucleic acid (e.g., a polynucleotide) of the invention in a form suitable for expression of the nucleic acid in a host cell, which means that the recombinant expression vectors include one or more regulatory elements, which can be selected on the basis of the host cells to be used for expression, that is operatively-linked to the nucleic acid sequence to be expressed. Within a recombinant expression vector, "operably linked" and "operatively-linked" are used interchangeably herein and further defined elsewhere herein. In the context of a vector, the term "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Advantageous vectors include lentiviruses and adeno-associated viruses, and types of such vectors can also be selected for targeting particular types of cells. These and other aspects of the vectors and vector systems are described elsewhere herein.

In some aspects, the vector can be a bicistronic vector. In some aspects, a bicistronic vector can be used for one or more of the engineered southern green stink bug pheromone enzymes or systems thereof described herein. In some aspects, expression of elements of the engineered southern green stink bug pheromone enzymes or systems thereof described herein can be driven by the beta acting, CAG, CMV or other suitable constitutive, tissue specific, or inducible promoter. Where the element of capable of producing one or more engineered southern green stink bug pheromone enzymes or systems thereof described herein is an RNA, its expression can be driven by a Pol III promoter, such as a U6 promoter. In some aspects, the two are combined.

Cell-Based Vector Amplification and Expression

Vectors can be designed for expression of one or more elements of the engineered southern green stink bug pheromone enzymes or systems described herein (e.g., nucleic acid transcripts, proteins, enzymes, and combinations thereof) in a suitable host cell. In some aspects, the suitable host cell is a prokaryotic cell. Suitable host cells include, but are not limited to, bacterial cells, yeast cells, insect cells, and mammalian cells. The vectors can be viral-based or non-viral based. In some aspects, the suitable host cell is a eukaryotic cell. In some aspects, the suitable host cell is a suitable bacterial cell. Suitable bacterial cells include, but are not limited to bacterial cells from the bacteria of the species *Escherichia coli*. Many suitable strains of *E. coli* are known in the art for expression of vectors. These include, but are not limited toPir1, Stbl2, Stbl3, Stbl4, TOP10, XL1 Blue, and XL10 Gold. In some aspects, the host cell is a suitable insect cell. Suitable insect cells include those from *Spodoptera frugiperda*. Suitable strains of *S. frugiperda* cells include, but are not limited to Sf9 and Sf21. In some aspects, the host cell is a suitable yeast cell. In some aspects, the yeast cell can be from *Saccharomyces cerevisiae*. In some aspects, the host cell is a suitable mammalian cell. Many types of mammalian cells have been developed to express vectors. Suitable mammalian cells include, but are not limited to, HEK293, Chinese Hamster Ovary Cells (CHOs), mouse myeloma cells, HeLa, U2OS, A549, HT1080, CAD, P19, NIH 3T3, L929, N2a, MCF-7, Y79, SO-Rb50, HepG G2, DIKX-X11, J558L, Baby hamster kidney cells (BHK), and chicken embryo fibroblasts (CEFs). Suitable host cells are discussed further in Goeddel, GENE EXPRESSION TECHNOLOGY: METHODS IN ENZYMOLOGY 185, Academic Press, San Diego, Calif. (1990).

In some aspects, the vector can be a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in Yeast Protocols, 2nd edition, Xiao, W., ed. (Humana Press, New York, 2007) and Buckholz, R. G. and Gleeson, M.A. (1991) Biotechnology (NY) 9(11): 1067-72. Yeast vectors can contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2p plasmids, yeast integrative plasmids, yeast replicative plasmids, shuttle vectors, and episomal plasmids.

In some aspects, the vector is a baculovirus vector or expression vector and can be suitable for expression of polynucleotides and/or proteins in insect cells. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39). rAAV (recombinant Adeno-associated viral) vectors are preferably produced in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

In some embodiments, the vector is a mammalian expression vector. In some aspects, the mammalian expression vector is capable of expressing one or more polynucleotides and/or polypeptides in a mammalian cell. Examples of mammalian expression vectors include, but are not limited to, pCDM8 (Seed, 1987. Nature 329: 840) and pMT2PC (Kaufman, et al., 1987. EMBO J. 6: 187-195). The mammalian expression vector can include one or more suitable regulatory elements capable of controlling expression of the one or more polynucleotides and/or proteins in the mammalian cell. For example, commonly used promoters are derived from polyoma, adenovirus 2, cytomegalovirus, simian virus 40, and others disclosed herein and known in the art. More detail on suitable regulatory elements are described elsewhere herein.

For other suitable expression vectors and vector systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Nat/. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other aspects can utilize viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element can be operably linked to one or more elements of a southern green stink bug pheromone enzyme or enzyme system so as to drive expression of the one or more elements of the southern green stink bug pheromone enzyme or enzyme system described herein.

Vectors may be introduced and propagated in a prokaryote or prokaryotic cell. In some aspects, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some aspects, a prokaryote is used to amplify copies of a vector and express one or more nucleic acids, such as to provide a source of one or more proteins for delivery to a host cell or host organism.

In some aspects, the vector can be a fusion vector or fusion expression vector. In some aspects, fusion vectors add a number of amino acids to a protein encoded therein, such as to the amino terminus, carboxy terminus, or both of a recombinant protein. Such fusion vectors can serve one or more purposes, such as: (i) to increase expression of recombinant protein; (ii) to increase the solubility of the recombinant protein; and (iii) to aid in the purification of the recombinant protein by acting as a ligand in affinity purification. In some aspects, expression of polynucleotides (such as non-coding polynucleotides) and proteins in prokaryotes can be carried out in *Escherichia coli* with vectors containing constitutive or inducible promoters directing the expression of either fusion or non-fusion polynucleotides and/or proteins. In some aspects, the fusion expression vector can include a proteolytic cleavage site, which can be introduced at the junction of the fusion vector backbone or other fusion moiety and the recombinant polynucleotide or protein to enable separation of the recombinant polynucleotide or protein from the fusion vector backbone or other fusion moiety subsequent to purification of the fusion polynucleotide or protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, one or more vectors driving expression of one or more elements of one or more southern green stink bug pheromone enzymes or systems thereof described herein are introduced into a host cell such that expression of the elements of the engineered delivery system described herein direct formation of one or more southern green stink bug pheromone enzymes or systems thereof described herein. For example, different elements of one or more southern green stink bug pheromone enzymes or systems thereof described herein can each be operably linked to separate regulatory elements on separate vectors. RNA(s) of different elements of the engineered delivery system described herein can be delivered to an animal or mammal or cell thereof to produce an animal or mammal or cell thereof that constitutively or inducibly or conditionally expresses different elements of one or more southern green stink bug pheromone enzymes or systems thereof described herein that incorporates one or more elements of one or more southern green stink bug pheromone enzymes or systems thereof described herein or contains one or more cells that incorporates and/or expresses one or more elements of one or more southern green stink bug pheromone enzymes or systems thereof described herein.

In some aspects, two or more of the elements expressed from the same or different regulatory element(s), can be combined in a single vector, with one or more southern green stink bug pheromone enzyme and/or enzyme system polynucleotides that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding one or more engineered southern green stink bug pheromone enzymes, embedded within one or more intron sequences (e.g., each in a different intron, two or more in at least one intron, or all in a single intron). In some embodiments, the engineered southern green stink bug pheromone enzymes polynucleotide(s) can be operably linked to and expressed from the same promoter.

Vector Features

The vectors can include additional features that can confer one or more functionalities to the vector, the polynucleotide to be delivered, a virus particle produced there from, or polypeptide expressed thereof. Such features include, but are not limited to, regulatory elements, selectable markers, molecular identifiers (e.g., molecular barcodes), stabilizing elements, and the like. It will be appreciated by those skilled in the art that the design of the expression vector and additional features included can depend on such factors as the choice of the host cell to be transformed, the level of expression desired, etc.

Regulatory Elements

In aspects, the polynucleotides and/or vectors thereof described herein (such as the engineered southern green stink bug enzyme polynucleotide(s) described herein) can include one or more regulatory elements that can be operatively linked to the polynucleotide. The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter can direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the R-actin promoter, the phosphoglycerol kinase (PGK) promoter, and the EF1a promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit p-globin (Proc. Natl. Acad. Sci. USA., Vol. 78(3), p. 1527-31, 1981).

In some aspects, the regulatory sequence can be a regulatory sequence described in U.S. Pat. No. 7,776,321, U.S. Pat. Pub. No. 2011/0027239, and PCT publication WO 2011/028929, the contents of which are incorporated by reference herein in their entirety. In some aspects, the vector can contain a minimal promoter. In some aspects, the minimal promoter is the Mecp2 promoter, tRNA promoter, or U6. In a further embodiment, the minimal promoter is tissue specific. In some aspects, the length of the vector polynucleotide the minimal promoters and polynucleotide sequences is less than 4.4Kb.

To express a polynucleotide, the vector can include one or more transcriptional and/or translational initiation regulatory sequences, e.g. promoters, that direct the transcription of the gene and/or translation of the encoded protein in a cell. In some aspects a constitutive promoter may be employed. Suitable constitutive promoters for mammalian cells are generally known in the art and include, but are not limited to SV40, CAG, CMV, EF-1a, R-actin, RSV, and PGK. Suitable constitutive promoters for bacterial cells, yeast cells, and fungal cells are generally known in the art, such as a T-7 promoter for bacterial expression and an alcohol dehydrogenase promoter for expression in yeast.

In some aspects, the regulatory element can be a regulated promoter. "Regulated promoter" refers to promoters that direct gene expression not constitutively, but in a temporally- and/or spatially-regulated manner, and includes tissue-specific, tissue-preferred and inducible promoters. Regulated promoters include conditional promoters and inducible promoters. In some aspects, conditional promoters can be employed to direct expression of a polynucleotide in a specific cell type, under certain environmental conditions, and/or during a specific state of development. Suitable tissue specific promoters can include, but are not limited to, liver specific promoters (e.g., APOA2, SERPIN A1 (hAAT), CYP3A4, and MIR122), pancreatic cell promoters (e.g., INS, IRS2, Pdx1, Alx3, Ppy), cardiac specific promoters (e.g., Myh6 (alpha MHC), MYL2 (MLC-2v), TN13 (cTnl), NPPA (ANF), Slc8al (Ncxl)), central nervous system cell promoters (SYN1, GFAP, INA, NES, MOBP, MBP, TH, FOXA2 (HNF3 beta)), skin cell specific promoters (e.g., FLG, K14, TGM3), immune cell specific promoters, (e.g., ITGAM, CD43 promoter, CD14 promoter, CD45 promoter, CD68 promoter), urogenital cell specific promoters (e.g., Pbsn, Upk2, Sbp, Fer1 14), endothelial cell specific promoters (e.g. ENG), pluripotent and embryonic germ layer cell specific promoters (e.g., Oct4, NANOG, Synthetic Oct4, T brachyury, NES, SOX17, FOXA2, MIR122), and muscle cell specific promoter (e.g., Desmin). Other tissue and/or cell specific promoters are generally known in the art and are within the scope of this disclosure.

Inducible/conditional promoters can be positively inducible/conditional promoters (e.g., a promoter that activates transcription of the polynucleotide upon appropriate interaction with an activated activator, or an inducer (compound, environmental condition, or other stimulus) or a negative/conditional inducible promoter (e.g., a promoter that is repressed (e.g., bound by a repressor) until the repressor condition of the promotor is removed (e.g., inducer binds a repressor bound to the promoter stimulating release of the promoter by the repressor or removal of a chemical repressor from the promoter environment).The inducer can be a compound, environmental condition, or other stimulus. Thus, inducible/conditional promoters can be responsive to any suitable stimuli such as chemical, biological, or other molecular agents, temperature, light, and/or pH. Suitable inducible/conditional promoters include, but are not limited to, Tet-On, Tet-Off, Lac promoter, pBad, AlcA, LexA, Hsp70 promoter, Hsp90 promoter, pDawn, XVE/OlexA, GVG, and pOp/LhGR.

Where expression in a plant cell is desired, the components of the one or more engineered southern green stink bug pheromone enzymes described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. Different promoters may direct the expression of a gene in different tissues or cell types, or at different stages of development, or in response to different environmental conditions. In particular embodiments, one or more of the engineered southern green stink bug pheromone enzymes are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the expression of one or more of the engineered southern green stink bug enzymes and systems thereof are found in Kawamata et al., (1997) Plant Cell Physiol 38:792-803; Yamamoto et al., (1997) Plant J 12:255-65; Hire et al, (1992) Plant Mol Biol 20:207-18,Kuster et al, (1995) Plant Mol Biol 29:759-72, and Capana et al., (1994) Plant Mol Biol 25:681-91.

Examples of promoters that are inducible and that can allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome)., such as a Light Inducible Transcriptional Effector (LITE) that direct changes in transcriptional activity in a sequence-specific manner. The components of a light inducible system may include one or more elements of the one or more engineered southern green stink bug pheromone enzymes and/or systems thereof described herein, a light-responsive cytochrome heterodimer (e.g., from *Arabidopsis thaliana*), and a transcriptional activation/repression domain. In some aspects, the vector can include one or more of the inducible DNA binding proteins provided in PCT publication WO 2014/018423 and US Publications, 2015/0291966, 2017/0166903, 2019/0203212, which describe e.g., aspects of inducible DNA binding proteins and methods of use and can be adapted for use with the present invention.

In some aspects, transient or inducible expression can be achieved by including, for example, chemical-regulated promotors, i.e. whereby the application of an exogenous chemical induces gene expression. Modulation of gene expression can also be obtained by including a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) Plant Cell Physiol 38:568-77), the maize GST promoter (GST-II-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

In some aspects, the vector or system thereof can include one or more elements capable of translocating and/or expressing one or more engineered to/in a specific cell component or organelle. Such organelles can include, but are not limited to, nucleus, ribosome, endoplasmic reticulum, golgi apparatus, chloroplast, mitochondria, vacuole, lysosome, cytoskeleton, plasma membrane, cell wall, peroxisome, centrioles, etc.

Selectable Markers and Tags

One or more of the engineered southern green stink bug enzyme polynucleotides can be can be operably linked, fused to, or otherwise modified to include a polynucleotide that encodes or is a selectable marker or tag, which can be a polynucleotide or polypeptide. In some aspects, the polypeptide encoding a polypeptide selectable marker can be incorporated in the engineered southern green stink bug enzyme polynucleotide such that the selectable marker polypeptide, when translated, is inserted between two amino acids between the N- and C-terminus of the engineered southern green stink bug enzyme polypeptide or at the N- and/or C-terminus of the engineered southern green stink bug enzyme polypeptide. In some aspects, the selectable marker or tag is a polynucleotide barcode or unique molecular identifier (UMI).

It will be appreciated that the polynucleotide encoding such selectable markers or tags can be incorporated into a polynucleotide encoding one or more components of one or more of the engineered southern green stink bug enzymes or systems thereof described herein in an appropriate manner to allow expression of the selectable marker or tag. Such techniques and methods are described elsewhere herein and will be instantly appreciated by one of ordinary skill in the art in view of this disclosure. Many such selectable markers and tags are generally known in the art and are intended to be within the scope of this disclosure.

Suitable selectable markers and tags include, but are not limited to, affinity tags, such as chitin binding protein (CBP), maltose binding protein (MBP), glutathione-S-transferase (GST), poly(His) tag; solubilization tags such as thioredoxin (TRX) and poly(NANP), MBP, and GST; chromatography tags such as those consisting of polyanionic amino acids, such as FLAG-tag; epitope tags such as V5-tag, Myc-tag, HA-tag and NE-tag; protein tags that can allow specific enzymatic modification (such as biotinylation by biotin ligase) or chemical modification (such as reaction with FIAsH-EDT2 for fluorescence imaging), DNA and/or RNA segments that contain restriction enzyme or other enzyme cleavage sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipient cell (e.g., tRNA genes, auxotrophic markers); DNA and/or RNA segments that encode products which can be readily identified (e.g., phenotypic markers such as R-galactosidase, GUS; fluorescent proteins such as green fluorescent protein (GFP), cyan (CFP), yellow (YFP), red (RFP), luciferase, and cell surface proteins); polynucleotides that can generate one or more new primer sites for PCR (e.g., the juxtaposition of two DNA sequences not previously juxtaposed), DNA sequences not acted upon or acted upon by a restriction endonuclease or other DNA modifying enzyme, chemical, etc.; epitope tags (e.g., GFP, FLAG- and His-tags), and, DNA sequences that make a molecular barcode or unique molecular identifier (UMI), DNA sequences required for a specific modification (e.g., methylation) that allows its identification. Other suitable markers will be appreciated by those of skill in the art.

Selectable markers and tags can be operably linked to one or more components of one or more of the engineered southern green stink bug enzymes or systems thereof described herein via suitable linker, such as a glycine or glycine serine linkers as short as GS or GG up to (GGGGG)$_3$ or (GGGGS)$_3$. Other suitable linkers are described elsewhere herein.

The vector or vector system can include one or more polynucleotides encoding one or more targeting moieties. In some aspects, the targeting moiety encoding polynucleotides can be included in the vector or vector system, such as a viral vector system, such that they are expressed within and/or on the virus particle(s) produced such that the virus particles can be targeted to specific cells, tissues, organs, etc. In some aspects, the targeting moiety encoding polynucleotides can be included in the vector or vector system such that the engineered southern green stink bug enzymes or systems thereof polynucleotide(s) and/or products expressed therefrom include the targeting moiety and can be targeted to specific cells, tissues, organs, etc. In some aspects, such as non-viral carriers, the targeting moiety can be attached to the carrier (e.g., polymer, lipid, inorganic molecule etc.) and can be capable of targeting the carrier and any attached or associated engineered southern green stink bug enzymes or systems thereof polynucleotide(s) to specific cells, tissues, organs, etc.

Cell-free Vector and Polynucleotide Expression

In some aspects, the polynucleotide encoding one or more features of the one or more of the engineered southern green stink bug enzymes or systems thereof can be expressed from a vector or suitable polynucleotide in a cell-free in vitro system. In other words, the polynucleotide can be transcribed and optionally translated in vitro. In vitro transcription/translation systems and appropriate vectors are generally known in the art and commercially available. Generally, in vitro transcription and in vitro translation systems replicate the processes of RNA and protein synthesis, respectively, outside of the cellular environment. Vectors and suitable polynucleotides for in vitro transcription can include T7, SP6, T3, promoter regulatory sequences that can be recognized and acted upon by an appropriate polymerase to transcribe the polynucleotide or vector.

In vitro translation can be stand-alone (e.g., translation of a purified polyribonucleotide) or linked/coupled to transcription. In some aspects, the cell-free (or in vitro) translation system can include extracts from rabbit reticulocytes, wheat germ, and/or *E. coli*. The extracts can include various macromolecular components that are needed for translation of exogenous RNA (e.g., 70S or 80S ribosomes, tRNAs, aminoacyl-tRNA, synthetases, initiation, elongation factors, termination factors, etc.). Other components can be included or added during the translation reaction, including but not limited to, amino acids, energy sources (ATP, GTP), energy regenerating systems (creatine phosphate and creatine phosphokinase (eukaryotic systems)) (phosphoenol pyruvate and pyruvate kinase for bacterial systems), and other co-factors (Mg2+, K+, etc.). As previously mentioned, in vitro translation can be based on RNA or DNA starting material. Some translation systems can utilize an RNA template as starting material (e.g., reticulocyte lysates and wheat germ extracts). Some translation systems can utilize a DNA template as a starting material (e.g., *E coli*-based systems). In these systems transcription and translation are coupled and DNA is first transcribed into RNA, which is subsequently translated. Suitable standard and coupled cell-free translation systems are generally known in the art and are commercially available.

Codon Optimization of Vector Polynucleotides

As described elsewhere herein, the polynucleotide encoding one or more engineered southern green stink bug enzymes or systems thereof described herein can be codon optimized. In some aspects, one or more polynucleotides contained in a vector ("vector polynucleotides") described herein that are in addition to an optionally codon optimized polynucleotide encoding engineered southern green stink bug enzymes or systems thereof described herein can be codon optimized. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at http://www.yeastgenome.org/community/codon_usage.shtml, or Codon selection in yeast, Bennetzen and Hall, J Biol Chem. 1982 Mar. 25; 257(6):3026-31. As to codon usage in plants including algae, reference is made to *Codon usage in higher plants, green algae, and cyanobacteria*, Campbell and Gowri, Plant Physiol. 1990 January; 92(1): 1-11.; as well as *Codon usage in plant genes*, Murray et al, Nucleic Acids Res. 1989 Jan. 25; 17(2):477-98; or *Selection on the codon bias of chloroplast and cyanelle genes in different plant and algal lineages*, Morton BR, J Mol Evol. 1998 April; 46(4):449-59.

The vector polynucleotide can be codon optimized for expression in a specific cell-type, tissue type, organ type, and/or subject type. In some aspects, a codon optimized sequence is a sequence optimized for expression in a eukaryote, e.g., humans (i.e. being optimized for expression in a human or human cell), or for another eukaryote, such as another animal (e.g., a mammal or avian) as is described elsewhere herein. Such codon optimized sequences are within the ambit of the ordinary skilled artisan in view of the description herein. In some aspects, the polynucleotide is codon optimized for a specific cell type. Such cell types can include, but are not limited to, epithelial cells (including skin cells, cells lining the gastrointestinal tract, cells lining other hollow organs), nerve cells (nerves, brain cells, spinal column cells, nerve support cells (e.g., astrocytes, glial cells, Schwann cells etc.), muscle cells (e.g., cardiac muscle, smooth muscle cells, and skeletal muscle cells), connective tissue cells (fat and other soft tissue padding cells, bone cells, tendon cells, cartilage cells), blood cells, stem cells and other progenitor cells, immune system cells, germ cells, and combinations thereof. Such codon optimized sequences are within the ambit of the ordinary skilled artisan in view of the description herein. In some aspects, the polynucleotide is codon optimized for a specific tissue type. Such tissue types can include, but are not limited to, muscle tissue, connective tissue, connective tissue, nervous tissue, and epithelial tissue. Such codon optimized sequences are within the ambit of the ordinary skilled artisan in view of the description herein. In some aspects, the polynucleotide is codon optimized for a specific organ. Such organs include, but are not limited to, muscles, skin, intestines, liver, spleen, brain, lungs, stomach, heart, kidneys, gallbladder, pancreas, bladder, thyroid, bone, blood vessels, blood, and combinations thereof. Such codon optimized sequences are within the ambit of the ordinary skilled artisan in view of the description herein.

In some embodiments, a vector polynucleotide is codon optimized for expression in particular cells, such as prokaryotic or eukaryotic cells. The eukaryotic cells may be those of or derived from a particular organism, such as a plant, bacteria, or yeast cell.

Non-Viral Vectors and Carriers

In some aspects, the vector is a non-viral vector or carrier. In some aspects, non-viral vectors can have the advantage(s) of reduced toxicity and/or immunogenicity and/or increased bio-safety as compared to viral vectors. The terms of art "Non-viral vectors and carriers" and as used herein in this context refers to molecules and/or compositions that are not based on one or more component of a virus or virus genome (excluding any nucleotide to be delivered and/or expressed by the non-viral vector) that can be capable of attaching to, incorporating, coupling, and/or otherwise interacting with an engineered southern green stink bug enzymes or systems thereof polynucleotide described herein and can be capable of ferrying the polynucleotide to a cell and/or expressing the polynucleotide. It will be appreciated that this does not exclude the inclusion of a virus-based polynucleotide that is to be delivered. For example, if a gRNA to be delivered is directed against a virus component and it is inserted or otherwise coupled to an otherwise non-viral vector or carrier, this would not make said vector a "viral vector". Non-viral vectors and carriers include naked polynucleotides, chemical-based carriers, polynucleotide (non-viral) based vectors, and particle-based carriers. It will be appreciated that the term "vector" as used in the context of non-viral vectors and carriers refers to polynucleotide vectors and "carriers" used in this context refers to a non-nucleic acid or polynucleotide molecule or composition that be attached to or otherwise interact with a polynucleotide to be delivered, such as an engineered southern green stink bug enzymes or systems thereof polynucleotide(s) of the present invention.

Naked Polynucleotides

In some aspects, one or more engineered southern green stink bug enzymes or systems thereof polynucleotide(s) described elsewhere herein can be included in a naked polynucleotide. The term of art "naked polynucleotide" as used herein refers to polynucleotides that are not associated with another molecule (e.g., proteins, lipids, and/or other molecules) that can often help protect it from environmental factors and/or degradation. As used herein, associated with includes, but is not limited to, linked to, adhered to, adsorbed to, enclosed in, enclosed in or within, mixed with, and the like. Naked polynucleotides that include one or more of the engineered southern green stink bug enzymes or systems thereof polynucleotides described herein can be delivered directly to a host cell and optionally expressed therein. The naked polynucleotides can have any suitable two- and three-dimensional configurations. By way of non-limiting examples, naked polynucleotides can be single-stranded molecules, double stranded molecules, circular molecules (e.g., plasmids and artificial chromosomes), molecules that contain portions that are single stranded and portions that are double stranded (e.g., ribozymes), and the like. In some aspects, the naked polynucleotide contains only the engineered southern green stink bug enzymes or systems thereof polynucleotide(s) of the present invention. In some aspects, the naked polynucleotide can contain other nucleic acids and/or polynucleotides in addition to the engineered southern green stink bug enzymes or systems thereof polynucleotide(s) of the present invention. The naked polynucleotides can include one or more elements of a transposon system. Transposons and system thereof are described in greater detail elsewhere herein.

Non-Viral Polynucleotide Vectors

In some aspects, one or more of the engineered southern green stink bug enzymes or systems thereof polynucleotides can be included in a non-viral polynucleotide vector. Suitable non-viral polynucleotide vectors include, but are not limited to, transposon vectors and vector systems, plasmids, bacterial artificial chromosomes, yeast artificial chromosomes, AR(antibiotic resistance)-free plasmids and miniplasmids, circular covalently closed vectors (e.g., minicircles, minivectors, miniknots,), linear covalently closed vectors ("dumbbell shaped"), MIDGE (minimalistic immunologically defined gene expression) vectors, MiLV (micro-linear vector) vectors, Ministrings, mini-intronic plasmids, PSK systems (post-segregationally killing systems), ORT (operator repressor titration) plasmids, and the like. See e.g., Hardee et al. 2017. Genes. 8(2):65.

In some aspects, the non-viral polynucleotide vector can have a conditional origin of replication. In some aspects, the non-viral polynucleotide vector can be an ORT plasmid. In some aspects, the non-viral polynucleotide vector can have a minimalistic immunologically defined gene expression. In some aspects, the non-viral polynucleotide vector can have one or more post-segregationally killing system genes. In some aspects, the non-viral polynucleotide vector is AR-free. In some aspects, the non-viral polynucleotide vector is a minivector. In some aspects, the non-viral polynucleotide vector includes a nuclear localization signal. In some aspects, the non-viral polynucleotide vector can include one or more CpG motifs. In some aspects, the non-viral polynucleotide vectors can include one or more scaffold/matrix attachment regions (S/MARs). See e.g., Mirkovitch et al. 1984. Cell. 39:223-232, Wong et al. 2015. Adv. Genet. 89:113-152, whose techniques and vectors can be adapted for use in the present invention. S/MARs are AT-rich sequences that play a role in the spatial organization of chromosomes through DNA loop base attachment to the nuclear matrix. S/MARs are often found close to regulatory elements such as promoters, enhancers, and origins of DNA replication. Inclusion of one or S/MARs can facilitate a once-per-cell-cycle replication to maintain the non-viral polynucleotide vector as an episome in daughter cells. In aspects, the S/MAR sequence is located downstream of an actively transcribed polynucleotide (e.g., one or more engineered southern green stink bug enzymes or systems thereof polynucleotides) included in the non-viral polynucleotide vector. In some aspects, the S/MAR can be a S/MAR from the beta-interferon gene cluster. See e.g., Verghese et al. 2014. Nucleic Acid Res. 42:e53; Xu et al. 2016. Sci. China Life Sci. 59:1024-1033; Jin et al. 2016. 8:702-711; Koirala et al. 2014. Adv. Exp. Med. Biol. 801:703-709; and Nehlsen et al. 2006. Gene Ther. Mol. Biol. 10:233-244, whose techniques and vectors can be adapted for use in the present invention.

In some aspects, the non-viral vector is a transposon vector or system thereof. As used herein, "transposon" (also referred to as transposable element) refers to a polynucleotide sequence that is capable of moving form location in a genome to another. There are several classes of transposons. Transposons include retrotransposons and DNA transposons. Retrotransposons require the transcription of the polynucleotide that is moved (or transposed) in order to transpose the polynucleotide to a new genome or polynucleotide. DNA transposons are those that do not require reverse transcription of the polynucleotide that is moved (or transposed) in order to transpose the polynucleotide to a new genome or polynucleotide. In some aspects, the non-viral polynucleotide vector can be a retrotransposon vector. In some aspects, the retrotransposon vector includes long terminal repeats. In some aspects, the retrotransposon vector does not include long terminal repeats. In some aspects, the non-viral polynucleotide vector can be a DNA transposon vector. DNA transposon vectors can include a polynucleotide sequence encoding a transposase. In some aspects, the transposon vector is configured as a non-autonomous transposon vector, meaning that the transposition does not occur spontaneously on its own. In some of these aspects, the transposon vector lacks one or more polynucleotide sequences encoding proteins required for transposition. In some aspects, the non-autonomous transposon vectors lack one or more Ac elements.

In some aspects a non-viral polynucleotide transposon vector system can include a first polynucleotide vector that contains the engineered southern green stink bug enzymes or systems thereof polynucleotide(s) of the present invention flanked on the 5' and 3' ends by transposon terminal inverted repeats (TIRs) and a second polynucleotide vector that includes a polynucleotide capable of encoding a transposase coupled to a promoter to drive expression of the transposase. When both are expressed in the same cell the transposase can be expressed from the second vector and can transpose the material between the TIRs on the first vector (e.g., the engineered southern green stink bug enzymes or systems thereof polynucleotide(s) of the present invention) and integrate it into one or more positions in the host cell's genome. In some aspects the transposon vector or system thereof can be configured as a gene trap. In some aspects, the TIRs can be configured to flank a strong splice acceptor site followed by a reporter and/or other gene (e.g., one or more of the engineered southern green stink bug enzymes or systems thereof polynucleotide(s) of the present invention) and a strong poly A tail. When transposition occurs while using this vector or system thereof, the transposon can insert into an intron of a gene and the inserted reporter or other gene can provoke a mis-splicing process and as a result it in activates the trapped gene.

Any suitable transposon system can be used. Suitable transposon and systems thereof can include, Sleeping Beauty transposon system (Tc1/mariner superfamily) (see e.g., Ivics et al. 1997. Cell. 91(4): 501-510), piggyBac (piggyBac superfamily) (see e.g., Li et al. 2013 110(25): E2279-E2287 and Yusa et al. 2011. PNAS. 108(4): 1531-1536), Tol2 (superfamily hAT), Frog Prince (Tc1/mariner superfamily) (see e.g., Miskey et al. 2003 Nucleic Acid Res. 31(23):6873-6881) and variants thereof.

Chemical Carriers

In some aspects the engineered southern green stink bug enzymes or systems thereof polynucleotide(s) can be coupled to a chemical carrier. Chemical carriers that can be suitable for delivery of polynucleotides can be broadly classified into the following classes: (i) inorganic particles, (ii) lipid-based, (iii) polymer-based, and (iv) peptide based. They can be categorized as (1) those that can form condensed complexes with a polynucleotide (such as the engineered southern green stink bug enzymes or systems thereof polynucleotide(s) of the present invention), (2) those capable of targeting specific cells, (3) those capable of increasing delivery of the polynucleotide (such as the engineered southern green stink bug enzymes or systems thereof polynucleotide(s) of the present invention) to the nucleus or cytosol of a host cell, (4) those capable of disintegrating from DNA/RNA in the cytosol of a host cell, and (5) those capable of sustained or controlled release. It will be appreciated that any one given chemical carrier can include features from multiple categories. The term "particle" as used herein, refers to any suitable sized particles for delivery of the engineered southern green stink bug enzymes or systems thereof components described herein. Suitable sizes include macro-, micro-, and nano-sized particles.

In some aspects, the non-viral carrier can be an inorganic particle. In some aspects, the inorganic particle, can be a nanoparticle. The inorganic particles can be configured and optimized by varying size, shape, and/or porosity. In some aspects, the inorganic particles are optimized to escape from the reticulo endothelial system. In some aspects, the inorganic particles can be optimized to protect an entrapped molecule from degradation. Suitable inorganic particles that can be used as non-viral carriers in this context can include, but are not limited to, calcium phosphate, silica, metals (e.g., gold, platinum, silver, palladium, rhodium, osmium, iridium, ruthenium, mercury, copper, rhenium, titanium, niobium, tantalum, and combinations thereof), magnetic compounds, particles, and materials, (e.g., supermagnetic iron oxide and magnetite), quantum dots, fullerenes (e.g., carbon nanoparticles, nanotubes, nanostrings, and the like), and combinations thereof. Other suitable inorganic non-viral carriers are discussed elsewhere herein.

In some aspects, the non-viral carrier can be lipid-based. Suitable lipid-based carriers are also described in greater detail herein. In some aspects, the lipid-based carrier includes a cationic lipid or an amphiphilic lipid that is capable of binding or otherwise interacting with a negative charge on the polynucleotide to be delivered (e.g., such as an engineered southern green stink bug enzymes or systems thereof polynucleotide(s). In some aspects, chemical non-viral carrier systems can include a polynucleotide such as the engineered southern green stink bug enzymes or systems thereof polynucleotide(s) of the present invention) and a lipid (such as a cationic lipid). These are also referred to in the art as lipoplexes. Other aspects of lipoplexes are described elsewhere herein. In some aspects, the non-viral lipid-based carrier can be a lipid nano emulsion. Lipid nano emulsions can be formed by the dispersion of an immiscible liquid in another stabilized emulsifying agent and can have particles of about 200 nm that are composed of the lipid, water, and surfactant that can contain the polynucleotide to be delivered (e.g., the engineered southern green stink bug enzymes or systems thereof polynucleotide(s) of the present invention). In some aspects, the lipid-based non-viral carrier can be a solid lipid particle or nanoparticle.

In some aspects, the non-viral carrier can be peptide-based. In some aspects, the peptide-based non-viral carrier can include one or more cationic amino acids. In some aspects, 35 to 40, 45, 50, 55, 60, 65, 70, 75, 80, 85, 90, 95, 99 or 100% of the amino acids are cationic. In some aspects, peptide carriers can be used in conjunction with other types of carriers (e.g., polymer-based carriers and lipid-based carriers to functionalize these carriers). In some aspects, the functionalization is targeting a host cell. Suitable polymers that can be included in the polymer-based non-viral carrier can include, but are not limited to, polyethylenimine (PEI), chitosan, poly (D,L-lactide) (PLA), poly (D,L-Lactide-coglycoside) (PLGA), dendrimers (see e.g., US Pat. Pub. 2017/0079916 whose techniques and compositions can be adapted for use with the engineered southern green stink bug enzymes or systems thereof polynucleotide(s), polymethacrylate, and combinations thereof.

In some aspects, the non-viral carrier can be configured to release an engineered delivery system polynucleotide that is associated with or attached to the non-viral carrier in response to an external stimulus, such as pH, temperature, osmolarity, concentration of a specific molecule or composition (e.g., calcium, NaCl, and the like), pressure and the like. In some aspects, the non-viral carrier can be a particle that is configured includes one or more of the engineered southern green stink bug enzymes or systems thereof polynucleotide(s) describe herein and a environmental triggering agent response element, and optionally a triggering agent. In some aspects, the particle can include a polymer that can be selected from the group of polymethacrylates and polyacrylates. In some aspects, the non-viral particle can include one or more aspects of the compositions microparticles described in US Pat. Pubs. 20150232883 and 20050123596, whose techniques and compositions can be adapted for use in the present invention.

In some aspects, the non-viral carrier can be a polymer-based carrier. In some aspects, the polymer is cationic or is predominantly cationic such that it can interact in a charge-dependent manner with the negatively charged polynucleotide to be delivered (such as the engineered southern green stink bug enzymes or systems thereof polynucleotide(s) described herein). Polymer-based systems are described in greater detail elsewhere herein.

Viral Vectors

In some aspects, the vector is a viral vector. The term of art "viral vector" and as used herein in this context refers to polynucleotide based vectors that contain one or more elements from or based upon one or more elements of a virus that can be capable of expressing and packaging a polynucleotide, such as an engineered southern green stink bug enzymes or systems thereof polynucleotide(s) described herein, into a virus particle and producing said virus particle when used alone or with one or more other viral vectors (such as in a viral vector system). Viral vectors and systems thereof can be used for producing viral particles for delivery of and/or expression of one or more components of the engineered southern green stink bug enzymes or systems thereof described herein. The viral vector can be part of a viral vector system involving multiple vectors. In some aspects, systems incorporating multiple viral vectors can increase the safety of these systems. Suitable viral vectors can include retroviral-based vectors, lentiviral-based vectors, adenoviral-based vectors, adeno associated vectors, helper-dependent adenoviral (HdAd) vectors, hybrid adenoviral vectors, herpes simplex virus-based vectors, poxvirus-based vectors, and Epstein-Barr virus-based vectors. Other aspects of viral vectors and viral particles produce therefrom are described elsewhere herein. In some aspects, the viral vectors are configured to produce replication incompetent viral particles for improved safety of these systems.

Retroviral and Lentiviral Vectors

Retroviral vectors can be composed of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Suitable retroviral vectors for the one or more engineered southern green stink bug enzymes or systems thereof polynucleotide(s) can include those based upon murine leukemia virus (MuLV), gibbon ape leukemia virus (GaLV), Simian immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). Selection of a retroviral gene transfer system may therefore depend on the target tissue.

The tropism of a retrovirus can be altered by incorporating foreign envelope proteins, expanding the potential target population of target cells. Lentiviral vectors are retroviral vectors that are able to transduce or infect non-dividing cells and are described in greater detail elsewhere herein. A retrovirus can also be engineered to allow for conditional expression of the inserted transgene, such that only certain cell types are infected by the lentivirus.

Lentiviruses are complex retroviruses that have the ability to infect and express their genes in both mitotic and post-mitotic cells. Advantages of using a lentiviral approach can include the ability to transduce or infect non-dividing cells and their ability to typically produce high viral titers, which can increase efficiency or efficacy of production and delivery. Suitable lentiviral vectors include, but are not limited to, human immunodeficiency virus (HIV)-based lentiviral vectors, feline immunodeficiency virus (FIV)-based lentiviral vectors, simian immunodeficiency virus (SIV)-based lentiviral vectors, Moloney Murine Leukaemia Virus (Mo-MLV), Visna-maedi virus (VMV)-based lentiviral vector, caprine arthritis-encephalitis virus (CAEV)-based lentiviral vector, bovine immune deficiency virus (BIV)-based lentiviral vector, and Equine infectious anemia (EIAV)-based lentiviral vector. In some embodiments, an HIV-based lentiviral vector system can be used. In some embodiments, a FIV-based lentiviral vector system can be used.

In some aspects, the lentiviral vector is an EIAV-based lentiviral vector or vector system. EIAV vectors have been used to mediate expression, packaging, and/or delivery in other contexts, such as for ocular gene therapy (see, e.g., Balagaan, J Gene Med 2006; 8: 275-285). In another embodiment, RetinoStat®, (see, e.g., Binley et al., HUMAN GENE THERAPY 23:980-991 (September 2012)), which describes RetinoStat®, an equine infectious anemia virus-based lentiviral gene therapy vector that expresses angiostatic proteins endostatin and angiostatin that is delivered via a subretinal injection for the treatment of the wet form of age-related macular degeneration. Any of these vectors described in these publications can be modified for the engineered southern green stink bug enzymes or systems thereof described herein.

In some aspects, the lentiviral vector or vector system thereof can be a first-generation lentiviral vector or vector system thereof. First-generation lentiviral vectors can contain a large portion of the lentivirus genome, including the gag and pol genes, other additional viral proteins (e.g., VSV-G) and other accessory genes (e.g., vif, vprm vpu, nef, and combinations thereof), regulatory genes (e.g., tat and/or rev) as well as the gene of interest between the LTRs. First generation lentiviral vectors can result in the production of virus particles that can be capable of replication in vivo, which may not be appropriate for some instances or applications.

In some aspects, the lentiviral vector or vector system thereof can be a second-generation lentiviral vector or vector system thereof. Second-generation lentiviral vectors do not contain one or more accessory virulence factors and do not contain all components necessary for virus particle production on the same lentiviral vector. This can result in the production of a replication-incompetent virus particle and thus increase the safety of these systems over first-generation lentiviral vectors. In some aspects, the second-generation vector lacks one or more accessory virulence factors (e.g., vif, vprm, vpu, nef, and combinations thereof). Unlike the first-generation lentiviral vectors, no single second generation lentiviral vector includes all features necessary to express and package a polynucleotide into a virus particle. In some aspects, the envelope and packaging components are split between two different vectors with the gag, pol, rev, and tat genes being contained on one vector and the envelope protein (e.g., VSV-G) are contained on a second vector. The gene of interest, its promoter, and LTRs can be included on a third vector that can be used in conjunction with the other two vectors (packaging and envelope vectors) to generate a replication-incompetent virus particle.

In some aspects, the lentiviral vector or vector system thereof can be a third-generation lentiviral vector or vector system thereof. Third-generation lentiviral vectors and vector systems thereof have increased safety over first- and second-generation lentiviral vectors and systems thereof because, for example, the various components of the viral genome are split between two or more different vectors but used together in vitro to make virus particles, they can lack the tat gene (when a constitutively active promoter is included up-stream of the LTRs), and they can include one or more deletions in the 3'LTR to create self-inactivating (SIN) vectors having disrupted promoter/enhancer activity of the LTR. In some aspects, a third-generation lentiviral vector system can include (i) a vector plasmid that contains the polynucleotide of interest and upstream promoter that are flanked by the 5' and 3' LTRs, which can optionally include one or more deletions present in one or both of the LTRs to render the vector self-inactivating; (ii) a "packaging vector(s)" that can contain one or more genes involved in packaging a polynucleotide into a virus particle that is produced by the system (e.g., gag, pol, and rev) and upstream regulatory sequences (e.g., promoter(s)) to drive expression of the features present on the packaging vector, and (iii) an "envelope vector" that contains one or more envelope protein genes and upstream promoters. In aspects, the third-generation lentiviral vector system can include at least two packaging vectors, with the gag-pol being present on a different vector than the rev gene.

In some aspects, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) can be used and/or adapted to the engineered southern green stink bug enzymes or systems thereof described herein.

In some aspects, the pseudotype and infectivity or tropism of a lentivirus particle can be tuned by altering the type of envelope protein(s) included in the lentiviral vector or system thereof. As used herein, an "envelope protein" or "outer protein" means a protein exposed at the surface of a viral particle that is not a capsid protein. For example, envelope or outer proteins typically comprise proteins embedded in the envelope of the virus. In some aspects, a lentiviral vector or vector system thereof can include a VSV-G envelope protein. VSV-G mediates viral attachment to an LDL receptor (LDLR) or an LDLR family member present on a host cell, which triggers endocytosis of the viral particle by the host cell. Because LDLR is expressed by a wide variety of cells, viral particles expressing the VSV-G envelope protein can infect or transduce a wide variety of cell types. Other suitable envelope proteins can be incorporated based on the host cell that a user desires to be infected by a virus particle produced from a lentiviral vector or system thereof described herein and can include, but are not limited to, feline endogenous virus envelope protein (RD114) (see e.g., Hanawa et al. Molec. Ther. 2002 5(3) 242-251), modified Sindbis virus envelope proteins (see e.g., Morizono et al. 2010. J. Virol. 84(14) 6923-6934; Morizono et al. 2001. J. Virol. 75:8016-8020; Morizono et al. 2009. J. Gene Med. 11:549-558; Morizono et al. 2006 Virology 355:71-81; Morizono et al J. Gene Med. 11:655-663, Morizono et al. 2005 Nat. Med. 11:346-352), baboon retroviral envelope protein (see e.g., Girard-Gagnepain et al. 2014. Blood. 124: 1221-1231); Tupaia paramyxovirus glycoproteins (see e.g., Enkirch T. et al., 2013. Gene Ther. 20:16-23); measles virus glycoproteins (see e.g., Funke et al. 2008. Molec. Ther. 16(8): 1427-1436), rabies virus envelope proteins, MLV envelope proteins, Ebola envelope proteins, baculovirus envelope proteins, filovirus envelope proteins, hepatitis E1 and E2 envelope proteins, gp41 and gp120 of HIV, hemagglutinin, neuraminidase, M2 proteins of influenza virus, and combinations thereof.

In some aspects, the tropism of the resulting lentiviral particle can be tuned by incorporating cell targeting peptides into a lentiviral vector such that the cell targeting peptides are expressed on the surface of the resulting lentiviral particle. In some aspects, a lentiviral vector can contain an envelope protein that is fused to a cell targeting protein (see e.g., Buchholz et al. 2015. Trends Biotechnol. 33:777-790; Bender et al. 2016. PLoS Pathog. 12(e1005461); and Friedrich et al. 2013. Mol. Ther. 2013. 21: 849-859.

In some aspects, a split-intein-mediated approach to target lentiviral particles to a specific cell type can be used (see e.g., Chamoun-Emaneulli et al. 2015. Biotechnol. Bioeng. 112:2611-2617, Ramirez et al. 2013. Protein. Eng. Des. Sel. 26:215-233. In these aspects, a lentiviral vector can contain one half of a splicing-deficient variant of the naturally split intein from *Nostoc punctiforme* fused to a cell targeting peptide and the same or different lentiviral vector can contain the other half of the split intein fused to an envelope protein, such as a binding-deficient, fusion-competent virus envelope protein. This can result in production of a virus particle from the lentiviral vector or vector system that includes a split intein that can function as a molecular Velcro linker to link the cell-binding protein to the pseudotyped lentivirus particle. This approach can be advantageous for use where surface-incompatibilities can restrict the use of, e.g., cell targeting peptides.

In some aspects, a covalent-bond-forming protein-peptide pair can be incorporated into one or more of the lentiviral vectors described herein to conjugate a cell targeting peptide to the virus particle (see e.g., Kasaraneni et al. 2018. Sci. Reports (8) No. 10990). In some aspects, a lentiviral vector can include an N-terminal PDZ domain of InaD protein (PDZ1) and its pentapeptide ligand (TEFCA) from NorpA, which can conjugate the cell targeting peptide to the virus particle via a covalent bond (e.g., a disulfide bond). In some aspects, the PDZ1 protein can be fused to an envelope protein, which can optionally be binding deficient and/or fusion competent virus envelope protein and included in a lentiviral vector. In some aspects, the TEFCA can be fused to a cell targeting peptide and the TEFCA-CPT fusion construct can be incorporated into the same or a different lentiviral vector as the PDZ1-envelope protein construct. During virus production, specific interaction between the PDZ1 and TEFCA facilitates producing virus particles covalently functionalized with the cell targeting peptide and thus capable of targeting a specific cell-type based upon a specific interaction between the cell targeting peptide and cells expressing its binding partner. This approach can be advantageous for use where surface-incompatibilities can restrict the use of, e.g., cell targeting peptides.

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015. Any of these systems or a variant thereof can be used to deliver an engineered southern green stink bug pheromone enzyme or system thereof polynucleotide described herein to a cell.

In some aspects, a lentiviral vector system can include one or more transfer plasmids. Transfer plasmids can be generated from various other vector backbones and can include one or more features that can work with other retroviral and/or lentiviral vectors in the system that can, for example, improve safety of the vector and/or vector system, increase virial titers, and/or increase or otherwise enhance expression of the desired insert to be expressed and/or packaged into the viral particle. Suitable features that can be included in a transfer plasmid can include, but are not limited to, 5'LTR, 3'LTR, SIN/LTR, origin of replication (Ori), selectable marker genes (e.g., antibiotic resistance genes), Psi (Ψ), RRE (rev response element), cPPT (central polypurine tract), promoters, WPRE (woodchuck hepatitis post-transcriptional regulatory element), SV40 polyadenylation signal, pUC origin, SV40 origin, F1 origin, and combinations thereof.

Adenoviral Vectors, Helper-Dependent Adenoviral Vectors, and Hybrid Adenoviral Vectors In some aspects, the vector can be an adenoviral vector. In some aspects, the adenoviral vector can include elements such that the virus particle produced using the vector or system thereof can be serotype 2 or serotype 5. In some aspects, the polynucleotide to be delivered via the adenoviral particle can be up to about 8 kb. Thus, in some aspects, an adenoviral vector can include a DNA polynucleotide to be delivered that can range in size from about 0.001 kb to about 8 kb. Adenoviral vectors have been used successfully in several contexts (see e.g., Teramato et al. 2000. Lancet. 355:1911-1912; Lai et al. 2002. DNA Cell. Biol. 21:895-913; Flotte et al., 1996. Hum. Gene. Ther. 7:1145-1159; and Kay et al. 2000. Nat. Genet. 24:257-261.

In some aspects the vector can be a helper-dependent adenoviral vector or system thereof. These are also referred to in the art as "gutless" or "gutted" vectors and are a modified generation of adenoviral vectors (see e.g., Thrasher et al. 2006. Nature. 443:E5-7). In aspects of the helper-dependent adenoviral vector system one vector (the helper) can contain all the viral genes required for replication but contains a conditional gene defect in the packaging domain. The second vector of the system can contain only the ends of the viral genome, one or more engineered southern green stink bug enzyme or system thereof polynucleotides, and the native packaging recognition signal, which can allow selective packaged release from the cells (see e.g., Cideciyan et al. 2009. N Engl J Med. 361:725-727). Helper-dependent adenoviral vector systems have been successful for gene delivery in several contexts (see e.g., Simonelli et al. 2010. J Am Soc Gene Ther. 18:643-650; Cideciyan et al. 2009. N Engl J Med. 361:725-727; Crane et al. 2012. Gene Ther. 19(4):443-452; Alba et al. 2005. Gene Ther. 12:18-S27; Croyle et al. 2005. Gene Ther. 12:579-587; Amalfitano et al. 1998. J. Virol. 72:926-933; and Morral et al. 1999. PNAS. 96:12816-12821). The techniques and vectors described in these publications can be adapted for inclusion and delivery of the engineered southern green stink bug enzyme or system thereof polynucleotides described herein. In some aspects, the polynucleotide to be delivered via the viral particle produced from a helper-dependent adenoviral vector or system thereof can be up to about 37 kb. Thus, in some aspects, a adenoviral vector can include a DNA polynucleotide to be delivered that can range in size from about 0.001 kb to about 37 kb (see e.g., Rosewell et al. 2011. J. Genet. Syndr. Gene Ther. Suppl. 5:001).

In some aspects, the vector is a hybrid-adenoviral vector or system thereof. Hybrid adenoviral vectors are composed of the high transduction efficiency of a gene-deleted adenoviral vector and the long-term genome-integrating potential of adeno-associated, retroviruses, lentivirus, and transposon based-gene transfer. In some aspects, such hybrid vector systems can result in stable transduction and limited integration site. See e.g., Balague et al. 2000. Blood. 95:820-828; Morral et al. 1998. Hum. Gene Ther. 9:2709-2716; Kubo and Mitani. 2003. J. Virol. 77(5): 2964-2971; Zhang et al. 2013. PloS One. 8(10) e76771; and Cooney et al. 2015. Mol. Ther. 23(4):667-674), whose techniques and vectors described therein can be modified and adapted for use with the engineered southern green stink bug pheromone enzymes and systems thereof polynucleotide(s) described herein. In some aspects, a hybrid-adenoviral vector can include one or more features of a retrovirus and/or an adeno-associated virus. In some aspects the hybrid-adenoviral vector can include one or more features of a spuma retrovirus or foamy virus (FV). See e.g., Ehrhardt et al. 2007. Mol. Ther. 15:146-156 and Liu et al. 2007. Mol. Ther. 15:1834-1841, whose techniques and vectors described therein can be modified and adapted for use with the engineered southern green stink bug pheromone enzymes and systems thereof polynucleotide(s) described herein. Advantages of using one or more features from the FVs in the hybrid-adenoviral vector or system thereof can include the ability of the viral particles produced therefrom to infect a broad range of cells, a large packaging capacity as compared to other retroviruses, and the ability to persist in quiescent (non-dividing) cells. See also e.g., Ehrhardt et al. 2007. Mol. Ther. 156:146-156 and Shuji et al. 2011. Mol. Ther. 19:76-82, whose techniques and vectors described therein can be modified and adapted for use with the engineered southern green stink bug pheromone enzymes and systems thereof polynucleotide(s) described herein.

Adeno Associated Viral (AAV) Vectors

In an embodiment, the vector can be an adeno-associated virus (AAV) vector. See, e.g., West et al., Virology 160:38-47 (1987); U.S. Pat. No. 4,797,368; WO 93/24641; Kotin, Human Gene Therapy 5:793-801 (1994); and Muzyczka, J. Clin. Invest. 94:1351 (1994). Although similar to adenoviral vectors in some of their features, AAVs have some deficiency in their replication and/or pathogenicity and thus can be safer that adenoviral vectors. In some aspects the AAV can integrate into a specific site on chromosome 19 of a human cell with no observable side effects. In some aspects, the capacity of the AAV vector, system thereof, and/or AAV particles can be up to about 4.7 kb.

The AAV vector or system thereof can include one or more regulatory molecules. In some aspects the regulatory molecules can be promoters, enhancers, repressors and the like, which are described in greater detail elsewhere herein. In some aspects, the AAV vector or system thereof can include one or more polynucleotides that can encode one or more regulatory proteins. In some aspects, the one or more regulatory proteins can be selected from Rep78, Rep68, Rep52, Rep40, variants thereof, and combinations thereof.

The AAV vector or system thereof can include one or more polynucleotides that can encode one or more capsid proteins. The capsid proteins can be selected from VP1, VP2, VP3, and combinations thereof. The capsid proteins can be capable of assembling into a protein shell of the AAV virus particle. In some aspects, the AAV capsid can contain 60 capsid proteins. In some aspects, the ratio of VP1:VP2:VP3 in a capsid can be about 1:1:10.

In some aspects, the AAV vector or system thereof can include one or more adenovirus helper factors or polynucleotides that can encode one or more adenovirus helper factors. Such adenovirus helper factors can include, but are not limited, E1A, E1B, E2A, E4ORF6, and VA RNAs. In some aspects, a producing host cell line expresses one or more of the adenovirus helper factors.

The AAV vector or system thereof can be configured to produce AAV particles having a specific serotype. In some aspects, the serotype can be AAV-1, AAV-2, AAV-3, AAV-4, AAV-5, AAV-6, AAV-8, AAV-9 or any combinations thereof. In some aspects, the AAV can be AAV1, AAV-2, AAV-5 or any combination thereof. One can select the AAV of the AAV with regard to the cells to be targeted; e.g., one can select AAV serotypes 1, 2, 5 or a hybrid capsid AAV-1, AAV-2, AAV-5 or any combination thereof for targeting brain and/or neuronal cells; and one can select AAV-4 for targeting cardiac tissue; and one can select AAV8 for delivery to the liver. Thus, in some aspects, an AAV vector or system thereof capable of producing AAV particles capable of targeting the brain and/or neuronal cells can be configured to generate AAV particles having serotypes 1, 2, 5 or a hybrid capsid AAV-1, AAV-2, AAV-5 or any combination thereof. In some aspects, an AAV vector or system thereof capable of producing AAV particles capable of targeting cardiac tissue can be configured to generate an AAV particle having an AAV-4 serotype. In some aspects, an AAV vector or system thereof capable of producing AAV particles capable of targeting the liver can be configured to generate an AAV having an AAV-8 serotype. In some aspects, the AAV vector is a hybrid AAV vector or system thereof. Hybrid AAVs are AAVs that include genomes with elements from one serotype that are packaged into a capsid derived from at least one different serotype. For example, if it is the rAAV2/5 that is to be produced, and if the production method is based on the helper-free, transient transfection method discussed above, the 1st plasmid and the 3rd plasmid (the adeno helper plasmid) will be the same as discussed for rAAV2 production. However, the 2nd plasmid, the pRepCap will be different. In this plasmid, called pRep2/Cap5, the Rep gene is still derived from AAV2, while the Cap gene is derived from AAV5. The production scheme is the same as the above-mentioned approach for AAV2 production. The resulting rAAV is called rAAV2/5, in which the genome is based on recombinant AAV2, while the capsid is based on AAV5. It is assumed the cell or tissue-tropism displayed by this AAV2/5 hybrid virus should be the same as that of AAV5.

In some aspects, the AAV vector or system thereof is configured as a "gutless" vector, similar to that described in connection with a retroviral vector. In some aspects, the "gutless" AAV vector or system thereof can have the cis-acting viral DNA elements involved in genome amplification and packaging in linkage with the heterologous sequences of interest (e.g., the engineered southern green stink bug pheromone enzymes and systems thereof polynucleotide(s) described herein).

Herpes Simplex Viral Vectors

In some aspects, the vector can be a Herpes Simplex Viral (HSV)-based vector or system thereof. HSV systems can include the disabled infections single copy (DISC) viruses, which are composed of a glycoprotein H defective mutant HSV genome. When the defective HSV is propagated in complementing cells, virus particles can be generated that are capable of infecting subsequent cells permanently replicating their own genome but are not capable of producing more infectious particles. See e.g., 2009. Trobridge. Exp. Opin. Biol. Ther. 9:1427-1436, whose techniques and vectors described therein can be modified and adapted for use with the engineered southern green stink bug pheromone enzymes and systems thereof polynucleotide(s) described herein. In some aspects where an HSV vector or system thereof is utilized, the host cell can be a complementing cell. In some aspects, HSV vector or system thereof can be capable of producing virus particles capable of delivering a polynucleotide cargo of up to 150 kb. Thus, in some aspect the engineered southern green stink bug pheromone enzymes and systems thereof polynucleotide(s) described herein included in the HSV-based viral vector or system thereof can sum from about 0.001 to about 150 kb. HSV-based vectors and systems thereof have been successfully used in several contexts including various models of neurologic disorders. See e.g., Cockrell et al. 2007. Mol. Biotechnol. 36:184-204; Kafri T. 2004. Mol. Biol. 246:367-390; Balaggan and Ali. 2012. Gene Ther. 19:145-153; Wong et al. 2006. Hum. Gen. Ther. 2002. 17:1-9; Azzouz et al. J. Neruosci. 22L10302-10312; and Betchen and Kaplitt. 2003. Curr. Opin. Neurol. 16:487-493, whose techniques and vectors described therein can be modified and adapted for use with the engineered southern green stink bug pheromone enzymes and systems thereof polynucleotide(s) described herein.

Poxvirus Vectors

In some aspects, the vector can be a poxvirus vector or system thereof. In some aspects, the poxvirus vector can result in cytoplasmic expression of one or more engineered southern green stink bug pheromone enzymes and systems thereof polynucleotide(s) described herein. In some aspects the capacity of a poxvirus vector or system thereof can be about 25 kb or more.

Vector Construction

The vectors described herein can be constructed using any suitable process or technique. In some aspects, one or more suitable recombination and/or cloning methods or techniques can be used to the vector(s) described herein. Suitable recombination and/or cloning techniques and/or methods can include, but not limited to, those described in U.S. Application publication No. US 2004-0171156 A1. Other suitable methods and techniques are described elsewhere herein.

Construction of recombinant AAV vectors are described in a number of publications, including U.S. Pat. No. 5,173, 414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Any of the techniques and/or methods can be used and/or adapted for constructing an AAV or other vector described herein. rAAV vectors are discussed elsewhere herein.

In some embodiments, the vector can have one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors.

Delivery vehicles, vectors, particles, nanoparticles, formulations and components thereof for expression of one or more elements of the engineered southern green stink bug pheromone enzymes and systems thereof and/or polynucleotide(s) described herein described herein are as used in the foregoing documents, such as WO 2014/093622 (PCT/US2013/074667) and are discussed in greater detail herein.

Virus Particle Production from Viral Vectors

Retroviral Production

In some aspects, one or more viral vectors and/or system thereof can be delivered to a suitable cell line for production of virus particles containing the polynucleotide or other payload to be delivered to a host cell. Suitable host cells for virus production from viral vectors and systems thereof described herein are known in the art and are commercially available. For example, suitable host cells include HEK 293 cells and its variants (HEK 293T and HEK 293TN cells). In some aspects, the suitable host cell for virus production from viral vectors and systems thereof described herein can stably express one or more genes involved in packaging (e.g., pol, gag, and/or VSV-G) and/or other supporting genes.

In some aspects, after delivery of one or more viral vectors to the suitable host cells for or virus production from viral vectors and systems thereof, the cells are incubated for an appropriate length of time to allow for viral gene expression from the vectors, packaging of the polynucleotide to be delivered (e.g., an engineered southern green stink bug pheromone enzymes and systems thereof polynucleotide(s) described herein), and virus particle assembly, and secretion of mature virus particles into the culture media. Various other methods and techniques are generally known to those of ordinary skill in the art.

Mature virus particles can be collected from the culture media by a suitable method. In some aspects, this can involve centrifugation to concentrate the virus. The titer of the composition containing the collected virus particles can be obtained using a suitable method. Such methods can include transducing a suitable cell line (e.g., NIH 3T3 cells) and determining transduction efficiency, infectivity in that cell line by a suitable method. Suitable methods include PCR-based methods, flow cytometry, and antibiotic selection-based methods. Various other methods and techniques are generally known to those of ordinary skill in the art. The concentration of virus particle can be adjusted as needed. In some aspects, the resulting composition containing virus particles can contain $1\times10^{1}$-$1\times10^{20}$ particles/mL.

AAV Particle Production

There are two main strategies for producing AAV particles from AAV vectors and systems thereof, such as those described herein, which depend on how the adenovirus helper factors are provided (helper v. helper free). In some aspects, a method of producing AAV particles from AAV vectors and systems thereof can include adenovirus infection into cell lines that stably harbor AAV replication and capsid encoding polynucleotides along with AAV vector containing the polynucleotide to be packaged and delivered by the resulting AAV particle (e.g., the engineered southern green stink bug pheromone enzymes and systems thereof polynucleotide(s) described herein). In some aspects, a method of producing AAV particles from AAV vectors and systems thereof can be a "helper free" method, which includes co-transfection of an appropriate producing cell line with three vectors (e.g., plasmid vectors): (1) an AAV vector that contains a polynucleotide of interest (e.g., the engineered southern green stink bug pheromone enzymes and systems thereof polynucleotide(s) described herein between 2 ITRs; (2) a vector that carries the AAV Rep-Cap encoding polynucleotides; and (helper polynucleotides. One of skill in the art will appreciate various methods and variations thereof that are both helper and -helper free and as well as the different advantages of each system.

Vector and Virus Particle Delivery

A vector (including non-viral carriers) described herein can be introduced into host cells to thereby produce transcripts, proteins, or peptides, including fusion proteins or peptides encoded by nucleic acids as described herein (e.g., engineered southern green stink bug pheromone enzymes and systems thereof described herein transcripts, proteins, enzymes, mutant forms thereof, fusion proteins thereof, etc.), and virus particles (such as from viral vectors and systems thereof).

One or more engineered southern green stink bug pheromone enzymes and systems thereof polynucleotide(s) described herein can be delivered using adeno associated virus (AAV), lentivirus, adenovirus or other plasmid or viral vector types, in particular, using formulations and doses from, for example, U.S. Pat. Nos. 8,454,972 (formulations, doses for adenovirus), 8,404,658 (formulations, doses for AAV) and 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus.

For plasmid delivery, the route of administration, formulation and dose can be as in U.S. Pat. No. 5,846,946 and as in clinical studies involving plasmids. In some aspects, doses can be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into or otherwise delivered to the tissue or cell of interest.

In terms of in vivo delivery, AAV is advantageous over other viral vectors for a couple of reasons such as low toxicity (this may be due to the purification method not requiring ultra-centrifugation of cell particles that can activate the immune response) and a low probability of causing insertional mutagenesis because it doesn't integrate into the host genome.

The vector(s) and virus particles described herein can be delivered in to a host cell in vitro, in vivo, and/or ex vivo. Delivery can occur by any suitable method including, but not limited to, physical methods, chemical methods, and biological methods. Physical delivery methods are those methods that employ physical force to counteract the membrane barrier of the cells to facilitate intracellular delivery of the vector. Suitable physical methods include, but are not limited to, needles (e.g., injections), ballistic polynucleotides (e.g., particle bombardment, micro projectile gene transfer, and gene gun), electroporation, sonoporation, photoporation, magnetofection, hydroporation, and mechanical massage. Chemical methods are those methods that employ a chemical to elicit a change in the cells membrane permeability or other characteristic(s) to facilitate entry of the vector into the cell. For example, the environmental pH can be altered which can elicit a change in the permeability of the cell membrane. Biological methods are those that rely and capitalize on the host cell's biological processes or biological characteristics to facilitate transport of the vector (with or without a carrier) into a cell. For example, the vector and/or its carrier can stimulate an endocytosis or similar process in the cell to facilitate uptake of the vector into the cell.

Delivery of the engineered southern green stink bug pheromone enzymes and systems thereof polynucleotide(s) described herein components (e.g., polynucleotides encoding engineered southern green stink bug pheromone enzymes and systems thereof polypeptides) to cells via particles. The term "particle" as used herein, refers to any suitable sized particles for delivery of the engineered southern green stink bug pheromone enzymes and systems thereof polynucleotide(s) and/or polypeptides described herein components described herein. Suitable sizes include macro-, micro-, and nano-sized particles. In some aspects, any of the engineered southern green stink bug pheromone enzymes and systems thereof polynucleotide(s) described herein components (e.g., polypeptides, polynucleotides, vectors and combinations thereof described herein) can be attached to, coupled to, integrated with, otherwise associated with one or more particles or component thereof as described herein. The particles described herein can then be administered to a cell or organism by an appropriate route and/or technique. In some aspects, particle delivery can be selected and be advantageous for delivery of the polynucleotide or vector components. It will be appreciated that in aspects, particle delivery can also be advantageous for other engineered southern green stink bug pheromone enzymes and systems thereof described herein molecules and formulations described elsewhere herein.

Modified Cells and Organisms

One or more of the polynucleotides and/or vectors can be delivered to and/or expressed in heterologous cells to produce modified cells. In some aspects, the cell is a plant cell. In some aspects, the plant is suitable as a trap crop for management of the Southern green stink bug. As such, also described herein are cells that can include and/or express one or more one or more engineered polynucleotides or vectors capable of producing one or more engineered southern green stink bug pheromone enzymes described herein. Thus, also contemplated herein are organisms that can express in one or more cells one or more one or more engineered polynucleotides or vectors capable of producing one or more engineered southern green stink bug pheromone enzymes described herein. In some instances, the organism is a mosaic. In some instances, the organism can express one or more of the engineered polynucleotides or vectors capable of producing one or more engineered southern green stink bug pheromone enzymes described herein in all cells. The polypeptides, polynucleotides, and vectors described herein can be used to modify one or more cells and/or be used to generate organisms to contain one or more modified cells.

As used herein, the term "transgenic cell" refers to a cell, such as a eukaryotic cell, in which one or more of the engineered polynucleotides capable of producing one or more engineered southern green stink bug pheromone enzymes described herein (the "transgene") has been genomically integrated. The nature, type, or origin of the cell are not particularly limiting according to the present invention. Also, the way the transgene is introduced in the cell can vary and can be any method as is known in the art. In certain embodiments, the transgenic cell is obtained by introducing the transgene in an isolated cell. In certain other embodiments, the transgenic cell is obtained by isolating cells from a transgenic organism.

Modified Cells

In some aspects the modified cell can be a prokaryotic cell. The prokaryotic cells can be bacterial cells. The bacterial cell can be any suitable strain of bacterial cell.

In some aspects the modified cell can be a eukaryotic cell. The eukaryotic cells may be those of or derived from a particular organism, such as a plant or a mammal, including but not limited to, human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded.

In certain embodiments, the methods as described herein may comprise providing a transgenic cell in which one or more nucleic acids encoding one or more engineered southern green stink bug pheromone enzymes described herein are provided or introduced operably connected in the cell with a regulatory element comprising a promoter of one or more gene of interest. By means of example, and without limitation, the transgenic cell as referred to herein may be derived from a transgenic eukaryote, such as a knock-in eukaryote. Any suitable genetic modification method can be used to modify the cells (e.g., convention recombinant techniques and cloning, Cre-Lox systems, Zinc Finger nucleases, TALE nucleases, CRISPR-Cas systems, and the like). Delivery systems for transgenes are well known in the art. By means of example, the transgene may be delivered in for instance eukaryotic cell by means of vector (e.g., AAV, adenovirus, lentivirus) and/or particle and/or nanoparticle delivery, as also described herein elsewhere.

The host cell for modification can be any cell. A wide variety of cell lines for tissue culture are known in the art.

Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN /OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some aspects, the cell is a plant cell. In some aspects, the cell is from a plant suitable for use as a trap crop for a stink bug. In some aspects, the cell is from a plant suitable for use as a trap crop of the southern green stink bug. In some aspects, the plant cell is from a sunflower plant, a squash plant, a zucchini plant, a pumpkin plant, a hollyhock plant, buckwheat, triticale, crimson clover, vetch sorghum, and millet. Other plants may be suitable for use as trap crops. Characteristics of suitable trap crops are described in greater detail elsewhere herein.

In some embodiments, a cell transfected with one or more vectors described herein is used to establish a new cell line comprising one or more polynucleotide and/or vector-derived sequences. In some embodiments, a cell transiently transfected with one or more engineered southern green stink bug pheromone enzymes described herein as described herein (such as by transient transfection of one or more vectors, or transfection with RNA), is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In one aspect, the invention provides a eukaryotic host cell comprising (a) a first regulatory element operably linked to one or more engineered southern green stink bug pheromone enzymes described herein, wherein when expressed, produces the one or more enzymes encoded by one or more engineered southern green stink bug pheromone enzyme polynucleotides described herein.

Modified Organisms

A wide variety of animals, plants, algae, fungi, yeast, etc. and animal, plant, algae, fungus, yeast cell or tissue systems may be engineered for the desired physiological and agronomic characteristics described herein using the nucleic acid constructs of the present disclosure and the various transformation methods mentioned elsewhere herein. In aspects, one or more cells of a plant, animal, algae, fungus, yeast contain one or more polynucleotides, vectors encoding one or more engineered southern green stink bug enzymes described herein. In some aspects, the polynucleotide(s) encoding one or more engineered southern green stink bug enzymes described herein can be stably or transiently incorporated into one or more cells of a plant, animal, algae, fungus, yeast and/or tissue system. In some aspects, one or more engineered southern green stink bug enzymes described herein are genomically incorporated into one or more cells of a plant, animal, algae, fungus, yeast and/or tissue system. Further aspects of the modified organisms and systems are described elsewhere herein.

The engineered southern green stink bug pheromone enzyme polynucleotides described can be used to confer desired traits (e.g., pheromone and/or pheromone precursor production) on essentially any animal plant, algae, fungus, yeast, etc. A wide variety of animals, plants, algae, fungus, yeast, etc. and plant algae, fungus, yeast cell, or tissue systems may be engineered for the desired physiological and agronomic characteristics described herein using the nucleic acid constructs of the present disclosure and the various transformation methods mentioned above. Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants.

In some aspects, one or more engineered southern green stink bug enzymes described herein are expressed in one or more cells of the plant, animal, algae, fungus, yeast, or tissue systems. In some aspects, one or more engineered southern green stink bug enzymes described herein can be transcribed and/or translated by a cell to produce one or more engineered southern green stink bug pheromone enzymes described elsewhere herein. In an aspect, described herein is a non-human eukaryotic organism (such as a plant); preferably a multicellular eukaryotic organism, comprising a eukaryotic host cell containing one or more components of a non-class I engineered CRISPR-Cas system described herein according to any of the described embodiments.

Thus, the described herein a plant, animal or cell, produced by the present methods and incorporating one or more of the polynucleotides and/or enzymes described herein, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants.

The methods described herein generally result in the generation of "improved animals, plants, algae, fungi, yeast, etc." in that they have one or more desirable traits compared to the wildtype animal, plant, algae, fungi, yeast, etc. In particular embodiments, the plants, algae, fungi, yeast, etc., cells or parts obtained are transgenic plants, comprising an exogenous DNA sequence incorporated into the genome of all or part of the cells. In particular embodiments, non-transgenic genetically modified animals, plants, algae, fungi, yeast, etc., parts or cells are obtained, in that no exogenous DNA sequence is incorporated into the genome of any of the cells of the modified animals, plants, algae, fungi, yeast, etc. In such embodiments, the improved animals, plants, algae, fungi, yeast, etc. are non-transgenic. Accordingly, as used herein, a "non-transgenic" animal, plant, algae, fungi, yeast, etc. or cell thereof is an animal, plant, algae, fungi, yeast, etc. or cell thereof which does not contain a foreign DNA stably integrated into its genome.

Modified Plants and Algae

Described herein are plants cells obtainable and obtained by the methods provided herein. The improved plants obtained by the methods described herein may be useful in food or feed production through expression of genes which, for instance ensure tolerance to plant pests, herbicides, drought, low or high temperatures, excessive water, etc.

The modified plants described herein can be used as trap crops that can be used to control southern green stink bug infestation. The trap crops can be planted one or more times a year. In some aspects, the modified trap crop expressing one or more engineered southern green stink bug polynucleotides vectors and/or enzymes as described elsewhere herein. In some aspects, the modified trap crop a sunflower plant, a squash plant, a zucchini plant, a pumpkin plant, a hollyhock plant, buckwheat, triticale, crimson clover, vetch sorghum, and millet. Other plants may be suitable for use as trap crops. Suitable trap crops can have one or more of the following characteristics: attracts the target pests (e.g., southern green stink bug), seeds are readily available, cost effective relative to other management strategies, culture and the management of the plant is well known, the plant is hardy in the geographical location needed and/or time of year needed, has minimal side effects (e.g., it is not invasive, other herbivores on it are benign or beneficial), an optimal maturity time (range is short to long), duration is extendable (by ratooning), the physical properties can be variable (height for barrier; foliage color), is multi-functional (e.g., attracts pollinators, beneficial insects, etc.).

In aspects more than one type of engineered trap crop can be used in the same area. In aspects, more than one type of trap crop can be used throughout the year. The physical appearance and height of the engineered trap crop plants can be important and their efficacy as a barrier can be improved by using pole or climbing species or cultivars on a vertical lattice of wire fencing on posts placed in the ground or in portable containers. The default (lack of knowledge) approach relative to placement would be to ring the entire cash crop with the trap crop. Alternatively, to reduce the amount of space and expense required for the trap crop, one may exploit stink bug behavior and use the "source-sink" approach to determine where to strategically place smaller trap crop plots in the most probable pathways that stink bugs will use to arrive at the cash crop from their previous hosts.

In aspects, the efficiency of the engineered trap crop can be further enhanced by the addition of visual and semiochemical attractants. The yellow pyramid trap baited with the species-specific attractant chemical(s) will attract and capture stink bugs and attract natural enemies. Simple 5-7 gallon plant pots or 3×36 inch mailing tubes painted safety yellow #K7744 will also attract both stink bugs and natural enemies to the trap crops. Stink bugs may be consumed by birds and other animals when exposed off the plant. Specific insect natural enemies include hymenopterous egg parasitoids and parasitic flies (Tachinidae). The mortality exerted on the various stink bug species by these parasitoids is not well documented but it is known that tachinid flies do respond to the semiochemicals released by stink bugs. Thus, the addition of semiochemicals to trap crops may increase natural enemy populations there, bringing them into more frequent contact with stink bugs.

The invention also provides for improved parts of a plant. Plant parts include, but are not limited to, leaves, stems, roots, tubers, seeds, endosperm, ovule, and pollen. Plant parts as envisaged herein may be viable, nonviable, regenerable, and/or non-regeneratable.

It is also encompassed herein to provide plant cells and plants generated according to the methods of the invention. Gametes, seeds, embryos, either zygotic or somatic, progeny or hybrids of plants comprising the genetic modification, which are produced by traditional breeding methods, are also included within the scope of the present invention. Such plants may contain a heterologous or foreign DNA sequence inserted at or instead of a target sequence. Alternatively, such plants may contain only an alteration (mutation, deletion, insertion, substitution) in one or more nucleotides. As such, such plants will only be different from their progenitor plants by the presence of the particular modification.

In some aspects, the modified organism is a plant. In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants. Specifically, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, *eucalyptus*, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, *papaya*, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini. The term plant also encompasses Algae, which are mainly photoautotrophs unified primarily by their lack of roots, leaves and other organs that characterize higher plants.

Plants can be modified to express one or more of the engineered southern green stink bug pheromones using a suitable modification technique, including but not limited to recombinant technology techniques and various genome editing systems, e.g., a CRISPR-Cas system, TALENs, Zinc-finger nucleases, can be used to confer desired traits on essentially any plant. Such methods are known in the art. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, a broad range of plants, such as for example with dicotyledonous plants can be modified belonging to the orders Magnoliales, Illiciales, Laurales, Piperales, Aristolochiaceae, Nymphaeales, Ranunculales, Papaveraceae, Sarraceniaceae, Trochodendrales, Hamamelidales, Eucommiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales; the methods and CRISPR-Cas systems can be used with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Liliales, and Orchid ales, or with plants belonging to Gymnospermae, e.g those belonging to the orders Pinales, Ginkgoales, Cycadales, Araucariales, Cupressales and Gnetales.

Other plants that can be modified as described herein include those in the non-limitative list of dicot, monocot or gymnosperm genera hereunder: *Atropa, Alseodaphne, Anacardium, Arachis, Beilschmiedia, Brassica*, Carthamus, Cocculus, Croton, *Cucumis, Citrus, Citrullus, Capsicum, Catharanthus, Cocos, Coffea, Cucurbita, Daucus, Duguetia, Eschscholzia, Ficus*, Fragaria, Glaucium, Glycine, *Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca*, Vilis, and *Vigna*; and the genera *Allium, Andropogon, Eragrostis, Asparagus, Avena, Cynodon, Elaeis, Festuca, Festulolium, Hemerocallis, Hordeum, Lemna, Lolium, Musa, Oryza, Panicum, Pennisetum, Phleum, Poa, Secale, Sorghum, Triticum, Zea, Abies, Cunninghamia, Ephedra, Picea, Pinus*, and *Pseudotsuga*.

As used herein "algae" or "algae cells" that can be modified as described herein include, but are not limited to, algae selected from several eukaryotic phyla, including the Rhodophyta (red algae), Chlorophyta (green algae), Phaeophyta (brown algae), Bacillariophyta (diatoms), Eustigmatophyta and dinoflagellates as well as the prokaryotic phylum Cyanobacteria (blue-green algae). The term "algae" includes for example algae selected from: Amphora, *Anabaena, Ankistrodesmus, Botryococcus, Chaetoceros, Chlamydomonas, Chlorella*, Chlorococcum, Cyclotella, Cylindrotheca, *Dunaliella, Emiliania, Euglena, Haematococcus, Isochrysis*, Monochrysis, Monoraphidium, Nannochloris, *Nannochloropsis*, Navicula, Nephrochloris, Nephroselmis, *Nitzschia, Nodularia, Nostoc*, Ochromonas, Oocystis, Oscillartoria, Pavlova, *Phaeodactylum, Playtmonas, Pleurochrysis, Porphyra*, Pseudoanabaena, Pyramimonas, Stichococcus, Synechococcus, *Synechocystis, Tetraselmis, Thalassiosira*, and *Trichodesmium*. *A part of a plant, i.e., a "plant tissue" may be treated according to the methods of the present invention to produce an improved plant. Plant tissue also encompasses plant cells. The term "plant cell" as used herein refers to individual units of a living plant, either in an intact whole plant or in an isolated form grown in in vitro tissue cultures, on media or agar, in suspension in a growth media or buffer or as a part of higher organized unites, such as, for example, plant tissue, a plant organ, or a whole plant.*

A "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

The term "transformation" broadly refers to the process by which a plant host is genetically modified by the introduction of DNA by means of Agrobacteria or one of a variety of chemical or physical methods. As used herein, the term "plant host" refers to plants, including any cells, tissues, organs, or progeny of the plants. Many suitable plant tissues or plant cells can be transformed and include, but are not limited to, protoplasts, somatic embryos, pollen, leaves, seedlings, stems, calli, stolons, microtubers, and shoots. A plant tissue also refers to any clone of such a plant, seed, progeny, propagule whether generated sexually or asexually, and descendants of any of these, such as cuttings or seed.

The term "transformed" as used herein, refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is transmitted to the subsequent progeny. In these embodiments, the "transformed" or "transgenic" cell or plant may also include progeny of the cell or plant and progeny produced from a breeding program employing such a transformed plant as a parent in a cross and exhibiting an altered phenotype resulting from the presence of the introduced DNA molecule. Preferably, the transgenic plant is fertile and capable of transmitting the introduced DNA to progeny through sexual reproduction.

The term "progeny", such as the progeny of a transgenic plant, is one that is born of, begotten by, or derived from a plant or the transgenic plant. The introduced DNA molecule may also be transiently introduced into the recipient cell such that the introduced DNA molecule is not inherited by subsequent progeny and thus not considered "transgenic".

The term "plant promoter" as used herein is a promoter capable of initiating transcription in plant cells, whether or not its origin is a plant cell. Exemplary suitable plant promoters include, but are not limited to, those that are obtained from plants, plant viruses, and bacteria such as *Agrobacterium* or *Rhizobium* which comprise genes expressed in plant cells.

In particular embodiments, the DNA construct may be introduced into the plant cell using techniques such as but not limited to electroporation, microinjection, aerosol beam injection of plant cell protoplasts, or the DNA constructs can be introduced directly to plant tissue using biolistic methods, such as DNA particle bombardment (see also Fu et al., Transgenic Res. 2000 Feb; 9(1):11-9). The basis of particle bombardment is the acceleration of particles coated with gene/s of interest toward cells, resulting in the penetration of the protoplasm by the particles and typically stable integration into the genome. (See e.g., Klein et al, Nature (1987), Klein et ah, Bio/Technology (1992), Casas et ah, Proc. Natl. Acad. Sci. USA (1993).).

In particular embodiments, the DNA constructs containing one or more engineered southern green stink bug pheromone polynucleotides described herein may be introduced into the plant by *Agrobacterium*-mediated transformation. The DNA constructs may be combined with suitable T-DNA flanking regions and introduced into a conventional *Agrobacterium tumefaciens* host vector. The foreign DNA can be incorporated into the genome of plants by infecting the plants or by incubating plant protoplasts with *Agrobacterium* bacteria, containing one or more Ti (tumor-inducing) plasmids. (see e.g., Fraley et al., (1985), Rogers et al., (1987) and U.S. Pat. No. 5,563,055).

CRISPR or other RNA-guided gene modification systems generally known in the art can be used to introduce targeted double-strand or single-strand breaks and/or to introduce into one or more plant cells or entire plant gene activator and/or repressor systems and without being limitative, can be used for gene targeting, gene replacement, targeted mutagenesis, targeted deletions or insertions, targeted inversions and/or targeted translocations. By co-expression of multiple targeting polynucleotides (e.g.,) RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

In particular embodiments, the methods described herein are used to modify endogenous genes or to modify their expression without the permanent introduction into the genome of the plant, including those encoding CRISPR components, so as to avoid the presence of foreign DNA in the genome of the plant. This can be of interest as the regulatory requirements for non-transgenic plants are less rigorous.

1. Chloroplast Targeting

In particular embodiments, it is envisaged that the transgenes are expressed specifically in the chloroplast. For this purpose, use is made of chloroplast transformation methods or compartmentalization of the engineered vectors or polynucleotides described herein to the chloroplast. For instance, the introduction of genetic modifications in the plastid genome can reduce biosafety issues such as gene flow through pollen. Methods of chloroplast transformation are known in the art and include Particle bombardment, PEG treatment, and microinjection. Additionally, methods involving the translocation of transformation cassettes from the nuclear genome to the plastid can be used as described in WO2010061186.

Alternatively, it is envisaged to target one or more of the engineered vectors or polynucleotides described herein to the plant chloroplast. This is achieved by incorporating in the expression construct a sequence encoding a chloroplast transit peptide (CTP) or plastid transit peptide, operably linked to the 5' region of the sequence encoding the CRISPR-Cas protein. The CTP is removed in a processing step during translocation into the chloroplast. Chloroplast targeting of expressed proteins is well known to the skilled artisan (see for instance Protein Transport into Chloroplasts, 2010, Annual Review of Plant Biology, Vol. 61: 157-180). In such embodiments it is also desired to target the guide RNA to the plant chloroplast. Methods and constructs which can be used for translocating guide RNA into the chloroplast by means of a chloroplast localization sequence are described, for instance, in US 20040142476, incorporated herein by reference. Such variations of constructs can be incorporated into the expression systems of the invention to efficiently translocate the CRISPR-Cas-guide RNA.

2. Introduction of Polynucleotides in Algal Cells

Transgenic algae (or other plants such as rape) may be particularly useful for the expression and/or production of the southern green stink bug pheromone enzymes described herein. These may be engineered to express or overexpress high levels of oil or alcohols for use in the oil or biofuel industries.

U.S. Pat. No. 8,945,839 describes a method for engineering Micro-Algae (*Chlamydomonas reinhardtii* cells) using Cas9. Using similar tools, the methods of the CRISPR-Cas system described herein can be applied on *Chlamydomonas* species and other algae. Electroporation protocols are available to the skilled person such as the standard recommended protocol from the GeneArt *Chlamydomonas* Engineering kit.

Organisms such as microalgae are widely used for synthetic biology. Stovicek et al. (Metab. Eng. Comm., 2015; 2:13 describes genome editing of industrial yeast, for example, *Saccharomyces cerevisiae*, to efficiently produce robust strains for industrial production. Stovicek used a CRISPR—The methods of Stovicek and Hlavová may be applied and/or adapted to produce a modified microalgae expression one or more of the engineered vectors, polynucleotides, and/or polypeptides described herein 3. Transient Expression of the Engineered Polynucleotides and/or Vectors in Plant Cells In particular embodiments, it is envisaged that one or more of the engineered vectors or polynucleotides described herein are transiently expressed in the plant cell. In these embodiments, expression of the transgene(s) is transient, plants regenerated from such plant cells typically contain no foreign DNA. In particular embodiments, one or more of the engineered vectors or polynucleotides described herein can be introduced in the plant cells using a plant viral vector (Scholthof et al. 1996, Annu Rev Phytopathol. 1996; 34:299-323). In further particular embodiments, said viral vector is a vector from a DNA virus. For example, geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). In other particular embodiments, said viral vector is a vector from an RNA virus. For example, tobravirus (e.g., tobacco rattle virus, tobacco mosaic virus), potexvirus (e.g., potato virus X), or hordeivirus (e.g., barley stripe mosaic virus). The replicating genomes of plant viruses are non-integrative vectors.

In particular embodiments, the vector used for transient expression of the transgene(s) for instance a pEAQ vector, which is tailored for *Agrobacterium*-mediated transient expression (Sainsbury F. et al., Plant Biotechnol J. 2009 September; 7(7):682-93) in the protoplast.

In particular embodiments, double-stranded DNA fragments encoding the engineered southern green stink bug pheromone enzymes described herein can be transiently introduced into the plant cell. In such embodiments, the introduced double-stranded DNA fragments are provided in sufficient quantity to modify the cell but do not persist after a contemplated period of time has passed or after one or more cell divisions. Methods for direct DNA transfer in plants are known by the skilled artisan (see for instance Davey et al. Plant Mol Biol. 1989 September; 13(3):273-85.)

In other embodiments, an RNA polynucleotide encoding the engineered southern green stink bug pheromone enzymes described herein is/are introduced into the plant cell, which is then translated and processed by the host cell generating the protein in sufficient quantity to modify the cell (in the presence of at least one guide RNA) but which does not persist after a contemplated period of time has passed or after one or more cell divisions. Methods for introducing mRNA to plant protoplasts for transient expression are known by the skilled artisan (see for instance in Gallie, Plant Cell Reports (1993), 13;119-122).

Combinations of the different methods described above are also envisaged.

Delivery of engineered polynucleotides, vectors, and polypeptides to a plant cell In particular embodiments, it is of interest to deliver one or more engineered polynucleotides, vectors and/or polypeptides described herein directly to the plant cell. This is of interest, inter alia, for the generation of non-transgenic plants (see e.g., elsewhere herein). In particular embodiments, one or more engineered polynucleotides, vectors and/or polypeptides described herein is prepared outside the plant or plant cell and delivered to the cell. For instance, in particular embodiments, the engineered southern green stink bug pheromone protein(s) is/are prepared in vitro prior to introduction to the plant cell. Such protein(s) can be prepared by various methods known by one of skill in the art and include recombinant production. After expression, the engineered protein(s) described herein is/are isolated, refolded if needed, purified and optionally treated to remove any purification tags, such as a His-tag. Once crude, partially purified, or more completely purified engineered protein(s) is/are obtained, the protein may be introduced to the plant cell.

In particular embodiments, the engineered polypeptides, polynucleotides, and/or vectors described herein are introduced into the plant cells using nanoparticles. The components, either as protein or nucleic acid or in a combination thereof, can be uploaded onto or packaged in nanoparticles and applied to the plants (such as for instance described in WO 2008042156 and US 20130185823). In some embodiments, cell penetrating peptides can be used to introduce one or more of the engineered polypeptides, polynucleotides, and/or vectors described herein into a plant cell. Accordingly, in particular, embodiments the invention comprises compositions comprising a cell penetrating peptide linked to one or more of the engineered protein(s) described herein. In particular embodiments, one or more of the engineered protein(s) described herein is coupled to one or more CPPs to effectively transport them inside plant protoplasts. In other embodiments, the engineered proteins are encoded by one or more circular or non-circular DNA molecule(s) which are coupled to one or more CPPs for plant protoplast delivery. The plant protoplasts are then regenerated to plant cells and further to plants. CPPs are generally described as short peptides of fewer than 35 amino acids either derived from proteins or from chimeric sequences which are capable of transporting biomolecules across cell membrane in a receptor independent manner. CPP can be cationic peptides, peptides having hydrophobic sequences, amphipathic peptides, peptides having proline-rich and anti-microbial sequence, and chimeric or bipartite peptides (Pooga and Langel 2005). CPPs are able to penetrate biological membranes and as such trigger the movement of various biomolecules across cell membranes into the cytoplasm and to improve their intracellular routing, and hence facilitate interaction of the biomolecule with the target. Examples of CPP include amongst others: Tat, a nuclear transcriptional activator protein required for viral replication by HIV type1, penetratin, Kaposi fibroblast growth factor (FGF) signal peptide sequence, integrin P3 signal peptide sequence; polyarginine peptide Args sequence, Guanine rich-molecular transporters, sweet arrow peptide, etc.

In particular embodiments, the methods described herein are used to modify endogenous genes or to modify their expression without the permanent introduction into the genome of the plant of any foreign gene, including those one or more of the engineered polypeptides described elsewhere herein, so as to avoid the presence of foreign DNA in the genome of the plant. This can be of interest as the regulatory requirements for non-transgenic plants are less rigorous.

In particular embodiments, the engineered polypeptides, polynucleotides and/or vectors are introduced in the plant cell, protoplast or plant tissue either separately or in mixture, with the aid of particulate delivering molecules such as nanoparticles or CPP molecules as described herein above.

Detecting modifications in the plant genome—selectable markers

Where the method involves introduction of a transgene, a transformed plant cell, callus, tissue or plant may be identified and isolated by selecting or screening the engineered plant material for the presence of the transgene or for traits encoded by the transgene. Physical and biochemical methods may be used to identify plant or plant cell transformants containing inserted gene constructs or an endogenous DNA modification. These methods include but are not limited to: 1) Southern analysis or PCR amplification for detecting and determining the structure of the recombinant DNA insert or modified endogenous genes; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct or expression is affected by the genetic modification; 4) protein gel electrophoresis, Western blot techniques, immunoprecipitation, or enzyme-linked immunoassays, where the gene construct or endogenous gene products are proteins. Additional techniques, such as in situ hybridization, enzyme staining, and immunostaining, also may be used to detect the presence or expression of the recombinant construct or detect a modification of endogenous gene in specific plant organs and tissues. The methods for doing all these assays are well known to those skilled in the art. Additionally (or alternatively), the expression system encoding the engineered polypeptides is typically designed to comprise one or more selectable or detectable markers that provide a means to isolate or efficiently select cells that contain and/or have been modified by the transgene system at an early stage and on a large scale.

In the case of *Agrobacterium*-mediated transformation, the marker cassette may be adjacent to or between flanking T-DNA borders and contained within a binary vector. In another embodiment, the marker cassette may be outside of the T-DNA. A selectable marker cassette may also be within or adjacent to the same T-DNA borders as the expression cassette or may be somewhere else within a second T-DNA on the binary vector (e.g., a 2 T-DNA system). For particle bombardment or with protoplast transformation, the expression system can comprise one or more isolated linear fragments or may be part of a larger construct that might contain bacterial replication elements, bacterial selectable markers or other detectable elements. The expression cassette(s) comprising the engineered polynucleotides described herein may be physically linked to a marker cassette or may be mixed with a second nucleic acid molecule encoding a marker cassette. The marker cassette is comprised of necessary elements to express a detectable or selectable marker that allows for efficient selection of transformed cells.

The selection procedure for the cells based on the selectable marker will depend on the nature of the marker gene. In particular embodiments, use is made of a selectable marker, i.e. a marker which allows a direct selection of the cells based on the expression of the marker. A selectable marker can confer positive or negative selection and is conditional or non-conditional on the presence of external substrates (Miki et al. 2004, 107(3): 193-232). Most commonly, antibiotic or herbicide resistance genes are used as a marker, whereby selection is be performed by growing the engineered plant material on media containing an inhibitory amount of the antibiotic or herbicide to which the marker gene confers resistance. Examples of such genes are genes that confer resistance to antibiotics, such as hygromycin (hpt) and kanamycin (nptll), and genes that confer resistance to herbicides, such as phosphinothricin (bar) and chlorosulfuron (als).

Transformed plants and plant cells may also be identified by screening for the activities of a visible marker, typically an enzyme capable of processing a colored substrate (e.g., the p-glucuronidase, luciferase, B or C1 genes). Such selection and screening methodologies are well known to those skilled in the art.

4. Plant Cultures and Regeneration

In particular embodiments, plant cells which have a modified genome and that are produced or obtained by any of the methods described herein, can be cultured to regenerate a whole plant which possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In further particular embodiments, plant regeneration is obtained from cultured protoplasts, plant callus, explants, organs, pollens, embryos or parts thereof (see e.g., Evans et al. (1983), Handbook of Plant Cell Culture, Klee et al (1987) Ann. Rev. of Plant Phys.).

In particular embodiments, transformed or improved plants as described herein can be self-pollinated to provide seed for homozygous improved plants of the invention (homozygous for the DNA modification) or crossed with non-transgenic plants or different improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the improved plants and comprising the genetic modification (which can be a recombinant DNA) are referred to herein as "progeny". Progeny plants are plants descended from the original transgenic plant and containing the genome modification or recombinant DNA molecule introduced by the methods provided herein. Alternatively, genetically modified plants can be obtained by one of the methods described supra using a genome modification technique whereby no foreign DNA is incorporated into the genome. Progeny of such plants, obtained by further breeding may also contain the genetic modification. Breedings are performed by any breeding methods that are commonly used for different crops (e.g., Allard, Principles of Plant Breeding, John Wiley & Sons, NY, U. of CA, Davis, CA, 50-98 (1960).

Modified Fungi

In some embodiments, the modified organism can be a fungus. As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell. As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerevisiae, Kluyveromyces marxianus*, or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and Issatchenkia spp. (e.g., Issatchenkia *orientalis*, a.k.a. *Pichia* kudriavzevii and *Candida* acidothermophilum). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella* isabellina).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains may include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, inactivation, activation, or modification of meiosis, cytokinesis, or DNA replication). A polyploid cell may refer to a cell whose entire genome is polyploid, or it may refer to a cell that is polyploid in a particular genomic locus of interest.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

The yeast can be modified using any suitable technique, which are generally known in the art and can include recombinant engineering techniques, cloning, TALEs, CRISPR-Cas, and the like. Methods for transforming yeast cells which can be used to introduce the engineered polynucleotides described herein are well known to the artisan as can be exemplified are reviewed by Kawai et al., 2010, Bioeng Bugs. 2010 Nov-Dec; 1(6): 395-403). Non-limiting examples include transformation of yeast cells by lithium acetate treatment (which may further include carrier DNA and PEG treatment), bombardment or by electroporation.

Modified Microorganisms

In some aspects, the modified organism is a modified micro-organism.

In particular embodiments, the micro-organism is selected from the genus *Escherichia, Bacillus, Lactobacillus, Rhodococcus, Synechococcus, Synechocystis, Pseudomonas, Aspergillus, Trichoderma, Neurospora, Fusarium, Humicola, Rhizomucor, Kluyveromyces, Pichia, Mucor, Myceliophthora, Penicillium, Phanerochaete, Pleurotus, Trametes, Chrysosporium, Saccharomyces, Stenotrophomonas, Schizosaccharomyces, Yarrowia,* or *Streptomyces.*

Any of the modified plants described herein can be used to manage

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

This Example can demonstrate the identification of two *N. viridula* IDS-type genes and encoded enzymes. One gene (abbreviated NvTPS1) can encode an enzyme encodes an enzyme that converts (E,E)-FPP to (Z)-α-bisabolene as the likely precursor of trans-/cis-(Z)-α-bisabolene epoxide. The second gene can have bona fide IDS activity producing (E,E)-FPP. As is further demonstrated herein NvTPS1 is highly expressed in the tissue associated with the abdominal sternites of mature males, which correlates with (Z)-α-bisabolene activity in crude protein extracts of males, while low NvTPS1 transcript levels and enzyme activity were observed in females.

Materials and Methods

Chemicals and Reagents. [1-$^3$H]-FPP (20 Ci/mmol) was ob-tained from American Radiolabeled Chemicals (St. Louis, MO). Opoponax oil, a source of (Z)-α-bisabolene, was obtain-ed from Floracopeia (Grass Valley, CA; reported source, *Commiphora guidotti*, Sapindales: Burseraceae). All other chemicals were from Sigma-Aldrich (St. Louis, MO).

Preparations of Reference Standards. Preparation of (+)-(S,Z)-α-bisabolene: Opopanax oil (45 ml) was distilled in vacuum to provide (among others) a fraction (2.71 g) with the boiling point 77-78° C. /0.1-0.2 mg Hg. The content of (+)-(S,Z)-α-bisabolene in this fraction according to GC-MS analysis was 65%. This was flash chromatographed on silica with hexanes to provide a fraction (500 mg) containing 87% (+)-(S,Z)-α-bisabolene, which was further purified by chromatography on $AgNO_3$—$SiO_2$ eluting with hexanes/ethyl acetate, 97:3, to furnish the desired product (142 mg) of 95% chemical purity. [α]D20+2.0 (c 1.17, EtOH); lit. (Delay and Ohloff 0.1979. Helv Chim Acta 62:369-377) [α]D20+4.15 (1%, EtOH).

Preparation of (−)-(R,Z)-α-bisabolene: trans-(R,Z)-α-bisabolene epoxide, the enantiomer of the main component of the *N. viridula* sex pheromone, was prepared from a (+)-limonene oxide mixture following Chen et al. (2000. Synthesis. 269-272) [α]D20+8.2 (c 2.65, CH2C12); lit. (Baker et al. 1987. J Chem Soc Chem Commun: 414-416) [α]D20+ 19.1 (c 0.53, CH2C12). The retention time and the mass-spectrum of the product were identical to those of an authentic sample of trans-(S,Z)-α-bisabolene epoxide prepared previously from (−)-limonene oxide Chen et al. (2000. Synthesis. 269-272). This epoxide (50 mg, 0.23 mmol) was deoxygenated by stirring at r.t. with zinc (83 mg,1.27 mmol), sodium iodide (272 mg, 1.81 mmol), sodium acetate (93 mg, 1.13 mmol), and acetic acid (249 µl) in dichloromethane (2 ml) for 18 h following (Scalabrino et al.2003. Org Biomol Chem 1:318-327) The mixture was filtered through Celite, the filtrate was further diluted with $CH_2Cl_2$, then washed with $NaHCO_3$, brine, and dried with $Na_2SO_4$. After evaporation of the solvent, the residue was chromatographed on silica with hexanes to provide (R,Z)-α-bisabolene (27 mg, 58%), which matched (+)-(S,Z)-α-bisabolene by GC retention time and mass-spectrum but was levorotatory with [α]D20-2.3 (c 1.0, EtOH) and optical purity 66% (ee), as determined by GC analysis on an enantioselective Hydrodex-R-6TBDM column.

Insects. A colony of *N. viridula* originated with field collections near Tifton, Georgia, USA. Insects were reared in venti-lated plastic cylinders (21 cm×21 cm o.d.) on a diet of organ-ic green beans, shelled raw sunflower seeds and buckwheat seeds (2:1 w/w), glued onto squares of brown wrapping paper with wheat-based wallpaper paste. Distilled water was sup-plied in two cotton-stopped 7 cm×2 cm o.d. shell vials held together with a rubber band. Insects were reared in a climate controlled growth chamber (25±5° C., 16:8 h L:D, 65% RH). Eggs were collected weekly and hatched in plastic Petri dishes with a water vial, and after molting to second-instars, the nymphs were transferred to the larger rearing cages as de-scribed above for the remaining four instars. Newly enclosed adults were removed from cages three times weekly and moved to new cages, isolating males and females. Insects were kept until the immature (2-3 day post molt) or mature (14-15 day post molt) adult stage.

Crude Protein Extracts of *N. viridula*. Abdominal cuticles from one mature (14-15 days post molt) adult male and female *N. viridula* were used for crude protein assays. Insects were fixed with hexane vapor in a screw top jar and dissected in phosphate buffered saline (PBS) (137 mM NaCl, 8.1 mM Na2HPO4, 1.5 mM NaH2PO4, 2.7 mM KCl, pH 7.2). Head, thorax and abdominal soft tissues were removed except for epithelial cells lining the cuticle. Abdominal cuticles were then frozen in liquid nitrogen, pulverized with a mortar and pestle, and suspended in assay buffer (25 mM HEPES, 5 mM MgCl2, 10% glycerol, 1 mM DTT, pH 7). Protein concentrations were determined with a Bradford Assay (Bio-Rad, Hercules, CA) according to the manufacturer's protocol resulting in a protein concentration of 1.2 µg/µl and 0.8 µg/µl for female and male tissue, respectively.

RNAseq and De Novo Transcriptome Assembly. Total RNA was extracted each from pooled abdominal sternites of five mature (14-15 days post molt) male and five mature female *N. viridula* using Trizol Reagent (Invitrogen, Thermo Fisher Scientific) according to the manufacturer's protocol. RNA was DNase treated with RQ1 DNase I (Promega, Madison, WI) and purified using the RNeasy Plant Mini Kit (Qiagen, Germantown, MD). RNA integrity was analyzed on a Bioanalyzer 2100 (Agilent Technologies, Santa Clara, CA). RNAseq was performed by Beckman Coulter Genomics (Danvers, MA) on an Illumina HiSeq instrument using paired-end (2×100 bp) reads resulting in approximately 82 M reads per sample. Quality of fastq files was assessed using the publicly available software FastQC. Based on quality scores, reads were truncated by 9 bp using Trimmomatic (Bolger et al. 2014) to remove low quality se-quence and the resulting reads were reanalyzed by FastQC. High quality reads were assembled de novo using Trinity (Grabherr et al. 2011) and assembly quality was verified by aligning processed reads to the assembled transcriptome using Bowtie2 (Langmead and Salzberg. 2012. PNAS 115:E8634-E8641). RNAseq data and gene accession numbers are deposited in GenBank.

Identification and Cloning of IDS Type Genes. Three putative isoprenyl diphosphate synthase like genes (NvIDS1-NvIDS3) were identified from the transcriptome data with tblastn searches using query sequences of functionally characterized TPS and FPPS from *M. histrionica* and the bifunctional IDS/TPS from *I. pini* (Gilg et al. 2005. PNAS 102:9760-9765; Lancaster et al. 2018. PNAS 1150: 115: E8534-E8641; Sparks et al. 2017. Insects 8:55). Primers were designed to clone full-length NvIDS1 (NvTPS_1F/NvTPS_1137R), NvIDS2 (NvFPPS_1F/NvFPPS_1212R) and NvIDS3 (NvIDS3_1F/NvIDS3_1134R) (Table 1). cDNAs were generated from total RNA using GoScript reverse transcriptase (Promega). NvIDS1 and NvIDS2 cDNAs were amplified with Q5 proofreading DNA polymerase (New England Biolabs) and ligated into the pGEM-T Easy vector (Promega). Sequences for NvIDS1 and NvIDS2 were verified before cloning into expression vectors. Sequences have been deposited in the GenBank database under accession numbers MG748543 (NvIDS1/NvTPS), MG748544 (NvIDS2/NvFPPS) and MG748545 (NvIDS3). A cDNA from NvIDS3 was not be amplified.

TABLE 1

List of primers used in Example 1

| Gene | Primers (5'→3') | Amplicon size (bp) | Purpose |
|---|---|---|---|
| NvIDS1/NvTPS | NcTPS-F<br>ATGGCAGCAAGGGCACCCGTACA SEQ ID NO: 80<br>NVTPS-R<br>TTAGTTATTTAATACGCTTTCAGCTTCT SEQ ID NO: 81 | 1137 | Blunt-end cloning into pGEM-T easy vector |
| | NvTPS-QF<br>GTTTGGGCTTCCGTGTGTG SEQ ID NO: 82<br>NvTPS-QR<br>TACCGAAGTGGCGCTTAACC SEQ ID NO: 83 | 100 | qRT-PCR |
| NvIDS2/NvFPPS | NvFPPS-F<br>ATGCCACTTGCAAAACTGTG SEQ ID NO: 84<br>NvFPPS-R<br>CTACTGCTTTCTGCCATATGTTTTATG SEQ ID NO: 85 | 1212 | Blunt-end cloning into pGEM-T easy vector |
| NvIDS3 | NvIDS3-F<br>ATGGCAGCAAGGGCATC SEQ ID NO: 86 | 1134 | Blunt-end cloning into pGEM-T easy vector |

TABLE 1-continued

List of primers used in Example 1

| Gene | Primers (5'→3') | Amplicon size (bp) | Purpose |
|---|---|---|---|
| | NvIDS3-R TTAAACATACACTTTTATTCTTTCAATTTG SEQ ID NO: 87 | | |
| RpS4 | NvRpS4-F GCTCGTGGTCCCAAAAAGC SEQ ID NO: 88 NvRpS4-R GACCTGAGCTGGGCCTTG SEQ ID NO: 89 | 100 | qRT-PCR |

Heterologous Expression of Recombinant NvFPPS. For expression in bacterial cells, full-length NvFPPS (NvIDS2) cDNA was amplified from the pGEM-T Easy construct with Q5 DNA polymerase and cloned into the pEXP5-NT/TOPO expression vector (Invitrogen, Thermo Fisher Scientific) generating an N-terminal 6× histidine tag. Following transformation of the vector into *Escherichia coli* BL21(DE3) pLysS (Invitrogen), cells (50 ml) were grown at 37° C. and 220 rpm and induced with 1 mM IPTG at an OD600 of 0.6. Cells were cultivated at 18° C. for another 18 h before the cell pellet was incubated at 4° C. for 30 min in 2 ml extraction buffer (50 mM Tris HCl, pH 7.5, 20 mM imidazole, 300 mM NaCl, 10% glycerol [v/v], 5 mM MgCl2, 2 mM DTT) supplemented with 0.3 mg/ml lysozyme (AppliChem, Maryland Heights, MO), 2.5 U/ml benzonase (EMD Millipore, Novagen) and proteinase inhibitors (Protease Inhibitor Mix HP, Serva, Heidelberg, Germany). Upon sonication (4×30 s treatment, Bandelin UW2070, Berlin, Germany; 50%) the recombinant protein was purified from cell lysates on Ni-NTA Spin Columns (Qiagen) according to the manufacturer's instructions. In preparation for enzyme assays, a buffer exchange to 25 mM 3-(N-morpholino)-2-hydroxypropanesulfonic acid (MOPSO, pH 7.2, 10% [v/v] glycerol, 1 mM DTT, 5 mM MgCl2) was conducted on PD-10 Desalting Columns (GE Healthcare Life Sciences, Pittsburgh, PA).

Heterologous Expression of Recombinant NvTPS. Full-length NvTPS (NvIDS1) cDNA was cloned into the pEXP5-NT/TOPO (Invitrogen) expression vector as described above and transformed into *E. coli* BL21(DE3)pLysS cells. Single colonies were selected at 18° C. on LB with ampicillin (100 µg/ml) and chloramphenicol (34 µg/ml). Expression cultures (200 ml of the same medium) were started from 5 ml overnight cultures and incubated at 18° C. for 4-8h. Following induction at an OD600 of 0.50 with 0.5 mM IPTG, cells were cultivated for another 48 h, then washed in 100 ml wash buffer (20 mM Tris-HCl, 50 mM KCl, pH 7), pelleted, and resuspended in 15 ml cell lysis buffer (50 mM NaH2PO4, 300 mM NaCl, 5 mM imidazole, 0.5 mM PMSF, 2 mM DTT, pH 8). Upon sonication for 2×30 s (on ice, 1 min interval, 20% amplitude, Branson Digital Sonifier), the recombinant protein was purified with Ni-NTA agarose (Qiagen) using three washes of 30 mM imidazole and elution as a 1 ml fraction with 250 mM imidazole. Buffer exchange into TPS assay buffer (25 mM HEPES, 10 mM MgCl$_2$, 10% glycerol, pH 7) was performed on PD MiniTrap G-25 desalting columns (GE Healthcare Life Sciences).

IDS Activity Assay and Analysis. IDS enzyme assays were perfumed with 96 µl of purified protein mixed with 2 µl 50 µM isopentenyl diphosphate (IPP; Sigma-Aldrich) and 2 µl 50 µM dimethylallyl diphosphate (DMAPP; Sigma-Aldrich). Upon incubation at 30° C. for 2 h, IDS enzyme products were analyzed on an Agilent 1260 HPLC system (Agilent Technologies) coupled to an API 5000 triple-quadrupole mass spectrometer (AB Sciex Instruments) following the protocol described by Beran et al. 2016. PNAS. 113:2922-2927.

TPS Activity Assay. To determine terpene synthase activity in crude protein extracts of male and female abdominal cuticle tissue, 50 µM (E,E)-FPP was added to protein extracts in assay buffer (see above) containing 50 pg protein at a final volume of 200 µl and with a 200 µl hexane overlay to collect volatiles. Following incubation for 12 h at 30° C., enzyme products were extracted by mixing for 15 s using a vortex and phases were separated by centrifuging at 4000×g for 10 min. One µl of the hexane extract was analyzed by GC-MS.

TPS activity of purified, recombinant NvTPS protein was determined in assay buffer (see above) with 1 mM DTT and 50 µM allylic substrate [(E,E)-, (Z,E)- or (Z,Z)-FPP] in a total volume of 100 µl and with a 100 µl hexane overlay. Upon incubation at 30° C. for 1 h, assays were stopped on ice and compounds extracted by mixing using a vortex at maximum speed for 15 s. Phases were separated by centrifuging at 4000×g for 10 min and the hexane phase was removed and dried over MgSO4. One µL of the hexane extract was analyzed by GC-MS.

To determine the apparent Km value of NvTPS for (E,E)-FPP, 0.05 pg of recombinant protein was incubated with increasing concentrations of [1-3H]-(E,E)-FPP (64 pCi mmol-1) in a total volume of 50 pl. Assays were incubated at 30° C. for 5 min prior to extraction of the enzyme product with 250 µl hexane. Assays were performed in triplicate. Quantification of the radioactive product was as described by Tholl et al. (2005. Plant. J. 42:757-771). The Km value was calculated by rectangular hyperbolic regression analysis using Hyperbolic Regression Analysis software (HYPER 1.01) (J. S. Easterby, University of Liverpool).

Gas Chromatography-Mass Spectrometry Analysis and Determination of Absolute Configuration of NvTPS Products. GC-MS analysis of hexane extracts from assays with crude protein lysates or NvTPS recombinant protein was performed using split injection (5:1 ratio) at an injection temperature of 240° C. Compounds were separated on a GC-2010 gas chromatograph (Shimadzu, Kyoto, Japan) with a 30 m×0.25 mm i.d.×0.25 µm film Zebron ZB-XLB column (Phenomenex, Torrance, CA) coupled to a QP2010S mass spectrometer (Shimadzu). Separation steps were as follows: initial 2 min hold at 40° C., followed by a 5° C./min ramp to 220° C., then a 70° C./min ramp to 240° C. followed by a 2 min hold time at 240° C. Mass spectrometry was performed with a 240° C. ion source temperature, 280° C. interface temperature, electron ionization (EI) potential of 70 eV, and scan range of 50 to 400 amu. Helium was used as a carrier gas at 1.9 ml/min. Enzyme products were identified by library suggestions and comparison to a reference standard (Opoponax oil) for (Z)-α-bisabolene.

The absolute configurations of the (Z)-α-bisabolene product of NvTPS was determined by separation on a chiral Hydrodex R-6TBDM column (25 m×0.25 mm, ID) in comparison with the synthetic reference standards (+) and (−)-(Z)-α-bisabolenes. Samples were injected without split at a concentration of about 40 pg/ml (in hexane) and separated at a gradient from 40(5) to 200° C. at 10° C./min with H2 as the carrier gas (2 ml/min), a detector temperature of 200° C., and an injection temperature of 200° C. Comparative analysis of reference standards was performed with a 25:1 split injection of about 1 mg/ml hexane solutions. Separation occurred isothermally at 200° C. with H2 as the carrier gas (2 ml/min), a detector temperature of 200° C., and an injection temperature of 200° C.

Gene Expression Analysis. For sex-specific gene expression analysis from whole bugs, mature (15 days post molt) male and female insects were fixed by adding hexane to a sealed jar and then frozen in liquid nitrogen. To determine gene transcript abundance in the cuticle tissue, three mature males or females were treated with hexane and individuals were dissected in PBS. All tissues were removed except the epithelial cells attached to the cuticle. Tissues were kept frozen in liquid nitrogen between dissections. Pooled tissue samples from males and females were stored at −80° C. prior to RNA extraction. cDNAs of RNA extracted from whole bugs of cuticle tissue were generated as described above. Relative transcript abundance was measured by quantitative (Real Time)-Reverse Transcription PCR (qRT-PCR) using the ddCt method and normalized to the 30S ribosomal protein S4 (RpS4) (Livak and Schmittgen. 2001. Methods 25:402-408). Primers were designed to amplify a fragment of approximately 100 bp using Geneious (v. 7.1.9) (Table 1) and tested for non-specific binding. Reaction plates contained 2 µl cDNA (1 ng/µl), 0.6 µL of each primer (300 nM final concentration), 6.8 µl dH2O and 10 µl PowerSYBR Green PCR Master Mix (Applied Biosystems, Thermo Fisher Scientific) per well. The samples were analyzed using an Applied Biosystems 7300 with default settings (50° C. 2 min, 95° C. 10 min followed by 40 cycles of 95° C. 15 s, 60° C. 1 min). Primers were tested for non-specific amplification by analyzing the dissociation curve after PCR. Significance was measured using Student's t test.

Amino Acid Sequence Alignment and Phylogenetic Analysis. Amino acid sequence alignments were performed in Geneious (v. 7.1.9) using MAFFT with automatic algorithm selection. For phylogenetic analysis, poorly conserved positions were removed using Gblocks (v. 0.91b) with default settings. A consensus tree was built from Bayesian phylogenetic posterior probabilities using MrBayes (v. 3.2.5). Analysis was performed with 2 parallel processes each of 4 MCMC chains sampled every 1000 generations until the standard deviation of split frequencies reached <0.01. The first 25% of saved trees were discarded prior to analysis.

Results

Figure 6:
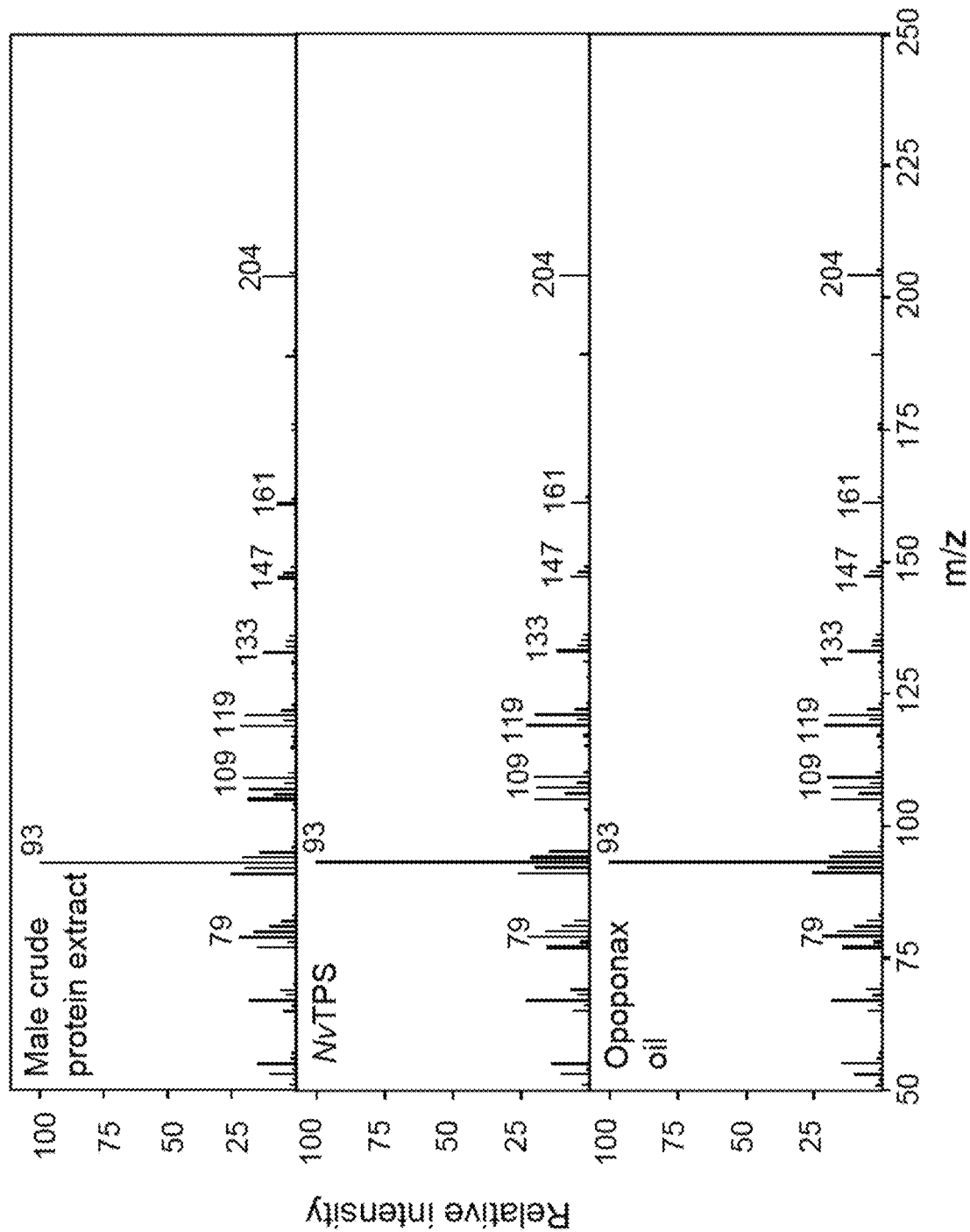
FIG. 6 shows mass spectra of the enzymatic product from male crude protein extract (top), recombinant NvTPS protein (middle), and (Z)-α-bisabolene from Opoponax oil (bottom).

Determination of (Z)-α-Bisabolene Synthase Activity in Crude Protein Extracts. Since the sex pheromone of *N. viridula* is released from glands at the ventral abdomen of mature males but not from females, we prepared crude protein extracts from the tissue associated with the ventral sternites of males and females and comparatively examined these extracts for the presence or absence of TPS activity. Incubation with (E,E)-FPP and subsequent analysis of hexane-extracted products by GC-MS showed the formation of (Z)-α-bisabolene in extracts from males while only little activity was found in females (FIGS. 1 and 6). Additional putative sesquiterpene products found at low abundance were β-bisabolene and nerolidol isomers.

Identification and Functional Characterization of IDS-Like Genes in *N. viridula*. To identify possible IDS-like genes associated with the (Z)-α-bisabolene synthase activity in male *N. viridula* a comparative transcriptome data from tissue associated with the ventral sternites of mature males and females was generated. A tblastn search was performed to search for IDS-type sequences using MhTPS (MG662378.1) and MhFPPS (MG662379.1) from *M. histrionica* as well as the bifunctional GPPS/TPS (AAX55632.1) and FPPS (AAX55631.1) from Ips *pini* as query sequences. Three IDS-like sequences (NvIDS1-3, accession numbers MG748543 (NVIDS1) (SEQ ID NO: 1), MG748544 (NvIDS2) (SEQ ID NO: 2), and MG748545 (NvIDS3) (SEQ ID NO: 3), respectively) were found, while no plant or microbial type TPS sequences could be identified. Full length cDNAs of two of these sequences were further amplified: cDNA of NvIDS1 was obtained from RNA extracted from the cuticle associated tissue of mature males and cDNA of NvIDS2 was amplified from the same tissue of mature males and females. The NvIDS1 cDNA (SEQ ID NO: 1) encodes a 43.32 kDa protein containing 379 amino acids (SEQ ID NO: 4) (NvTPS) and the cDNA of NvIDS2 (NvFPPS) (SEQ ID NO: 2) encodes a 46.00 kDa protein consisting of 403 amino acids and can had a sequence according to SEQ ID NO: 5.

SEQ ID NO: 1
ATGGCAGCAAGGGCACCCGTACACCTCAGAGGATTTATTGCAAGAGTCG

CCCTTAACAAGAAAAATCTTCATGCAAGACATAAGCTAGACACAGATAT

TGACAAATATTATTACACGCTCCACAATGTAATAATTCCAGATTTTATG

GATATGGTTAAGGAAATACCAGGTTATCCAGAAAGGATTAAGAAGTGCG

TTGCTCACACCACCCCATCATATTTTGAAGGATGGGCCTTCAGCACCGA

ATTAATATACAAAACAGTGGCAGATAAACAACATCAAACAGAAAGGAAC

TTAGAAAAGTGTAGAATCATCAGAGCTTTGATGGATATGAGCTATGCGA

TGGCAGGAATACTTGATGACTATGTTGACAAAGGTGAGTTCAGACGAGG

TAAGAAGGTTTGGGCTTCCGTGTGTGAGGGAGGCCAAGAAGCTGCAATC

TACGACTCCATTGCTGTCACCTACTTGATGTCACTTATGGTTAAGCGCC

ACTTCGGTACGGATCCAGGATATAGCAAGCTGATAGAATTATTTAATAT

GGTTCCTGGCACAGCGGCGATAGGGAACACGCTGGATATCCTTGACCGT

CACGACACAAACTACTATGATGATACAATGTGGAAACATTCCGTCCAAA

ACAAAGCAGCAAATACTGTATTTCCTGCAGCAACTGCTGGCCTAATTCA

TGCAGGAGTACTCTGTGATGACCTACTTGATAGAACTAGTGAAGTGTTT

GGCTACACTGGACATCTGTTTCAAGTCTGGGATGATTTCATGGAACACT

ACGCTGTGAAAGAACAATCTGGCAAAGGTGCTCCAGATACCAAATATAA

-continued
CGCAAAAACTTGGGCAACGTTGACTGCAATGGCCCACTTTAATGAAGCC

CAAGCCAAGGAGTTTAAGGCCTGCTACGGGTCCACCGATCCAGCCAAAA

GATCGAGAGTGCGCGAACTATATGATGAAGTGAATTTACGAGGACTATA

TATTGATTATCTCAGAAATACTTATATGGTCGTGGAAGAAAAAATCAGC

AAAATTCCCGATCCCAGAATACAAAGTGCCTGTAGAAGCTACATGGATT

GGTTGCTTGTTGAACCACCCCAGGATGAAGAAGAAGCTGAAAGCGTATT

AAATAACTGA

SEQ ID NO: 2
ATGCCACTTGCAAAACTGTGCGCGAAAAAACTTTCAAGCCCTTTAATGA

AATTATGTTACCCTAATTTGAACGGAAAATTGCCCTTTAGTAATTTATC

TAATATCTTAGACAATTCTTCTTTAAAATTTCATAGCTGCAATCCTCAT

ATTACCTGCAGAGGGCTTAGCACAGTTGCACTACGTCCACAGACTATAA

CAAAAGATGATAAGAGAGATTTTATGGCTGTATTTCCAGACATTGTTCG

GGATTTGACACAACTGAATCCTGGAATATCAGATCTCAGTACTTTAATT

TCTAAGATTATGCAATATAATGTATCAGGAGGAAAGAAAGTAAGAGGGC

TGACTGTTGTTTATAGTTATCGCATGCTTGCTCCTGACCATGCTTTAAC

ACCAGAAAACATCAGGCTGGCCCAGATTTTAGGGTGGTGCGTTGAAATG

CTCCAAGGATTTTTCTTAGTTATTGATGATCTTGCTGATCAGTCTATAA

CTAGAAGGGGAAGACCCTGTTGGTATAGAAATCCTGATGTTGGACTTCG

TGCTGGTTCTGATGCTCTTCTTATACAGTCAGGAACTTTTCAACTGCTT

CAACAACATTGCAAAGATAGAGAGTTCTATATTGATCTTGTTGAATTAT

TTTTGGATGCTGTAAGGCGTACTACCTATGGACAAACATTAGATCACGT

TTCTTCATTTCCTAACATCACTCACTTAACAATGGATAGGTATAACTTT

ATCACAAAATATAAACATCGTACTACACTTTCCATTTGCCAGTAGCCA

CTGCAATGTATATGGCTGGTATTTACAATACTGAATTGCATCGTCAAGC

TAAAAGTGTTTTACTTGAAATGGGACATTACTTTCAAGTTCAGGATGAC

TATCTTGATGTGTTTGGTGATGAAGAAGTTATCGGAAAGATAGGTACTG

ATATTCAGGAAGGAAAGTGCACATGGCTAGCTATTGTTGCATTTCAAAG

AGCTTCACCATCTCAGAGAGAAATTTTAGAGTCCTGCTATGGAAGTAAA

GACCCAGAAAAAATTAAAAAAGTGAAGGATACTTTTATAGAAATTGGTG

TTCCTGCAGTTTTTCATGCTTATGAAGAAGAAACATATAATTTGATCAC

AAGACAAATACAACAATTAAGTCAAGGCCTGCCTCATGAATTATTTCTT

ACATTATTACATAAAACATATGGCAGAAAGCAGTAG

SEQ ID NO: 3
ATGGCAGCAAGGGCATCGGTAAATCTAAGAGGTTTTTTAGCAAGAGTCG

CGCAAAATAAGGAAAATGTTCATGTAAGACATAAGTTGGACACAGAAAT

TGACAAATATTATAAGACACTCCACAATGTAGTCATTCCAGATTGTATG

GATTTGGTGAAGGAAATACCAGGTTATCCACAAAGGGTTAAAGAGTGCA

TTTCACACACCACCCCATCATATTATGACGGGTGGAACTTCAGCATCGA

ATTAATGTATAAAACAGTGGCAGATGAACACCATCAAACAGAAAAGAAC

TTGGAAAAGTGTAGAATACTCAGAGCCTTGAAGGATATGAGCTATGCGA

TGGCAGGTATAGTTGATGACTATGCTGATAAAGGTGAATACAGACATGG

-continued
TAAGAAGGTTTGGGCTTCCATATGCGAAGGAGGCCAAGAAGCTGCAATC

TACGACTCCGTCGCAGTCAACTACTTGATACTACTGATGCTTCATCGCC

ACTTCAGGAATGATCCAGGATACAGCAGGCTGTTAGAACTATATAATAT

GGTTCCTGGCACAGCAGCGATAGGAAACACGCTGGATATCCTTGACCGT

TACAACTCAAACTACAGTGATGATATATGGAAACATACTGTCCAAAACA

AAGCAATGAATTCAATATGTACTGCAGGAGGTACAGGCCTAGTTCATGC

TGGAGTTATCTGTGATGACCTGATTGCTAAAACTTGTGATGTTTTTCGC

TACACTGGACTTCTGTTTCAAGTGTGGGATGATTTCATGGAATACTATG

CTTTGCAAGAACAATCTGGTAAAGGTTCTCCAGATAGCGAATATAATAT

AAAATCCTGGGCAACTGTGACTGCAATGGCCCACTTTAATGAAGCCCAA

GCTAAGGAGTTTAGGGCCTGCTACGGGTCCAGCGATCCAGCCAAAAGAT

CAAGAGTGCGGGAGCTGTATGATGAAGTGAATTTACCAGGACTATACAT

GGATTATCTTAGAAATATTCATATGACAATGGAAAAAAAAATTAGCATT

ATTCCAAATCCAAGAATACGAAGCGCCTGCACTAGCTATATGGAATGGT

TGCTCGTTGAACCACCCAACGTTGAAGAACAAATTGAAAGAATAAAAGT

GTATTAA

SEQ ID NO: 4
MAARAPVHLRGFIARVALNKKNLHARHKLDTDIDKYYYTLHNVIIPDFM

DMVKEIPGYPERIKKCVAHTTPSYFEGWAFSTELIYKTVADKQHQTERN

LEKCRIIRALMDMSYAMAGILDDYVDKGEFRRGKKVWASVCEGGQEAAI

YDSIAVTYLMSLMVKRHFGTDPGYSKLIELFNMVPGTAAIGNTLDILDR

HDTNYYDDTMWKHSVQNKAANTVFPAATAGLIHAGVLCDDLLDRTSEVF

GYTGHLFQVWDDFMEHYAVKEQSGKGAPDTKYNAKTWATLTAMAHFNEA

QAKEFKACYGSTDPAKRSRVRELYDEVNLRGLYIDYLRNTYMVVEEKIS

KIPDPRIQSACRSYMDWLLVEPPQDEEEAESVLNN*

SEQ ID NO: 5
MPLAKLCAKKLSSPLMKLCYPNLNGKLPFSNLSNILDNSSLKFHSCNPH

ITCRGLSTVALRPQTITKDDKRDFMAVFPDIVRDLTQLNPGISDLSTLI

SKIMQYNVSGGKKVRGLTVVYSYRMLAPDHALTPENIRLAQILGWCVEM

LQGFFLVIDDLADQSITRRGRPCWYRNPDVGLRAGSDALLIQSGTFQLL

QQHCKDREFYIDLVELFLDAVRRTTYGQTLDHVSSFPNITHLTMDRYNF

ITKYKTSYYTFHLPVATAMYMAGIYNTELHRQAKSVLLEMGHYFQVQDD

YLDVFGDEEVIGKIGTDIQEGKCTWLAIVAFQRASPSQREILESCYGSK

DPEKIKKVKDTFIEIGVPAVFHAYEEETYNLITRQIQQLSQGLPHELFL

TLLHKTYGRKQ

Figure 7:
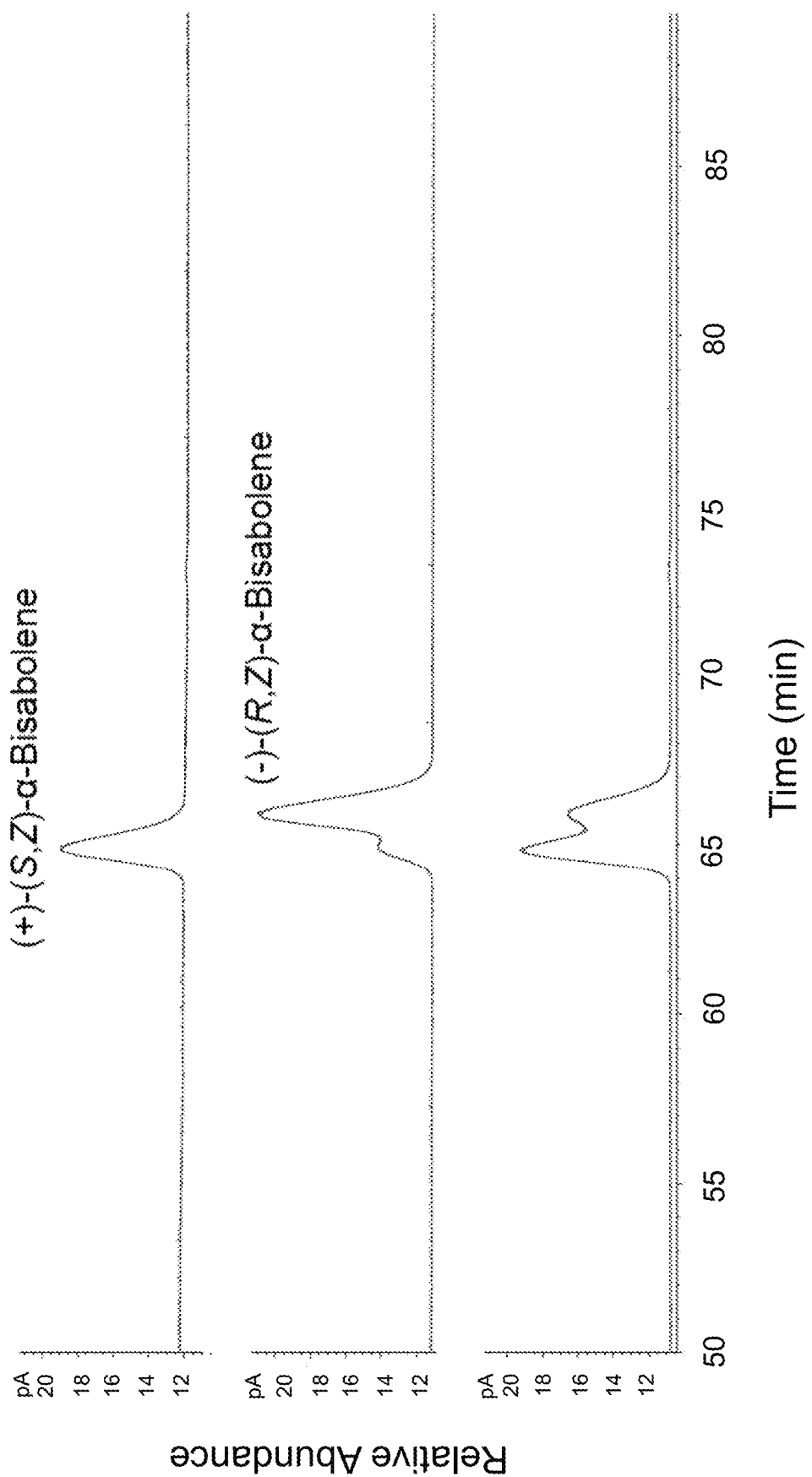
FIG. 7 can demonstrate Separation of α-bisabolene reference standards on a Hydrodex-β-6TBDM column. GC-MS chromatograms of (+)-(S,Z)-α-bisabolene from Opoponax oil (top), synthetic (−)-(R,Z)-α-bisabolene (middle), and a mixture of (+)- and (−)-bisabolenes (bottom). Conditions for separation are described in Methods and Materials of Example 1.

To functionally characterize these genes, both full length cDNAs were cloned into the bacterial expression vector pEXP5 generating an N-terminal histidine fusion tag. When tested for TPS activity, partially purified recombinant NvIDS1 protein converted (E,E)-FPP to (Z)-α-bisabolene as the main product (FIGS. 2A and 6). Although (+)-(S,Z)- and (−)-(R,Z)-bisabolene stereoisomers could only be partially separated on a Hydrodex-R-6TBDM GC column, it was still possible to clearly identify the NvIDS1 product as (+)-(S,Z)-α-bisabolene (FIGS. 3 and 7). No enzymatic products were detected when NvIDS1 was provided with (Z,E)-FPP or (Z,Z)-FPP (FIG. 2A). Further, no activity was observed with isopentenyl diphosphate (IPP) and dimethyl allyl diphosphate (DMAPP) indicating that the enzyme did not exhibit IDS activity. Recombinant NvIDS2 did not show any TPS activity when provided with different FPP isomers, but instead converted IPP and DMAPP to (E,E)-FPP as the sole product (FIG. 2B). Because of the TPS activity of NvIDS1 and IDS activity of NvIDS2, designated NvTPS and NvFPPS, respectively. Kinetic analysis of NvTPS with (E,E)-FPP as the substrate showed an apparent Km value of 0.95±0.37 μM, which is similar to that of the sesquipiperitol synthase from M. histrionica (Lancaster et al. 2018. PNAS 1150: 115: E8534-E8641) and Km values of plant sesqui-TPS enzymes (Cai et al. 2002. Phytochemistry.61:523-529). A synthetic scheme for this pathway is shown in FIG. 2C. (Z)-α-Bisabolene can be produced from (E,E)-FPP by NvTPS, which is further converted to trans- or cis-(Z)-α-bisabolene epoxide by epoxidation along the C3-C4 double-bond by a cytochrome P450 epoxidase. Kinetic analysis of NvTPS with (E,E)-FPP as the substrate showed an apparent Km value of 0.95±0.37 μM and a Vmax of 11.83±2.14 pkat/mg. The kcat value was $5.41 \times 10^{-4} \pm 9.76 \times 10^{-5}$ s-1 and kcat/Km=$0.57 \pm 4.46 \times 10^{-9}$ s-1 mM-1. Km, kcat and kcat/Km values of NvTPS were similar to those of other plant sesqui-TPS enzymes such as (E)-β-caryophyllene synthase from Artemisia annua (Cai et al., 2002) and γ-humulene synthase from Abies grandis (Little and Croteau, 2002).

Tissue and Sex Specificity of NvTPS and NvFPPS Gene Expression. The sex pheromone of N. viridula is released by mature males from unicellular pheromone glands located in epithelial cells of the abdominal sternites (Cribb et al. 2006. J Morphol 267:831-840). To determine to what extent the TPS activity found in crude lysates of this tissue (FIG. 1) correlates with the expression of the NvTPS gene, NvTPS transcript abundance was examined in whole male and female bugs and their abdominal sternites by qRT-PCR (FIGS. 4A-4B). Accumulation of the NvTPS transcript was significantly higher in mature males than in females (FIG. 4A) and high transcript abundance was observed in the tissue lining the cuticle of the abdominal sternites of mature males (FIG. 4B). By contrast, NvFPPS was more equally expressed in both mature males and females (FIG. 8).

Figure 10:
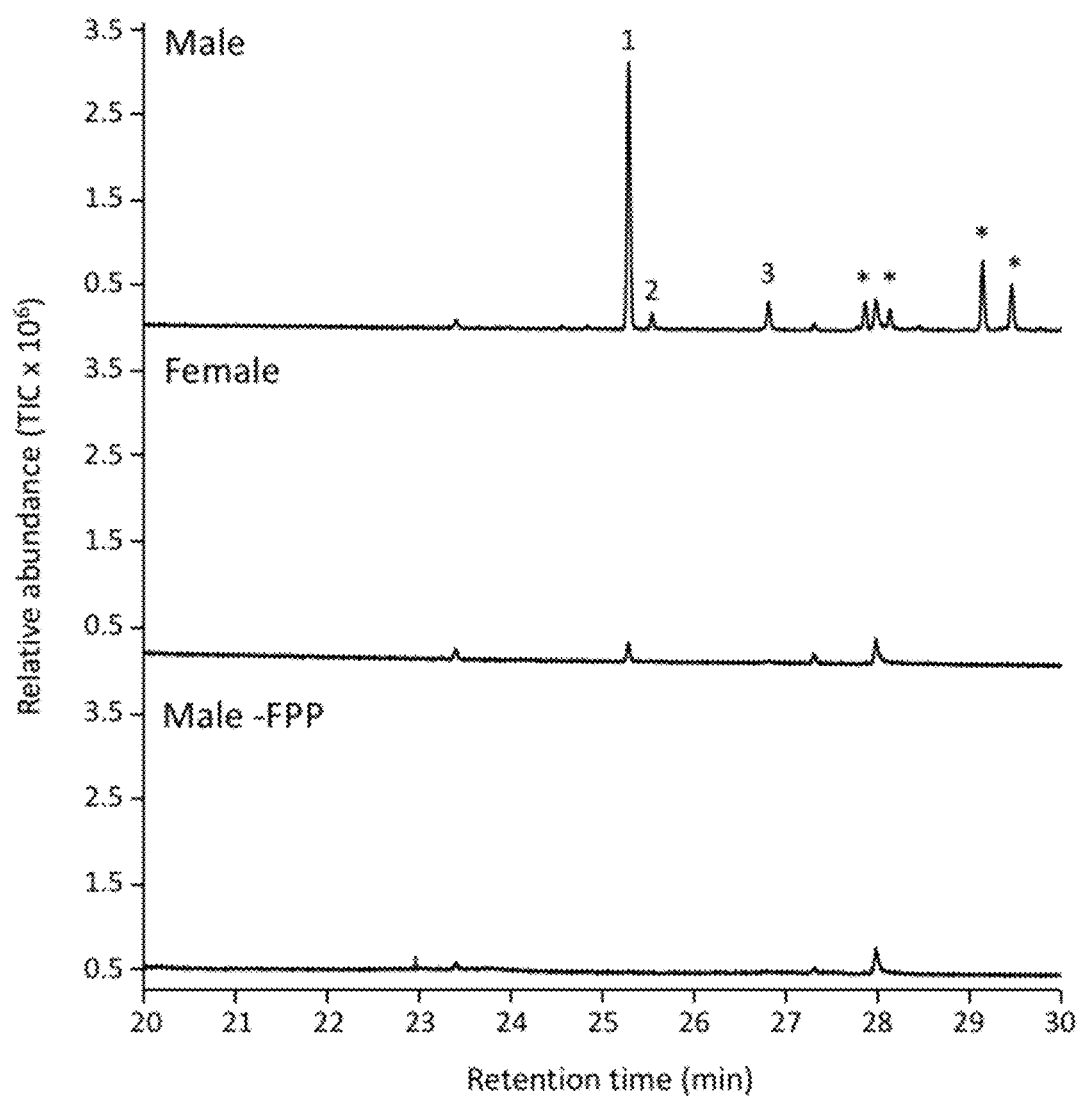
FIG. 10 can demonstrates results after the tissue of abdominal cuticle from mature male and female *N. viridula* was homogenized in assay buffer and assayed with 100 μM (E,E)-FPP. Volatile products were extracted with an equal volume of hexane and analyzed with GC-MS. 1, α-bisabolene, 2, β-bisabolene, 3, nerolidol, *, unknown sesquiterpene.

Enzyme Activity in Crude Protein Assay. Enzyme activity was measured in crude protein extract from whole male and female bugs to determine possible products from enzymes that accept (E,E)-FPP. The supernatant from homogenized bugs was incubated with the substrate and analyzed products extracted by hexane using GC-MS. Chromatographs show (Z)-α-bisabolene present in crude protein from males but not females (see e.g., FIGS. 1 and 10). Also, several sesquiterpenes were found in low abundance that were not found in assays of partially purified NvTPS.

Figure 5:
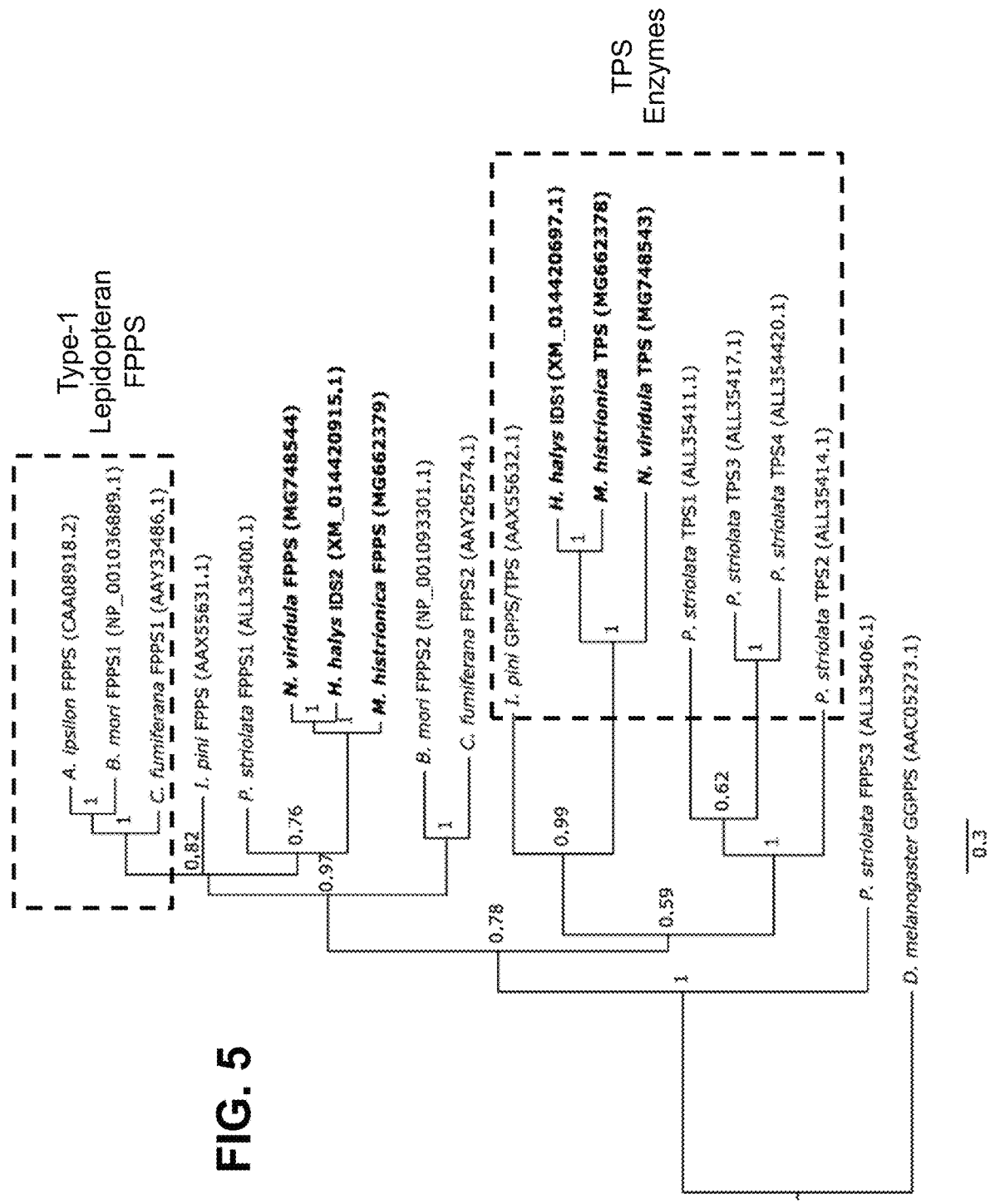
FIG. 5 shows the majority-rule phylogram based on Bayesian posterior probabilities with functionally characterized insect IDS and TPS proteins. Pentatomid proteins are highlighted in bold. *H. halys* IDS1 and IDS2 proteins are considered to have putative TPS and FPPS function, respectively. Node values are Bayesian probability scores and the scale represents expected changes per site. The tree was rooted using a geranylgeranyl diphosphate synthase (GGPPS) from *D. melanogaster*.
Figure 13:
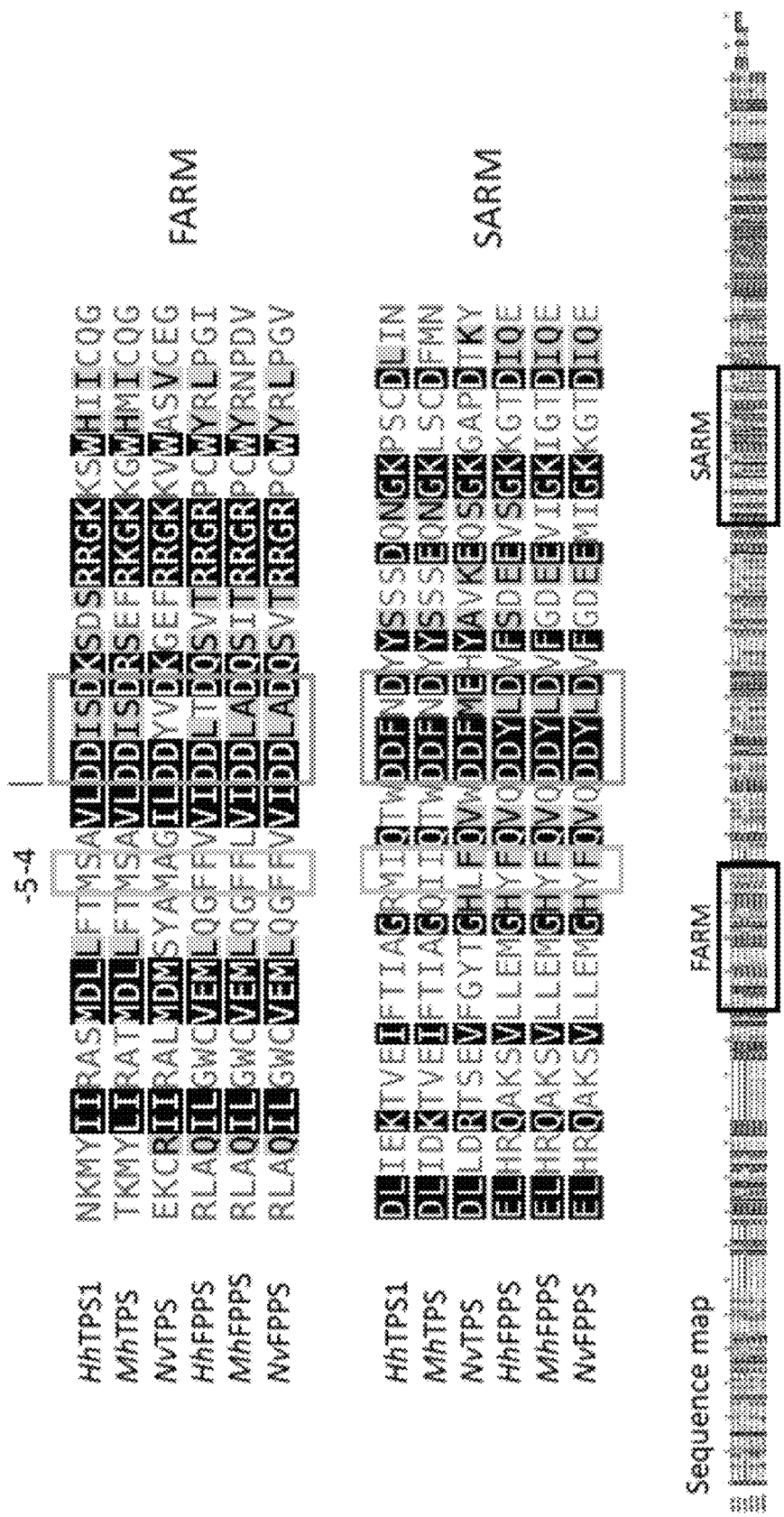
FIG. 13 shows an amino acid sequence alignment of the FARM and SARM regions of various different stink bugs, including the Southern green stink bug enzyme described herein (NvTPS and NvFPPS).

Sequence Comparison and Phylogenetic Analysis of N. viridula IDS and TPS with Other IDS-Like Proteins from Pentatomidae. NvTPS maintains the non-aromatic residues at the fourth and fifth positions upstream of the first aspartate-rich motif (FARM) similar to HB and BMSB but shows a phenylalanine at the fourth position upstream of the second aspartate-rich motif (SARM) (FIG. 13). A majority-rule phylogenetic tree based on alignments of NvTPS and NvFPPS with other recently characterized insect IDS and TPS proteins was constructed using Bayesian posterior probabilities to examine possible evolutionary relationships between these proteins (FIG. 5). Selected sequences were from functionally characterized IDSs and IDS-type TPSs of Lepidoptera, Coleoptera and Hemiptera, and also included putative TPS and FPPS proteins (IDS1, IDS2) from H. halys. While most IDS proteins are considered to form homodimers (Wallrapp et al. 2013. PNAS. 110:E1196-E1202), type I and II FPPSs from Lepidoptera can produce allylic diphosphates as heterodimers (Sen et al. 2007. Insect Biochem Mol Biol 37:819-828). According to the phylogenetic analysis, pentatomid TPSs clustered together and formed a clade with the Ips pini bifunctional GPPS/TPS, while only weak phylogenetic support was provided for a clade containing both TPSs from pentatomids and P. striolata. IDS-type TPSs formed a clade separate from that of bona fide (E,E)-FPPSs including those from pentatomids. Interestingly, the (Z,E)-FPPS from P. striolata (FPPS3) appears to have diverged early from a putative trans-IDS pro-genitor of (E,E)-FPPSs and IDS-type TPSs.

Figure 9:
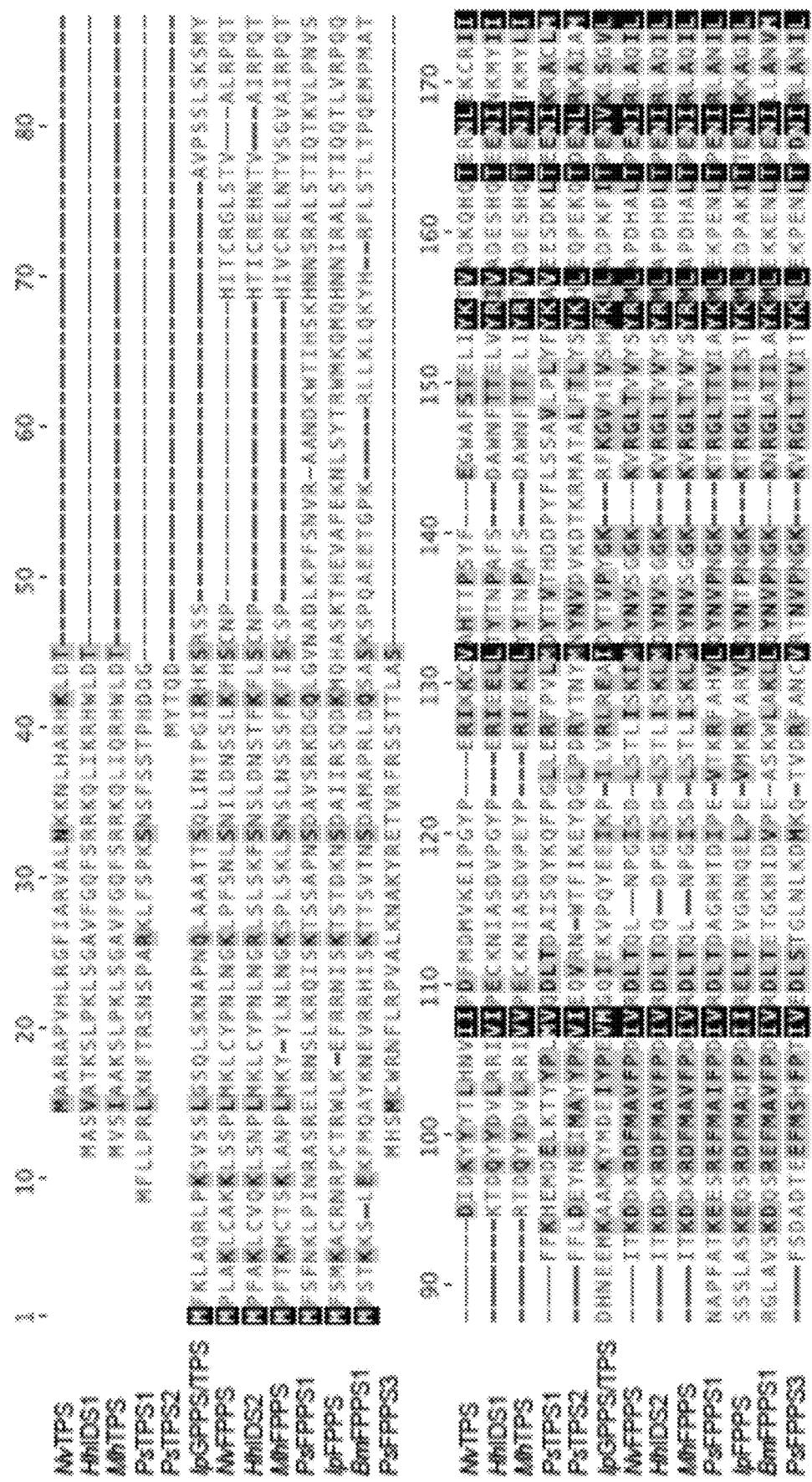
FIG. 9 shows an amino acid sequence alignment of functionally characterized pentatomid FPPS and TPS proteins. The first and second aspartate rich motifs (FARM, SARM) are marked with dashed boxes. Amino acid residues at positions 4 and 5 upstream of the FARM are marked with a sold line box. Accession or gene model numbers are given in FIG. 5.

An alignment of several proteins used for phylogenetic comparison showed low sequence identities between IDS-type TPSs and the more highly conserved IDS (FPPS) proteins (FIG. 9). FIG. 13 shows an amino acid sequence alignment of the FARM and SARM regions of various different stink bugs, including the Southern green stink bug enzyme described herein (NvTPS and NvFPPS). NvTPS shares only 19%-23% sequence identity with NvFPPS and FPPSs from M. histrionica and other insects. By contrast, the NvFPPS protein is 88% identical to M. histrionica FPPS and 40-46% identical to other insect FPPSs. NvTPS had less sequence similarity compared to M. histronica TPS and Halyomorpha halys TPS1. See e.g., FIGS. 9,12 and 13. The divergence between IDS-like TPS and FPPS enzymes is also apparent in sequence variations of the TPS proteins at two aspartate rich motifs, the first aspartate rich motif (FARM) and the second aspartate rich motif (SARM), which facilitate coordinated binding of Mg2+ions with the allylic substrate to initiate catalysis through carbocation formation in IDS enzymes (Christianson. 2017. Chem Rev. 117:11570-11648). For example, two aromatic amino acids at position 4 and 5 upstream of the FARM of FPPS proteins are substituted by non-aromatic amino acids in pentatomid TPSs and most other insect TPSs (FIG. 9). Similar substitutions can be observed upstream of the SARM. Furthermore, in NvTPS, the third aspartate residue of the SARM is replaced by a glutamate indicating residue changes at this conserved motif in conjunction with the emergence of TPS activity. FIG. 11 shows a table showing BLAST query sequences. FIG. 12 shows an identity matrix table of pentatomid IDS and TPS proteins developed from the alignment of proteins listed in FIG. 11.

N. viridula Produces the Sesquiterpene Pheromone Precursor (Z)-α-bisabolene. This Example can demonstrate identification NvTPS as an IDS-type TPS, which produces the cyclic sesquiterpene (Z)-α-bisabolene as the presumed precursor of the N. viridula sex pheromone isomers trans- and cis-(Z)-α-bisabolene epoxide. The (S) configuration of the identified a-bisabolene matched those of trans- and cis-epoxides and thus provided an unequivocal support for its role as an intermediate in the biosynthesis of the N. viridula sex pheromone.

(E,E)-FPP, the substrate of NvTPS, is most likely provided by NvFPPS, which was identified as a true trans-IDS enzyme. Conversion of the NvTPS product (Z)-α-bisabolene to trans- or cis-(Z)-α-bisabolene epoxide is presumably catalyzed by a cytochrome P450 epoxidase activity. Similar epoxidations occur in the biosynthesis of fatty acid-derived pheromones and the final step in juvenile hormone biosynthesis (Belles et al. 2005. J Chem Ecol. 27:2397-2423; Blomquist and Vogt. 2003. Insect pheromone biochemistry and molecular biology. The biosynthesis and detection of pheromones and plant volatiles. Elsevier, London). This Example focused on the southeastern United States ecotype of *N. viridula*, which releases a pheromone with a 3:1 ratio of trans:cis-(Z)-α-bisabolene epoxide (Aldrich et al. 1987. J Exp. Zool 244:171-175). By contrast, a French ecotype emits a 2:1 ratio (Brezot et al. 1994. J Chem Ecol. 20:4133-3147 and Brezot et al. 1993 J Chem Ecol), while the pheromone of a Brazilian ecotype contains no cis isomer (Baker et al. 1987. J Chem Soc Chem Commun: 414-416). It is likely that these ecotype-specific variations in pheromone isomeric composition are generated by differences in product specificity of the final P450 epoxidation step.

High expression of NvTPS in cells lining the abdominal sternites of *N. viridula* mature males was observed (FIG. 4B). This tissue was shown to carry unicellular pheromone glands, which are absent in females and fifth-instar nymphs (Cribb et al. 2006. J Morphol 267:831-840). Bisabolene epoxides are released via ducts from the glands onto the ventral abdominal surface. It is possible that (Z)-α-bisabolene is directly produced and converted to trans/cis-(Z)-α-bisabolene epoxides in the glandular cells. Alternatively, the terpene olefin may be made in neighboring cells or cuticle-associated specialized cells called oenocytes and then transported to the glandular cells, where the com-pound undergoes epoxidation. Similar scenarios have been described for hydrocarbon sex pheromones. For example, in the gypsy moth *Lymantria dispar* (Lepidoptera: Erebidae), the alkene hydrocarbon precursor to the sex pheromone disparlure is biosynthesized in oenocyte cells. Following transport through the hemolymph by lipophorin, the precursor is taken up by gland cells for epoxidation and subsequent release (Jurenka et al. 2003). A localization of TPS activity in tissue associated with the ventral abdominal cuticle has also been demonstrated in males of *M. histrionica* (Lancaster et al. 2018. PNAS 1150: 115: E8534-E8641).

Evolution of Terpene Synthase Genes in Pentatomidae and Other Insect Lineages. The demonstrated identification of an a-bisabolene producing TPS enzyme in *N. viridula* is in agreement with similar findings of a homologous TPS enzyme in *M. histrionica* (Lancaster et al. 2018. PNAS 1150: 115: E8534-E8641), and supports the notion that TPS enzymes have evolved from IDS proteins for de novo biosynthesis of sesquiterpene pheromones in stink bugs. Since similar findings have been reported for the biosynthesis of sesquiterpene and monoterpene aggregation pheromones in *P. striolata* and Ips *pini*, respectively, it is likely that TPS homologs have emerged throughout the evolution of different insect lineages. Volatile terpenes are released by insects not only as aggregation and sex pheromones but also exhibit important functions as alarm pheromones such as (E)-R-farnesene in aphids (Pickett et al. 2013. Nat. Prod. Rep 30:1277-1283) or a-farnesene in advanced termites (Sobotnik et al. 2008. J Chem Ecol: 34:478-486). Moreover, terpenes serve as defensive compounds as in the case of papilionid larvae, which release blends of monoterpenes and sesquiterpenes from special organs called osmeteria to ward off predators (Honda 1981. J. Chem Ecol. 7:1089-1113; Omura et al. 2006. J Chem Ecol. 32:1999-2012). Based on the common use of specialized terpenes in insect interactions, it was hypothesized that IDS-derived TPS enzymes have been recruited by various insects in the evolution of distinct intra- and inter-specific communication signals. This can be supported by similar findings of biosynthetic enzymes in the formation of iridoid defense metabolites in larvae of chrysomelid beetles (Bodemann et al. 2012. Proc RSoc B. 279:4126-4134).

Recent studies of sesquiterpene pheromone biosynthesis in *M. histrionica* (Lancaster et al. 2018. PNAS 1150: 115: E8534-E8641) and *P. striolata* (Beran et al. 2016. PNAS. 113:2922-2927), together with the phylogenetic comparison of insect IDS and TPS proteins presented here, suggest that the clades of bona fide IDS enzymes and proteins with TPS function diverged early from a progenitor with trans-IDS activity. It is possible that a clade encompassing all insect TPSs has descended from a common TPS ancestor that emerged from this trans-IDS progenitor; however, the current results provide only weak support for a monophyletic evolution of insect TPS proteins, and more homologs from diverse insect lineages have to be identified to corroborate this assumption.

Sequence comparisons among the IDS-type TPS proteins in pentatomids show that the TPS from *N. viridula* is only 38% identical to that of *M. histrionica* and a putative TPS (IDS-1) from *H. halys*. NvTPS also shares only 17-19% identity with the TPS enzymes from *P. striolata* and I. *pini* indicating plasticity and diversification in the functional evolution of these enzymes similar to those observed for TPS enzymes from other organisms (Chen et al. 2011. Plant J 66:212-229; Dickschat 2016. Nat Prod Rep. 33:87-110). An evolutionary analysis of FPPS and TPS proteins from *P. striolata* and other insects confirmed that selection of members of the TPS clade is under more relaxed constraints in contrast to a strong purifying selection among true FPPS proteins (Beran et al. 2016. PNAS. 113:2922-2927). Furthermore, in *Phyllotreta* species, TPSs have diversified into small gene families. This sequence diversification, although at a limited scale, resembles that of plants and microbes; however, it is not apparent in all species since I. *pini* and the investigated pentatomids seem to have evolved only single TPS proteins with function in pheromone biosynthesis.

The structural changes underlying the transition from IDS to TPS function in insects are currently unknown. Sequence comparisons demonstrate distinct amino acid differences between bona fide IDS and TPS proteins as indicated for residues at the FARM and SARM motifs (FIG. 9). Homology modeling of the *M. histrionica* TPS on an avian FPPS and docking experiments with (E,E)-FPP suggested that the aromatic amino acid substitutions at positions 4 and 5 upstream of the FARM likely cause a different orientation of the prenyl side chain of the FPP substrate that may facilitate a cyclization to terpene products in the TPS enzyme (Lancaster et al. 2018. PNAS 1150: 115: E8534-E8641). Substitution of these amino acids in the TPS of *M. histrionica* abolished its enzymatic activity and thereby supports a critical role of these residues in TPS function (Lancaster et al. 2018. PNAS 1150: 115: E8534-E8641). However, a combination of several residue substitutions was likely led the evolutionary transition from IDS to TPS enzymatic function. Taken together, this Example can demonstrate IDS-type TPS proteins in the evolution of terpene semiochemicals in insects, particularly the southern green stink bug. Terpene biosynthetic genes such as the one identified in *N. viridula* can be useful as targets in RNAi-based pest management or for metabolic engineering of trap crops and plant/microbial based pheromone production platforms as is described elsewhere herein.

We claim:

1. An engineered polynucleotide comprising:
one or more polynucleotides, wherein the one or more polynucleotides
   (a) have a sequence that is 95% to 100% identical to SEQ ID NO: 1 or 3 and encode a terpene synthase (TPS) protein comprising an amino acid sequence that is about 95% to 100% identical to SEQ ID NO: 4;
   (b) have a sequence that is 95% to 100% identical to SEQ ID NO: 2 and
encode an isoprenyl diphosphate synthase (IDS) protein comprising an amino acid sequence that is about 95% to 100% identical to SEQ ID NO: 5; or
   (c) have both (a) and (b); and one or more heterologous regulatory polynucleotides operably coupled to the one or more polynucleotides.

2. A vector comprising:
one or more engineered polynucleotides of claim 1.

3. A cell comprising:
the engineered polynucleotide of claim 1, or a vector comprising the engineered polynucleotide, wherein the engineered polynucleotide encodes a terpene synthase (TPS) protein comprising an amino acid sequence that is about 95% to 100% identical to SEQ ID NO: 4 or encodes an isoprenyl diphosphate synthase (IDS) protein comprising an amino acid sequence that is about 95% to 100% identical to SEQ ID NO: 5, or a combination thereof.

4. The cell of claim 3, wherein the cell is a plant cell.

5. The cell of claim 3, wherein the plant cell is from a plant species suitable for use as a trap crop for management of the southern green stink bug.

6. The cell of claim 3, wherein the cell is capable of producing a southern green stink bug pheromone, a southern green stink bug pheromone intermediate, or both.

7. A genetically modified plant comprising: the cell of claim 3 or a population thereof.

8. The genetically modified plant of claim 7, wherein the genetically modified plant is of a species suitable for use as a trap crop for management of the southern green stink bug.

9. A method of managing southern green stink bug infestation of a desired crop, the method comprising:
planting the genetically modified plant of claim 8.

10. The method of claim 9, wherein the genetically modified plant is planted in a location next to or near the desired crop.

11. The cell of claim 6, wherein the cell is a sunflower plant cell, a squash plant cell, a zucchini plant cell, a pumpkin plant cell, a hollyhock cell, a buckwheat cell, a triticale cell, a crimson clover cell, a vetch sorghum cell, or a millet cell.

12. The genetically modified plant of claim 8, wherein the genetically modified plant is a sunflower plant, a squash plant, a zucchini plant, a pumpkin plant, hollyhock, buckwheat, triticale, crimson clover, vetch sorghum, or millet.

13. The method of claim 10, wherein the desired crop is a cash crop.

14. The method of claim 10, further comprising positioning a visual attractant near the genetically modified plant, positioning semiochemical attractants near the genetically modified plant, or both.

15. The method of claim 10, wherein the genetically modified plant is effective as a trap crop for the southern green stink bug.

16. The engineered polynucleotide of claim 1, further comprising a polynucleotide that encodes a cytochrome P450 protein comprising an amino acid sequence that is about 100% identical to any one of SEQ ID NOs: 6-79.

17. The engineered polynucleotide of claim 1, wherein the TPS protein comprises a first aspartate rich motif (FARM).

18. The engineered polynucleotide of claim 1, wherein the IDS protein comprises a second aspartate rich motif SARM.

19. The cell of claim 3, further comprising a cytochrome P450 protein comprising an amino acid sequence that is about 100% identical to any one of SEQ ID NOs: 6-79.

20. The genetically modified plant of claim 7, wherein the cell further comprises a cytochrome P450 protein comprising an amino acid sequence that is about 100% identical to any one of SEQ ID NOs: 6-79.

\* \* \* \* \*